(12) United States Patent
Zhang

(10) Patent No.: US 7,575,876 B2
(45) Date of Patent: Aug. 18, 2009

(54) BIOMARKERS FOR NEURODEGENERATIVE DISORDERS

(75) Inventor: Jing Zhang, Mercer Island, WA (US)

(73) Assignee: The University of Washington, Seattle, WA (US)

( * ) Notice: Subject to any disclaimer, the term of this patent is extended or adjusted under 35 U.S.C. 154(b) by 0 days.

(21) Appl. No.: 11/441,384

(22) Filed: May 24, 2006

(65) Prior Publication Data

US 2007/0099203 A1    May 3, 2007

Related U.S. Application Data

(60) Provisional application No. 60/731,339, filed on Oct. 27, 2005.

(51) Int. Cl.
| | |
|---|---|
| A61B 5/00 | (2006.01) |
| G01N 33/00 | (2006.01) |
| G01N 33/53 | (2006.01) |
| G01N 33/566 | (2006.01) |
| G01N 33/48 | (2006.01) |
| G01N 31/00 | (2006.01) |
| A61K 38/00 | (2006.01) |
| C07K 16/00 | (2006.01) |

(52) U.S. Cl. .................. 435/7.1; 436/86; 436/501; 435/7.9; 530/300; 530/387.9; 600/300; 702/19; 702/23

(58) Field of Classification Search ................. None
See application file for complete search history.

(56) References Cited

OTHER PUBLICATIONS

Blennow, Journal of Internal Medicine 256:224-234, Sep. 2004.*
Earley et al., Cytometry 50(5): 239-42, Oct. 15, 2002.*
Otto et al., Methods, 44: 289-298 (2008).*
Hickey et al., Current Alzheimer Research, 5:52-60, 2008.*
Bacskai et al., "Imaging Amyloid-β Deposits In Vivo", J Cereb Blood Flow Metab, 2002. 22(9): p. 1035-41.
Klunk et al., "Imaging Aβ Plaques in Living Transgenic Mice with Multiphoton and Methoxy-X04, a Systemically Administered Congo Red Derivative", J Neuropathol Exp Neurol, 2002. 61(9): p. 797-805.
Small et al., "In Vivo Brain Imaging of Tangle Burden in Humans", J Mol Neurosci, 2002. 19(3): p. 323.
Jankovic et al., "The Evolution of Diagnosis in Early Parkinson Disease", Arch Neurol, 2000. 57(3): p. 369.
Hughes et al., "The accuracy of Diagnosis of Parkinsonian Syndromes in a Specialist Movement Disorder Service", Brain, 2002. 125(Pt 4): p. 861.
Litvan et al., "Accuracy of the Clinical Diagnoses of Lewy Body Disease, Parkinson Disease, and Dementia with Lewy Bodies", Arch Neurol, 1998. 55(7): p. 969.
Rajput et al., "Accuracy of Clinical Diagnosis in Parkinsonism—A Prospective Study", Can J Neurol Sci, 1991. 18(3): p. 275.
Hughes et al., "Accuracy of Clinical Diagnosis of Idiopathic Parkinson's Disease: a clinico-Pathological Study of 100 Cases", J Neurol Neurosurg Psychiatry, 1992. 55(3): p. 181-184.
McKeith et al., "Dementia with Lewy Bodies", Semin Clin Neuropsychiatry, 2003. 8(1): p. 46.
Love et al., "Post Mortem Sampling of the Brain and other Tissues in Neurodegenerative Disease", Histopathology, 2004. 44(4): p. 309.
Olsson et al., "Simultaneous Measurement of β-Amyloid $_{(1-42)}$, Total Tau, and Phosphorylated Tau (Thr$^{181}$) in Cerebrospinal Fluid by the xMAP Technology", Clin Chem, 2005. 51(2): p. 336.
Zhang et al., "Quantitative Proteomic Analysis of Age-Related Changes in Human Cerebrospinal Fuid", Neurobiol Aging, 2005. 26(2): p. 207.
Zhang et al., "Quantitative Proteomic of Cerebrospinal Fluid from Patients with Alzheirmer Disease", J Alzheimers Dis, 2005. 7(2): p. 125.

* cited by examiner

*Primary Examiner*—Olga N Chernyshev
*Assistant Examiner*—Stacey MacFarlane
(74) *Attorney, Agent, or Firm*—Edward J. Baba; Bozicevic, Field & Francis LLP

(57) ABSTRACT

The present invention provides methods for diagnosing neurodegenerative disease, such as Alzheimer's Disease, Parkinson's Disease, and dementia with Lewy body disease by detecting a pattern of gene product expression in a cerebrospinal fluid sample and comparing the pattern of gene product expression from the sample to a library of gene product expression pattern known to be indicative of the presence or absence of a neurodegenerative disease. The methods also provide for monitoring neurodegenerative disease progression and assessing the effects of therapeutic treatment. Also provided are kits, systems and devices for practicing the subject methods.

6 Claims, 97 Drawing Sheets

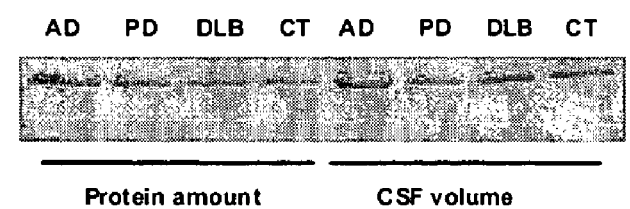
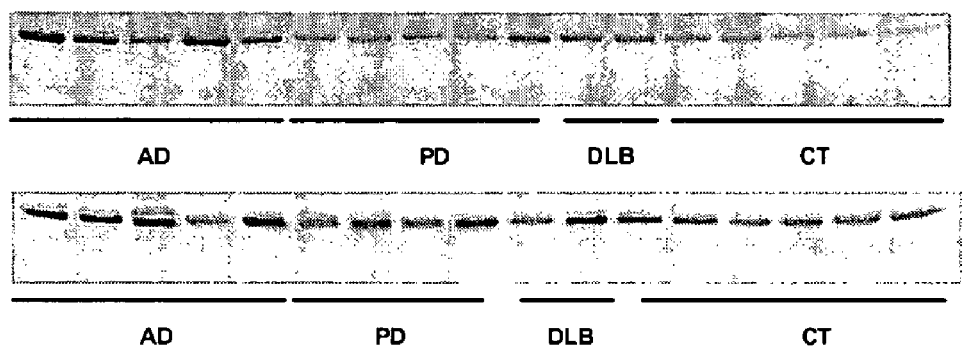
FIG. 2

Proteins With Changes In Expression Level

| Protein Name | IPI # | Peptide Sequences | iTRAQ Ratios ||||||
|---|---|---|---|---|---|---|---|---|
| | | | AD | | PD | | DLB | |
| I. Proteins unique to AD and identified by 2 or more peptides ||||||||||
| Neuronal Activities/Signal Transduction ||||||||||
| Brain abundant, membrane attached signal protein 1 | IPI00299024 | AEPPKAPEQEQAAPGPAAGGEAPK (SEQ ID NO:1) | 0.39 | ↓↓ | 0.92 | NC | 1.34 | ↑ |
| | | EADVVAR (SEQ ID NO:2) | | | | | | |
| | | EKPDQDAEGK (SEQ ID NO:3) | | | | | | |
| | | ESEPQAAAEPAEAK (SEQ ID NO:4) | | | | | | |
| Brain-derived neurotrophic factor BDNF1 | IPI00336003 | AAPMK (SEQ ID NO:5) | 0.6 | ↓↓ | 0.84 | NC | 0.91 | NC |
| | | GQGGLAYPGVR (SEQ ID NO:6) | | | | | | |
| | | IDTSCVCTLTIK (SEQ ID NO:7) | | | | | | |
| | | NYLDAANMSMRVR (SEQ ID NO:8) | | | | | | |
| Cell growth regulator with EF hand domain 1 | IPI00337548 | ELPGETLESK (SEQ ID NO:9) | 0.77 | ↓ | 1.67 | ↑↑ | 1.12 | NC |
| | | ESLDPVQEPGGQAEADGDVPGPR (SEQ ID NO:10) | | | | | | |
| | | GEAEGQAEAK (SEQ ID NO:11) | | | | | | |
| | | GEAGGQAEAEGDAPGPR (SEQ ID NO:12) | | | | | | |
| | | GEAGGQAEAR (SEQ ID NO:13) | | | | | | |
| | | HVEPGEPLAPSPQEPQAVGR (SEQ ID NO:14) | | | | | | |
| | | NTQNDFEVHIVQVENDEI (SEQ ID NO:15) | | | | | | |
| | | QETQEAPGPR (SEQ ID NO:16) | | | | | | |
| | | RESLDPVQEPGGQAEADGDVPGPR (SEQ ID NO:17) | | | | | | |
| | | TEVQLEHLSR (SEQ ID NO:18) | | | | | | |
| Chromogranin A | IPI00419463 | AEGNNQAPGEEEEEEEEATNTHPP (SEQ ID NO:19) | 0.58 | ↓↓ | 0.91 | NC | 0.83 | NC |
| | | EAVEEPSSK (SEQ ID NO:20) | | | | | | |
| | | EEEEMAVVPQGLFR (SEQ ID NO:21) | | | | | | |
| | | ELQDLALQGAK (SEQ ID NO:22) | | | | | | |
| | | EWEDSK (SEQ ID NO:23) | | | | | | |
| | | GEQEHSQQKEEEEMAVVPQGLFR | | | | | | |

FIG. 5A

| Protein Name | IPI # | Peptide Sequences | iTRAQ Ratios | | | | | |
|---|---|---|---|---|---|---|---|---|
| | | | AD | | PD | | DLB | |
| | | (SEQ ID NO:24) | | | | | | |
| | | GLSAEPGWQAK (SEQ ID NO:25) | | | | | | |
| | | GYPEEK (SEQ ID NO:26) | | | | | | |
| | | HQNLLK (SEQ ID NO:27) | | | | | | |
| | | ILSILR (SEQ ID NO:28) | | | | | | |
| | | SEALAVDGAGKPGAEEAQDPEGK (SEQ ID NO:29) | | | | | | |
| | | SGEATDGARPQALPEPMQESK (SEQ ID NO:30) | | | | | | |
| | | SGELEQEEER (SEQ ID NO:31) | | | | | | |
| | | VAHQLQALR (SEQ ID NO:32) | | | | | | |
| | | YPGPQAEGDSEGLSQGLVDR (SEQ ID NO:33) | | | | | | |
| | | YPGPQAEGDSEGLSQGLVDREK (SEQ ID NO:34) | | | | | | |
| Chromogranin B | IPI00006601 | ADQTVLTEDEK (SEQ ID NO:35) | 0.49 | ↓↓ | 1.7 | ↑↑ | 1.09 | NC |
| | | ADQTVLTEDEKK (SEQ ID NO:36) | | | | | | |
| | | ASEEEPEYGEEIK (SEQ ID NO:37) | | | | | | |
| | | AYFMSDTR (SEQ ID NO:38) | | | | | | |
| | | CHEVLSNALSK (SEQ ID NO:39) | | | | | | |
| | | DKETTENENTK (SEQ ID NO:40) | | | | | | |
| | | DPADASEAHESSSR (SEQ ID NO:41) | | | | | | |
| | | EDEEEEEGENYQK (SEQ ID NO:42) | | | | | | |
| | | ELDRNYLNYGEEGAPGK (SEQ ID NO:43) | | | | | | |
| | | ELENLAAMDLELQK (SEQ ID NO:44) | | | | | | |
| | | GEAGAPGEEDIQGPTK (SEQ ID NO:45) | | | | | | |
| | | GLEPGK (SEQ ID NO:46) | | | | | | |
| | | GYPGVQAPEDLEWER (SEQ ID NO:47) | | | | | | |
| | | HLEEPGETQNAFLNER (SEQ ID NO:48) | | | | | | |
| | | KELENLAAMDLELQK (SEQ ID NO:49) | | | | | | |
| | | MAHGYGEESEEER (SEQ ID NO:50) | | | | | | |
| | | NHNEGMVTR (SEQ ID NO:51) | | | | | | |
| | | NYLNYGEEGAPGK (SEQ ID NO:52) | | | | | | |
| | | NYPSLELDK (SEQ ID NO:53) | | | | | | |
| | | QASAIK (SEQ ID NO:54) | | | | | | |

FIG. 5B

| Protein Name | IPI # | Peptide Sequences | iTRAQ Ratios ||||||
|---|---|---|---|---|---|---|---|---|
| | | | AD || PD || DLB ||
| | | SQREDEEEEEGENYQK (SEQ ID NO:55) | | | | | | |
| | | SSAPPITPECR (SEQ ID NO:56) | | | | | | |
| | | SSQESGEEAGSQENHPQESK (SEQ ID NO:57) | | | | | | |
| | | SSQGGSLPSEEK (SEQ ID NO:58) | | | | | | |
| | | VAQLDQLLHYR (SEQ ID NO:59) | | | | | | |
| | | VQENQMDK (SEQ ID NO:60) | | | | | | |
| | | WAEGGGHSR (SEQ ID NO:61) | | | | | | |
| | | WQQQGDLQDTK (SEQ ID NO:62) | | | | | | |
| Insulin-like growth factor binding protein 5 precursor | IPI00029236 | AVYLPNCDR (SEQ ID NO:63) | 1.51 | ↑↑ | 0.79 | ↓ | 0.85 | NC |
| | | GICWCVDK (SEQ ID NO:64) | | | | | | |
| | | GVCLNEK (SEQ ID NO:65) | | | | | | |
| | | HMEASLQELK (SEQ ID NO:66) | | | | | | |
| | | QESEQGPCR (SEQ ID NO:67) | | | | | | |
| Neurexin 1-alpha precursor | IPI00442299 | DCSQEDNNVEGLAHLMMGDQGK (SEQ ID NO:68) | 0.47 | ↓↓ | 2.14 | ↑↑ | 1.17 | NC |
| | | DMTVFSGLFVGGLPPELR (SEQ ID NO:69) | | | | | | |
| | | EPYPGSAEVIR (SEQ ID NO:70) | | | | | | |
| | | MGTALLQR (SEQ ID NO:71) | | | | | | |
| | | NGDIDYCELNAR (SEQ ID NO:72) | | | | | | |
| | | NNGMCR (SEQ ID NO:73) | | | | | | |
| | | QGDPK (SEQ ID NO:74) | | | | | | |
| | | TLQRNGLMLHTGK (SEQ ID NO:75) | | | | | | |
| Neuronal pentraxin I precursor | IPI00220562 | FQLTFPLR (SEQ ID NO:76) | 0.46 | ↓↓ | 0.99 | NC | 1.43 | ↑ |
| | | IDELER (SEQ ID NO:77) | | | | | | |
| | | LENLEQYSR (SEQ ID NO:78) | | | | | | |
| | | QPGSGKNTMGDLSR (SEQ ID NO:79) | | | | | | |
| | | TPAAETLSQLGQTLQSLK (SEQ ID NO:80) | | | | | | |
| | | VNTLEEGK (SEQ ID NO:81) | | | | | | |
| | | WTFEACR (SEQ ID NO:82) | | | | | | |
| Neuronal pentraxin receptor | IPI00031289 | ADQDTIRELTGK (SEQ ID NO:83) | 0.64 | ↓↓ | 1.13 | NC | 1.11 | NC |
| | | DTMADGPWDSPALILELEDAVR (SEQ ID NO:84) | | | | | | |

FIG. 5C

| Protein Name | IPI # | Peptide Sequences | iTRAQ Ratios | | | | | |
|---|---|---|---|---|---|---|---|---|
| | | | AD | | PD | | DLB | |
| | | EELLLLQSTAEQLR (SEQ ID NO:85) | | | | | | |
| | | ELDVLQGR (SEQ ID NO:86) | | | | | | |
| | | ELTGK (SEQ ID NO:87) | | | | | | |
| | | GLQGAGPRR (SEQ ID NO:88) | | | | | | |
| | | IDRLEELPAR (SEQ ID NO:89) | | | | | | |
| | | ISIPIR (SEQ ID NO:90) | | | | | | |
| | | LEELPAR (SEQ ID NO:91) | | | | | | |
| | | LVEAFGGATK (SEQ ID NO:92) | | | | | | |
| | | MDQLEGQLLAQVLALEK (SEQ ID NO:93) | | | | | | |
| | | QRQEVEKELDVLQGR (SEQ ID NO:94) | | | | | | |
| | | QTALQQEAR (SEQ ID NO:95) | | | | | | |
| | | QTALQQEARIR (SEQ ID NO:96) | | | | | | |
| | | VALSHSSR (SEQ ID NO:97) | | | | | | |
| PLXDC2 protein | IPI00073777 | EITVATGGFIYTGEVVHR (SEQ ID NO:98) | 0.67 | ↓↓ | 0.83 | NC | 1.26 | ↑ |
| | | IQQIPNVR (SEQ ID NO:99) | | | | | | |
| PREDICTED: lunatic fringe homolog | IPI00455739 | GRRALR (SEQ ID NO:100) | 0.47 | ↓↓ | 1.03 | NC | 1.79 | ,↑↑, |
| | | HPTMLK (SEQ ID NO:101) | | | | | | |
| | | MAVEYDR (SEQ ID NO:102) | | | | | | |
| | | MSPAVRR (SEQ ID NO:103) | | | | | | |
| | | MSPWASGGHFMNTAER (SEQ ID NO:104) | | | | | | |
| | | SLAGPAGAAPAPGLGAAAAAP (SEQ ID NO:105) | | | | | | |
| | | TGAGPGRGGLRAR (SEQ ID NO:106) | | | | | | |
| Prostatic binding protein | IPI00219446 | CDEPILSNR (SEQ ID NO:107) | 0.46 | ↓↓ | 0.91 | NC | 0.84 | NC |
| | | LYTLVLTDPDAPSR (SEQ ID NO:108) | | | | | | |
| Protein KIAA0494 | IPI00006130 | AAQLRPISLPGVSSTEDLQDLFR (SEQ ID NO:109) | 0.66 | ↓↓ | 0.95 | NC | 0.96 | NC |
| | | FSQFLGDPVEK (SEQ ID NO:110) | | | | | | |
| | | LTYQEIWTSLGSAMPEPESLR (SEQ ID NO:111) | | | | | | |
| | | QSLDQVTNR (SEQ ID NO:112) | | | | | | |
| | | TGQDVDGK (SEQ ID NO:113) | | | | | | |
| | | YSFLELR (SEQ ID NO:114) | | | | | | |
| Reticulocalbin 2 | IPI00029628 | DRFVNDYDK (SEQ ID NO:115) | 1.25 | ↑ | 0.99 | NC | 0.87 | NC |

FIG. 5D

| Protein Name | IPI # | Peptide Sequences | iTRAQ Ratios | | | | | |
|---|---|---|---|---|---|---|---|---|
| | | | AD | | PD | | DLB | |
| precursor | | | | | | | | |
| | | LGHEEQQK (SEQ ID NO:116) | | | | | | |
| | | VIDFDENTALDDAEEESFR (SEQ ID NO:117) | | | | | | |
| Secretogranin I precursor | IPI00006601 | ADQTVLTEDEK (SEQ ID NO:118) | 0.65 | ↓↓ | 1.06 | NC | 0.84 | NC |
| | | ASEEEPEYGEEIK (SEQ ID NO:119) | | | | | | |
| | | AYFMSDTR (SEQ ID NO:120) | | | | | | |
| | | GEDSSEEK (SEQ ID NO:121) | | | | | | |
| | | GLEPGK (SEQ ID NO:122) | | | | | | |
| | | GSEEYR (SEQ ID NO:123) | | | | | | |
| | | HPQGAWK (SEQ ID NO:124) | | | | | | |
| | | KEELVAR (SEQ ID NO:125) | | | | | | |
| | | NHNEGMVTR (SEQ ID NO:126) | | | | | | |
| | | NYLNYGEEGAPGK (SEQ ID NO:127) | | | | | | |
| | | NYPSLELDK (SEQ ID NO:128) | | | | | | |
| | | QASAIK (SEQ ID NO:129) | | | | | | |
| | | SSAPPITPECR (SEQ ID NO:130) | | | | | | |
| | | SSQGGSLPSEEK (SEQ ID NO:131) | | | | | | |
| | | TRHSEK (SEQ ID NO:132) | | | | | | |
| | | VAQLDQLLHYR (SEQ ID NO:133) | | | | | | |
| | | VQENQMDK (SEQ ID NO:134) | | | | | | |
| | | WAEGGGHSR (SEQ ID NO:135) | | | | | | |
| | | WQQQGDLQDTK (SEQ ID NO:136) | | | | | | |
| Secretogranin III precursor | IPI00292071 | AITEK (SEQ ID NO:137) | 0.65 | ↓↓ | 1.03 | NC | 0.98 | NC |
| | | AVFDK (SEQ ID NO:138) | | | | | | |
| | | DFINK (SEQ ID NO:139) | | | | | | |
| | | ELSAERPLNEQIAEAAEEDK (SEQ ID NO:140) | | | | | | |
| | | ELSAERPLNEQIAEAAEEDKIK (SEQ ID NO:141) | | | | | | |
| | | EYGSLK (SEQ ID NO:142) | | | | | | |
| | | FQDDPDGLHQLDGTPLTAEDIVHK (SEQ ID NO:143) | | | | | | |
| | | GNKEDYDLSK (SEQ ID NO:144) | | | | | | |
| | | IYEENDR (SEQ ID NO:145) | | | | | | |
| | | KLIDDYDSTK (SEQ ID NO:146) | | | | | | |

FIG. 5E

| Protein Name | IPI # | Peptide Sequences | iTRAQ Ratios ||||||
|---|---|---|---|---|---|---|---|---|
| | | | AD | | PD | | DLB | |
| | | LIDDYDSTK (SEQ ID NO:147) | | | | | | |
| | | NIEWLK (SEQ ID NO:148) | | | | | | |
| | | YGTISPEEGVSYLENLDEMIALQTK (SEQ ID NO:149) | | | | | | |
| Splice isoform 2 of insulin-like growth factor II precursor | IPI00215977 | ELEAFR (SEQ ID NO:150) | 1.57 | ↑↑ | 1.07 | NC | 1.11 | NC |
| | | FFQYDTWK (SEQ ID NO:151) | | | | | | |
| | | GFYFR (SEQ ID NO:152) | | | | | | |
| | | GHVLAK (SEQ ID NO:153) | | | | | | |
| | | GIVEECCFR (SEQ ID NO:154) | | | | | | |
| | | GLPALLR (SEQ ID NO:155) | | | | | | |
| | | SCDLALLETYCATPAK (SEQ ID NO:156) | | | | | | |
| | | YPVGK (SEQ ID NO:157) | | | | | | |
| Splice isoform 3 of calcium/calmodulin-dependent protein kinase type II beta chain | IPI00219165 | FYFENLLAK (SEQ ID NO:158) | 0.64 | ↓↓ | 0.85 | NC | 1.05 | NC |
| | | GAILTTMLATR (SEQ ID NO:159) | | | | | | |
| TBC1 domain family member 10 | IPI00011167 | FDELDMSPGDPK (SEQ ID NO:160) | 1.25 | ↑ | 1.03 | NC | 1.04 | NC |
| | | GGHGQQDLFRVLK (SEQ ID NO:161) | | | | | | |
| | | GIPPSLR (SEQ ID NO:162) | | | | | | |
| | | LRSLSPK (SEQ ID NO:163) | | | | | | |
| | | YLPGYYSEK (SEQ ID NO:164) | | | | | | |
| Cadherin-13 precursor | IPI00024046 | DIQGSLQDIFK (SEQ ID NO:165) | 0.55 | ↓↓ | 1.11 | NC | 0.84 | NC |
| | | GIFRINENTGSVSVTR (SEQ ID NO:166) | | | | | | |
| | | TLFVHAR (SEQ ID NO:167) | | | | | | |
| | | TPHAEDMAELVIVGGK (SEQ ID NO:168) | | | | | | |
| | | VDCNAAGALR (SEQ ID NO:169) | | | | | | |
| | | VNSDGGLVALR (SEQ ID NO:170) | | | | | | |
| | | YEVSSPYFK (SEQ ID NO:171) | | | | | | |
| Glucosidase II beta subunit precursor | IPI00026154 | ILIEDWK (SEQ ID NO:172) | 0.64 | ↓↓ | 1.11 | NC | 1.07 | NC |
| | | TVKEEAEKPER (SEQ ID NO:173) | | | | | | |
| Golgi autoantigen, | IPI00004671 | AEMEEK (SEQ ID NO:174) | 0.47 | ↓↓ | 2.14 | ↑↑ | 1.17 | NC |

FIG. 5F

| Protein Name | IPI # | Peptide Sequences | iTRAQ Ratios | | | | | |
|---|---|---|---|---|---|---|---|---|
| | | | AD | | PD | | DLB | |
| golgin subfamily B member 1 | | | | | | | | |
| | | AQEIYEK (SEQ ID NO:175) | | | | | | |
| | | DLVEMEQK (SEQ ID NO:176) | | | | | | |
| | | DVQLQQK (SEQ ID NO:177) | | | | | | |
| | | EALKENKSLQEELSLAR (SEQ ID NO:178) | | | | | | |
| | | EEDVSYLSGQLSEKEAALTK (SEQ ID NO:179) | | | | | | |
| | | EIKELENLLSQEEEENIVLEEENK (SEQ ID NO:180) | | | | | | |
| | | ELLQR (SEQ ID NO:181) | | | | | | |
| | | ELLSQLEETR (SEQ ID NO:182) | | | | | | |
| | | EMKQMEGEGIAPIKMK (SEQ ID NO:183) | | | | | | |
| | | ENENIGDQLR (SEQ ID NO:184) | | | | | | |
| | | ENLAQAVEHR (SEQ ID NO:185) | | | | | | |
| | | LDELQK (SEQ ID NO:186) | | | | | | |
| | | LLMVTK (SEQ ID NO:187) | | | | | | |
| | | NETETAEER (SEQ ID NO:188) | | | | | | |
| | | QDGDK (SEQ ID NO:189) | | | | | | |
| | | SMSSLQNDRDR (SEQ ID NO:190) | | | | | | |
| | | SSKIAESTEWQEK (SEQ ID NO:191) | | | | | | |
| | | SSWEIHER (SEQ ID NO:192) | | | | | | |
| Latent transforming growth factor beta binding protein 2 | IPI00465145 | AQPGWGSPR (SEQ ID NO:193) | 1.71 | ↑↑ | 1.08 | NC | 0.82 | ↓ |
| | | EQDAPVAGLQPVER (SEQ ID NO:194) | | | | | | |
| | | RPGGSYPAAAAAK (SEQ ID NO:195) | | | | | | |
| | | STPLGQQQPAPR (SEQ ID NO:196) | | | | | | |
| | | YEPAGGDANR (SEQ ID NO:197) | | | | | | |
| Neuroblastoma suppressor of tumorigenicity 1 precursor | IPI00013299 | LALFPDK (SEQ ID NO:198) | 1.55 | ↑↑ | 1.13 | NC | 1.09 | NC |
| | | SAWCEAK (SEQ ID NO:199) | | | | | | |
| Splice isoform 1 of SWI/SNF-related, matrix associated, actin-dependent | IPI00220119 | ANTPDSDITEK (SEQ ID NO:200) | 1.61 | ↑↑ | 0.96 | NC | 0.71 | ↓ |

FIG. 5G

| Protein Name | IPI # | Peptide Sequences | iTRAQ Ratios | | | | | |
|---|---|---|---|---|---|---|---|---|
| | | | AD | | PD | | DLB | |
| regulator | | | | | | | | |
| | | HGLNGILADEMGLGK (SEQ ID NO:201) | | | | | | |
| | | NLFNLDR (SEQ ID NO:202) | | | | | | |
| | | QELREVLK (SEQ ID NO:203) | | | | | | |
| | | SADEQSIYEKER (SEQ ID NO:204) | | | | | | |
| | | SLFRRLK (SEQ ID NO:205) | | | | | | |
| | | VFAEDQDMQYASQSEVPNGK (SEQ ID NO:206) | | | | | | |
| | | YQHLMTINANNR (SEQ ID NO:207) | | | | | | |
| Cell Structure/Motility/Transport/Traffic | | | | | | | | |
| 107 kDa protein | IPI00476999 | AEDHFSVIDFNQNIR (SEQ ID NO:208) | 0.28 | ↓↓ | 0.85 | NC | 0.99 | NC |
| | | AHGLIGQFMQEPK (SEQ ID NO:209) | | | | | | |
| | | AHVSFKPTVAQQR (SEQ ID NO:210) | | | | | | |
| | | FQLVAENR (SEQ ID NO:211) | | | | | | |
| | | FYNQVSTPLLR (SEQ ID NO:212) | | | | | | |
| | | IQPSGGTNINEALLR (SEQ ID NO:213) | | | | | | |
| | | IYGNQDTSSQLK (SEQ ID NO:214) | | | | | | |
| | | SLAPTAAAK (SEQ ID NO:215) | | | | | | |
| | | SSALDMENFR (SEQ ID NO:216) | | | | | | |
| | | YIEK (SEQ ID NO:217) | | | | | | |
| Alpha-1-acid glycoprotein 1 precursor | IPI00022429 | EQLGEFYEALDCLR (SEQ ID NO:218) | 2.49 | ↑↑ | 0.71 | ↓ | 1.02 | NC |
| | | KQEEGES (SEQ ID NO:219) | | | | | | |
| | | TEDTIFLR (SEQ ID NO:220) | | | | | | |
| | | WFYIASAFR (SEQ ID NO:221) | | | | | | |
| Apolipoprotein A-II precursor | IPI00021854 | DLMEK (SEQ ID NO:222) | 1.99 | ↑↑ | 0.66 | ↓↓ | 1.06 | NC |
| | | EPCVESLVSQYFQTVTDYGK (SEQ ID NO:223) | | | | | | |
| | | EQLTPLIK (SEQ ID NO:224) | | | | | | |
| | | SKEQLTPLIK (SEQ ID NO:225) | | | | | | |
| | | SPELQAEAK (SEQ ID NO:226) | | | | | | |
| | | SYFEK (SEQ ID NO:227) | | | | | | |
| | | VKSPELQAEAK (SEQ ID NO:228) | | | | | | |
| Apolipoprotein C-1 precursor | IPI00021855 | EFGNTLEDK (SEQ ID NO:229) | 1.59 | ↑↑ | 0.78 | ↓ | 1.05 | NC |

FIG. 5H

| Protein Name | IPI # | Peptide Sequences | iTRAQ Ratios ||||||
|---|---|---|---|---|---|---|---|---|
| | | | AD || PD || DLB ||
| | | EWFSETFQK (SEQ ID NO:230) | | | | | | |
| | | LKEFGNTLEDK (SEQ ID NO:231) | | | | | | |
| | | QSELSAK (SEQ ID NO:232) | | | | | | |
| Apolipoprotein D precursor | IPI00006662 | CPNPPVQENFDVNK (SEQ ID NO:233) | 1.63 | ↑↑ | 0.96 | NC | 1.16 | NC |
| | | IKVLNQELR (SEQ ID NO:234) | | | | | | |
| | | MTVTDQVNCPK (SEQ ID NO:235) | | | | | | |
| | | NILTSNNIDVK (SEQ ID NO:236) | | | | | | |
| | | NPNLPPETVDSLK (SEQ ID NO:237) | | | | | | |
| | | VLNQELR (SEQ ID NO:238) | | | | | | |
| | | WYEIEK (SEQ ID NO:239) | | | | | | |
| Apolipoprotein E precursor | IPI00021842 | AATVGSLAGQPLQER (SEQ ID NO:240) | 0.77 | ↓ | 1.14 | NC | 0.93 | NC |
| | | ALMDETMK (SEQ ID NO:241) | | | | | | |
| | | AQAWGER (SEQ ID NO:242) | | | | | | |
| | | DADDLQK (SEQ ID NO:243) | | | | | | |
| | | DRLDEVK (SEQ ID NO:244) | | | | | | |
| | | EGAERGLSAIR (SEQ ID NO:245) | | | | | | |
| | | ELQAAQAR (SEQ ID NO:246) | | | | | | |
| | | EQVAEVR (SEQ ID NO:247) | | | | | | |
| | | FWDYLR (SEQ ID NO:248) | | | | | | |
| | | LASHLR (SEQ ID NO:249) | | | | | | |
| | | LEEQAQQIR (SEQ ID NO:250) | | | | | | |
| | | LGADMEDVCGR (SEQ ID NO:251) | | | | | | |
| | | LGPLVEQGR (SEQ ID NO:252) | | | | | | |
| | | LQAEAFQAR (SEQ ID NO:253) | | | | | | |
| | | QQTEWQSGQR (SEQ ID NO:254) | | | | | | |
| | | QWAGLVEK (SEQ ID NO:255) | | | | | | |
| | | SELEEQLTPVAEETR (SEQ ID NO:256) | | | | | | |
| | | SWFEPLVEDMQR (SEQ ID NO:257) | | | | | | |
| | | VEQAVETEPEPELR (SEQ ID NO:258) | | | | | | |
| | | WELALGR (SEQ ID NO:259) | | | | | | |
| Apolipoprotein H | IPI00298828 | ATVVYQGER (SEQ ID NO:260) | 1.22 | ↑ | 0.66 | ↓↓ | 0.84 | NC |
| | | KATVVYQGER (SEQ ID NO:261) | | | | | | |
| | | VSFFCK (SEQ ID NO:262) | | | | | | |
| Collagen alpha 2(I) chain precursor | IPI00304962 | GEAGAAGPAGPAGPR (SEQ ID NO:263) | 1.53 | ↑↑ | 1.02 | NC | 1.18 | NC |

FIG. 5I

| Protein Name | IPI # | Peptide Sequences | iTRAQ Ratios | | | | | |
|---|---|---|---|---|---|---|---|---|
| | | | AD | | PD | | DLB | |
| | | GETGPSGPVGPAGAVGPR (SEQ ID NO:264) | | | | | | |
| | | GPAGPSGPAGK (SEQ ID NO:265) | | | | | | |
| | | GVVGPQGAR (SEQ ID NO:266) | | | | | | |
| Divalent cation tolerant protein CUTA | IPI00034319 | LLLLPR (SEQ ID NO:267) | 0.82 | ↓ | 0.96 | NC | 2.07 | ↑↑ |
| | | TQSSLVPALTDFVR (SEQ ID NO:268) | | | | | | |
| Golgi phosphoprotein 2 | IPI00171411 | DLSENNDQR (SEQ ID NO:269) | 2.08 | ↑↑ | 0.89 | NC | 0.77 | ↓ |
| | | DQLVIPDGQEEEQEAAGEGR (SEQ ID NO:270) | | | | | | |
| | | DTINLLDQR (SEQ ID NO:271) | | | | | | |
| | | EETNEIQVVNEEPQR (SEQ ID NO:272) | | | | | | |
| | | EQVVEDRPVGGR (SEQ ID NO:273) | | | | | | |
| | | GFGGAGELGQTPQVQAA (SEQ ID NO:274) | | | | | | |
| | | GFGGAGELGQTPQVQAALSVSQ (SEQ ID NO:275) | | | | | | |
| | | LPQEPGR (SEQ ID NO:276) | | | | | | |
| | | LSVSQENPEMEGPER (SEQ ID NO:277) | | | | | | |
| | | MGLGNGRRSMK (SEQ ID NO:278) | | | | | | |
| | | NIDVFNVEDQK (SEQ ID NO:279) | | | | | | |
| | | NIDVFNVEDQKR (SEQ ID NO:280) | | | | | | |
| | | NQTNLERKFSYDLSQCINQMK (SEQ ID NO:281) | | | | | | |
| | | QQLQALSEPQPR (SEQ ID NO:282) | | | | | | |
| | | RDTINLLDQREK (SEQ ID NO:283) | | | | | | |
| Hypothetical protein FLJ25530 | IPI00167215 | DKDSPETEENPAPEPR (SEQ ID NO:284) | 0.59 | ↓↓ | 0.99 | NC | 0.87 | NC |
| | | SATEPGPPGYSVSPAVPGR (SEQ ID NO:285) | | | | | | |
| | | SPGLPIRSARR (SEQ ID NO:286) | | | | | | |
| Hypothetical protein MOT8 | IPI00001399 | AGLAKPPAAAK (SEQ ID NO:287) | 2.18 | ↑↑ | 0.65 | ↓↓ | 1.08 | NC |
| | | DQAAALVPK (SEQ ID NO:288) | | | | | | |
| | | MWIQQLLGLSSMSIR (SEQ ID NO:289) | | | | | | |
| | | SSPSLASSSSSSSSAVAGGAPE (SEQ ID NO:290) | | | | | | |

FIG. 5J

| Protein Name | IPI # | Peptide Sequences | iTRAQ Ratios | | | | | |
|---|---|---|---|---|---|---|---|---|
| | | | AD | | PD | | DLB | |
| KIAA1291 protein | IPI00413206 | DIQQTLTQNMER (SEQ ID NO:291) | 1.76 | ↑↑ | 1.14 | NC | 0.7 | ↓ |
| | | LEALK (SEQ ID NO:292) | | | | | | |
| | | RPPRPGTNGWSRR (SEQ ID NO:293) | | | | | | |
| | | SSTQMTWGALFR (SEQ ID NO:294) | | | | | | |
| | | WNGMSRLEK (SEQ ID NO:295) | | | | | | |
| Neurofascin isoform 2 | IPI00477942 | LTVSWLK (SEQ ID NO:296) | 0.59 | ↓↓ | 0.87 | NC | 0.91 | NC |
| | | NLILAPGEDGR (SEQ ID NO:297) | | | | | | |
| | | TSGAPPESNPGDVK (SEQ ID NO:298) | | | | | | |
| | | VIAINEVGSSHPSLPSER (SEQ ID NO:299) | | | | | | |
| | | YVVGQTPVYVPYEIR (SEQ ID NO:300) | | | | | | |
| Receptor-type tyrosine-protein phosphatase-like N precursor | IPI00004440 | AEAPALFSR (SEQ ID NO:301) | 0.33 | ↓↓ | 0.89 | NC | 0.85 | NC |
| | | AEDSPEGYEK (SEQ ID NO:302) | | | | | | |
| | | DTAELPAR (SEQ ID NO:303) | | | | | | |
| | | GEKPASPAVQPDAALQR (SEQ ID NO:304) | | | | | | |
| | | KTMEGPVEGR (SEQ ID NO:305) | | | | | | |
| | | KTMEGPVEGRDTAELPAR (SEQ ID NO:306) | | | | | | |
| | | LAAVLAGYGVELR (SEQ ID NO:307) | | | | | | |
| | | LPEQGSSSR (SEQ ID NO:308) | | | | | | |
| | | NPGGVVNVGADIK (SEQ ID NO:309) | | | | | | |
| | | SELEAQTGLQILQTGVGQR (SEQ ID NO:310) | | | | | | |
| | | TMEGPVEGR (SEQ ID NO:311) | | | | | | |
| Ly-6/neurotoxin-like protein 1 precursor | IPI00289058 | CFETVYDGYSK (SEQ ID NO:312) | 0.48 | ↓↓ | 1.03 | NC | 0.94 | NC |
| | | TYYTPTR (SEQ ID NO:313) | | | | | | |
| Sortilin 1, preproprotein | IPI00383591 | ERPWGAADGLSR (SEQ ID NO:314) | 1.54 | ↑↑ | 1.06 | NC | 0.65 | ↓↓ |
| | | IYSFGLGGR (SEQ ID NO:315) | | | | | | |
| | | LDAPPPPAAPLPR (SEQ ID NO:316) | | | | | | |
| | | LRKSSVCQNGR (SEQ ID NO:317) | | | | | | |
| Tetranectin precursor | IPI00009028 | CFLAFTQTK (SEQ ID NO:318) | 0.63 | ↓↓ | 0.98 | NC | 1.35 | ↑ |
| | | DQLPYICQFGIV (SEQ ID NO:319) | | | | | | |
| | | EQQALQTVCLK (SEQ ID NO:320) | | | | | | |

FIG. 5K

| Protein Name | IPI # | Peptide Sequences | iTRAQ Ratios | | | | | |
|---|---|---|---|---|---|---|---|---|
| | | | AD | | PD | | DLB | |
| | | GGTLSTPQTGSENDALYEYLR (SEQ ID NO:321) | | | | | | |
| | | KIVNAK (SEQ ID NO:322) | | | | | | |
| | | LDTLAQEVALLK (SEQ ID NO:323) | | | | | | |
| | | MFEELK (SEQ ID NO:324) | | | | | | |
| | | NWETEITAQPDGGK (SEQ ID NO:325) | | | | | | |
| | | TFHEASEDCISR (SEQ ID NO:326) | | | | | | |
| | | WFDK (SEQ ID NO:327) | | | | | | |
| Angiotensinogen precursor | IPI00032220 | AAMVGMLANFLGFR (SEQ ID NO:328) | 0.61 | ↓↓ | 1.02 | NC | 1.7 | ↑↑ |
| | | ALQDQLVLVAAK (SEQ ID NO:329) | | | | | | |
| | | DPTFIPAPIQAK (SEQ ID NO:330) | | | | | | |
| | | FMQAVTGWK (SEQ ID NO:331) | | | | | | |
| | | LDTEDKLR (SEQ ID NO:332) | | | | | | |
| | | QPFVQGLALYTPVVLPR (SEQ ID NO:333) | | | | | | |
| | | SLDFTELDVAAEK (SEQ ID NO:334) | | | | | | |
| | | TSPVDEK (SEQ ID NO:335) | | | | | | |
| | | VANPLSTA (SEQ ID NO:336) | | | | | | |
| | | VLSALQAVQGLLVAQGR (SEQ ID NO:337) | | | | | | |
| Enolase 2 | IPI00216171 | AAVPSGASTGIYEALELR (SEQ ID NO:338) | 0.57 | ↓↓ | 1 | NC | 1.32 | ↑ |
| | | GNPTVEVDLYTAK (SEQ ID NO:339) | | | | | | |
| | | YITGDQLGALYQDFVR (SEQ ID NO:340) | | | | | | |
| Hypothetical protein DKFZp686B0286 | IPI00465248 | AAVPSGASTGIYEALELR (SEQ ID NO:341) | 0.57 | ↓↓ | 1 | NC | 1.32 | ↑ |
| | | GNPTVEVDLFTSK (SEQ ID NO:342) | | | | | | |
| | | VVIGMDVAASEFFR (SEQ ID NO:343) | | | | | | |
| Kallikrein 6 precursor | IPI00023845 | AVIHPDYDAASHDQDIMLLR (SEQ ID NO:344) | 1.9 | ↑↑ | 0.8 | ↓ | 0.86 | NC |
| | | DSCQGDSGGPLVCGDHLR (SEQ ID NO:345) | | | | | | |
| | | EKPGVYTNVCR (SEQ ID NO:346) | | | | | | |
| | | ESSQEQSSVVR (SEQ ID NO:347) | | | | | | |
| | | GLVSWGNIPCGSK (SEQ ID NO:348) | | | | | | |
| | | KPNLQVFLGK (SEQ ID NO:349) | | | | | | |
| | | LSELIQPLPLER (SEQ ID NO:350) | | | | | | |

FIG. 5L

| Protein Name | IPI # | Peptide Sequences | iTRAQ Ratios ||||||
|---|---|---|---|---|---|---|---|---|
| | | | AD || PD || DLB ||
| | | LVHGGPCDK (SEQ ID NO:351) | | | | | | |
| | | TADGDFPDTIQCAYIHLVSR (SEQ ID NO:352) | | | | | | |
| | | YTNWIQK (SEQ ID NO:353) | | | | | | |
| Phosphatidylcholine-sterol acyltransferase precursor | IPI00022331 | ITTTSPWMFPSR (SEQ ID NO:354) | 0.6 | ↓↓ | 1.08 | NC | 0.91 | NC |
| | | LEPGQQEEYYR (SEQ ID NO:355) | | | | | | |
| | | SSGLVSNAPGVQIR (SEQ ID NO:356) | | | | | | |
| | | STELCGLWQGR (SEQ ID NO:357) | | | | | | |
| ProSAAS precursor | IPI00002280 | AADHDVGSELPPEGVLGALLR (SEQ ID NO:358) | 0.65 | ↓↓ | 1.07 | NC | 1.11 | NC |
| | | AEAQEAEDQQAR (SEQ ID NO:359) | | | | | | |
| | | AGSPLLWGPR (SEQ ID NO:360) | | | | | | |
| | | ALAHLLEAER (SEQ ID NO:361) | | | | | | |
| | | ARAEAQEAEDQQAR (SEQ ID NO:362) | | | | | | |
| | | GEAAGAVQELAR (SEQ ID NO:363) | | | | | | |
| | | ILAGSADSEGVAAPR (SEQ ID NO:364) | | | | | | |
| | | ILAGSADSEGVAAPRR (SEQ ID NO:365) | | | | | | |
| | | LETPAPQVPAR (SEQ ID NO:366) | | | | | | |
| | | MAGSPLLWGPR (SEQ ID NO:367) | | | | | | |
| | | NSDPALGLDDDPDAPAAQLAR (SEQ ID NO:368) | | | | | | |
| | | VLAQLLR (SEQ ID NO:369) | | | | | | |
| | | VWGAPR (SEQ ID NO:370) | | | | | | |
| Superoxide dismutase 1, soluble | IPI00218733 | AVCVLK (SEQ ID NO:371) | 0.58 | ↓↓ | 1.06 | NC | 1.68 | ↑↑ |
| | | GDGPVQGIINFEQK (SEQ ID NO:372) | | | | | | |
| | | GGNEESTK (SEQ ID NO:373) | | | | | | |
| | | LACGVIGIAQ (SEQ ID NO:374) | | | | | | |
| | | VWGSIK (SEQ ID NO:375) | | | | | | |
| Transcription elongation regulator 1 | IPI00247871 | FKAIEK (SEQ ID NO:376) | 2.33 | ↑↑ | 0.94 | NC | 0.71 | ↓ |
| | | YLVLDCVPEERR (SEQ ID NO:377) | | | | | | |
| Vacuolar ATP synthase subunit S1 precursor | IPI00020430 | EVLTGNDEVIGQVLSTLK (SEQ ID NO:378) | 0.5 | ↓↓ | 0.96 | NC | 0.84 | NC |

FIG. 5M

| Protein Name | IPI # | Peptide Sequences | iTRAQ Ratios | | | | | |
|---|---|---|---|---|---|---|---|---|
| | | | AD | | PD | | DLB | |
| | | LGASPLHVDLATLR (SEQ ID NO:379) | | | | | | |
| | | LPYTASSGLMAPR (SEQ ID NO:380) | | | | | | |
| | | LSIEDFTAYGGVFGNK (SEQ ID NO:381) | | | | | | |
| | | MMAAMATARVRMGPR (SEQ ID NO:382) | | | | | | |
| | | NVLLFLQDK (SEQ ID NO:383) | | | | | | |
| | | SEDVPYTAALTAVRPSR (SEQ ID NO:384) | | | | | | |
| Extracellular Matrix/Cell Adhesion | | | | | | | | |
| Cochlin precursor | IPI00012386 | GVISNSGGPVR (SEQ ID NO:385) | 1.22 | ↑ | 0.62 | ↓↓ | 1.14 | NC |
| | | TFEISDIGAK (SEQ ID NO:386) | | | | | | |
| | | VYSLPGR (SEQ ID NO:387) | | | | | | |
| | | WSASFTVTK (SEQ ID NO:388) | | | | | | |
| Matrix Gla-protein precursor | IPI00028714 | ERSKPVHELNR (SEQ ID NO:389) | 1.51 | ↑↑ | 0.9 | NC | 0.97 | NC |
| | | NANTFISPQQR (SEQ ID NO:390) | | | | | | |
| Spondin 1 precursor | IPI00171473 | LCGGGIQER (SEQ ID NO:391) | 1.76 | ↑↑ | 0.9 | NC | 0.93 | NC |
| | | SEQLKEESEGEQFPGCR (SEQ ID NO:392) | | | | | | |
| | | SSQFTSCK (SEQ ID NO:393) | | | | | | |
| | | VVIERIAR (SEQ ID NO:394) | | | | | | |
| Immunity/Defense | | | | | | | | |
| 24 kDa protein | IPI00479531 | EQLGEFYEALDCLR (SEQ ID NO:395) | 3.02 | ↑↑ | 0.7 | ↓ | 1.05 | NC |
| | | KQEEGES (SEQ ID NO:396) | | | | | | |
| | | NEEYNK (SEQ ID NO:397) | | | | | | |
| | | NWGLSVYADKPETTK (SEQ ID NO:398) | | | | | | |
| | | SDVVYTDWK (SEQ ID NO:399) | | | | | | |
| | | TEDTIFLR (SEQ ID NO:400) | | | | | | |
| | | TYMLAFDVNDEK (SEQ ID NO:401) | | | | | | |
| | | WFYIASAFR (SEQ ID NO:402) | | | | | | |
| | | YVGGQEHFAHLLILR (SEQ ID NO:403) | | | | | | |
| AMBP protein precursor | IPI00022426 | AFIQLWAFDAVK (SEQ ID NO:404) | 2.09 | ↑↑ | 0.88 | NC | 1.1 | NC |
| | | ETLLQDFR (SEQ ID NO:405) | | | | | | |
| | | EYCGVPGDGDEELLR (SEQ ID NO:406) | | | | | | |
| | | FYSEK (SEQ ID NO:407) | | | | | | |

FIG. 5N

| Protein Name | IPI # | Peptide Sequences | iTRAQ Ratios | | | | | |
|---|---|---|---|---|---|---|---|---|
| | | | AD | | PD | | DLB | |
| | | GECVPGEQEPEPILIPR (SEQ ID NO:408) | | | | | | |
| | | GPCRAFIQLWAFDAVKGK (SEQ ID NO:409) | | | | | | |
| | | TVAACNLPIVR (SEQ ID NO:410) | | | | | | |
| | | VVAQGVGIPEDSIFTMADR (SEQ ID NO:411) | | | | | | |
| Complement C2 precursor | IPI00303963 | DFHINLFR (SEQ ID NO:412) | 0.59 | ↓↓ | 0.89 | NC | 1.07 | NC |
| | | QHLGDVLNFLPL (SEQ ID NO:413) | | | | | | |
| Cytokine-like protein C17 precursor | IPI00032876 | ALSQEITR (SEQ ID NO:414) | 1.65 | ↑↑ | 0.83 | NC | 1.1 | NC |
| | | DFNLLQVSEPSEPCVR (SEQ ID NO:415) | | | | | | |
| Fibrinogen beta chain precursor | IPI00298497 | AHYGGFTVQNEANK (SEQ ID NO:416) | 1.55 | ↑↑ | 0.97 | NC | 1.14 | NC |
| | | EDGGGWWYNR (SEQ ID NO:417) | | | | | | |
| | | EEAPSLRPAPPPISGGGYR (SEQ ID NO:418) | | | | | | |
| | | GSWYSMR (SEQ ID NO:419) | | | | | | |
| | | KGGETSEMYLIQPDSSVKPYR (SEQ ID NO:420) | | | | | | |
| | | KWDPYK (SEQ ID NO:421) | | | | | | |
| | | MGPTELLIEMEDWK (SEQ ID NO:422) | | | | | | |
| | | QDGSVDFGR (SEQ ID NO:423) | | | | | | |
| | | QGFGNVATNTDGK (SEQ ID NO:424) | | | | | | |
| | | SILENLR (SEQ ID NO:425) | | | | | | |
| | | YQISVNK (SEQ ID NO:426) | | | | | | |
| | | YYWGGQYTWDMAK (SEQ ID NO:427) | | | | | | |
| HLA class I histocompatibility antigen, B-27 alpha chain precursor | IPI00471986 | AQTDREDLR (SEQ ID NO:428) | 1.52 | ↑↑ | 1.13 | NC | 1.06 | NC |
| | | FDSDAASPR (SEQ ID NO:429) | | | | | | |
| | | LLRGYHQDAYDGK (SEQ ID NO:430) | | | | | | |
| | | YTCHVQHEGLPKPLTLR (SEQ ID NO:431) | | | | | | |
| HLA class I histocompatibility antigen, E alpha chain precursor | IPI00010362 | FDNDAASPR (SEQ ID NO:432) | 1.28 | ↑ | 1.08 | NC | 1.18 | NC |

FIG. 50

| Protein Name | IPI # | Peptide Sequences | iTRAQ Ratios ||||| 
|---|---|---|---|---|---|---|---|---|
| | | | AD || PD || DLB ||
| | | FISVGYVDDTQFVR (SEQ ID NO:433) | | | | | | |
| | | VNLRTLR (SEQ ID NO:434) | | | | | | |
| | | WAAVVVPSGEEQR (SEQ ID NO:435) | | | | | | |
| | | YLEK (SEQ ID NO:436) | | | | | | |
| Myosin-reactive immunoglobulin heavy chain variable region | IPI00007893 | KPGSSVK (SEQ ID NO:437) | 1.53 | ↑↑ | 0.86 | NC | 1.04 | NC |
| | | QAPGQGLEWMGR (SEQ ID NO:438) | | | | | | |
| Unknown | | | | | | | | |
| 132 kDa protein | IPI00477893 | ELGQMNLTER (SEQ ID NO:439) | 1.48 | ↑ | 0.49 | ↓↓ | 1.01 | NC |
| | | EVEEEMEK (SEQ ID NO:440) | | | | | | |
| | | FGEIYEK (SEQ ID NO:441) | | | | | | |
| | | FKNEVNTLEEEFLALK (SEQ ID NO:442) | | | | | | |
| | | KMNSEFHSAAK (SEQ ID NO:443) | | | | | | |
| | | LEDLGELHRAAR (SEQ ID NO:444) | | | | | | |
| | | LLIEER (SEQ ID NO:445) | | | | | | |
| | | NMLERGEGER (SEQ ID NO:446) | | | | | | |
| | | QMENMVSVLQNELSETKK (SEQ ID NO:447) | | | | | | |
| | | RNADMLYNK (SEQ ID NO:448) | | | | | | |
| | | SGDVPGVEHVLAPGDTGVDKR (SEQ ID NO:449) | | | | | | |
| | | SYMER (SEQ ID NO:450) | | | | | | |
| | | TSQEPEMAKDCDR (SEQ ID NO:451) | | | | | | |
| Haptoglobin precursor | IPI00478493 | DIAPTLTLYVGK (SEQ ID NO:452) | 1.97 | ↑↑ | 1.23 | ↑ | 1.14 | NC |
| | | DYAEVGR (SEQ ID NO:453) | | | | | | |
| | | DYAEVGRVGYVSGWGRNANFK (SEQ ID NO:454) | | | | | | |
| | | FTDHLK (SEQ ID NO:455) | | | | | | |
| | | GSFPWQAK (SEQ ID NO:456) | | | | | | |
| | | HYEGSTVPEK (SEQ ID NO:457) | | | | | | |
| | | HYEGSTVPEKK (SEQ ID NO:458) | | | | | | |
| | | ILGGHLDAK (SEQ ID NO:459) | | | | | | |
| | | LPECEAVCGKPK (SEQ ID NO:460) | | | | | | |
| | | NPANPVQR (SEQ ID NO:461) | | | | | | |
| | | NPANPVQR (SEQ ID NO:462) | | | | | | |

FIG. 5P

| Protein Name | IPI # | Peptide Sequences | iTRAQ Ratios ||||||
|---|---|---|---|---|---|---|---|---|
| | | | AD || PD || DLB ||
| | | QLVEIEK (SEQ ID NO:463) | | | | | | |
| | | QWINK (SEQ ID NO:464) | | | | | | |
| | | SPVGVQPILNEHTFCAGMSK (SEQ ID NO:465) | | | | | | |
| | | TEGDGVYTLNDK (SEQ ID NO:466) | | | | | | |
| | | TEGDGVYTLNNEK (SEQ ID NO:467) | | | | | | |
| | | VGYVSGWGR (SEQ ID NO:468) | | | | | | |
| | | VTSIQDWVQK (SEQ ID NO:469) | | | | | | |
| | | YQCK (SEQ ID NO:470) | | | | | | |
| | | YVMLPVADQDQCIR (SEQ ID NO:471) | | | | | | |
| Hypothetical protein | IPI00165652 | DLGLAADLPGGAEGAAA (SEQ ID NO:472) | 0.54 | ↓↓ | 0.9 | NC | 0.94 | NC |
| | | DLGPHAEGQLAPR (SEQ ID NO:473) | | | | | | |
| | | GGEDAAVQEPR (SEQ ID NO:474) | | | | | | |
| | | QPQAVLR (SEQ ID NO:475) | | | | | | |
| Hypothetical protein DKFZp566O224 | IPI00383815 | ASWEGHWSPAPSSR (SEQ ID NO:476) | 1.76 | ↑↑ | 0.76 | ↓ | 1.16 | NC |
| | | KIHEEEVR (SEQ ID NO:477) | | | | | | |
| | | LALDIEIATYR (SEQ ID NO:478) | | | | | | |
| Hypothetical protein FLJ33620 | IPI00216853 | NAVMRLCFLKAR (SEQ ID NO:479) | 1.56 | ↑↑ | 1.15 | NC | 1.06 | NC |
| | | NFEIDTEGK (SEQ ID NO:480) | | | | | | |
| | | NFEIDTEGKNAVMR (SEQ ID NO:481) | | | | | | |
| | | QLCQEK (SEQ ID NO:482) | | | | | | |
| Hypothetical protein FLJ33674 | IPI00301019 | GAVEAPGTPK (SEQ ID NO:483) | 0.66 | ↓↓ | 1.18 | NC | 1.17 | NC |
| | | GFPRPLENSEIPMIPGAHPK (SEQ ID NO:484) | | | | | | |
| | | GSVGSEPQAFDVFPENPR (SEQ ID NO:485) | | | | | | |
| | | QADLPDAK (SEQ ID NO:486) | | | | | | |
| | | RGLIRVTTQR (SEQ ID NO:487) | | | | | | |
| | | SLPPAEELPVETPK (SEQ ID NO:488) | | | | | | |
| Hypothetical protein PSEC0072 | IPI00168884 | ANSVFEDLSVTLR (SEQ ID NO:489) | 0.65 | ↓↓ | 1.04 | NC | 0.87 | NC |
| | | SFDTSLIR (SEQ ID NO:490) | | | | | | |
| Inter-alpha-trypsin inhibitor heavy chain H1 precursor | IPI00292530 | AAISGENAGLVR (SEQ ID NO:491) | 1.55 | ↑↑ | 0.98 | NC | 0.98 | NC |

FIG. 5Q

| Protein Name | IPI # | Peptide Sequences | iTRAQ Ratios ||||||
|---|---|---|---|---|---|---|---|---|
| | | | AD || PD || DLB ||
| | | FAHYVVTSQVVNTANEAR (SEQ ID NO:492) | | | | | | |
| | | GSLVQASEANLQAAQDFVR (SEQ ID NO:493) | | | | | | |
| | | QYYEGSEIVVAGR (SEQ ID NO:494) | | | | | | |
| KIAA1318 protein | IPI00002353 | APASGGVSSPLVR (SEQ ID NO:495) | 1.23 | ↑ | 0.9 | NC | 1.17 | NC |
| | | ASVSGSMPMPLPR (SEQ ID NO:496) | | | | | | |
| | | FLEGLSEAVTTKMGRIFLK (SEQ ID NO:497) | | | | | | |
| | | MATAPIRASASGAR (SEQ ID NO:498) | | | | | | |
| | | VTSTSQMMPTASGDMCTLPVR (SEQ ID NO:499) | | | | | | |
| Uveal autoantigen | IPI00173359 | EHEK (SEQ ID NO:500) | 0.61 | ↓↓ | 1 | NC | 1.1 | NC |
| | | EHLTSEAASGNHR (SEQ ID NO:501) | | | | | | |
| | | ELEAMR (SEQ ID NO:502) | | | | | | |
| | | IQQEQRILLDK (SEQ ID NO:503) | | | | | | |
| | | KELEAMR (SEQ ID NO:504) | | | | | | |
| | | LEMEK (SEQ ID NO:505) | | | | | | |
| | | LMKAAER (SEQ ID NO:506) | | | | | | |
| | | NLTHMQDEVNVK (SEQ ID NO:507) | | | | | | |
| | | SLNGTIENLK (SEQ ID NO:508) | | | | | | |
| | | TNRELLDVK (SEQ ID NO:509) | | | | | | |
| VPS10 domain-containing receptor SorCS3 precursor | IPI00010381 | AGPELLPQQGGGR (SEQ ID NO:510) | 0.66 | ↓↓ | 1.08 | NC | 1.05 | NC |
| | | AQMCPGKAPRGLHVVTTDGR (SEQ ID NO:511) | | | | | | |
| | | AVASQWPEELASAR (SEQ ID NO:512) | | | | | | |
| | | GGEMQVEAGGTSPAGER (SEQ ID NO:513) | | | | | | |
| | | GGEMQVEAGGTSPAGERR (SEQ ID NO:514) | | | | | | |
| | | GIPAPAK (SEQ ID NO:515) | | | | | | |
| | | GLHVVTTDGR (SEQ ID NO:516) | | | | | | |
| II. Proteins unique to AD and identified by single peptide |||||||||
| Neuronal Activities/Signal Transduction |||||||||
| Bone morphogenetic protein 15 precursor | IPI00001485 | VLLSILR (SEQ ID NO:517) | 0.64 | ↓↓ | 1.06 | NC | 1.08 | NC |
| G protein-coupled sphingolipid receptor | IPI00015343 | SSVSDYVNYDIIVR (SEQ ID NO:518) | 0.62 | ↓↓ | 0.86 | NC | 0.96 | NC |

FIG. 5R

| Protein Name | IPI # | Peptide Sequences | iTRAQ Ratios | | | | | |
|---|---|---|---|---|---|---|---|---|
| | | | AD | | PD | | DLB | |
| IL-17RC | IPI00303074 | DDVLLLETR (SEQ ID NO:519) | 0.63 | ↓↓ | 0.96 | NC | 0.87 | NC |
| Interleukin-1 receptor-associated kinase-like 2 | IPI00304986 | DFSTSIPK (SEQ ID NO:520) | 0.58 | ↓↓ | 1 | NC | 0.88 | NC |
| Metallothionein-III | IPI00016666 | GGEAAEAEAEK (SEQ ID NO:521) | 0.47 | ↓↓ | 0.95 | NC | 0.97 | NC |
| Neural proliferation differentiation and control protein-1 precursor | IPI00299699 | LEDEIDFLAQELAR (SEQ ID NO:522) | 0.51 | ↓↓ | 1.01 | NC | 1.05 | NC |
| Potassium voltage-gated channel subfamily KQT member 3 | IPI00012857 | DGTLLLEGGGR (SEQ ID NO:523) | 0.62 | ↓↓ | 0.96 | NC | 0.9 | NC |
| Putative 4 repeat voltage-gated ion channel | IPI00217996 | SLQLEELLAR (SEQ ID NO:524) | 0.64 | ↓↓ | 1.26 | ↑ | 0.91 | NC |
| Splice Isoform 1 of protachykinin 1 precursor | IPI00023571 | EELPEPFEHLLQR (SEQ ID NO:525) | 0.43 | ↓↓ | 1.01 | NC | 0.87 | NC |
| Splice isoform 2 of UDP-N-acetylglucosamine--peptide N-acetylglucosaminyltransferase 11 | IPI00219856 | IVLNGIDLK (SEQ ID NO:526) | 1.62 | ↑↑ | 0.87 | NC | 1.01 | NC |
| Voltage-dependent calcium channel gamma-6 subunit | IPI00011072 | GAEFLLR (SEQ ID NO:527) | 1.53 | ↑↑ | 0.94 | NC | 1.2 | NC |
| Cell Cycle/Death | | | | | | | | |
| AlphA 1 type XIII collagen isoform 3 | IPI00375409 | GEAGLDGAK (SEQ ID NO:528) | 1.26 | ↑ | 0.63 | ↓↓ | 0.94 | NC |
| Integral membrane protein 2B | IPI00031821 | IENIDHLGFFIYR (SEQ ID NO:529) | 1.8 | ↑↑ | 0.94 | NC | 1.08 | NC |
| Cell Structure/Motility/Transport/Traffic | | | | | | | | |
| Actin, aortic smooth muscle | IPI00008603 | SYELPDGQVITIGNER (SEQ ID NO:530) | 1.72 | ↑↑ | 1.05 | NC | 1.09 | NC |
| Cohesin subunit SA-1 | IPI00025158 | TQIDDR (SEQ ID NO:531) | 1.64 | ↑↑ | 0.91 | NC | 1.12 | NC |
| Hepatocellular carcinoma associated protein TB6 | IPI00293898 | LFAEEK (SEQ ID NO:532) | 1.57 | ↑↑ | 1.01 | NC | 1.05 | NC |
| SAA1 protein | IPI00452748 | FFGHGAEDSLADQAANEWGR (SEQ ID NO:533) | 1.86 | ↑↑ | 0.78 | ↓ | 0.91 | NC |
| SAYY8238 | IPI00432771 | LQDMEK (SEQ ID NO:534) | 0.59 | ↓↓ | 0.86 | NC | 1.05 | NC |
| Splice isoform 1 of | IPI00337307 | VILAIR (SEQ ID NO:535) | 0.65 | ↓↓ | 0.95 | NC | 1.14 | NC |

FIG. 5S

| Protein Name | IPI # | Peptide Sequences | iTRAQ Ratios ||||||
|---|---|---|---|---|---|---|---|---|
| | | | AD | | PD | | DLB | |
| hpaII tiny fragments locus 9c protein | | | | | | | | |
| Splice isoform 2 of development and differentiation-enhancing factor 2 | IPI00409613 | EIISEVQR (SEQ ID NO:536) | 1.96 | ↑↑ | 0.93 | NC | 1.03 | NC |
| Splice isoform 2 of putative polypeptide N-acetylgalactosaminyltransferase-like protein | IPI00456715 | AYLSAK (SEQ ID NO:537) | 0.66 | ↓↓ | 1.07 | NC | 0.89 | NC |
| TRIF-related adapter molecule | IPI00329281 | INSCPLSLSWGKR (SEQ ID NO:538) | 1.87 | ↑↑ | 0.94 | NC | 1.03 | NC |
| Metabolism | | | | | | | | |
| ADAM 10 precursor | IPI00013897 | DTSLFSDEFK (SEQ ID NO:539) | 1.54 | ↑↑ | 0.99 | NC | 0.91 | NC |
| Alpha-1,3-mannosyl-glycoprotein 2-beta-N-acetylglucosaminyltransferase | IPI00000138 | WALGQVFR (SEQ ID NO:540) | 0.49 | ↓↓ | 1.02 | NC | 0.91 | NC |
| Cytochrome P450 1A1 | IPI00218839 | VIIFGMGK (SEQ ID NO:541) | 0.55 | ↓↓ | 1.03 | NC | 0.88 | NC |
| DNA-directed RNA polymerase I largest subunit | IPI00031960 | SITNPR (SEQ ID NO:542) | 0.59 | ↓↓ | 0.89 | NC | 1.32 | ↑ |
| Heat shock 10kDa protein 1 (chaperonin 10) | IPI00220362 | FLPLFDR (SEQ ID NO:543) | 1.71 | ↑↑ | 1.19 | NC | 0.97 | NC |
| Hect domain and RLD 4 | IPI00333067 | KSDFFINK (SEQ ID NO:544) | 1.62 | ↑↑ | 0.67 | ↓ | 0.9 | NC |
| Mosaic serine protease | IPI00012505 | NKPGVYTK (SEQ ID NO:545) | 1.84 | ↑↑ | 1.12 | NC | 1.06 | NC |
| PPIB protein | IPI00419262 | VIFGLFGK (SEQ ID NO:546) | 0.55 | ↓↓ | 1.03 | NC | 0.88 | NC |
| Splice isoform 2 of insulin receptor precursor | IPI00220325 | VTDLMR (SEQ ID NO:547) | 0.59 | ↓↓ | 0.87 | NC | 0.86 | NC |
| Transcriptional activator SRCAP | IPI00009101 | LEAEGMRGR (SEQ ID NO:548) | 0.59 | ↓↓ | 0.94 | NC | 0.84 | NC |
| Zinc finger protein 95 homolog | IPI00032316 | ELEERR (SEQ ID NO:549) | 2.8 | ↑↑ | 1.17 | NC | 1.19 | NC |
| ZNF627 protein | IPI00029023 | RNISHIPER (SEQ ID NO:550) | 3.04 | ↑↑ | 0 | 0 | 0 | 0 |
| Extracellular Matrix/Cell Adhesion | | | | | | | | |
| Inhibin beta A chain precursor | IPI00028670 | EGSDLSVVER (SEQ ID NO:551) | 0.66 | ↓↓ | 1.14 | NC | 1.06 | NC |

FIG. 5T

| Protein Name | IPI # | Peptide Sequences | iTRAQ Ratios | | | | | |
|---|---|---|---|---|---|---|---|---|
| | | | AD | | PD | | DLB | |
| KIAA1730 protein | IPI00155199 | EAEAWAKPGAAARR (SEQ ID NO:552) | 1.63 | ↑↑ | 1.18 | NC | 0.66 | ↓↓ |
| PREDICTED: KIAA0527 protein | IPI00297224 | GSGEQQIMR (SEQ ID NO:553) | 0.66 | ↓↓ | 1.04 | NC | 0.98 | NC |
| PREDICTED: odz, odd Oz/ten-m homolog 3 | IPI00398020 | NTMAMK (SEQ ID NO:554) | 1.91 | ↑↑ | 0.72 | ↓ | 0.99 | NC |
| Splice isoform 1 of ADAMTS-16 precursor | IPI00386697 | GEYDLVSAYEVDHR (SEQ ID NO:555) | 0.64 | ↓↓ | 0.87 | NC | 0.93 | NC |
| Immunity/Defense | | | | | | | | |
| Pregnancy-specific beta-1-glycoprotein 8 precursor | IPI00334256 | LQLSETNR (SEQ ID NO:556) | 2.79 | ↑↑ | 1.07 | NC | 0.88 | NC |
| Unknown | | | | | | | | |
| 141 kDa protein | IPI00478948 | TQLDDR (SEQ ID NO:557) | 1.64 | ↑↑ | 0.91 | NC | 1.12 | NC |
| 15 kDa protein | IPI00413387 | IVEPYVTFGFPNPK (SEQ ID NO:558) | 1.51 | ↑↑ | 0.93 | NC | 1.1 | NC |
| 25 kDa protein | IPI00477989 | LGEHNIEVLEGNEQFINAAK (SEQ ID NO:559) | 2.38 | ↑↑ | 1 | NC | 1.13 | NC |
| Antigen MLAA-20 | IPI00447178 | ERVTALVR (SEQ ID NO:560) | 1.56 | ↑↑ | 1.1 | NC | 1.14 | NC |
| C1 or f40 protein | IPI00304374 | DLTLLITER (SEQ ID NO:561) | 0.63 | ↓↓ | 0.96 | NC | 0.87 | NC |
| DJ977L11.1 | IPI00478622 | LQEAAEIVK (SEQ ID NO:562) | 1.55 | ↑↑ | 0.61 | ↓↓ | 0.94 | NC |
| FLJ00199 protein | IPI00291731 | GLAAAAGGR (SEQ ID NO:563) | 0.83 | ↓ | 1.15 | NC | 1.15 | NC |
| Hypothetical protein | IPI00032525 | DLLLEK (SEQ ID NO:564) | 1.66 | ↑↑ | 1.09 | NC | 1.09 | NC |
| Hypothetical protein | IPI00333324 | AAHAGER (SEQ ID NO:565) | 1.57 | ↑↑ | 1.13 | NC | 1.01 | NC |
| Hypothetical protein | IPI00470772 | TDQEVLGELVR (SEQ ID NO:566) | 0.67 | ↓↓ | 1.1 | NC | 1 | NC |
| Hypothetical protein DKFZp434A2017 | IPI00295380 | EADVVAR (SEQ ID NO:567) | 1.67 | ↑↑ | 1.01 | NC | 1.08 | NC |
| Hypothetical protein DKFZp666G229 | IPI00470388 | DGGELPDPDR (SEQ ID NO:568) | 0.6 | ↓↓ | 1.09 | NC | 1.12 | NC |
| Hypothetical protein DKFZp686A06175 | IPI00478616 | EQIVAQYPSLK (SEQ ID NO:569) | 1.58 | ↑↑ | 1.13 | NC | 0.85 | NC |
| Hypothetical protein DKFZp761H2024 | IPI00185662 | APAKPPGSGLDLADALDDQDDGR (SEQ ID NO:570) | 0.32 | ↓↓ | 0.93 | NC | 1.19 | NC |
| Hypothetical protein DKFZp781A0122 | IPI00470805 | DAEEDMPQR (SEQ ID NO:571) | 0.66 | ↓↓ | 1.14 | NC | 1.06 | NC |
| Hypothetical protein PSEC0200 | IPI00166392 | SDDSVIQLLNPNR (SEQ ID NO:572) | 1.54 | ↑↑ | 1 | NC | 1.11 | NC |
| KARCA1 protein | IPI00168703 | WLCVVGGWDGSRR (SEQ ID NO:573) | 5.81 | ↑↑ | 1.06 | NC | 0.57 | ↓↓ |
| Kelch/ankyrin repeat containing cyclin A1 interacting protein | IPI00449308 | WLCVVGGWDGSRR (SEQ ID NO:574) | 5.65 | ↑↑ | 1.09 | NC | 0.76 | ↓ |

FIG. 5U

| Protein Name | IPI # | Peptide Sequences | iTRAQ Ratios | | | | | |
|---|---|---|---|---|---|---|---|---|
| | | | AD | | PD | | DLB | |
| Optic atrophy 1 isoform 4 | IPI00107749 | LHLVSR (SEQ ID NO:575) | 2.2 | ↑↑ | 1.02 | NC | 1.05 | NC |
| PREDICTED: hypothetical protein XP_374046 | IPI00397059 | YGEEIK (SEQ ID NO:576) | 0.66 | ↓↓ | 1.04 | NC | 0.84 | NC |
| PREDICTED: similar to melanoma antigen, family A, 10 | IPI00455972 | VLEAILR (SEQ ID NO:577) | 0.64 | ↓↓ | 1.06 | NC | 1.08 | NC |
| Similar to expressed sequence AI593442 | IPI00217781 | TFASPNASGSGNTGAR (SEQ ID NO:578) | 0.45 | ↓↓ | 1.18 | NC | 0.86 | NC |
| III. Proteins unique to PD and identified by 2 or more peptides | | | | | | | | |
| Neuronal Activities/Signal Transduction | | | | | | | | |
| Amyloid-like protein 1 precursor | IPI00020012 | AALEGFLAALQADPPQAER (SEQ ID NO:579) | 1.11 | NC | 0.66 | ↓↓ | 0.91 | NC |
| | | DDTPMTLPK (SEQ ID NO:580) | | | | | | |
| | | DELAPAGTGVSR (SEQ ID NO:581) | | | | | | |
| | | EWAMADNQSK (SEQ ID NO:582) | | | | | | |
| | | FLHQER (SEQ ID NO:583) | | | | | | |
| | | GGLQPPDSK (SEQ ID NO:584) | | | | | | |
| | | GSTEQDAASPEK (SEQ ID NO:585) | | | | | | |
| | | GSTEQDAASPEKEK (SEQ ID NO:586) | | | | | | |
| | | LVETHATR (SEQ ID NO:587) | | | | | | |
| | | MDQCESSTR (SEQ ID NO:588) | | | | | | |
| | | MNPLEQYER (SEQ ID NO:589) | | | | | | |
| | | QMYPELQIAR (SEQ ID NO:590) | | | | | | |
| | | VEQATQAIPMER (SEQ ID NO:591) | | | | | | |
| | | VIALINDQR (SEQ ID NO:592) | | | | | | |
| | | VLEYCR (SEQ ID NO:593) | | | | | | |
| | | VLLALR (SEQ ID NO:594) | | | | | | |
| | | WEPDPQR (SEQ ID NO:595) | | | | | | |
| Cell growth regulator with EF hand domain 1 | IPI00337548 | ELPGETLESK (SEQ ID NO:596) | 0.77 | ↓ | 1.67 | ↑↑ | 1.12 | NC |
| | | ESLDPVQEPGGQAEADGDVP (SEQ ID NO:597) | | | | | | |
| | | GEAEGQAEAK (SEQ ID NO:598) | | | | | | |
| | | GEAGGQAEAEGDAPGPR (SEQ ID NO:599) | | | | | | |
| | | GEAGGQAEAR (SEQ ID NO:600) | | | | | | |
| | | HVEPGEPLAPSPQEPQAVGR (SEQ ID | | | | | | |

FIG. 5V

| Protein Name | IPI # | Peptide Sequences | iTRAQ Ratios |||||| 
|---|---|---|---|---|---|---|---|---|
| | | | AD || PD || DLB ||
| | | NO:601) | | | | | | |
| | | NTQNDFEVHIVQVENDEI (SEQ ID NO:602) | | | | | | |
| | | QETQEAPGPR (SEQ ID NO:603) | | | | | | |
| | | RESLDPVQEPGGQAEADGDV (SEQ ID NO:604) | | | | | | |
| | | TEVQLEHLSR (SEQ ID NO:605) | | | | | | |
| Chromogranin B | IPI00006601 | ADQTVLTEDEK (SEQ ID NO:606) | 0.49 | ↓↓ | 1.7 | ↑↑ | 1.09 | NC |
| | | ADQTVLTEDEKK (SEQ ID NO:607) | | | | | | |
| | | ASEEEPEYGEEIK (SEQ ID NO:608) | | | | | | |
| | | AYFMSDTR (SEQ ID NO:609) | | | | | | |
| | | CIIEVLSNALSK (SEQ ID NO:610) | | | | | | |
| | | DKETTENENTK (SEQ ID NO:611) | | | | | | |
| | | DPADASEAHESSSR (SEQ ID NO:612) | | | | | | |
| | | EDEEEEEGENYQK (SEQ ID NO:613) | | | | | | |
| | | ELDRNYLNYGEEGAPGK (SEQ ID NO:614) | | | | | | |
| | | ELENLAAMDLELQK (SEQ ID NO:615) | | | | | | |
| | | GEAGAPGEEDIQGPTK (SEQ ID NO:616) | | | | | | |
| | | GLEPGK (SEQ ID NO:617) | | | | | | |
| | | GYPGVQAPEDLEWER (SEQ ID NO:618) | | | | | | |
| | | HLEEPGETQNAFLNER (SEQ ID NO:619) | | | | | | |
| | | KELENLAAMDLELQ (SEQ ID NO:620) | | | | | | |
| | | MAHGYGEESEEER (SEQ ID NO:621) | | | | | | |
| | | NHNEGMVTR (SEQ ID NO:622) | | | | | | |
| | | NYLNYGEEGAPGK (SEQ ID NO:623) | | | | | | |
| | | NYPSLELDK (SEQ ID NO:624) | | | | | | |
| | | QASAIK (SEQ ID NO:625) | | | | | | |
| | | SQREDEEEEGENYQK (SEQ ID NO:626) | | | | | | |
| | | SSAPPITPECR (SEQ ID NO:627) | | | | | | |
| | | SSQESGEEAGSQENHPQESK (SEQ ID NO:628) | | | | | | |
| | | SSQGGSLPSEEK (SEQ ID NO:629) | | | | | | |
| | | VAQLDQLLHYR (SEQ ID NO:630) | | | | | | |

FIG. 5W

| Protein Name | IPI # | Peptide Sequences | iTRAQ Ratios ||||||
|---|---|---|---|---|---|---|---|---|
| | | | AD | | PD | | DLB | |
| | | VQENQMDK (SEQ ID NO:631) | | | | | | |
| | | WAEGGGHSR (SEQ ID NO:632) | | | | | | |
| | | WQQQGDLQDTK (SEQ ID NO:633) | | | | | | |
| C-type natriuretic peptide precursor | IPI00012075 | APGGGGANLKGDRSR (SEQ ID NO:634) | 0.87 | NC | 1.54 | ↑↑ | 1 | NC |
| | | TPPAEELAEPQAAGGGQK (SEQ ID NO:635) | | | | | | |
| DA141H5.1 | IPI00478414 | CCKVCPGK (SEQ ID NO:636) | 0.98 | NC | 1.31 | ↑ | 0.55 | ↓↓ |
| | | EELPGQSFDNK (SEQ ID NO:637) | | | | | | |
| | | GDGELSWEHSDGDIFR (SEQ ID NO:638) | | | | | | |
| | | LTCAFPVSVPDSCCRVCR (SEQ ID NO:639) | | | | | | |
| | | VLYLERSEK (SEQ ID NO:640) | | | | | | |
| | | YPCK (SEQ ID NO:641) | | | | | | |
| Insulin-like growth factor binding protein 5 precursor | IPI00029236 | AVYLPNCDR (SEQ ID NO:642) | 1.51 | ↑↑ | 0.79 | ↓ | 0.85 | NC |
| | | GICWCVDK (SEQ ID NO:643) | | | | | | |
| | | GVCLNEK (SEQ ID NO:644) | | | | | | |
| | | HMEASLQELK (SEQ ID NO:645) | | | | | | |
| | | QESEQGPCR (SEQ ID NO:646) | | | | | | |
| Neurexin 1-alpha precursor | IPI00442299 | DCSQEDNNVEGLAHLMMGDQGK (SEQ ID NO:647) | 0.47 | ↓↓ | 2.14 | ↑↑ | 1.17 | NC |
| | | DMTVFSGLFVGGLPPELR (SEQ ID NO:648) | | | | | | |
| | | EPYPGSAEVIR (SEQ ID NO:649) | | | | | | |
| | | MGTALLQR (SEQ ID NO:650) | | | | | | |
| | | NGDIDYCELNAR (SEQ ID NO:651) | | | | | | |
| | | NNGMCR (SEQ ID NO:652) | | | | | | |
| | | QGDPK (SEQ ID NO:653) | | | | | | |
| | | TLQRNGLMLHTGK (SEQ ID NO:654) | | | | | | |
| Prion protein | IPI00382843 | ESQAYYQR (SEQ ID NO:655) | 1 | NC | 1.57 | ↑↑ | 1 | NC |
| | | GENFTETDVK (SEQ ID NO:656) | | | | | | |
| | | QHTVTTTTK (SEQ ID NO:657) | | | | | | |
| | | VVEQMCITQYER (SEQ ID NO:658) | | | | | | |
| | | YPGQGSPGGNR (SEQ ID NO:659) | | | | | | |
| Protein tyrosine phosphatase, non-receptor type | IPI00332887 | AKPSAPVVSGPAAR (SEQ ID NO:660) | 1 | NC | 1.52 | ↑↑ | 0.71 | ↓ |

FIG. 5X

| Protein Name | IPI # | Peptide Sequences | iTRAQ Ratios ||||||
|---|---|---|---|---|---|---|---|---|
| | | | AD | | PD | | DLB | |
| substrate 1 Precursor | | | | | | | | |
| | | ELIYNQK (SEQ ID NO:661) | | | | | | |
| | | GSPDDVEFK (SEQ ID NO:662) | | | | | | |
| | | MEPAGPAPGR (SEQ ID NO:663) | | | | | | |
| | | SVLVAAGETATLR (SEQ ID NO:664) | | | | | | |
| | | TETASTVTENK (SEQ ID NO:665) | | | | | | |
| | | VPPTLEVTQQPVR (SEQ ID NO:666) | | | | | | |
| Serine/threonine-protein kinase PLK2 | IPI00302787 | MEYALNMLLQR (SEQ ID NO:667) | 0.91 | NC | 0.44 | ↓↓ | 1.06 | NC |
| | | NPEDRPSLDDIIR (SEQ ID NO:668) | | | | | | |
| | | QQIGDAIR (SEQ ID NO:669) | | | | | | |
| Splice isoform 1 of basigin precursor | IPI00218019 | EDALPGQK (SEQ ID NO:670) | 0.98 | NC | 1.21 | ↑ | 0.67 | ↓↓ |
| | | GGVVLK (SEQ ID NO:671) | | | | | | |
| Splice isoform 1 of lysosomal trafficking regulator | IPI00017094 | LLDAYFAR (SEQ ID NO:672) | 1.05 | NC | 0.36 | ↓↓ | 0.95 | NC |
| | | SVANDELHVMMQR (SEQ ID NO:673) | | | | | | |
| Splice isoform 7 of amyloid beta A4 protein precursor | IPI00219187 | CLVGEFVSDALLVPDK (SEQ ID NO:674) | 0.93 | NC | 1.57 | ↑↑ | 0.97 | NC |
| | | LVFFAEDVGSNK (SEQ ID NO:675) | | | | | | |
| | | THPHFVIPYR (SEQ ID NO:676) | | | | | | |
| Cell Cycle/Death | | | | | | | | |
| Golgi autoantigen, golgin subfamily B member 1 | IPI00004671 | AEMEEK (SEQ ID NO:677) | 0.47 | ↓↓ | 2.14 | ↑↑ | 1.17 | NC |
| | | AQEIYEK (SEQ ID NO:678) | | | | | | |
| | | DLVEMEQK (SEQ ID NO:679) | | | | | | |
| | | DVQLQQK (SEQ ID NO:680) | | | | | | |
| | | EALKENKSLQEELSLAR (SEQ ID NO:681) | | | | | | |
| | | EEDVSYLSGQLSEKEAALTK (SEQ ID NO:682) | | | | | | |
| | | EIKELENLLSQEEEENIVLEEENK (SEQ ID NO:683) | | | | | | |
| | | ELLQR (SEQ ID NO:684) | | | | | | |
| | | ELLSQLEETR (SEQ ID NO:685) | | | | | | |
| | | EMKQMEGEIAPIKMK (SEQ ID NO:686) | | | | | | |

FIG. 5Y

| Protein Name | IPI # | Peptide Sequences | iTRAQ Ratios ||||||
|---|---|---|---|---|---|---|---|---|
| | | | AD || PD || DLB ||
| | | ENENIGDQLR (SEQ ID NO:687) | | | | | | |
| | | ENLAQAVEHR (SEQ ID NO:688) | | | | | | |
| | | LDELQK (SEQ ID NO:689) | | | | | | |
| | | LLMVTK (SEQ ID NO:690) | | | | | | |
| | | NETETAEER (SEQ ID NO:691) | | | | | | |
| | | QDGDK (SEQ ID NO:692) | | | | | | |
| | | SMSSLQNDRDR (SEQ ID NO:693) | | | | | | |
| | | SSKIAESTEWQEK (SEQ ID NO:694) | | | | | | |
| | | SSWEIHER (SEQ ID NO:695) | | | | | | |
| Heparin-binding EGF-like growth factor precursor | IPI00012948 | DLQEADLDLLR (SEQ ID NO:696) | 0.84 | NC | 0.64 | ↓↓ | 0.84 | NC |
| | | LGMTNSH (SEQ ID NO:697) | | | | | | |
| Cell Structure/Motility/Transport/Traffic | | | | | | | | |
| Alpha-1-acid glycoprotein 1 precursor | IPI00022429 | EQLGEFYEALDCLR (SEQ ID NO:698) | 2.49 | ↑↑ | 0.71 | ↓ | 1.02 | NC |
| | | KQEEGES (SEQ ID NO:699) | | | | | | |
| | | TEDTIFLR (SEQ ID NO:700) | | | | | | |
| | | WFYIASAFR (SEQ ID NO:701) | | | | | | |
| Apolipoprotein A-II precursor | IPI00021854 | DLMEK (SEQ ID NO:702) | 1.99 | ↑↑ | 0.66 | ↓↓ | 1.06 | NC |
| | | EPCVESLVSQYFQTVTDYGK (SEQ ID NO:703) | | | | | | |
| | | EQLTPLIK (SEQ ID NO:704) | | | | | | |
| | | SKEQLTPLIK (SEQ ID NO:705) | | | | | | |
| | | SPELQAEAK (SEQ ID NO:706) | | | | | | |
| | | SYFEK (SEQ ID NO:707) | | | | | | |
| | | VKSPELQAEAK (SEQ ID NO:708) | | | | | | |
| Apolipoprotein C-I precursor | IPI00021855 | EFGNTLEDK (SEQ ID NO:709) | 1.59 | ↑↑ | 0.78 | ↓↓ | 1.05 | NC |
| | | EWFSETFQK (SEQ ID NO:710) | | | | | | |
| | | LKEFGNTLEDK (SEQ ID NO:711) | | | | | | |
| | | QSELSAK (SEQ ID NO:712) | | | | | | |
| Apolipoprotein C-III precursor | IPI00021857 | DALSSVQESQVAQQAR (SEQ ID NO:713) | 0.89 | NC | 0.57 | ↓↓ | 1.28 | ↑ |
| | | DYWSTVK (SEQ ID NO:714) | | | | | | |
| | | GWVTDGFSSLK (SEQ ID NO:715) | | | | | | |
| Apolipoprotein H | IPI00298828 | ATVVYQGER (SEQ ID NO:716) | 1.22 | ↑ | 0.66 | ↓↓ | 0.84 | NC |

FIG. 5Z

| Protein Name | IPI # | Peptide Sequences | iTRAQ Ratios ||||||
|---|---|---|---|---|---|---|---|---|
| | | | AD | | PD | | DLB | |
| | | KATVVYQGER (SEQ ID NO:717) | | | | | | |
| | | VSFFCK (SEQ ID NO:718) | | | | | | |
| Apolipoprotein M | IPI00030739 | AFLLTPR (SEQ ID NO:719) | 1.11 | NC | 0.6 | ↓↓ | 0.91 | NC |
| | | CVEEFK (SEQ ID NO:720) | | | | | | |
| | | FLLYNR (SEQ ID NO:721) | | | | | | |
| | | WIYHLTEGSTDLR (SEQ ID NO:722) | | | | | | |
| Hook homolog 3 | IPI00031768 | CEELEK (SEQ ID NO:723) | 0.89 | NC | 0.63 | ↓↓ | 1.01 | NC |
| | | ETIEELR (SEQ ID NO:724) | | | | | | |
| | | KNELETENR (SEQ ID NO:725) | | | | | | |
| | | LASTGSGQSFLAR (SEQ ID NO:726) | | | | | | |
| | | LEEHLEK (SEQ ID NO:727) | | | | | | |
| | | LFHSLEK (SEQ ID NO:728) | | | | | | |
| | | LNQSDSIEDPNSPAGR (SEQ ID NO:729) | | | | | | |
| | | MLKLNQEGSDNEK (SEQ ID NO:730) | | | | | | |
| | | TERDSLK (SEQ ID NO:731) | | | | | | |
| | | YLEK (SEQ ID NO:732) | | | | | | |
| Hypothetical protein MOT8 | IPI00001399 | AGLAKPPAAAK (SEQ ID NO:733) | 2.18 | ↑↑ | 0.65 | ↓↓ | 1.08 | NC |
| | | DQAAALVPK (SEQ ID NO:734) | | | | | | |
| | | MWIQQLLGLSSMSIR (SEQ ID NO:735) | | | | | | |
| | | SSPSLASSSSSSSAVAGGAPEQ (SEQ ID NO:736) | | | | | | |
| KIAA1265 protein | IPI00008085 | GHQDLDPDNEGELR (SEQ ID NO:737) | 1.08 | NC | 0.55 | ↓↓ | 1.66 | ↑↑ |
| | | LSFFGLEK (SEQ ID NO:738) | | | | | | |
| KRT8 protein | IPI00418411 | AKQDMAR (SEQ ID NO:739) | 1.15 | NC | 0.64 | ↓↓ | 0.85 | NC |
| | | LALDIEIATYR (SEQ ID NO:740) | | | | | | |
| | | LESGMQNMSIHTK (SEQ ID NO:741) | | | | | | |
| | | QLETLGQEK (SEQ ID NO:742) | | | | | | |
| | | TARSNMDNMFESYINNLRR (SEQ ID NO:743) | | | | | | |
| | | VSTSGPR (SEQ ID NO:744) | | | | | | |
| Retinol binding protein 4, plasma | IPI00479848 | FSGTWYAMAK (SEQ ID NO:745) | 1.02 | NC | 0.63 | ↓↓ | 1.08 | NC |
| | | GNDDHWIVDTDYDTYAVQYSCR (SEQ ID NO:746) | | | | | | |
| | | LLNLDGTCADSYSFVFSR (SEQ ID NO:747) | | | | | | |

FIG. 5AA

| Protein Name | IPI # | Peptide Sequences | iTRAQ Ratios | | | | | |
|---|---|---|---|---|---|---|---|---|
| | | | AD | | PD | | DLB | |
| | | QEELCLAR (SEQ ID NO:748) | | | | | | |
| | | VKENFDK (SEQ ID NO:749) | | | | | | |
| | | YWGVASFLQK (SEQ ID NO:750) | | | | | | |
| Selenoprotein M precursor | IPI00103471 | EEINALVQELGFYR (SEQ ID NO:751) | 1.06 | NC | 0.66 | ↓↓ | 0.93 | NC |
| | | HLPGADPELVLLGR (SEQ ID NO:752) | | | | | | |
| Metabolism | | | | | | | | |
| Ceruloplasmin precursor | IPI00017601 | ALYLQYTDETFR (SEQ ID NO:753) | 0.93 | NC | 0.65 | ↓↓ | 0.84 | NC |
| | | DIASGLIGPLIICK (SEQ ID NO:754) | | | | | | |
| | | DIFTGLIGPMK (SEQ ID NO:755) | | | | | | |
| | | DLYSGLIGPLIVCR (SEQ ID NO:756) | | | | | | |
| | | DSLDKEK (SEQ ID NO:757) | | | | | | |
| | | EYTDASFTNR (SEQ ID NO:758) | | | | | | |
| | | GAYPLSIEPIGVR (SEQ ID NO:759) | | | | | | |
| | | GEFYIGSK (SEQ ID NO:760) | | | | | | |
| | | GPEEEHLGILGPVIWAEVGDTIR (SEQ ID NO:761) | | | | | | |
| | | GVYSSDVFDIFPGTYQTLEMFPR (SEQ ID NO:762) | | | | | | |
| | | IGGSYK (SEQ ID NO:763) | | | | | | |
| | | IYHSHIDAPK (SEQ ID NO:764) | | | | | | |
| | | KAEEEHLGILGPQLHADVGDK (SEQ ID NO:765) | | | | | | |
| | | LISVDTEHSNIYLQNGPDR (SEQ ID NO:766) | | | | | | |
| | | MYYSAVDPTKDIFTGLIGPMK (SEQ ID NO:767) | | | | | | |
| | | NNEGTYYSPNYNPQSR (SEQ ID NO:768) | | | | | | |
| | | QSEDSTFYLGER (SEQ ID NO:769) | | | | | | |
| | | QYTDSTFR (SEQ ID NO:770) | | | | | | |
| | | TTIEKPVWLGFLGPIIK (SEQ ID NO:771) | | | | | | |
| | | TYSDHPEK (SEQ ID NO:772) | | | | | | |
| | | VDKDNEDFQESNR (SEQ ID NO:773) | | | | | | |
| | | VNKDDEEFIESNK (SEQ ID NO:774) | | | | | | |
| | | VTFHNK (SEQ ID NO:775) | | | | | | |
| | | VYVHLK (SEQ ID NO:776) | | | | | | |
| Cystatin C precursor | IPI00032293 | ALDFAVGEYNK (SEQ ID NO:777) | 0.88 | NC | 0.61 | ↓↓ | 0.89 | NC |

FIG. 5BB

| Protein Name | IPI # | Peptide Sequences | iTRAQ Ratios ||||| 
|---|---|---|---|---|---|---|---|---|
| | | | AD || PD || DLB ||
| | | ALQVVR (SEQ ID NO:778) | | | | | | |
| | | ASNDMYHSR (SEQ ID NO:779) | | | | | | |
| | | KQIVAGVNYFLDVELGR (SEQ ID NO:780) | | | | | | |
| | | LVGGPMDASVEEEGVR (SEQ ID NO:781) | | | | | | |
| | | LVGGPMDASVEEEGVRR (SEQ ID NO:782) | | | | | | |
| | | QIVAGVNYFLDVELGR (SEQ ID NO:783) | | | | | | |
| | | STCQDA (SEQ ID NO:784) | | | | | | |
| | | TQPNLDNCPFHDQPHLK (SEQ ID NO:785) | | | | | | |
| Hect domain and RLD 4 | IPI00333067 | KSDFFINK (SEQ ID NO:786) | 1.62 | ↑↑ | 0.67 | ↓ | 0.9 | NC |
| | | LIWFSDK (SEQ ID NO:787) | | | | | | |
| | | MGQIIQYDK (SEQ ID NO:788) | | | | | | |
| Kallikrein 6 precursor | IPI00023845 | AVIHPDYDAASHDQDIMLLR (SEQ ID NO:789) | 1.9 | ↑↑ | 0.8 | ↓ | 0.86 | NC |
| | | DSCQGDSGGPLVCGDHLR (SEQ ID NO:790) | | | | | | |
| | | EKPGVYTNVCR (SEQ ID NO:791) | | | | | | |
| | | ESSQEQSSVVR (SEQ ID NO:792) | | | | | | |
| | | GLVSWGNIPCGSK (SEQ ID NO:793) | | | | | | |
| | | KPNLQVFLGK (SEQ ID NO:794) | | | | | | |
| | | LSELIQPLPLER (SEQ ID NO:795) | | | | | | |
| | | LVHGGPCDK (SEQ ID NO:796) | | | | | | |
| | | TADGDFPDTIQCAYIHLVSR (SEQ ID NO:797) | | | | | | |
| | | YTNWIQK (SEQ ID NO:798) | | | | | | |
| Prothrombin precursor | IPI00019568 | ALSKHQDFNSAVQLVENFCR (SEQ ID NO:799) | 1.08 | NC | 0.57 | ↓↓ | 0.87 | NC |
| | | ELLESYIDGR (SEQ ID NO:800) | | | | | | |
| | | ISMLEK (SEQ ID NO:801) | | | | | | |
| | | IVEGSDAEIGMSPWQVMLFR (SEQ ID NO:802) | | | | | | |
| | | NFTENDLLVR (SEQ ID NO:803) | | | | | | |
| | | SEGSSVNLSPPLEQCVPDR (SEQ ID NO:804) | | | | | | |
| | | TATSEYQTFFNPR (SEQ ID NO:805) | | | | | | |
| | | VIDQFGE (SEQ ID NO:806) | | | | | | |

FIG. 5CC

| Protein Name | IPI # | Peptide Sequences | iTRAQ Ratios ||||||
|---|---|---|---|---|---|---|---|---|
| | | | AD | | PD | | DLB | |
| | | YGFYTHVFR (SEQ ID NO:807) | | | | | | |
| Pyruvate kinase 3 isoform 2 | IPI00220644 | GDYPLEAVR (SEQ ID NO:808) | 1.11 | NC | 1.8 | ↑↑ | 1.13 | NC |
| | | LDIDSPPITAR (SEQ ID NO:809) | | | | | | |
| | | LFEELVR (SEQ ID NO:810) | | | | | | |
| Selenium binding protein 1 | IPI00305719 | EEIVYLPCIYR (SEQ ID NO:811) | 1.16 | NC | 1.56 | ↑↑ | 1.19 | NC |
| | | NTGTEAPDYLATVDVDPK (SEQ ID NO:812) | | | | | | |
| Vitamin D-binding protein precursor | IPI00298853 | EDFTSLSLVLYSR (SEQ ID NO:813) | 1.06 | NC | 0.83 | ↓↓ | 1.01 | NC |
| | | EFSHLGK (SEQ ID NO:814) | | | | | | |
| | | ELPEHTVK (SEQ ID NO:815) | | | | | | |
| | | ELSSFIDK (SEQ ID NO:816) | | | | | | |
| | | GQELCADYSENTFTEYK (SEQ ID NO:817) | | | | | | |
| | | HLSLLTTLSNR (SEQ ID NO:818) | | | | | | |
| | | HQPQEFPTYVEPTNDEICEAFR (SEQ ID NO:819) | | | | | | |
| | | KFPSGTFEQVSQLVK (SEQ ID NO:820) | | | | | | |
| | | LAQKVPTADLEDVLPLAEDITNLSK (SEQ ID NO:821) | | | | | | |
| | | LSNLIK (SEQ ID NO:822) | | | | | | |
| | | RTHLPEVFLSK (SEQ ID NO:823) | | | | | | |
| | | THLPEVFLSK (SEQ ID NO:824) | | | | | | |
| | | VLEPTLK (SEQ ID NO:825) | | | | | | |
| | | VMDKYTFELSR (SEQ ID NO:826) | | | | | | |
| | | VPTADLEDVLPLAEDITNILSK (SEQ ID NO:827) | | | | | | |
| | | YTFELSR (SEQ ID NO:828) | | | | | | |
| Extracellular Matrix/Cell Adhesion | | | | | | | | |
| Cochlin precursor | IPI00012386 | GVISNSGGPVR (SEQ ID NO:829) | 1.22 | ↑ | 0.62 | ↓↓ | 0.96 | NC |
| | | TFEISDIGAK (SEQ ID NO:830) | | | | | | |
| | | VYSLPGR (SEQ ID NO:831) | | | | | | |
| | | WSASFTVTK (SEQ ID NO:832) | | | | | | |
| Extracellular matrix protein 1 | IPI00006969 | APYPNYDR (SEQ ID NO:833) | 0.97 | NC | 0.53 | ↓↓ | 1.05 | NC |
| | | DECFAR (SEQ ID NO:834) | | | | | | |
| | | DILTIDISR (SEQ ID NO:835) | | | | | | |

FIG. 5DD

| Protein Name | IPI # | Peptide Sequences | iTRAQ Ratios | | | | | |
|---|---|---|---|---|---|---|---|---|
| | | | AD | | PD | | DLB | |
| | | EVGPPLPQEAVPLQK (SEQ ID NO:836) | | | | | | |
| | | HKHIPGLIHNMTAR (SEQ ID NO:837) | | | | | | |
| | | LLPAQLPAEK (SEQ ID NO:838) | | | | | | |
| | | LTFINDLCGPR (SEQ ID NO:839) | | | | | | |
| | | QGETLNFLEIGYSR (SEQ ID NO:840) | | | | | | |
| Splice isoform 3 of integrin alpha-7 precursor | IPI00220749 | DMIGRCFVLSQDLAIR (SEQ ID NO:841) | 0.99 | NC | 0.64 | ↓↓ | 0.98 | NC |
| | | DSASRLVPEVMLSGER (SEQ ID NO:842) | | | | | | |
| | | ELEPPEQQEPGER (SEQ ID NO:843) | | | | | | |
| | | GAVVILR (SEQ ID NO:844) | | | | | | |
| | | GLVRAEELSFVAGAPR (SEQ ID NO:845) | | | | | | |
| | | VCGDAMFQLQENVK (SEQ ID NO:846) | | | | | | |
| | | VDQILETRDMIGR (SEQ ID NO:847) | | | | | | |
| | | YEARQR (SEQ ID NO:848) | | | | | | |
| Immunity/Defense | | | | | | | | |
| 21 kDa protein | IPI00477336 | EQLGEFYEALDCLR (SEQ ID NO:849) | 1.2 | NC | 1.59 | ↑↑ | 1.17 | NC |
| | | SDVVYTDWK (SEQ ID NO:850) | | | | | | |
| | | TEDTIFLR (SEQ ID NO:851) | | | | | | |
| | | WFYIASAFR (SEQ ID NO:852) | | | | | | |
| 24 kDa protein | IPI00479531 | EQLGEFYEALDCLR (SEQ ID NO:853) | 3.02 | ↑↑ | 0.7 | ↓ | 1.05 | NC |
| | | KQEEGES (SEQ ID NO:854) | | | | | | |
| | | NEEYNK (SEQ ID NO:855) | | | | | | |
| | | NWGLSVYADKPETTK (SEQ ID NO:856) | | | | | | |
| | | SDVVYTDWK (SEQ ID NO:857) | | | | | | |
| | | TEDTIFLR (SEQ ID NO:858) | | | | | | |
| | | TYMLAFDVNDEK (SEQ ID NO:859) | | | | | | |
| | | WFYIASAFR (SEQ ID NO:860) | | | | | | |
| | | YVGGQEHFAHLLILR (SEQ ID NO:861) | | | | | | |
| CD99L2 protein | IPI00434755 | APAKPPGSGLDLADALDDQDDGR (SEQ ID NO:862) | 1.11 | NC | 1.63 | ↑↑ | 0.42 | ↓↓ |
| | | APANTLGNDFDLADALDDR (SEQ ID NO:863) | | | | | | |
| Polymeric- | IPI00004573 | ASVDSGSSEEQGGSSR (SEQ ID | 1.12 | NC | 0.15 | ↓↓ | 1.52 | ↑↑ |

FIG. 5EE

| Protein Name | IPI # | Peptide Sequences | iTRAQ Ratios ||||||
|---|---|---|---|---|---|---|---|---|
| | | | AD || PD || DLB ||
| immunoglobulin receptor precursor | | NO:864) | | | | | | |
| | | LFAEEK (SEQ ID NO:865) | | | | | | |
| Unknown ||||||||| 
| 132 kDa protein | IPI00477893 | ELGQMNLTER (SEQ ID NO:866) | 1.48 | ↑ | 0.49 | ↓↓ | 1.01 | NC |
| | | EVEEEMEK (SEQ ID NO:867) | | | | | | |
| | | FGEIYEK (SEQ ID NO:868) | | | | | | |
| | | FKNEVNTLEEEFLALK (SEQ ID NO:869) | | | | | | |
| | | KMNSEFHSAAK (SEQ ID NO:870) | | | | | | |
| | | LEDLGELHRAAR (SEQ ID NO:871) | | | | | | |
| | | LLIEER (SEQ ID NO:872) | | | | | | |
| | | NMLERGEGER (SEQ ID NO:873) | | | | | | |
| | | QMENMVSVLQNELSETKK (SEQ ID NO:874) | | | | | | |
| | | RNADMLYNK (SEQ ID NO:875) | | | | | | |
| | | SGDVPGVEHVLAPGDTGVDKR (SEQ ID NO:876) | | | | | | |
| | | SYMER (SEQ ID NO:877) | | | | | | |
| | | TSQEPEMAKDCDR (SEQ ID NO:878) | | | | | | |
| Hypothetical protein DKFZp566O224 | IPI00383815 | ASWEGHWSPAPSSR (SEQ ID NO:879) | 1.76 | ↑↑ | 0.76 | ↓ | 1.16 | NC |
| | | KIHEEEVR (SEQ ID NO:880) | | | | | | |
| | | LALDIEIATYR (SEQ ID NO:881) | | | | | | |
| PREDICTED: G2 protein | IPI00176482 | AASGPK (SEQ ID NO:882) | 0.92 | NC | 1.28 | ↑ | 0.58 | ↓↓ |
| | | GFLNFMNTVLVAFTK (SEQ ID NO:883) | | | | | | |
| | | LLPISPTWPFTEVR (SEQ ID NO:884) | | | | | | |
| IV. Proteins unique to PD and identified by single peptide |||||||||
| Neuronal Activities/Signal Transduction |||||||||
| Activating receptor pilrbeta | IPI00186781 | VELDTR (SEQ ID NO:885) | 0.97 | NC | 0.72 | ↓ | 1.62 | ↑↑ |
| PREDICTED: KIAA1337 protein | IPI00002283 | ETPPLEDLAANQSEDPR (SEQ ID NO:886) | 0.97 | NC | 0.64 | ↓↓ | 1.49 | ↑ |
| PREDICTED: similar to 28 kDa heat- and acid-stable phosphoprotein (PDGF-associated protein) | IPI00376589 | ADLAQLAIIR (SEQ ID NO:887) | 0.84 | NC | 1.53 | ↑↑ | 0.62 | ↓↓ |

FIG. 5FF

| Protein Name | IPI # | Peptide Sequences | iTRAQ Ratios | | | | | |
|---|---|---|---|---|---|---|---|---|
| | | | AD | | PD | | DLB | |
| Reticulon 4, isoform D | IPI00335276 | GPLPAAPPVAPER (SEQ ID NO:888) | 0.98 | NC | 0.5 | ↓↓ | 0.99 | NC |
| | | GSSGSVVVDLLYWR (SEQ ID NO:889) | | | | | | |
| Rho-GTPase activating protein 10 | IPI00169307 | GSWGSGK (SEQ ID NO:890) | 1 | NC | 5.99 | ↑↑ | 0.48 | ↓↓ |
| Cell Cycle/Death | | | | | | | | |
| Alpha 1 type XIII collagen isoform 3 | IPI00375409 | GEAGLDGAK (SEQ ID NO:891) | 1.26 | ↑ | 0.63 | ↓↓ | 0.94 | NC |
| Cell Structure/Motility/Transport/Traffic | | | | | | | | |
| ATP-binding cassette, sub-family A, member 1 | IPI00293460 | QNTADILQDLTGR (SEQ ID NO:892) | 1.1 | NC | 1.57 | ↑↑ | 1.05 | NC |
| Hypothetical protein DKFZp434P097 | IPI00011232 | LSAEILRLEK (SEQ ID NO:893) | 1.1 | NC | 0.55 | ↓↓ | 0.89 | NC |
| Hypothetical protein FLJ32842 | IPI00480036 | DPQSTELIPR (SEQ ID NO:894) | 0.84 | NC | 0.46 | ↓↓ | 0.97 | NC |
| Putative 4 repeat voltage-gated ion channel | IPI00217996 | SLQLEELLAR (SEQ ID NO:895) | 0.64 | ↓↓ | 1.26 | ↑ | 0.91 | NC |
| Ribonuclease 4 precursor | IPI00029699 | YCNLMMQR (SEQ ID NO:896) | 0.88 | NC | 1.68 | ↑↑ | 1.08 | NC |
| Ribosomal protein L3-like | IPI00219335 | VAWAQARLEK (SEQ ID NO:897) | 1.1 | NC | 0.55 | ↓↓ | 0.89 | NC |
| SAA1 protein | IPI00452748 | FFGHGAEDSLADQAANEWGR (SEQ ID NO:898) | 1.86 | ↑↑ | 0.78 | ↓ | 0.91 | NC |
| Splice isoform 1 of transcription factor E2-alpha | IPI00013929 | AADGSLDTQPK (SEQ ID NO:899) | 0.84 | NC | 0.72 | ↓ | 1.74 | ↑↑ |
| Metabolism | | | | | | | | |
| Metabotropic glutamate receptor 3 precursor | IPI00478165 | ELIAAASR (SEQ ID NO:900) | 0.86 | NC | 0.51 | ↓↓ | 2.43 | ↑↑ |
| Extracellular matrix/Cell Adhesion | | | | | | | | |
| Laminin gamma-1 chain precursor | IPI00298281 | NTIEETGNLAEQAR (SEQ ID NO:901) | 0.93 | NC | 1.37 | ↑ | 0.6 | ↓↓ |
| Mammalian ependymin related protein 1 | IPI00259102 | AGGSHSDPGR (SEQ ID NO:902) | 1.14 | NC | 0.57 | ↓↓ | 1.55 | ↑↑ |
| PREDICTED: odz, odd Oz/ten-m homolog 3 | IPI00398020 | NTMAMK (SEQ ID NO:903) | 1.91 | ↑↑ | 0.72 | ↓ | 0.99 | NC |
| Splice Isoform 2 of integrin alpha-7 | IPI00220748 | ELEPPEQQEPGER (SEQ ID NO:904) | 1.18 | NC | 0.64 | ↓↓ | 1.04 | NC |

FIG. 5GG

| Protein Name | IPI # | Peptide Sequences | iTRAQ Ratios | | | | | |
|---|---|---|---|---|---|---|---|---|
| | | | AD | | PD | | DLB | |
| precursor | | | | | | | | |
| Immunity/Defense | | | | | | | | |
| Ig kappa chain V-1 region HK102 precursor | IPI00478600 | LLIYDASSLESGVPSR (SEQ ID NO:905) | 1.1 | NC | 1.53 | ↑↑ | 0.87 | NC |
| Unknown | | | | | | | | |
| 97 kDa protein | IPI00472544 | ELEERR (SEQ ID NO:906) | 0 | 0 | 2.75 | ↑↑ | 0 | 0 |
| DJ977L11.1 | IPI00478622 | LQEAAEIVK (SEQ ID NO:907) | 1.55 | ↑↑ | 0.61 | ↓↓ | 0.94 | NC |
| HRPE773 | IPI00060800 | YFSTTEDYDHEITGLR (SEQ ID NO:908) | 0.99 | NC | 0.44 | ↓↓ | 1.78 | ↑↑ |
| Hypothetical protein | IPI00470620 | HQCSIDLK (SEQ ID NO:909) | 1.08 | NC | 0.55 | ↓↓ | 1.12 | NC |
| Hypothetical protein FLJ16127 | IPI00442326 | MDRPSLVR (SEQ ID NO:910) | 1.13 | NC | 0.63 | ↓↓ | 0.93 | NC |
| Hypothetical protein FLJ46550 | IPI00443682 | AEAGGGWEGSASYK (SEQ ID NO:911) | 0.84 | NC | 1.69 | ↑↑ | 0.91 | NC |
| OTTHUMP00000021593 | IPI00374531 | TIEELAR (SEQ ID NO:912) | 0 | 0 | 2.75 | ↑↑ | 0 | 0 |
| V. Proteins unique to DLB and identified by 2 or more peptides | | | | | | | | |
| Neuronal Activities/Signal Transduction | | | | | | | | |
| 110 kDa protein | IPI00473056 | AALGESGEQADGPK (SEQ ID NO:913) | 0.91 | NC | 0.93 | NC | 0.63 | ↓↓ |
| | | DLLGQQPHSEPGAAAFGELQNQMPGPSK (SEQ ID NO:914) | | | | | | |
| | | EEQSLPAGAQEALSDGLQLEVQPSEEEAR (SEQ ID NO:915) | | | | | | |
| | | HLPFLEALSQAPASDVLAR (SEQ ID NO:916) | | | | | | |
| | | RPEASSPARPSKHSVGSER (SEQ ID NO:917) | | | | | | |
| | | VPAMDFYR (SEQ ID NO:918) | | | | | | |
| | | YEVSPVALQR (SEQ ID NO:919) | | | | | | |
| Brain abundant, membrane attached signal protein 1 | IPI00299024 | AEPPKAPEQEQAAPGPAAGGEAPK (SEQ ID NO:920) | 0.39 | ↓↓ | 0.92 | NC | 1.34 | ↑ |
| | | EADVVAR (SEQ ID NO:921) | | | | | | |
| | | EKPDQDAEGK (SEQ ID NO:922) | | | | | | |
| | | ESEPQAAAEPAEAK (SEQ ID NO:923) | | | | | | |
| Cocaine- and amphetamine-regulated transcript protein precursor | IPI00002925 | ALDIYSAVDDASHEK (SEQ ID NO:924) | 0.89 | NC | 1.07 | NC | 1.74 | ↑↑ |
| | | ELIEALQEVLK (SEQ ID NO:925) | | | | | | |

FIG. 5HH

| Protein Name | IPI # | Peptide Sequences | iTRAQ Ratios | | | | | |
|---|---|---|---|---|---|---|---|---|
| | | | AD | | PD | | DLB | |
| | | GTSCNSFLLK (SEQ ID NO:926) | | | | | | |
| DA141H5.1 | IPI00478414 | CCKVCPGK (SEQ ID NO:927) | 0.98 | NC | 1.31 | ↑ | 0.55 | ↓↓ |
| | | EELPGQSFDNK (SEQ ID NO:928) | | | | | | |
| | | GDGELSWEHSDGDIFR (SEQ ID NO:929) | | | | | | |
| | | LTCAFPVSVPDSCCRVCR (SEQ ID NO:930) | | | | | | |
| | | VLYLERSEK (SEQ ID NO:931) | | | | | | |
| | | YPCK (SEQ ID NO:932) | | | | | | |
| Latent transforming growth factor-beta binding protein 4 | IPI00395783 | EAPYGAPR (SEQ ID NO:933) | 0.97 | NC | 0.87 | NC | 1.59 | ↑↑ |
| | | FDMPDFEDDGGPYGESEAPAPPGPGTR (SEQ ID NO:934) | | | | | | |
| | | QGPVGSGR (SEQ ID NO:935) | | | | | | |
| | | REAPYGAPR (SEQ ID NO:936) | | | | | | |
| | | | | | | | | |
| | | | | | | | | |
| Neurexophilin 4 | IPI00376343 | AGAAGALPAQR (SEQ ID NO:937) | 1.04 | NC | 1 | NC | 0.72 | ↓ |
| | | SSDGLGVGR (SEQ ID NO:938) | | | | | | |
| Neuronal pentraxin I precursor | IPI00220562 | FQLTFPLR (SEQ ID NO:939) | 0.46 | ↓↓ | 0.99 | NC | 1.43 | ↑ |
| | | IDELER (SEQ ID NO:940) | | | | | | |
| | | LENLEQYSR (SEQ ID NO:941) | | | | | | |
| | | QPGSGKNTMGDLSR (SEQ ID NO:942) | | | | | | |
| | | TPAAETLSQLGQTLQSLK (SEQ ID NO:943) | | | | | | |
| | | VNTLEEGK (SEQ ID NO:944) | | | | | | |
| | | WTFEACR (SEQ ID NO:945) | | | | | | |
| Parvalbumin | IPI00219703 | AVGAFSATDSFDHK (SEQ ID NO:946) | 1.1 | NC | 1.14 | NC | 1.56 | ↑↑ |
| | | FFQMVGLK (SEQ ID NO:947) | | | | | | |
| | | GFSPDAR (SEQ ID NO:948) | | | | | | |
| | | IGVDEFSTLVAES (SEQ ID NO:949) | | | | | | |
| | | KFFQMVGLK (SEQ ID NO:950) | | | | | | |
| | | SGFIEEDELGFILK (SEQ ID NO:951) | | | | | | |
| PLXDC2 protein | IPI00073777 | EITVATGGFIYTGEVVHR (SEQ ID NO:952) | 0.67 | ↓↓ | 0.83 | NC | 1.26 | ↑ |

FIG. 5II

| Protein Name | IPI # | Peptide Sequences | iTRAQ Ratios | | | | | |
|---|---|---|---|---|---|---|---|---|
| | | | AD | | PD | | DLB | |
| | | IQQIPNVR (SEQ ID NO:953) | | | | | | |
| PREDICTED: lunatic fringe homolog | IPI00455739 | GRRALR (SEQ ID NO:954) | 0.47 | ↓↓ | 1.03 | NC | 1.79 | ↑↑ |
| | | HPTMLK (SEQ ID NO:955) | | | | | | |
| | | MAVEYDR (SEQ ID NO:956) | | | | | | |
| | | MSPAVRR (SEQ ID NO:957) | | | | | | |
| | | MSPWASGGHFMNTAER (SEQ ID NO:958) | | | | | | |
| | | SLAGPAGAAPAPGLGAAAAAPG (SEQ ID NO:959) | | | | | | |
| | | TGAGPGRGGLRAR (SEQ ID NO:960) | | | | | | |
| Proenkephalin A precursor | IPI00000828 | DAEEDDSLANSSDLLK (SEQ ID NO:961) | 0.97 | NC | 1.12 | NC | 0.62 | ↓↓ |
| | | ELLETGDNR (SEQ ID NO:962) | | | | | | |
| | | ELLQLSKPELPQDGTSTLR (SEQ ID NO:963) | | | | | | |
| | | ELLQLSKPELPQDGTSTLR (SEQ ID NO:964) | | | | | | |
| | | EVPEMEK (SEQ ID NO:965) | | | | | | |
| | | FAEALPSDEEGESYSK (SEQ ID NO:966) | | | | | | |
| | | IWETCK (SEQ ID NO:967) | | | | | | |
| | | LPSLK (SEQ ID NO:968) | | | | | | |
| | | RYGGFMRGLK (SEQ ID NO:969) | | | | | | |
| | | SPQLEDEAKELQKR (SEQ ID NO:970) | | | | | | |
| | | YGGFMK (SEQ ID NO:971) | | | | | | |
| | | YGGFMRGLKR (SEQ ID NO:972) | | | | | | |
| Protein tyrosine phosphatase, non-receptor type substrate 1 precursor | IPI00332887 | AKPSAPVVSGPAAR (SEQ ID NO:973) | 1 | NC | 1.52 | ↑↑ | 0.71 | ↓ |
| | | CTATSLIPVGPIQWFR (SEQ ID NO:974) | | | | | | |
| | | ELIYNQK (SEQ ID NO:975) | | | | | | |
| | | GSPDDVEFK (SEQ ID NO:976) | | | | | | |
| | | SVLVAAGETATLR (SEQ ID NO:977) | | | | | | |
| | | TETASTVTENK (SEQ ID NO:978) | | | | | | |
| | | VPPTLEVTQQPVR (SEQ ID NO:979) | | | | | | |
| Somatostatin precursor | IPI00000130 | LELQR (SEQ ID NO:980) | 0.89 | NC | 1.1 | NC | 0.56 | ↓↓ |
| | | LELQRSANSNPAMAPR (SEQ ID | | | | | | |

FIG. 5JJ

| Protein Name | IPI # | Peptide Sequences | iTRAQ Ratios | | | | | |
|---|---|---|---|---|---|---|---|---|
| | | | AD | | PD | | DLB | |
| | | NO:981) | | | | | | |
| | | QFLQK (SEQ ID NO:982) | | | | | | |
| | | SANSNPAMAPR (SEQ ID NO:983) | | | | | | |
| | | SLAAAAGK (SEQ ID NO:984) | | | | | | |
| Splice isoform 1 of basigin precursor | IPI00218019 | EDALPGQK (SEQ ID NO:985) | 0.98 | NC | 1.21 | ↑ | 0.67 | ↓↓ |
| | | GGVVLK (SEQ ID NO:986) | | | | | | |
| Splice isoform 1 of receptor-type tyrosine-protein phosphatase N2 precursor | IPI00334666 | LSATLGGLLQDHGSR (SEQ ID NO:987) | 0.92 | NC | 0.91 | NC | 0.54 | ↓↓ |
| | | LYQEVHR (SEQ ID NO:988) | | | | | | |
| | | SQTYSK (SEQ ID NO:989) | | | | | | |
| | | VALQK (SEQ ID NO:990) | | | | | | |
| | | VPAMDFYR (SEQ ID NO:991) | | | | | | |
| | | YEVSPVALQR (SEQ ID NO:992) | | | | | | |
| Splice isoform 3 of integrin alpha-7 precursor | IPI00220749 | DMIGRCFVLSQDLAIR (SEQ ID NO:993) | 1.13 | NC | 0.84 | NC | 1.51 | ↑↑ |
| | | DSASRLVPEVMLSGER (SEQ ID NO:994) | | | | | | |
| | | ELEPPEQQEPGER (SEQ ID NO:995) | | | | | | |
| | | GAVVILR (SEQ ID NO:996) | | | | | | |
| | | GLVRAEELSFVAGAPR (SEQ ID NO:997) | | | | | | |
| | | VCGDAMFQLQENVK (SEQ ID NO:998) | | | | | | |
| | | VDQILETRDMIGR (SEQ ID NO:999) | | | | | | |
| | | YEARQR (SEQ ID NO:1000) | | | | | | |
| Cell cycle/death | | | | | | | | |
| Fas apoptotic inhibitory molecule 2 | IPI00017569 | APGTEGQQQVHGEK (SEQ ID NO:1001) | 0.88 | NC | 0.85 | NC | 0.56 | ↓↓ |
| | | EAPAVPSAPPSYEEATSGEGMK (SEQ ID NO:1002) | | | | | | |
| | | LSVANK (SEQ ID NO:1003) | | | | | | |
| Hypothetical protein FLJ16490 | IPI00465099 | ICYVCK (SEQ ID NO:1004) | 1.11 | NC | 0.99 | NC | 0.63 | ↓↓ |
| | | EGQAVAVPSSK (SEQ ID NO:1005) | | | | | | |
| Latent transforming growth factor beta | IPI00465145 | AQPGWGSPR (SEQ ID NO:1006) | 1.71 | ↑↑ | 1.08 | NC | 0.82 | ↓ |

FIG. 5KK

| Protein Name | IPI # | Peptide Sequences | iTRAQ Ratios | | | | | |
|---|---|---|---|---|---|---|---|---|
| | | | AD | | PD | | DLB | |
| binding protein 2 | | | | | | | | |
| | | EQDAPVAGLQPVER (SEQ ID NO:1007) | | | | | | |
| | | RPGGSYPAAAAAK (SEQ ID NO:1008) | | | | | | |
| | | STPLGQQQPAPR (SEQ ID NO:1009) | | | | | | |
| | | YEPAGGDANR (SEQ ID NO:1010) | | | | | | |
| Splice isoform 1 of SWI/SNF-related, matrix associated, actin-dependent regulator | IPI00220119 | ANTPDSDITEK (SEQ ID NO:1011) | 1.61 | ↑↑ | 0.96 | NC | 0.71 | ↓ |
| | | HGLNGILADEMGLGK (SEQ ID NO:1012) | | | | | | |
| | | NLFNLDR (SEQ ID NO:1013) | | | | | | |
| | | QELREVLK (SEQ ID NO:1014) | | | | | | |
| | | SADEQSIYEKER (SEQ ID NO:1015) | | | | | | |
| | | SLFRRLK (SEQ ID NO:1016) | | | | | | |
| | | VFAEDQDMQYASQSEVPNGK (SEQ ID NO:1017) | | | | | | |
| | | YQHLMTINANNR (SEQ ID NO:1018) | | | | | | |
| Cell Structure/Motility/Transport/Traffic | | | | | | | | |
| 12 kDa protein | IPI00477183 | LQQTQAQVDEVVDIMR (SEQ ID NO:1019) | 1.04 | NC | 0.92 | NC | 0.57 | ↓↓ |
| | | MMIILGVICAIILIIIIVFFSG (SEQ ID NO:1020) | | | | | | |
| Apolipoprotein C-III precursor | IPI00021857 | DALSSVQESVAQQAR (SEQ ID NO:1021) | 0.89 | NC | 0.57 | ↓↓ | 1.28 | ↑ |
| | | DYWSTVK (SEQ ID NO:1022) | | | | | | |
| | | GWVTDGFSSLK (SEQ ID NO:1023) | | | | | | |
| Apolipoprotein C-II precursor | IPI00021856 | ESLSSYWESAK (SEQ ID NO:1024) | 1.13 | NC | 1 | NC | 1.57 | ↑↑ |
| | | STAAMSTYTGIFTDQVLSVLK (SEQ ID NO:1025) | | | | | | |
| | | TAAQNLYEK (SEQ ID NO:1026) | | | | | | |
| | | TYLPAVDEK (SEQ ID NO:1027) | | | | | | |
| Divalent cation tolerant protein CUTA | IPI00034319 | LLLLPR (SEQ ID NO:1028) | 0.82 | ↓ | 0.96 | NC | 2.07 | ↑↑ |
| | | TQSSLVPALTDFVR (SEQ ID NO:1029) | | | | | | |
| Golgi phosphoprotein | IPI00171411 | DLSENNDQR (SEQ ID NO:1030) | 2.08 | ↑↑ | 0.89 | NC | 0.77 | ↓ |

FIG. 5LL

| Protein Name | IPI # | Peptide Sequences | iTRAQ Ratios | | | | | |
|---|---|---|---|---|---|---|---|---|
| | | | AD | | PD | | DLB | |
| 2 | | | | | | | | |
| | | DQLVIPDGQEEEQEAAGEGR (SEQ ID NO:1031) | | | | | | |
| | | DTINLLDQR (SEQ ID NO:1032) | | | | | | |
| | | EETNEIQVVNEEPQR (SEQ ID NO:1033) | | | | | | |
| | | EQVVEDRPVGGR (SEQ ID NO:1034) | | | | | | |
| | | GFGGAGELGQTPQVQAA (SEQ ID NO:1035) | | | | | | |
| | | GFGGAGELGQTPQVQAALSVSQEN (SEQ ID NO:1036) | | | | | | |
| | | LPQEPGR (SEQ ID NO:1037) | | | | | | |
| | | LSVSQENPEMEGPER (SEQ ID NO:1038) | | | | | | |
| | | MGLGNGRRSMK (SEQ ID NO:1039) | | | | | | |
| | | NIDVFNVEDQK (SEQ ID NO:1040) | | | | | | |
| | | NIDVFNVEDQKR (SEQ ID NO:1041) | | | | | | |
| | | NQTNLERKFSYDLSQCINQMK (SEQ ID NO:1042) | | | | | | |
| | | QQLQALSEPQPR (SEQ ID NO:1043) | | | | | | |
| | | RDTINLLDQREK (SEQ ID NO:1044) | | | | | | |
| Hemopexin precursor | IPI00022488 | DYFMPCPGR (SEQ ID NO:1045) | 1.02 | NC | 1.05 | NC | 1.64 | ↑↑ |
| | | ELISER (SEQ ID NO:1046) | | | | | | |
| | | LHIMAGR (SEQ ID NO:1047) | | | | | | |
| | | LWWLDLK (SEQ ID NO:1048) | | | | | | |
| | | NFPSPVDAAFR (SEQ ID NO:1049) | | | | | | |
| | | VDGALCMEK (SEQ ID NO:1050) | | | | | | |
| | | VWVYPPEK (SEQ ID NO:1051) | | | | | | |
| | | YYCFQGNQFLR (SEQ ID NO:1052) | | | | | | |
| KIAA1265 protein | IPI00008085 | GHQDLDPDNEGELR (SEQ ID NO:1053) | 1.08 | NC | 0.55 | ↓↓ | 1.66 | ↑↑ |
| | | LSFFGLEK (SEQ ID NO:1054) | | | | | | |
| KIAA1291 protein | IPI00413206 | DIQQTLTQNMER (SEQ ID NO:1055) | 1.76 | ↑↑ | 1.14 | NC | 0.7 | ↓ |
| | | LEALK (SEQ ID NO:1056) | | | | | | |
| | | RPPRPGTNGWSRR (SEQ ID NO:1057) | | | | | | |
| | | SSTQMTWGALFR (SEQ ID NO:1058) | | | | | | |
| | | WNGMSRLEK (SEQ ID NO:1059) | | | | | | |
| Latent transforming growth factor-beta-binding protein 2 | IPI00292150 | AEEEELARPPR (SEQ ID NO:1060) | 1.03 | NC | 1 | NC | 1.25 | ↑ |

FIG. 5MM

| Protein Name | IPI # | Peptide Sequences | iTRAQ Ratios | | | | | |
|---|---|---|---|---|---|---|---|---|
| | | | AD | | PD | | DLB | |
| precursor | | | | | | | | |
| | | AQPGWGSPR (SEQ ID NO:1061) | | | | | | |
| | | DPCKGKGR (SEQ ID NO:1062) | | | | | | |
| | | EQDAPVAGLQPVER (SEQ ID NO:1063) | | | | | | |
| | | GHAPCSSVLGR (SEQ ID NO:1064) | | | | | | |
| | | GHRTTYTECCCQDGK (SEQ ID NO:1065) | | | | | | |
| | | LGTPQRSGAAPPTPPR (SEQ ID NO:1066) | | | | | | |
| | | SPNLRRSSAAGEGTLAR (SEQ ID NO:1067) | | | | | | |
| | | VTNDVCSEPLRGHR (SEQ ID NO:1068) | | | | | | |
| | | VYSLFR (SEQ ID NO:1069) | | | | | | |
| | | YEPAGGDANR (SEQ ID NO:1070) | | | | | | |
| MIC2L1 isoform E3'-E4'-E3-E4 | IPI00152491 | APAKPPGSGLDLADALDDQDDGR (SEQ ID NO:1071) | 0.86 | NC | 0.98 | NC | 0.57 | ↓↓ |
| | | APANTLGNDFDLADALDDR (SEQ ID NO:1072) | | | | | | |
| | | DLEDIVGGGEYKPDK (SEQ ID NO:1073) | | | | | | |
| | | ETSSVK (SEQ ID NO:1074) | | | | | | |
| | | GENLEAVVCEEPQVK (SEQ ID NO:1075) | | | | | | |
| | | KPGIGGR (SEQ ID NO:1076) | | | | | | |
| | | KPIAGGGGFSDK (SEQ ID NO:1077) | | | | | | |
| | | YSTLHTQSAEPPPPPEPAR (SEQ ID NO:1078) | | | | | | |
| Neuronal pentraxin receptor isoform 1 | IPI00334238 | AAFDVCK (SEQ ID NO:1079) | 0.94 | NC | 0.99 | NC | 0.64 | ↓↓ |
| | | ADQDTIR (SEQ ID NO:1080) | | | | | | |
| | | ADQDTIRELTGK (SEQ ID NO:1081) | | | | | | |
| | | EELLLLQSTAEQLR (SEQ ID NO:1082) | | | | | | |
| | | ELDVLQGR (SEQ ID NO:1083) | | | | | | |
| | | ELTGK (SEQ ID NO:1084) | | | | | | |
| | | GLQGAGPRR (SEQ ID NO:1085) | | | | | | |
| | | IDRLEQELPAR (SEQ ID NO:1086) | | | | | | |
| | | ISIPIR (SEQ ID NO:1087) | | | | | | |
| | | LEQELPAR (SEQ ID NO:1088) | | | | | | |

FIG. 5NN

| Protein Name | IPI # | Peptide Sequences | iTRAQ Ratios | | | | | |
|---|---|---|---|---|---|---|---|---|
| | | | AD | | PD | | DLB | |
| | | LVEAFGGATK (SEQ ID NO:1089) | | | | | | |
| | | MDQLEGQLLAQVLALEK (SEQ ID NO:1090) | | | | | | |
| | | QRQEVEKELDVLQGR (SEQ ID NO:1091) | | | | | | |
| | | QTALQQEAR (SEQ ID NO:1092) | | | | | | |
| | | VALSHSSR (SEQ ID NO:1093) | | | | | | |
| | | VAQLPLSLK (SEQ ID NO:1094) | | | | | | |
| Nucleobindin 1 precursor | IPI00295542 | APAAHPEGQLK (SEQ ID NO:1095) | 0.86 | NC | 1.13 | NC | 1.62 | ↑↑ |
| | | DLELLIQTATR (SEQ ID NO:1096) | | | | | | |
| | | EETPATESPDTGLYYHR (SEQ ID NO:1097) | | | | | | |
| | | EMEEERLRMR (SEQ ID NO:1098) | | | | | | |
| | | EVDTSEK (SEQ ID NO:1099) | | | | | | |
| | | FHPDTDDVPVPAPAGDQK (SEQ ID NO:1100) | | | | | | |
| | | LDELK (SEQ ID NO:1101) | | | | | | |
| | | LPEVEVPQHL (SEQ ID NO:1102) | | | | | | |
| | | LQAANAEDIK (SEQ ID NO:1103) | | | | | | |
| | | LVTLEEFLASTQR (SEQ ID NO:1104) | | | | | | |
| | | QQQQQQQGHK (SEQ ID NO:1105) | | | | | | |
| | | YLESLGEEQR (SEQ ID NO:1106) | | | | | | |
| | | YLQEVIDVLETDGHFR (SEQ ID NO:1107) | | | | | | |
| PREDICTED: dynein, cytoplasmic, heavy polypeptide 2 | IPI00171494 | AADLK (SEQ ID NO:1108) | 1.07 | NC | 0.94 | NC | 1.26 | ↑ |
| | | AEDLFR (SEQ ID NO:1109) | | | | | | |
| | | ALAIQNWVDK (SEQ ID NO:1110) | | | | | | |
| | | AYGATPSR (SEQ ID NO:1111) | | | | | | |
| | | CLLQSLK (SEQ ID NO:1112) | | | | | | |
| | | DIVNQVGDNR (SEQ ID NO:1113) | | | | | | |
| | | GTTLLSSEVQK (SEQ ID NO:1114) | | | | | | |
| | | INNMYR (SEQ ID NO:1115) | | | | | | |
| | | LCSIDYPER (SEQ ID NO:1116) | | | | | | |
| | | LMGIFDTSWVSMK (SEQ ID NO:1117) | | | | | | |
| | | NLSEVVNSIVWVR (SEQ ID NO:1118) | | | | | | |
| | | NSKAGSGGKSQITWDNPK (SEQ ID | | | | | | |

FIG. 50O

| Protein Name | IPI # | Peptide Sequences | iTRAQ Ratios ||||||
|---|---|---|---|---|---|---|---|---|
| | | | AD || PD || DLB ||
| | | NO:1119) | | | | | | |
| | | NYISEIQDSPQQLLQAFLK (SEQ ID NO:1120) | | | | | | |
| | | QVFAPMLLK (SEQ ID NO:1121) | | | | | | |
| | | SITAGSKFDR (SEQ ID NO:1122) | | | | | | |
| | | VDEDFR (SEQ ID NO:1123) | | | | | | |
| | | VEEHSVMTVK (SEQ ID NO:1124) | | | | | | |
| | | VLSFPGGSLLLAGR (SEQ ID NO:1125) | | | | | | |
| | | VVVLMNIDLLR (SEQ ID NO:1126) | | | | | | |
| | | WEGPEDPLQYLR (SEQ ID NO:1127) | | | | | | |
| | | YVRGEHLSPDHWLDLFR (SEQ ID NO:1128) | | | | | | |
| Protein FAM3C precursor | IPI00021923 | AIQDGTIVLMGTYDDGATK (SEQ ID NO:1129) | 1.04 | NC | 1.07 | NC | 1.71 | ↑↑ |
| | | DNWVFCGGK (SEQ ID NO:1130) | | | | | | |
| | | HFAFK (SEQ ID NO:1131) | | | | | | |
| | | ICLEDNVLMSGVK (SEQ ID NO:1132) | | | | | | |
| | | LIADLGSTSITNLGFR (SEQ ID NO:1133) | | | | | | |
| | | MASGAANVVGPK (SEQ ID NO:1134) | | | | | | |
| | | MDASLGNLFAR (SEQ ID NO:1135) | | | | | | |
| | | SALDTAAR (SEQ ID NO:1136) | | | | | | |
| | | SPFEQHIK (SEQ ID NO:1137) | | | | | | |
| | | TGEVLDTK (SEQ ID NO:1138) | | | | | | |
| | | | | | | | | |
| Sortilin 1, preproprotein | IPI00383591 | ERPWGAADGLSR (SEQ ID NO:1139) | 1.54 | ↑↑ | 1.06 | NC | 0.65 | ↓↓ |
| | | IYSFGLGGR (SEQ ID NO:1140) | | | | | | |
| | | LDAPPPPAAPLPR (SEQ ID NO:1141) | | | | | | |
| | | LRKSSVCQNGR (SEQ ID NO:1142) | | | | | | |
| Tetranectin precursor | IPI00009028 | CFLAFTQTK (SEQ ID NO:1143) | 0.63 | ↓↓ | 0.98 | NC | 1.35 | ↑ |
| | | DQLPYICQFGIV (SEQ ID NO:1144) | | | | | | |
| | | EQQALQTVCLK (SEQ ID NO:1145) | | | | | | |
| | | GGTLSTPQTGSENDALYEYLR (SEQ ID NO:1146) | | | | | | |
| | | KIVNAK (SEQ ID NO:1147) | | | | | | |
| | | LDTLAQEVALLK (SEQ ID NO:1148) | | | | | | |
| | | MFEELK (SEQ ID NO:1149) | | | | | | |

FIG. 5PP

| Protein Name | IPI # | Peptide Sequences | iTRAQ Ratios ||||||
|---|---|---|---|---|---|---|---|---|
| | | | AD | | PD | | DLB | |
| | | NWETEITAQPDGGK (SEQ ID NO:1150) | | | | | | |
| | | TFHEASEDCISR (SEQ ID NO:1151) | | | | | | |
| | | WFDK (SEQ ID NO:1152) | | | | | | |
| Transthyretin precursor | IPI00022432 | AADDTWEPFASGK (SEQ ID NO:1153) | 1.03 | NC | 1.16 | NC | 1.51 | ↑↑ |
| | | ALGISPFHEHAEVVFTANDSGPR (SEQ ID NO:1154) | | | | | | |
| | | CPLMVK (SEQ ID NO:1155) | | | | | | |
| | | DSGPR (SEQ ID NO:1156) | | | | | | |
| | | GSPAINVAVHVFR (SEQ ID NO:1157) | | | | | | |
| | | GSPAINVAVHVFRK (SEQ ID NO:1158) | | | | | | |
| | | KAADDTWEPFASGK (SEQ ID NO:1159) | | | | | | |
| | | RYTIAALLSPYSYSTTAVVTNPK (SEQ ID NO:1160) | | | | | | |
| | | SYWK (SEQ ID NO:1161) | | | | | | |
| | | TSESGELHGLTTEEEFVEGIYK (SEQ ID NO:1162) | | | | | | |
| | | VEIDTK (SEQ ID NO:1163) | | | | | | |
| | | VLDAVR (SEQ ID NO:1164) | | | | | | |
| | | YTIAALLSPYSYSTTAVVTNPK (SEQ ID NO:1165) | | | | | | |
| | | YTIAALLSPYSYSTTAVVTNPKE (SEQ ID NO:1166) | | | | | | |
| Metabolism | | | | | | | | |
| 2'-phosphodiesterase | IPI00174390 | DQSEPLGRVLSR (SEQ ID NO:1167) | 0.91 | NC | 0.97 | NC | 0.45 | ↓↓ |
| | | ELTGYNADVICLQEVDR (SEQ ID NO:1168) | | | | | | |
| | | LPGARAALR (SEQ ID NO:1169) | | | | | | |
| | | QNLIQK (SEQ ID NO:1170) | | | | | | |
| | | VIRTAVEK (SEQ ID NO:1171) | | | | | | |
| Angiotensinogen precursor | IPI00032220 | AAMVGMLANFLGFR (SEQ ID NO:1172) | 0.97 | NC | 0.96 | NC | 1.23 | ↑ |
| | | ALQDQLVLVAAK (SEQ ID NO:1173) | | | | | | |
| | | DPTFIPAPIQAK (SEQ ID NO:1174) | | | | | | |
| | | FMQAVTGWK (SEQ ID NO:1175) | | | | | | |
| | | LDTEDKLR (SEQ ID NO:1176) | | | | | | |
| | | QPFVQGLALYTPVVLPR (SEQ ID NO:1177) | | | | | | |

FIG. 5QQ

| Protein Name | IPI # | Peptide Sequences | iTRAQ Ratios ||||||
|---|---|---|---|---|---|---|---|---|
| | | | AD || PD || DLB ||
| | | SLDFTELDVAAEK (SEQ ID NO:1178) | | | | | | |
| | | TSPVDEK (SEQ ID NO:1179) | | | | | | |
| | | VANPLSTA (SEQ ID NO:1180) | | | | | | |
| | | VLSALQAVQGLLVAQGR (SEQ ID NO:1181) | | | | | | |
| Apolipoprotein C1 | IPI00021855 | EFGNTLEDK (SEQ ID NO:1182) | 1.18 | NC | 0.99 | NC | 0.48 | ↓↓ |
| | | EWFSETFQK (SEQ ID NO:1183) | | | | | | |
| | | LKEFGNTLEDK (SEQ ID NO:1184) | | | | | | |
| | | QSELSAK (SEQ ID NO:1185) | | | | | | |
| Coagulation factor V | IPI00419311 | ASEFLGYWEPR (SEQ ID NO:1186) | 1.16 | NC | 0.84 | NC | 0.65 | ↓↓ |
| | | EFNPLVIVGLSK (SEQ ID NO:1187) | | | | | | |
| Enolase 2 | IPI00216171 | AAVPSGASTGIYEALELR (SEQ ID NO:1188) | 0.57 | ↓↓ | 1 | NC | 1.32 | ↑ |
| | | GNPTVEVDLYTAK (SEQ ID NO:1189) | | | | | | |
| | | YITGDQLGALYQDFVR (SEQ ID NO:1190) | | | | | | |
| Hypothetical protein DKFZp686B0286 | IPI00465248 | AAVPSGASTGIYEALELR (SEQ ID NO:1191) | 0.57 | ↓↓ | 1 | NC | 1.32 | ↑ |
| | | GNPTVEVDLFTSK (SEQ ID NO:1192) | | | | | | |
| | | VVIGMDVAASEFFR (SEQ ID NO:1193) | | | | | | |
| Lysozyme C precursor | IPI00019038 | AWVAWR (SEQ ID NO:1194) | 0.96 | NC | 0.88 | NC | 3.1 | ↑↑ |
| | | GISLANWMCLAK (SEQ ID NO:1195) | | | | | | |
| | | STDYGIFQINSR (SEQ ID NO:1196) | | | | | | |
| N-acetyllactosaminide beta-1,3-N-acetylglucosaminyltransferase | IPI00009997 | EAENQHNK (SEQ ID NO:1197) | 1.1 | NC | 1.19 | NC | 1.88 | ↑↑ |
| | | EMLDQSNQWGGTALVVPAFEIR (SEQ ID NO:1198) | | | | | | |
| | | EPGEFALLR (SEQ ID NO:1199) | | | | | | |
| | | QYGFNR (SEQ ID NO:1200) | | | | | | |
| | | SCQEVFDK (SEQ ID NO:1201) | | | | | | |
| | | SVDQVK (SEQ ID NO:1202) | | | | | | |
| | | TALASGGVLDASGDYR (SEQ ID NO:1203) | | | | | | |
| | | TALASGGVLDASGDYRVYR (SEQ ID NO:1204) | | | | | | |
| | | VPTFDER (SEQ ID NO:1205) | | | | | | |

FIG. 5RR

| Protein Name | IPI # | Peptide Sequences | iTRAQ Ratios ||||||
|---|---|---|---|---|---|---|---|---|
| | | | AD | | PD | | DLB | |
| | | WEGPLSVSVFAATK (SEQ ID NO:1206) | | | | | | |
| | | YEAAVPDPR (SEQ ID NO:1207) | | | | | | |
| | | YPNSPR (SEQ ID NO:1208) | | | | | | |
| Probable endonuclease KIAA0830 precursor | IPI00001952 | DSDIIEDVMVK (SEQ ID NO:1209) | 0.88 | NC | 1 | NC | 1.75 | ↑↑ |
| | | ICQRAEGAER (SEQ ID NO:1210) | | | | | | |
| | | ILEVVNQIQDEER (SEQ ID NO:1211) | | | | | | |
| | | WYVNLHSLMDR (SEQ ID NO:1212) | | | | | | |
| Rho-associated protein kinase 1 | IPI00022542 | DVEMEPVQQAEK (SEQ ID NO:1213) | 0.85 | NC | 0.88 | NC | 0.79 | ↓ |
| | | GNEGQMR (SEQ ID NO:1214) | | | | | | |
| | | INEYQRKAEQENEK (SEQ ID NO:1215) | | | | | | |
| | | KANTQDLR (SEQ ID NO:1216) | | | | | | |
| | | LSQLQK (SEQ ID NO:1217) | | | | | | |
| | | NDQWAWETLR (SEQ ID NO:1218) | | | | | | |
| | | NINTERTLK (SEQ ID NO:1219) | | | | | | |
| | | QLEEANDLLR (SEQ ID NO:1220) | | | | | | |
| | | SQGGDGYYGR (SEQ ID NO:1221) | | | | | | |
| | | VVKNTSGK (SEQ ID NO:1222) | | | | | | |
| Similar to peptide N-glycanase homolog | IPI00165496 | ELLQR (SEQ ID NO:1223) | 0.91 | NC | 1.06 | NC | 0.66 | ↓↓ |
| | | FECGSVGLK (SEQ ID NO:1224) | | | | | | |
| | | GEMGLQR (SEQ ID NO:1225) | | | | | | |
| | | IRDLIAIERSSR (SEQ ID NO:1226) | | | | | | |
| | | KVETDWHMVYLARK (SEQ ID NO:1227) | | | | | | |
| | | QLFLSENRR (SEQ ID NO:1228) | | | | | | |
| | | YVWDYTELQRTLSLK (SEQ ID NO:1229) | | | | | | |
| Sortilin-related receptor precursor | IPI00022608 | DEQYLFLVR (SEQ ID NO:1230) | 1.06 | NC | 1.1 | NC | 1.4 | ↑ |
| | | GFLVVQGDPR (SEQ ID NO:1231) | | | | | | |
| | | IITENDHVLLFWKSLALK (SEQ ID NO:1232) | | | | | | |
| | | LNFGLGNR (SEQ ID NO:1233) | | | | | | |
| | | TDLGDSPLAFEHVMTR (SEQ ID NO:1234) | | | | | | |

FIG. 5SS

| Protein Name | IPI # | Peptide Sequences | iTRAQ Ratios | | | | | |
|---|---|---|---|---|---|---|---|---|
| | | | AD | | PD | | DLB | |
| | | TPEGLPDAPRNLQLSLPR (SEQ ID NO:1235) | | | | | | |
| Splice isoform 1 of neuroendocrine protein 7B2 precursor | IPI00008944 | DFSEDQGYPDPPNPCPVGK (SEQ ID NO:1236) | 0.89 | NC | 0.96 | NC | 0.71 | ↑ |
| | | EFQLHQHLFDPEHDYPGLGK (SEQ ID NO:1237) | | | | | | |
| | | LDNVVAK (SEQ ID NO:1238) | | | | | | |
| | | LLHGVMEQLGIARPR (SEQ ID NO:1239) | | | | | | |
| | | LLYEK (SEQ ID NO:1240) | | | | | | |
| | | SVNPYLQGQR (SEQ ID NO:1241) | | | | | | |
| | | SVPHFSDEDKDPE (SEQ ID NO:1242) | | | | | | |
| | | TADDGCLENTPDTAEFSR (SEQ ID NO:1243) | | | | | | |
| | | VSEADIQR (SEQ ID NO:1244) | | | | | | |
| Splice isoform 2 of ectonucleotide pyrophosphatase/phosphodiesterase 2 | IPI00303210 | GWECTK (SEQ ID NO:1245) | 1.04 | NC | 0.85 | NC | 0.24 | ↓↓ |
| | | IVGQLMDGLK (SEQ ID NO:1246) | | | | | | |
| | | QMSYGFLFPPYLSSSPEAK (SEQ ID NO:1247) | | | | | | |
| | | RIEDIHLLVER (SEQ ID NO:1248) | | | | | | |
| | | TEFLSNYLTNVDDITLVPGTLGR (SEQ ID NO:1249) | | | | | | |
| | | VWNYFQR (SEQ ID NO:1250) | | | | | | |
| | | WVEELMK (SEQ ID NO:1251) | | | | | | |
| | | WWGGQPLWITATK (SEQ ID NO:1252) | | | | | | |
| Sulfatase 2 isoform b precursor | IPI00384856 | CYILENDTVQCDLDLYK (SEQ ID NO:1253) | 0.93 | NC | 0.86 | NC | 0.65 | ↓↓ |
| | | SVAIEVDGR (SEQ ID NO:1254) | | | | | | |
| | | TFAVYLNSTGYRTAFFGK (SEQ ID NO:1255) | | | | | | |
| | | VDAQEENFLPK (SEQ ID NO:1256) | | | | | | |
| | | VYHVGLGDAAQPR (SEQ ID NO:1257) | | | | | | |
| Superoxide dismutase 1, soluble | IPI00218733 | AVCVLK (SEQ ID NO:1258) | 0.58 | ↓ | 1.06 | NC | 1.68 | ↑↑ |
| | | GDGPVQGIINFEQK (SEQ ID NO:1259) | | | | | | |
| | | GGNEESTK (SEQ ID NO:1260) | | | | | | |

FIG. 5TT

| Protein Name | IPI # | Peptide Sequences | iTRAQ Ratios ||||||
|---|---|---|---|---|---|---|---|---|
| | | | AD | | PD | | DLB | |
| | | LACGVIGIAQ (SEQ ID NO:1261) | | | | | | |
| | | VWGSIK (SEQ ID NO:1262) | | | | | | |
| Transcription elongation regulator 1 | IPI00247871 | FKAIEK (SEQ ID NO:1263) | 2.33 | ↑↑ | 0.94 | NC | 0.71 | ↓ |
| | | YLVLDCVPEERR (SEQ ID NO:1264) | | | | | | |
| Extracellular Matrix/Cell Adhesion | | | | | | | | |
| Hypothetical protein FLJ35635 | IPI00385748 | DLPETLNELHLDHNK (SEQ ID NO:1265) | 0.92 | NC | 0.89 | NC | 0.65 | ↓↓ |
| | | IQAIELEDLLR (SEQ ID NO:1266) | | | | | | |
| Neural cell adhesion molecule 1, 140 kDa isoform precursor | IPI00435020 | CGLFMCIAVNLCGK (SEQ ID NO:1267) | 1.15 | NC | 1.03 | NC | 0.61 | ↓↓ |
| | | DESKEPIVEVR (SEQ ID NO:1268) | | | | | | |
| | | FFLCQVAGDAK (SEQ ID NO:1269) | | | | | | |
| | | GLGEISAASEFK (SEQ ID NO:1270) | | | | | | |
| | | IFQK (SEQ ID NO:1271) | | | | | | |
| | | QDDGGSPIR (SEQ ID NO:1272) | | | | | | |
| | | TQPVQGEPSAPK (SEQ ID NO:1273) | | | | | | |
| | | VNLIK (SEQ ID NO:1274) | | | | | | |
| T-Cadherin | IPI00024046 | DIQGSLQDIFK (SEQ ID NO:1275) | 0.98 | NC | 0.58 | NC | 0.85 | ↓↓ |
| | | GIFRINENTGSVSVTR (SEQ ID NO:1276) | | | | | | |
| | | TLFVHAR (SEQ ID NO:1277) | | | | | | |
| | | TPHAEDMAELVIVGGK (SEQ ID NO:1278) | | | | | | |
| | | VDCNAAGALR (SEQ ID NO:1279) | | | | | | |
| | | VNSDGGLVALR (SEQ ID NO:1280) | | | | | | |
| | | YEVSSPYFK (SEQ ID NO:1281) | | | | | | |
| Immunity/Defense | | | | | | | | |
| CD99L2 protein | IPI00434755 | APAKPPGSGLDLADALDDQDDGR (SEQ ID NO:1282) | 1.11 | NC | 1.63 | ↑↑ | 0.42 | ↓↓ |
| | | APANTLGNDFDLADALDDR (SEQ ID NO:1283) | | | | | | |
| Polymeric-immunoglobulin receptor precursor | IPI00004573 | ASVDSGSSEEQGGSSR (SEQ ID NO:1284) | 1.12 | NC | 0.15 | ↓↓ | 1.52 | ↑↑ |
| | | LFAEEK (SEQ ID NO:1285) | | | | | | |
| Unknown | | | | | | | | |
| Hypothetical protein | IPI00301255 | DLDDTK (SEQ ID NO:1286) | 0.98 | NC | 1.1 | NC | 1.29 | ↑ |

FIG. 5UU

| Protein Name | IPI # | Peptide Sequences | iTRAQ Ratios ||||||
|---|---|---|---|---|---|---|---|---|
| | | | AD || PD || DLB ||
| FLJ90835 | | | | | | | | |
| | | DLDDTKMQKSLSLLDAENR (SEQ ID NO:1287) | | | | | | |
| | | IVMTPSR (SEQ ID NO:1288) | | | | | | |
| | | SLSLLDAENR (SEQ ID NO:1289) | | | | | | |
| | | TDGRMR (SEQ ID NO:1290) | | | | | | |
| PREDICTED: FLJ46675 protein | IPI00165319 | AGMLVSGLAGEK (SEQ ID NO:1291) | 1.17 | NC | 0.89 | NC | 0.62 | ↓↓ |
| | | ASTLTIGWRAQEMSEK (SEQ ID NO:1292) | | | | | | |
| | | DLEFEEDQR (SEQ ID NO:1293) | | | | | | |
| | | DVLEK (SEQ ID NO:1294) | | | | | | |
| | | EMFLMAAMGPPGGGR (SEQ ID NO:1295) | | | | | | |
| | | FHALSLGQGQAPIAAR (SEQ ID NO:1296) | | | | | | |
| | | FLILQTETMETTAHGLFRR (SEQ ID NO:1297) | | | | | | |
| | | IDSYLREIEGSFPNK (SEQ ID NO:1298) | | | | | | |
| | | LVEDLGLFPGR (SEQ ID NO:1299) | | | | | | |
| | | MFEKLINK (SEQ ID NO:1300) | | | | | | |
| | | MMEDALR (SEQ ID NO:1301) | | | | | | |
| | | NCHLALR (SEQ ID NO:1302) | | | | | | |
| | | NMEGGQGLK (SEQ ID NO:1303) | | | | | | |
| | | QELLAQANK (SEQ ID NO:1304) | | | | | | |
| | | VELDALQQIWEIAR (SEQ ID NO:1305) | | | | | | |
| | | VGRNGGEAEEK (SEQ ID NO:1306) | | | | | | |
| | | VIGQPRGNMLLVGIGGSGR (SEQ ID NO:1307) | | | | | | |
| | | YIREMFLMAAMGPPGGGR (SEQ ID NO:1308) | | | | | | |
| PREDICTED: G2 protein | IPI00176482 | AASGPK (SEQ ID NO:1309) | 0.92 | NC | 1.28 | ↑ | 0.58 | ↓↓ |
| | | GFLNFMNTVLVAFTK (SEQ ID NO:1310) | | | | | | |
| | | LLPISPTWPFTEVR (SEQ ID NO:1311) | | | | | | |
| PREDICTED: hypothetical protein XP_498788 | IPI00456355 | LLYEK (SEQ ID NO:1312) | 1.03 | NC | 0.97 | NC | 0.63 | ↓↓ |
| | | LYEK (SEQ ID NO:1313) | | | | | | |

FIG. 5VV

| Protein Name | IPI # | Peptide Sequences | iTRAQ Ratios ||||||
|---|---|---|---|---|---|---|---|---|
| | | | AD || PD || DLB ||
| | | RSTYPLADSTER (SEQ ID NO:1314) | | | | | | |
| | | SVSNLNYQR (SEQ ID NO:1315) | | | | | | |
| VI. Proteins unique to DLB and identified by single peptide |||||||||
| Neuronal Activities/Signal Transduction |||||||||
| Activating receptor pilrbeta | IPI00186781 | VELDTR (SEQ ID NO:1316) | 0.97 | NC | 0.72 | ↓ | 1.62 | ↑↑ |
| Hypothetical protein FLJ13782 | IPI00016576 | ASDSQEDQEK (SEQ ID NO:1317) | 0.85 | NC | 0.95 | NC | 0.65 | ↓↓ |
| Metabotropic glutamate receptor 3 precursor | IPI00478165 | ELIAAASR (SEQ ID NO:1318) | 0.86 | NC | 0.51 | ↓↓ | 2.43 | ↑↑ |
| PREDICTED: KIAA1337 protein | IPI00002283 | ETPPLEDLAANQSEDPR (SEQ ID NO:1319) | 0.97 | NC | 0.64 | ↓↓ | 1.49 | ↑ |
| PREDICTED: similar to 28 kDa heat- and acid-stable phosphoprotein (PDGF-associated protein) | IPI00376589 | ADLAQLAIIR (SEQ ID NO:1320) | 0.84 | NC | 1.53 | ↑↑ | 0.62 | ↓↓ |
| Rho-GTPase activating protein 10 | IPI00169307 | GSWGSGK (SEQ ID NO:1321) | 1 | NC | 5.99 | ↑↑ | 0.48 | ↓↓ |
| Splice isoform 2 of ephrin type-A receptor 5 precursor | IPI00215945 | IDTIAADESFTELDLGDR (SEQ ID NO:1322) | 0.88 | NC | 0.86 | NC | 0.51 | ↓↓ |
| Splice isoform 2 of metabotropic glutamate receptor 8 precursor | IPI00396012 | ASIDGFDR (SEQ ID NO:1323) | 0.93 | NC | 0.85 | NC | 0.65 | ↓↓ |
| Cell Structure/Motility/Transport/Traffic |||||||||
| Hypothetical protein FLJ32363 | IPI00374273 | LTQTSPR (SEQ ID NO:1324) | 1.09 | NC | 0.88 | NC | 0.58 | ↓↓ |
| Laminin gamma-1 chain precursor | IPI00298281 | NTIEETGNLAEQAR (SEQ ID NO:1325) | 0.93 | NC | 1.37 | ↑ | 0.6 | ↓↓ |
| MGAT3 protein | IPI00020406 | VDLVLPEDTTEYFVR (SEQ ID NO:1326) | 1 | NC | 1.02 | NC | 0.66 | ↓↓ |
| SH3-domain GRB2-like 1 | IPI00019169 | AVTEVLAR (SEQ ID NO:1327) | 1.18 | NC | 0.89 | NC | 0.65 | ↓↓ |
| Splice isoform 1 of transcription factor E2-alpha | IPI00013929 | AADGSLDTQPK (SEQ ID NO:1328) | 0.84 | NC | 0.72 | ↓ | 1.74 | ↑↑ |
| Splice isoform 2 of sodium/potassium/calcium exchanger 2 precursor | IPI00218809 | VAQGYHQR (SEQ ID NO:1329) | 1.05 | NC | 0.92 | NC | 0.48 | ↓↓ |

FIG. 5WW

| Protein Name | IPI # | Peptide Sequences | iTRAQ Ratios ||||||
|---|---|---|---|---|---|---|---|---|
| | | | AD | | PD | | DLB | |
| Metabolism | | | | | | | | |
| DNA-directed RNA polymerase I largest subunit | IPI00031960 | SITNPR (SEQ ID NO:1330) | 0.59 | ↓↓ | 0.89 | NC | 1.32 | ↑ |
| Hypothetical protein FLJ90551 | IPI00181556 | SLAAAFPR (SEQ ID NO:1331) | 0.89 | NC | 1.1 | NC | 0.56 | ↓↓ |
| MGAT3 protein | IPI00020406 | VDLVLPEDTTEYFVR (SEQ ID NO:1332) | 1 | NC | 1.02 | NC | 0.66 | ↓↓ |
| Neuroendocrine convertase 2 precursor | IPI00029131 | EELEEELDEAVER (SEQ ID NO:1333) | 1.14 | NC | 1.11 | NC | 1.65 | ↑↑ |
| SCMH1 protein | IPI00187110 | TLNGAEMAPIR (SEQ ID NO:1334) | 1.06 | NC | 1.02 | NC | 0.64 | ↓↓ |
| Selenoprotein P precursor | IPI00029061 | LPTDSELAPR (SEQ ID NO:1335) | 1.18 | NC | 0.97 | NC | 1.71 | ↑↑ |
| Splice isoform 2 of glutaryl-CoA dehydrogenase, mitochondrial precursor | IPI00218112 | NQLIQK (SEQ ID NO:1336) | 0.94 | NC | 0.93 | NC | 0.23 | ↓↓ |
| Splice isoform 3 of reelin precursor | IPI00298066 | ITIPLPNAALTR (SEQ ID NO:1337) | 1.05 | NC | 0.91 | NC | 0.65 | ↓↓ |
| Extracellular Matrix/Cell Adhesion | | | | | | | | |
| Dermatopontin precursor | IPI00292130 | GATTTFSAVER (SEQ ID NO:1338) | 1.02 | NC | 1.11 | NC | 0.66 | ↓↓ |
| KIAA1730 protein | IPI00155199 | EAEAWAKPGAAARR (SEQ ID NO:1339) | 1.63 | ↑↑ | 1.18 | NC | 0.66 | ↓↓ |
| LOC374654 protein | IPI00394856 | AAQALNR (SEQ ID NO:1340) | 1 | NC | 0.93 | NC | 0.44 | ↓↓ |
| Mammalian ependymin related protein 1 | IPI00259102 | AGGSHSDPGR (SEQ ID NO:1341) | 1.14 | NC | 0.57 | ↓↓ | 1.55 | ↑↑ |
| Myosin | IPI00218638 | VSGGGEK (SEQ ID NO:1342) | 1.13 | NC | 1.1 | NC | 1.56 | ↑↑ |
| Profilin 2 isoform | IPI00219468 | SQGGEPTYNVAVGR (SEQ ID NO:1343) | 1.12 | NC | 0.84 | NC | 1.64 | ↑↑ |
| Splice isoform 2 of collagen alpha 2(VI) chain precursor | IPI00220613 | GDPGDAGPR (SEQ ID NO:1344) | 0.85 | NC | 0.93 | NC | 0.55 | ↓↓ |
| Immunity/Defense | | | | | | | | |
| Hypothetical protein | IPI00384931 | ADSSPVK (SEQ ID NO:1345) | 1.03 | NC | 1.04 | NC | 2.48 | ↑↑ |
| Unknown | | | | | | | | |
| DKFZp434L142 protein | IPI00165044 | ASLQHGQAAEK (SEQ ID NO:1346) | 0.86 | NC | 0.85 | NC | 0.42 | ↓↓ |
| HGS_RE408 | IPI00290826 | GLAEAAGPR (SEQ ID NO:1347) | 0.85 | NC | 0.93 | NC | 0.55 | ↓↓ |
| HRPE773 | IPI00060800 | YFSTTEDYDHEITGLR (SEQ ID NO:1348) | 0.99 | NC | 0.44 | ↓↓ | 1.78 | ↑↑ |

FIG. 5XX

| Protein Name | IPI # | Peptide Sequences | iTRAQ Ratios | | | | | |
|---|---|---|---|---|---|---|---|---|
| | | | AD | | PD | | DLB | |
| Hypothetical protein FLJ10650 | IPI00018805 | TLQSTPR (SEQ ID NO:1349) | 1.09 | NC | 0.88 | NC | 0.58 | ↓↓ |
| KARCA1 protein | IPI00168703 | WLCVVGGWDGSRR (SEQ ID NO:1350) | 5.81 | ↑↑ | 1.06 | NC | 0.57 | ↓↓ |
| Kelch/ankyrin repeat containing cyclin A1 interacting protein | IPI00449308 | WLCVVGGWDGSRR (SEQ ID NO:1351) | 5.65 | ↑↑ | 1.09 | NC | 0.76 | ↓ |
| PREDICTED: similar to adrenoleukodystrophy protein (ALDP) | IPI00397198 | GFLSQRLFAR (SEQ ID NO:1352) | 1.17 | NC | 1.17 | NC | 1.56 | ↑↑ |
| Protein C20 or f98 | IPI00017231 | LEGIGEGEFLVLDQR (SEQ ID NO:1353) | 0.9 | NC | 0.96 | NC | 0.54 | ↓↓ |

FIG. 5YY

| Protein Name | IPI Address |
|---|---|
| 10 kDa protein | IPI00477452 |
| 10 kDa protein | IPI00478205 |
| 107 kDa protein | IPI00476999 |
| 11 kDa protein | IPI00479928 |
| 12 kDa protein | IPI00477183 |
| 132 kDa protein | IPI00412845 |
| 132 kDa protein | IPI00477893 |
| 154 kDa protein | IPI00472011 |
| 16 kDa protein | IPI00328348 |
| 19 kDa protein | IPI00181341 |
| 2,3-bisphosphoglycerate mutase | IPI00215979 |
| 21 kDa protein | IPI00477336 |
| 24 kDa protein | IPI00479531 |
| 25 kDa protein | IPI00334282 |
| 29 kDa protein | IPI00180776 |
| 2'-phosphodiesterase | IPI00174390 |
| 38 kDa protein | IPI00333662 |
| 39S ribosomal protein L9, mitochondrial precursor | IPI00307409 |
| 42 kDa protein | IPI00333429 |
| 44 kDa protein | IPI00479267 |
| 45 kDa calcium-binding protein precursor | IPI00106646 |
| 45 kDa protein | IPI00478761 |
| 54 kDa protein | IPI00473015 |
| 57 kDa protein | IPI00479902 |
| 59 kDa protein | IPI00479340 |
| 59 kDa protein | IPI00479977 |
| 61 kDa protein | IPI00334408 |
| 65 kDa protein | IPI00479169 |
| 72 kDa type IV collagenase precursor | IPI00027780 |
| 75 kDa protein | IPI00238755 |
| 75 kDa protein | IPI00413996 |
| 85 kDa protein | IPI00414205 |
| 9 kDa protein | IPI00477785 |
| Actin, alpha skeletal muscle | IPI00021428 |
| Actin, cytoplasmic 1 | IPI00021439 |
| Actin, cytoplasmic 2 | IPI00021440 |
| Adenovirus E3-14.7K interacting protein 1 | IPI00105620 |
| Adenylate cyclase type III | IPI00028513 |
| Adenylate cyclase, type IX | IPI00030099 |
| Adseverin | IPI00002606 |
| AF5q31 protein | IPI00004344 |

FIG. 6A

| Protein Name | IPI Address |
|---|---|
| Afamin precursor | IPI00019943 |
| Agrin | IPI00479925 |
| ALB protein | IPI00384697 |
| Alcadein alpha-1 | IPI00007257 |
| ALDOC protein | IPI00418262 |
| Alpha 2,6-sialyltransferase | IPI00479942 |
| AlphA 3 type VI collagen isoform 3 precursor | IPI00072917 |
| Alpha-1,3 | IPI00061448 |
| Alpha-1-acid glycoprotein 2 precursor | IPI00020091 |
| Alpha-1-antitrypsin precursor | IPI00305457 |
| Alpha-1B-glycoprotein precursor | IPI00022895 |
| Alpha-2-antiplasmin precursor | IPI00029863 |
| Alpha-2-glycoprotein 1, zinc | IPI00166729 |
| Alpha-2-HS-glycoprotein precursor | IPI00022431 |
| Alpha-2-macroglobulin precursor | IPI00478003 |
| Alpha-2-macroglobulin receptor-associated protein precursor | IPI00026848 |
| Alu subfamily SB sequence contamination warning entry | IPI00383860 |
| AMBP protein precursor | IPI00022426 |
| Amyloid-like protein 1 precursor | IPI00020012 |
| Angiotensinogen precursor | IPI00032220 |
| Antithrombin III variant | IPI00032179 |
| APOA4 protein | IPI00479805 |
| APOBEC-1 stimulating protein | IPI00299499 |
| Apolipoprotein A-I precursor | IPI00021841 |
| Apolipoprotein A-II precursor | IPI00021854 |
| Apolipoprotein A-IV precursor | IPI00304273 |
| Apolipoprotein C-I precursor | IPI00021855 |
| Apolipoprotein C-II precursor | IPI00021856 |
| Apolipoprotein C-III precursor | IPI00021857 |
| Apolipoprotein D precursor | IPI00006662 |
| Apolipoprotein E precursor | IPI00021842 |
| Apolipoprotein M | IPI00030739 |
| Associated molecule with the SH3 domain of STAM | IPI00290975 |
| ATP-binding cassette, sub-family A member 8 | IPI00479296 |
| ATP-binding cassette, sub-family A, member 2 isoform b | IPI00414303 |
| Baculoviral IAP repeat-containing protein 1 | IPI00011547 |
| Basement membrane-specific heparan sulfate proteoglycan core protein precursor | IPI00024284 |
| Beta galactosyltransferase | IPI00184094 |
| Beta-2-glycoprotein I precursor | IPI00298828 |
| Beta-2-microglobulin precursor | IPI00004656 |

FIG. 6B

| Protein Name | IPI Address |
|---|---|
| Beta-galactosidase Binding lectin precursor | IPI00219219 |
| Beta-globin gene from a thalassemia patient, complete cds | IPI00382950 |
| Betaglycan | IPI00304865 |
| Biotinidase precursor | IPI00218413 |
| BK134P22.1 | IPI00009619 |
| Bone morphogenetic protein 3b precursor | IPI00023315 |
| Bone-derived growth factor | IPI00015916 |
| Brain abundant, membrane attached signal protein 1 | IPI00299024 |
| Brain immunoglobulin receptor precursor | IPI00166048 |
| Brain-derived neurotrophic factor BDNF1 | IPI00336003 |
| Butyrophilin | IPI00384734 |
| C1orf16 protein | IPI00448672 |
| C4B1 | IPI00418163 |
| CAD protein | IPI00301263 |
| Cadherin EGF LAG seven-pass G-type receptor 2 precursor | IPI00015346 |
| Cadherin-13 precursor | IPI00024046 |
| Calcium binding protein | IPI00384644 |
| Calmodulin | IPI00075248 |
| Calmodulin-like 3 | IPI00216984 |
| CAP-binding protein complex interacting protein 1 isoform a | IPI00009724 |
| Carboxypeptidase E precursor | IPI00031121 |
| Cathepsin B precursor | IPI00295741 |
| Cathepsin D precursor | IPI00011229 |
| CD59 glycoprotein precursor | IPI00011302 |
| CD99L2 protein | IPI00434755 |
| Cell growth regulator with EF hand domain 1 | IPI00337548 |
| Cell growth regulator with EF hand domain 1 | IPI00008584 |
| Ceruloplasmin precursor | IPI00017601 |
| Chitinase-3 like protein 1 precursor | IPI00002147 |
| Cholecystokinins precursor | IPI00026174 |
| Chordin-like 1 | IPI00150751 |
| Chromogranin A | IPI00419463 |
| Chromogranin A precursor | IPI00290315 |
| Ciliary dynein heavy chain 9 | IPI00302453 |
| Ciliary rootlet coiled-coil, rootletin | IPI00456492 |
| Clusterin isoform 1 | IPI00400826 |
| Clusterin precursor | IPI00291262 |
| Coagulation factor V | IPI00419311 |
| Cocaine- and amphetamine-regulated transcript protein precursor | IPI00002925 |
| Cochlin precursor | IPI00012386 |

FIG. 6C

| Protein Name | IPI Address |
|---|---|
| Collagen alpha 1(I) chain precursor | IPI00297646 |
| Collagen alpha 1(VI) chain precursor | IPI00291136 |
| Collagen alpha 2(I) chain precursor | IPI00304962 |
| Collagen alpha 2(V) chain precursor | IPI00293881 |
| Complement C1r subcomponent precursor | IPI00296165 |
| Complement C1s subcomponent precursor | IPI00017696 |
| Complement C2 precursor | IPI00303963 |
| Complement C3 precursor | IPI00164623 |
| Complement C4 precursor | IPI00032258 |
| Complement C5 precursor | IPI00032291 |
| Complement Component 4B proprotein | IPI00453459 |
| Complement component C6 precursor | IPI00009920 |
| Complement component C7 precursor | IPI00296608 |
| Complement component C8 beta chain precursor | IPI00294395 |
| Complement component C8 gamma chain precursor | IPI00011261 |
| Complement component C9 precursor | IPI00022395 |
| Complement factor I precursor | IPI00291867 |
| Contactin 2 precursor | IPI00024966 |
| COP9 signalosome complex subunit 4 | IPI00171844 |
| Corticosteroid-binding globulin precursor | IPI00027482 |
| C-type natriuretic peptide precursor | IPI00012075 |
| Cyclophilin | IPI00419585 |
| Cystatin C precursor | IPI00032293 |
| Cytochrome P450 27, mitochondrial precursor | IPI00025307 |
| Cytokeratin type II | IPI00005859 |
| Cytosolic malate dehydrogenase | IPI00291005 |
| D1 dopamine receptor-interacting protein calcyon | IPI00024587 |
| DA141H5.1 | IPI00478414 |
| DEAD (Asp-Glu-Ala-Asp) box polypeptide 51 | IPI00217541 |
| Death-associated protein kinase 1 | IPI00021250 |
| Dickkopf related protein-3 precursor | IPI00002714 |
| Dihydropyridine-sensitive L-type, calcium channel alpha-2/delta subunits precursor | IPI00479514 |
| Divalent cation tolerant protein CUTA | IPI00034319 |
| DJ1071L10.1 | IPI00299633 |
| DPKL1915 | IPI00419630 |
| Dystroglycan precursor | IPI00028911 |
| Endothelin B receptor-like protein-2 precursor | IPI00032405 |
| EnolasE 2 | IPI00216171 |
| Ephrin type-A receptor 4 precursor | IPI00008318 |
| Ephrin-B2 precursor | IPI00005126 |

FIG. 6D

| Protein Name | IPI Address |
|---|---|
| Epididymal secretory protein E1 precursor | IPI00301579 |
| Esophageal cancer related gene 4 protein | IPI00031769 |
| EWI2 | IPI00056478 |
| Exostosin-like 2 | IPI00002732 |
| Extracellular matrix protein 1 | IPI00006969 |
| Extracellular matrix protein 1 precursor | IPI00003351 |
| Extracellular sulfatase Sulf-2 precursor | IPI00297252 |
| Extracellular superoxide dismutase [Cu-Zn] precursor | IPI00027827 |
| Far upstream element binding protein 2 | IPI00298363 |
| F-box only protein 10 | IPI00007295 |
| Fc fragment of IgG binding protein | IPI00242956 |
| Fibrinogen beta chain precursor | IPI00298497 |
| FK506-binding protein 1A | IPI00413778 |
| FLJ00120 protein | IPI00291811 |
| FLJ00268 protein | IPI00418544 |
| FLJ00271 protein | IPI00386204 |
| FLJ00412 protein | IPI00329668 |
| FLJ35220 protein | IPI00384512 |
| Follistatin-like 4 | IPI00477747 |
| Full-length cDNA 5-PRIME end of clone CS0DM009YC13 of Fetal liver of Homo sapiens | IPI00328609 |
| Full-length cDNA clone CS0DC025YL05 of Neuroblastoma of Homo sapiens | IPI00165125 |
| Full-length cDNA clone CS0DH002YN05 of T cells | IPI00375442 |
| Full-length cDNA clone CS0DI028YM15 of Placenta of Homo sapiens | IPI00384174 |
| Full-length cDNA clone CS0DI085YI08 of Placenta of Homo sapiens | IPI00382428 |
| Full-length cDNA clone CS0DN001YP04 of Adult brain of Homo sapiens | IPI00383975 |
| Furin precursor | IPI00018387 |
| G protein coupled receptor 158 | IPI00412541 |
| Galectin-3 binding protein precursor | IPI00023673 |
| Ganglioside GM2 activator precursor | IPI00018236 |
| GARS protein | IPI00465260 |
| GBP protein isoform a | IPI00383814 |
| Gelsolin isoform b | IPI00377087 |
| Glial fibrillary acidic protein, astrocyte | IPI00025363 |
| Glucosidase II beta subunit precursor | IPI00026154 |
| Glutamate receptor 4 precursor | IPI00007632 |
| Gm133 | IPI00477944 |

FIG. 6E

| Protein Name | IPI Address |
|---|---|
| GM2 activator protein | IPI00418376 |
| Golgi autoantigen, golgin subfamily B member 1 | IPI00004671 |
| Golgi phosphoprotein 2 | IPI00171411 |
| GolGin-67 isoform c | IPI00377137 |
| Growth/differentiation factor 11 precursor | IPI00030111 |
| Growth/differentiation factor 8 precursor | IPI00023751 |
| Growth-arrest-specific protein 2 | IPI00015130 |
| Haptoglobin precursor | IPI00478493 |
| Hect domain and RLD 4 | IPI00333067 |
| Hemoglobin alpha-1 globin chain | IPI00410714 |
| Hemoglobin gamma-G | IPI00464992 |
| Hemopexin precursor | IPI00022488 |
| Heparin-binding EGF-like growth factor precursor | IPI00012948 |
| HERC2 protein | IPI00005826 |
| HGFL(S) protein | IPI00384770 |
| Histidine-rich glycoprotein precursor | IPI00022371 |
| Histone deacetylase 11 | IPI00304324 |
| HLA class I histocompatibility antigen, alpha chain H precursor | IPI00004672 |
| HLA class I histocompatibility antigen, B-27 alpha chain precursor | IPI00471986 |
| HLA class I histocompatibility antigen, B-35 alpha chain precursor | IPI00472103 |
| HLA class I histocompatibility antigen, B-54 alpha chain precursor | IPI00472282 |
| HLA class I histocompatibility antigen, B-67 alpha chain precursor | IPI00472867 |
| HLA class I histocompatibility antigen, Cw-15 alpha chain precursor | IPI00471951 |
| HLA class I histocompatibility antigen, Cw-2 alpha chain precursor | IPI00472605 |
| HLA class I histocompatibility antigen, Cw-7 alpha chain precursor | IPI00144014 |
| HLA class I histocompatibility antigen, E alpha chain precursor | IPI00010362 |
| HLA-C protein | IPI00472612 |
| Hook homolog 3 | IPI00031768 |
| HSAJ1454 | IPI00419590 |
| HU-K4 | IPI00478097 |
| Hypothetical protein | IPI00439446 |
| Hypothetical protein | IPI00026195 |
| Hypothetical protein | IPI00154742 |
| Hypothetical protein | IPI00165652 |
| Hypothetical protein | IPI00384355 |
| Hypothetical protein | IPI00385332 |
| Hypothetical protein | IPI00386158 |
| Hypothetical protein | IPI00395435 |
| Hypothetical protein | IPI00419424 |
| Hypothetical protein | IPI00430820 |

FIG. 6F

| Protein Name | IPI Address |
|---|---|
| Hypothetical protein | IPI00430839 |
| Hypothetical protein | IPI00430842 |
| Hypothetical protein | IPI00439447 |
| Hypothetical protein | IPI00440577 |
| Hypothetical protein | IPI00441043 |
| Hypothetical protein | IPI00441196 |
| Hypothetical protein | IPI00448984 |
| Hypothetical protein | IPI00448985 |
| Hypothetical protein | IPI00472610 |
| Hypothetical protein | IPI00472961 |
| Hypothetical protein | IPI00473141 |
| Hypothetical protein | IPI00083708 |
| Hypothetical protein | IPI00170503 |
| Hypothetical protein DKFZp451B1418 | IPI00401676 |
| Hypothetical protein DKFZp566O224 | IPI00383815 |
| Hypothetical protein DKFZp686B0286 | IPI00465248 |
| Hypothetical protein DKFZp686C02220 | IPI00423461 |
| Hypothetical protein DKFZp686C15213 | IPI00426051 |
| Hypothetical protein DKFZp686E04229 | IPI00426062 |
| Hypothetical protein DKFZp686I15212 | IPI00418153 |
| Hypothetical protein DKFZp686J1375 | IPI00375843 |
| Hypothetical protein DKFZp686K11107 | IPI00464973 |
| Hypothetical protein DKFZp686L19235 | IPI00426056 |
| Hypothetical protein DKFZp686P15220 | IPI00423445 |
| Hypothetical protein DKFZp761H2024 | IPI00185662 |
| Hypothetical protein DKFZp761O0610 | IPI00328584 |
| Hypothetical protein FLJ14473 | IPI00386879 |
| Hypothetical protein FLJ16025 | IPI00446856 |
| Hypothetical protein FLJ16420 | IPI00442150 |
| Hypothetical protein FLJ16490 | IPI00465099 |
| Hypothetical protein FLJ16561 | IPI00442230 |
| Hypothetical protein FLJ20421 | IPI00015834 |
| Hypothetical protein FLJ23121 | IPI00332872 |
| Hypothetical protein FLJ25359 | IPI00307317 |
| Hypothetical protein FLJ25530 | IPI00167215 |
| Hypothetical protein FLJ31726 | IPI00043516 |
| Hypothetical protein FLJ33516 | IPI00383970 |
| Hypothetical protein FLJ33620 | IPI00216853 |
| Hypothetical protein FLJ33674 | IPI00301019 |
| Hypothetical protein FLJ35588 | IPI00300564 |

FIG. 6G

| Protein Name | IPI Address |
|---|---|
| Hypothetical protein FLJ35635 | IPI00385748 |
| Hypothetical protein FLJ42206 | IPI00446339 |
| Hypothetical protein FLJ43748 | IPI00479260 |
| Hypothetical protein FLJ43983 | IPI00479279 |
| Hypothetical protein FLJ44823 | IPI00444939 |
| Hypothetical protein FLJ46033 | IPI00444172 |
| Hypothetical protein FLJ46113 | IPI00418813 |
| Hypothetical protein FLJ90018 | IPI00384073 |
| Hypothetical protein FLJ90651 | IPI00007664 |
| Hypothetical protein FLJ90761 | IPI00296168 |
| Hypothetical protein FLJ90835 | IPI00301255 |
| Hypothetical protein gs103 | IPI00290358 |
| Hypothetical protein MOT8 | IPI00001399 |
| Hypothetical protein PSEC0072 | IPI00168884 |
| Hypothetical protein PSEC0164 | IPI00301143 |
| Hypothetical protein SGCE | IPI00418183 |
| Hypothetical protein WUGSC:H_NH0436C12.1 | IPI00218107 |
| Ig heavy chain V-I region HG3 precursor | IPI00217045 |
| Ig heavy chain V-I region V35 precursor | IPI00009792 |
| Ig heavy chain V-III region CAM | IPI00382482 |
| Ig kappa chain V-I region AG | IPI00387022 |
| Ig kappa chain V-I region DEE | IPI00387025 |
| Ig kappa chain V-I region EU | IPI00387026 |
| Ig kappa chain V-I region Ni | IPI00387106 |
| Ig kappa chain V-I region OU | IPI00387098 |
| Ig kappa chain V-III region B6 | IPI00387113 |
| Ig kappa chain V-III region WOL | IPI00387118 |
| Ig lambda chain V-I region WAH | IPI00385254 |
| IGHG1 protein | IPI00448938 |
| IGHG1 protein | IPI00472762 |
| IGHG4 protein | IPI00004618 |
| IGHM protein | IPI00479708 |
| Insulin-like growth factor binding protein 2 precursor | IPI00297284 |
| Insulin-like growth factor binding protein 4 precursor | IPI00305380 |
| Insulin-like growth factor binding protein 5 precursor | IPI00029236 |
| Insulin-like growth factor binding protein 6 precursor | IPI00029235 |
| Insulin-like growth factor binding protein 7 precursor | IPI00016915 |
| Insulin-like growth factor binding protein complex acid labile chain precursor | IPI00020996 |
| Integral membrane protein 2B | IPI00477987 |
| Inter-alpha-trypsin inhibitor heavy chain H1 precursor | IPI00292530 |

FIG. 6H

| Protein Name | IPI Address |
|---|---|
| ISLR precursor | IPI00023648 |
| JAW1-related protein MRVI1B short isoform | IPI00375596 |
| Kallikrein 6 precursor | IPI00023845 |
| Kappa 1 light chain variable region | IPI00382577 |
| Keratin 1 | IPI00220327 |
| Keratin 10 | IPI00295684 |
| Keratin 10 | IPI00383111 |
| Keratin 16 | IPI00217963 |
| Keratin 1b | IPI00376379 |
| Keratin 6 irs4 | IPI00479579 |
| Keratin 6C | IPI00479403 |
| Keratin 6L | IPI00241841 |
| Keratin 7 | IPI00306959 |
| Keratin 9 | IPI00019359 |
| Keratin, type I cytoskeletal 10 | IPI00009865 |
| Keratin, type II cuticular HB1 | IPI00182654 |
| Keratin, type II cuticular HB4 | IPI00300052 |
| Keratin, type II cytoskeletal 2 epidermal | IPI00021304 |
| Keratin, type II cytoskeletal 3 | IPI00290857 |
| Keratin, type II cytoskeletal 4 | IPI00290078 |
| Keratin, type II cytoskeletal 5 | IPI00009867 |
| Keratin, type II cytoskeletal 6D | IPI00386438 |
| Keratin, type II cytoskeletal 6F | IPI00296350 |
| KIAA0170 protein | IPI00291929 |
| KIAA0284 protein | IPI00180625 |
| KIAA0319 protein | IPI00006524 |
| KIAA0387 protein | IPI00024289 |
| KIAA0523 protein | IPI00305349 |
| KIAA0584 protein | IPI00413264 |
| KIAA0644 protein | IPI00006556 |
| KIAA0661 protein | IPI00162563 |
| KIAA0792 protein | IPI00006006 |
| KIAA1009 protein | IPI00007122 |
| KIAA1061 protein | IPI00298956 |
| KIAA1291 protein | IPI00413206 |
| KIAA1318 protein | IPI00002353 |
| KIAA1373 protein | IPI00002208 |
| KIAA1417 protein | IPI00165979 |
| KIAA1458 protein | IPI00020601 |
| KIAA1503 protein | IPI00292777 |

FIG. 61

| Protein Name | IPI Address |
|---|---|
| KIAA1529 protein | IPI00292836 |
| KIAA1838 protein | IPI00335946 |
| KIAA1877 protein | IPI00064125 |
| KIAA1922 protein | IPI00044709 |
| KRT17 protein | IPI00450768 |
| KRT8 protein | IPI00418411 |
| Kunitz-type protease inhibitor 2 precursor | IPI00011662 |
| Lactate dehydrogenase B | IPI00219217 |
| Latent TGF-beta binding protein-4 | IPI00020665 |
| Latent transforming growth factor beta binding protein 2 | IPI00465145 |
| Latent transforming growth factor-beta binding protein 4 | IPI00395783 |
| Latent transforming growth factor-beta-binding protein 2 precursor | IPI00292150 |
| Leishmanolysin-like peptidase, variant 2 | IPI00064742 |
| Leucine zipper protein 1 | IPI00395737 |
| Leucine-rich alpha-2-glycoprotein precursor | IPI00022417 |
| L-FILIP | IPI00297210 |
| Limbic system-associated membrane protein precursor | IPI00013303 |
| LIR-D1 | IPI00186736 |
| LISCH protein isoform 1 | IPI00329124 |
| LISCH protein, isoform 2 | IPI00409640 |
| LOC123872 protein | IPI00065458 |
| Lumican precursor | IPI00020986 |
| Ly-6/neurotoxin-like protein 1 precursor | IPI00289058 |
| Lymphocyte antigen Ly-6H precursor | IPI00014964 |
| Lysosomal alpha-glucosidase precursor | IPI00293088 |
| Lysozyme C precursor | IPI00019038 |
| Mannosyl-oligosaccharide 1,2-alpha-mannosidase IA | IPI00291641 |
| MANSC domain containing protein 1 precursor | IPI00032288 |
| Matrix Gla-protein precursor | IPI00028714 |
| Metalloproteinase inhibitor 2 precursor | IPI00027166 |
| MHC class I antigen precursor | IPI00478438 |
| MIC2L1 isoform E3'-E4'-E3-E4 | IPI00152491 |
| Mimecan precursor | IPI00025465 |
| MOG protein | IPI00333125 |
| Monocyte differentiation antigen CD14 precursor | IPI00029260 |
| Multiple coagulation factor deficiency protein 2 precursor | IPI00328680 |
| Multiple EGF-like-domain protein 4 | IPI00027310 |
| Multiple PDZ domain protein | IPI00163612 |
| Myelin-associated glycoprotein precursor | IPI00026237 |
| Myosin-reactive immunoglobulin heavy chain variable region | IPI00007893 |
| Myosin-reactive immunoglobulin heavy chain variable region | IPI00384391 |

FIG. 6J

| Protein Name | IPI Address |
|---|---|
| Myosin-reactive immunoglobulin heavy chain variable region | IPI00384392 |
| Myosin-reactive immunoglobulin heavy chain variable region | IPI00384400 |
| Myosin-reactive immunoglobulin heavy chain variable region | IPI00384404 |
| Myosin-reactive immunoglobulin heavy chain variable region | IPI00384406 |
| Myosin-reactive immunoglobulin heavy chain variable region | IPI00456637 |
| Myosin-reactive immunoglobulin light chain variable region | IPI00384398 |
| Myristoylated alanine-rich protein kinase C substrate | IPI00219301 |
| N-acetylgalactosamine-4-O-sulfotransferase | IPI00300838 |
| N-acetyllactosaminide beta-1,3-N-acetylglucosaminyltransferase | IPI00009997 |
| NACHT-, LRR- and PYD-containing protein 7 | IPI00103487 |
| Natural killer cell-specific antigen KLIP1 | IPI00329688 |
| Nebulin | IPI00303335 |
| Nebulin | IPI00418175 |
| Neural cell adhesion molecule | IPI00299059 |
| Neural cell adhesion molecule 1, 140 kDa isoform precursor | IPI00435020 |
| Neural cell adhesion molecule 2 | IPI00478109 |
| Neural-cadherin precursor | IPI00290085 |
| Neurexin 1-alpha precursor | IPI00442299 |
| Neurexophilin 1 precursor | IPI00048230 |
| Neurexophilin 4 | IPI00376343 |
| Neuroblastoma suppressor of tumorigenicity 1 precursor | IPI00013299 |
| Neuroblastoma-amplified protein | IPI00333913 |
| Neurocan core protein precursor | IPI00159927 |
| Neuroendocrine convertase 1 precursor | IPI00301961 |
| Neurofascin isoform 2 | IPI00477942 |
| Neurofilament triplet H protein | IPI00021751 |
| Neuroligin 2 precursor | IPI00176424 |
| Neuron navigator 1 | IPI00478767 |
| Neuron specific protein family member 1 | IPI00002334 |
| Neuronal pentraxin I precursor | IPI00220562 |
| Neuronal pentraxin receptor | IPI00031289 |
| Neuronal pentraxin receptor isoform 1 | IPI00334238 |
| Neuronal potassium channel alpha subunit | IPI00164159 |
| Neuropeptide Y precursor | IPI00001506 |
| Neurosecretory protein VGF precursor | IPI00289501 |
| Nidogen-2 precursor | IPI00028908 |
| Nociceptin precursor | IPI00013701 |
| Nogo receptor-like 3 | IPI00328746 |
| Notch homolog 2 | IPI00480098 |
| NOV protein homolog precursor | IPI00011140 |

FIG. 6K

| Protein Name | IPI Address |
|---|---|
| Novel protein | IPI00292567 |
| Novel protein | IPI00412286 |
| Novel protein | IPI00440580 |
| Novex-3 Titin Isoform | IPI00397522 |
| Nucleobindin 1 precursor | IPI00295542 |
| Obscurin | IPI00100715 |
| P15 protein | IPI00011301 |
| P15 protein | IPI00385559 |
| P60 | IPI00179473 |
| Paraoxonase 1 | IPI00218732 |
| Parvalbumin | IPI00219703 |
| PBP family protein precursor | IPI00163563 |
| PePtidylglycine alPha-amidating monooxygenase isoform a, PreProProtein | IPI00177543 |
| Pericentrin 2 | IPI00412869 |
| Periplakin | IPI00298057 |
| PF6 | IPI00174345 |
| Phosphatidylcholine-sterol acyltransferase precursor | IPI00022331 |
| Phosphatidylinositol 3-kinase-related protein kinase | IPI00395672 |
| Pigment epithelium-derived factor precursor | IPI00006114 |
| Plasma glutathione peroxidase precursor | IPI00026199 |
| Plasma protease C1 inhibitor precursor | IPI00291866 |
| Plasma retinol-binding protein precursor | IPI00022420 |
| Plasma serine protease inhibitor precursor | IPI00007221 |
| Plasminogen precursor | IPI00019580 |
| Platelet-derived growth factor beta isoform 2, PreProProtein | IPI00334195 |
| Plectin 10 | IPI00398778 |
| Plectin 2 | IPI00398775 |
| Plectin 3 | IPI00420096 |
| Plectin 6 | IPI00186711 |
| Plectin 8 | IPI00398777 |
| PLXDC2 protein | IPI00073777 |
| Potassium/sodium hyperpolarization-activated cyclic nucleotide-gated channel 1 | IPI00031506 |
| Potassium/sodium hyperpolarization-activated cyclic nucleotide-gated channel 3 | IPI00163724 |
| Potassium/sodium hyperpolarization-activated cyclic nucleotide-gated channel 4 | IPI00023164 |
| PREDICTED: dynein, cytoplasmic, heavy polypeptide 2 | IPI00171494 |
| PREDICTED: FLJ46675 protein | IPI00165319 |
| PREDICTED: G2 protein | IPI00176482 |

FIG. 6L

| Protein Name | IPI Address |
|---|---|
| PREDICTED: hemicentin-2 | IPI00335009 |
| PREDICTED: hypothetical protein FLJ13305 | IPI00175083 |
| PREDICTED: hypothetical protein XP_291007 | IPI00216817 |
| PREDICTED: hypothetical protein XP_373647 | IPI00374504 |
| PREDICTED: hypothetical protein XP_373957 | IPI00398676 |
| PREDICTED: hypothetical protein XP_375869 | IPI00456680 |
| PREDICTED: hypothetical protein XP_498788 | IPI00456355 |
| PREDICTED: KIAA1076 protein | IPI00165459 |
| PREDICTED: KIAA1836 protein | IPI00306483 |
| PREDICTED: leucine rich repeat containing 4B | IPI00300241 |
| PREDICTED: lunatic fringe homolog | IPI00455739 |
| PREDICTED: MAX dimerization protein 5 | IPI00163866 |
| PREDICTED: similar to ataxin-1 ubiquitin-like interacting protein | IPI00175126 |
| PREDICTED: similar to bA92K2.2 (similar to ubiquitin) | IPI00397808 |
| PREDICTED: similar to Beta-1,3-N-acetylglucosaminyltransferase lunatic fringe (O-fucosy | IPI00454960 |
| PREDICTED: similar to Centromeric protein E (CENP-E protein) | IPI00063523 |
| PREDICTED: similar to contains transmembrane (TM) region | IPI00247243 |
| PREDICTED: similar to FKSG30 | IPI00455552 |
| PREDICTED: similar to hypothetical protein | IPI00166622 |
| PREDICTED: similar to Keratin, type I cytoskeletal 18 (Cytokeratin 18) (K18) (CK 18) | IPI00455689 |
| PREDICTED: similar to KIAA1501 protein | IPI00399193 |
| PREDICTED: similar to KIAA1501 protein | IPI00455296 |
| PREDICTED: similar to KIAA1693 protein | IPI00455450 |
| PREDICTED: similar to Phosphatidylethanolamine-binding protein (PEBP) (Prostatic bindin | IPI00454722 |
| PREDICTED: similar to POTE2A | IPI00455547 |
| PREDICTED: similar to pregnancy specific beta-1-glycoprotein 7 | IPI00455395 |
| PREDICTED: similar to ribosomal protein L7 | IPI00018680 |
| PREDICTED: similar to ribosomal protein L7 | IPI00457083 |
| PREDICTED: similar to ribosomal protein S27a | IPI00398132 |
| PREDICTED: similar to RIKEN cDNA 4732495G21 gene | IPI00003269 |
| PREDICTED: similar to RIKEN cDNA 4930583C14 | IPI00232276 |
| PREDICTED: similar to tripartite motif-containing 43 | IPI00455440 |
| PREDICTED: similar to Zgc:66168 protein | IPI00296120 |
| Prepro-alpha2(I) collagen precursor | IPI00164755 |
| Preprotachykinin B | IPI00385187 |
| Prion protein | IPI00382843 |
| Probable endonuclease KIAA0830 precursor | IPI00001952 |
| Probable G protein-coupled receptor 37 precursor | IPI00006166 |

FIG. 6M

| Protein Name | IPI Address |
|---|---|
| Procollagen C-proteinase enhancer protein precursor | IPI00299738 |
| Proenkephalin A precursor | IPI00000828 |
| Proline-rich acidic protein | IPI00465255 |
| ProSAAS precursor | IPI00002280 |
| Prostaglandin-H2 D-isomerase precursor | IPI00013179 |
| Protease, serine, 3 | IPI00220839 |
| Protein FAM3C precursor | IPI00021923 |
| Protein KIAA0494 | IPI00006130 |
| Protein kinase C-binding protein NELL2 precursor | IPI00015260 |
| Protein phosphatase 3 | IPI00413731 |
| Protein tyrosine Phosphatase, non-receptor type substrate 1 Precursor | IPI00332887 |
| Protein tyrosine Phosphatase, receptor type, D isoform 2 Precursor | IPI00375547 |
| Protein tyrosine Phosphatase, receptor type, D isoform 3 Precursor | IPI00375548 |
| Protein tyrosine Phosphatase, receptor type, N Polypeptide 2 isoform 2 Precursor | IPI00472249 |
| Protein tyrosine Phosphatase, receptor type, sigma isoform 3 Precursor | IPI00293275 |
| Prothrombin precursor | IPI00019568 |
| PRRG1 protein | IPI00000459 |
| PTPRN2 protein | IPI00450961 |
| Pyruvate kinase 3 isoform 2 | IPI00220644 |
| Quiescin | IPI00003590 |
| Ran binding protein 2 | IPI00472789 |
| Ran-binding protein 2 | IPI00221325 |
| Ras GTPase-activating protein 2 | IPI00015811 |
| Ras GTPase-activating-like protein IQGAP1 | IPI00009342 |
| Receptor-type tyrosine-protein phosphatase gamma precursor | IPI00011651 |
| Receptor-type tyrosine-protein phosphatase-like N precursor | IPI00004440 |
| Reticulocalbin 2 precursor | IPI00029628 |
| Reticulon 4, isoform D | IPI00335276 |
| Retinoblastoma-associated factor 600 | IPI00180305 |
| Retinol binding protein 4, plasma | IPI00479848 |
| Retinol binding protein 4, plasma | IPI00480192 |
| Rho-associated protein kinase 1 | IPI00022542 |
| RTN3-A1 | IPI00398795 |
| RUN and TBC1 domain containing 3 | IPI00236852 |
| SARG904 | IPI00432405 |
| Scotin | IPI00166039 |
| Scrapie-responsive protein 1 precursor | IPI00026800 |

FIG. 6N

| Protein Name | IPI Address |
|---|---|
| Secreted phoSphoprotein 1 (osteopontin, bone sialoprotein I, early T-lymphocyte activat | IPI00306339 |
| Secretogranin I precursor | IPI00006601 |
| Secretogranin II precursor | IPI00009362 |
| Secretogranin III precursor | IPI00292071 |
| Selenium binding protein 1 | IPI00305719 |
| Selenium-binding protein 1 | IPI00012303 |
| Selenoprotein M precursor | IPI00103471 |
| Semaphorin 7A precursor | IPI00025257 |
| Semaphorin sem2 | IPI00024570 |
| Serine protease inhibitor Kazal-type 5 precursor | IPI00478816 |
| Serine/threonine protein phosphatase 2B catalytic subunit, alpha isoform | IPI00179415 |
| Serine/threonine-protein kinase PLK2 | IPI00302787 |
| Serotransferrin precursor | IPI00022463 |
| SERPINC1 protein | IPI00165421 |
| SERPIND1 protein | IPI00292950 |
| Serum albumin precursor | IPI00022434 |
| Serum amyloid A-4 protein precursor | IPI00019399 |
| Seven transmembrane helix receptor | IPI00297188 |
| SH3 and multiple ankyrin repeat domains 2 isoform 1 | IPI00220490 |
| Similar to peptide N-glycanase homolog | IPI00165496 |
| SIN3B long isoform | IPI00464980 |
| Single chain Fv | IPI00007899 |
| Single-chain Fv | IPI00470653 |
| SNC73 protein | IPI00478462 |
| Sodium channel beta-3 subunit precursor | IPI00020747 |
| Somatostatin precursor | IPI00000130 |
| Sortilin 1, preproprotein | IPI00383591 |
| Sortilin-related receptor precursor | IPI00022608 |
| SPARC precursor | IPI00014572 |
| SPARC-like 1 | IPI00384293 |
| SPARC-like protein 1 precursor | IPI00296777 |
| Spectrin beta chain, brain 4 | IPI00219168 |
| Splice Isoform 1 Of 85 kDa calcium-independent phospholipase A2 | IPI00031476 |
| Splice Isoform 1 Of Acyl-CoA-binding protein | IPI00010182 |
| Splice Isoform 1 Of Amyloid beta A4 protein precursor | IPI00006608 |
| Splice Isoform 1 Of Amyloid-like protein 2 precursor | IPI00031030 |
| Splice Isoform 1 Of Astrotactin 1 | IPI00022367 |
| Splice Isoform 1 Of Basigin precursor | IPI00218019 |
| Splice Isoform 1 Of Brevican core protein precursor | IPI00456623 |

FIG. 60

| Protein Name | IPI Address |
|---|---|
| Splice Isoform 1 Of Calcyclin-binding protein | IPI00395627 |
| Splice Isoform 1 Of Cannabinoid receptor 1 | IPI00009396 |
| Splice Isoform 1 Of Cartilage acidic protein 1 precursor | IPI00451624 |
| Splice Isoform 1 Of CD44 antigen precursor | IPI00305064 |
| Splice Isoform 1 Of Complement factor B precursor | IPI00019591 |
| Splice Isoform 1 Of Complement factor H precursor | IPI00029739 |
| Splice Isoform 1 Of Connective tissue growth factor precursor | IPI00020977 |
| Splice Isoform 1 Of Contactin 1 precursor | IPI00029751 |
| Splice Isoform 1 Of EGF-containing fibulin-like extracellular matrix protein 1 precursor | IPI00029658 |
| Splice Isoform 1 Of Engulfment and cell motility protein 1 | IPI00219532 |
| Splice Isoform 1 Of Fibrinogen alpha/alpha-E chain precursor | IPI00021885 |
| Splice Isoform 1 Of Fibrinogen gamma chain precursor | IPI00021891 |
| Splice Isoform 1 Of Fibronectin precursor | IPI00022418 |
| Splice Isoform 1 Of Fibulin-1 precursor | IPI00296534 |
| Splice Isoform 1 Of GDNF family receptor alpha 2 precursor | IPI00011732 |
| Splice Isoform 1 Of HLA class I histocompatibility antigen, Cw-16 alpha chain precursor | IPI00472711 |
| Splice Isoform 1 Of Insulin-like growth factor II precursor | IPI00001611 |
| Splice Isoform 1 Of Inter-alpha-trypsin inhibitor heavy chain H4 precursor | IPI00294193 |
| Splice Isoform 1 Of Latrophilin 1 precursor | IPI00183445 |
| Splice Isoform 1 Of Lysosome-associated membrane glycoprotein 2 precursor | IPI00009030 |
| Splice Isoform 1 Of Macrophage colony stimulating factor-1 precursor | IPI00015881 |
| Splice Isoform 1 Of Matrix metalloproteinase-17 precursor | IPI00008533 |
| Splice Isoform 1 Of Neural cell adhesion molecule 1, 120 kDa isoform precursor | IPI00411478 |
| Splice Isoform 1 Of Neurexin 2-alpha precursor | IPI00007921 |
| Splice Isoform 1 Of Neuroendocrine protein 7B2 precursor | IPI00008944 |
| Splice Isoform 1 Of Pantothenate kinase 2, mitochondrial precursor | IPI00171176 |
| Splice Isoform 1 Of Phosphatidylinositol 3,4,5-trisphosphatedependent Rac exchanger 1 | IPI00295252 |
| Splice Isoform 1 Of Phospholipid transfer protein precursor | IPI00022733 |
| Splice Isoform 1 Of Platelet-derived growth factor, A chain precursor | IPI00021833 |
| Splice Isoform 1 Of Plectin 1 | IPI00014898 |
| Splice Isoform 1 Of Proactivator polypeptide precursor | IPI00012503 |
| Splice Isoform 1 Of Receptor-type tyrosine-protein phosphatase N2 precursor | IPI00334666 |

FIG. 6P

| Protein Name | IPI Address |
|---|---|
| Splice Isoform 1 Of Receptor-type tyrosine-protein phosphatase zeta precursor | IPI00291099 |
| Splice Isoform 1 Of Reticulon 1 | IPI00003971 |
| Splice Isoform 1 Of Reticulon 4 | IPI00021766 |
| Splice Isoform 1 Of Serine/threonine-protein kinase Haspin | IPI00397836 |
| Splice Isoform 1 Of Serologically defined colon cancer antigen 1 | IPI00301618 |
| Splice Isoform 1 Of Stromal cell-derived factor 1 precursor | IPI00413781 |
| Splice Isoform 1 Of SWI/SNF-related, matrix associated, actin-dependent regulator of ch | IPI00220119 |
| Splice Isoform 1 Of Testican-3 precursor | IPI00478890 |
| Splice Isoform 2 Of Acyl-CoA-binding protein | IPI00218836 |
| Splice Isoform 2 Of Alpha-mannosidase IIx | IPI00220303 |
| Splice Isoform 2 Of Amyloid-like protein 2 precursor | IPI00220977 |
| Splice Isoform 2 Of Apoptotic protease activating factor 1 | IPI00217460 |
| Splice Isoform 2 Of Collagen alpha 1(XVIII) chain precursor | IPI00414694 |
| Splice Isoform 2 Of Connective tissue growth factor precursor | IPI00220647 |
| Splice Isoform 2 Of Contactin 1 precursor | IPI00216641 |
| Splice Isoform 2 Of Ectonucleotide pyrophosphatase/phosphodiesterase 2 | IPI00303210 |
| Splice Isoform 2 Of Far upstream element binding protein 1 | IPI00163782 |
| Splice Isoform 2 Of Fibrinogen alpha/alpha-E chain precursor | IPI00029717 |
| Splice Isoform 2 Of HIV-1 Rev binding protein-like protein | IPI00418239 |
| Splice Isoform 2 Of HpaII tiny fragments locus 9c protein | IPI00472176 |
| Splice Isoform 2 Of Insulin-like growth factor II precursor | IPI00215977 |
| Splice Isoform 2 Of Kininogen precursor | IPI00215894 |
| Splice Isoform 2 Of Latrophilin 1 precursor | IPI00410210 |
| Splice Isoform 2 Of Neural cell adhesion molecule L1 precursor | IPI00334532 |
| Splice Isoform 2 Of Neuroendocrine protein 7B2 precursor | IPI00470716 |
| Splice Isoform 2 Of Neuroligin 3 precursor | IPI00184861 |
| Splice Isoform 2 Of Neuronal cell adhesion molecule precursor | IPI00333777 |
| Splice Isoform 2 Of Osteopontin precursor | IPI00218874 |
| Splice Isoform 2 Of Platelet-derived growth factor, A chain precursor | IPI00220454 |
| Splice Isoform 2 Of Proactivator polypeptide precursor | IPI00219824 |
| Splice Isoform 2 Of Receptor-type tyrosine-protein phosphatase N2 precursor | IPI00334667 |
| Splice Isoform 2 Of Sex hormone-binding globulin precursor | IPI00219583 |
| Splice Isoform 2 Of Signal-regulatory protein beta-2 precursor | IPI00218600 |
| Splice Isoform 2 Of SPARC related modular calcium-binding protein 1 precursor | IPI00412898 |
| Splice Isoform 3 Of A-kinase anchor protein 9 | IPI00220625 |
| Splice Isoform 3 Of Amyloid beta A4 protein precursor | IPI00219183 |

FIG. 6Q

| Protein Name | IPI Address |
| --- | --- |
| Splice Isoform 3 Of Amyloid-like protein 2 precursor | IPI00220978 |
| Splice Isoform 3 Of Bullous pemphigoid antigen 1, isoforms 6/9/10 | IPI00473119 |
| Splice Isoform 3 Of EGF-containing fibulin-like extracellular matrix protein 1 precursor | IPI00220814 |
| Splice Isoform 3 Of Integrin alpha-7 precursor | IPI00220749 |
| Splice Isoform 3 Of Myelin-oligodendrocyte glycoprotein precursor | IPI00398722 |
| Splice Isoform 3 Of Neuronal cell adhesion molecule precursor | IPI00333778 |
| Splice Isoform 3 Of Neurotrimin precursor | IPI00442298 |
| Splice Isoform 3 Of Peptidyl-glycine alpha-amidating monooxygenase precursor | IPI00219042 |
| Splice Isoform 3 Of Proactivator polypeptide precursor | IPI00219825 |
| Splice Isoform 3 Of Receptor-type tyrosine-protein phosphatase S precursor | IPI00332272 |
| Splice Isoform 3 Of SH3 and multiple ankyrin repeat domains protein 1 | IPI00220165 |
| Splice Isoform 3 Of WAP four-disulfide core domain protein 2 precursor | IPI00183629 |
| Splice Isoform 4 Of EGF-containing fibulin-like extracellular matrix protein 1 precursor | IPI00220815 |
| Splice Isoform 4 Of Fibulin-1 precursor | IPI00296537 |
| Splice Isoform 4 Of Integrin beta-1 precursor | IPI00217562 |
| Splice Isoform 4 Of Nesprin 1 | IPI00247295 |
| Splice Isoform 4 Of Nuclear autoantigen Sp-100 | IPI00218326 |
| Splice Isoform 4 Of Osteopontin precursor | IPI00385896 |
| Splice Isoform 4 Of Seizure 6-like protein precursor | IPI00220334 |
| Splice Isoform 5 Of Amyloid beta A4 protein precursor | IPI00219185 |
| Splice Isoform 6 Of Amyloid beta A4 protein precursor | IPI00219186 |
| Splice Isoform 7 Of Amyloid beta A4 protein precursor | IPI00219187 |
| Splice Isoform 7 Of Myelin-oligodendrocyte glycoprotein precursor | IPI00376382 |
| Splice Isoform 8 Of Amyloid beta A4 protein precursor | IPI00412924 |
| Splice Isoform 8 Of Myelin-oligodendrocyte glycoprotein precursor | IPI00473134 |
| Splice Isoform 9 Of Amyloid beta A4 protein precursor | IPI00412681 |
| Spondin 1 precursor | IPI00171473 |
| SPUF protein precursor | IPI00002525 |
| Sulfatase 2 isoform b precursor | IPI00384856 |
| Superoxide dismutase 1, Soluble | IPI00218733 |
| Synaptotagmin-11 | IPI00027875 |
| TA p63 alpha | IPI00301360 |
| TBC1 domain family member 10 | IPI00011167 |
| T-cell activation Rho GTPase activating protein | IPI00166033 |
| Tenascin-R | IPI00160552 |

FIG. 6R

| Protein Name | IPI Address |
| --- | --- |
| Testican-1 precursor | IPI00005292 |
| Testican-2 precursor | IPI00006128 |
| Tetranectin precursor | IPI00009028 |
| Tetratricopeptide repeat protein 14 | IPI00043402 |
| Thioredoxin | IPI00216298 |
| Threonine aspartase 1 | IPI00302837 |
| Thy-1 membrane glycoprotein precursor | IPI00022892 |
| Thymosin, beta 10 | IPI00220827 |
| Thymosin, beta 4 | IPI00220828 |
| Thymosin, beta 4, Y chromosome | IPI00219803 |
| Thymosin-like 3 | IPI00180240 |
| Thyroxine-binding globulin precursor | IPI00292946 |
| Titin | IPI00179357 |
| Titin isoform novex-1 | IPI00375498 |
| Titin, heart isoform N2-B | IPI00455173 |
| Toll-like receptor 7 precursor | IPI00009812 |
| Transforming growth factor-beta induced protein IG-H3 precursor | IPI00018219 |
| Transient receptor potential cation channel subfamily M member 7 | IPI00290032 |
| Transthyretin precursor | IPI00022432 |
| Tripartite motif protein 26 | IPI00010948 |
| Type I inner root sheath specific keratin 25 irs3 | IPI00328103 |
| Type XV collagen | IPI00477770 |
| Ubiquitin 4 | IPI00024502 |
| Ubiquitin and ribosomal protein L40 precUrsor | IPI00456429 |
| Ubiquitin and ribosomal protein S27a precUrsor | IPI00179330 |
| Usher syndrome 1C binding protein 1 | IPI00297559 |
| Uveal autoantigen | IPI00173359 |
| Vacuolar ATP synthase subunit S1 precursor | IPI00020430 |
| VGFG2573 | IPI00383014 |
| VH3 protein | IPI00383732 |
| Villin 1 | IPI00218852 |
| Vitamin D-binding protein precursor | IPI00298853 |
| Vitamin K-dependent protein S precursor | IPI00294004 |
| Vitronectin precursor | IPI00298971 |
| VPS10 domain-containing receptor SorCS2 precursor | IPI00044600 |
| VPS10 domain-containing receptor SorCS3 precursor | IPI00010381 |
| WAP four-disulfide core domain protein 1 precursor | IPI00008997 |
| Werner helicase interacting protein | IPI00290314 |
| WUGSC:DJ515N1.2 protein | IPI00298388 |
| WUGSC:H_DJ0747G18.3 protein | IPI00069058 |
| WW domain containing adaptor with coiled-coil | IPI00478665 |

FIG. 6S

| Protein Name | IPI Address |
|---|---|
| WW domain-containing adapter with a coiled-coil region, isoform 1 | IPI00010241 |
| Xylosyltransferase I | IPI00183487 |
| Zona pellucida sperm-binding protein 2 precursor | PIP00016870 |

FIG. 6T

| Protein Name | IPI Address |
|---|---|
| 101 kDa protein | IPI00478742 |
| 101 kDa protein | IPI00291316 |
| 11 kDa protein | IPI00382841 |
| 110 kDa protein | IPI00473056 |
| 130 kD Golgi-localized phosphoprotein | IPI00004962 |
| 14 kDa protein | IPI00478089 |
| 141 kDa protein | IPI00478948 |
| 15 kDa protein | IPI00413031 |
| 15 kDa protein | IPI00413387 |
| 25 kDa protein | IPI00412608 |
| 25 kDa protein | IPI00477989 |
| 28S ribosomal protein S18c, mitochondrial precursor | IPI00007049 |
| 344 kDa protein | IPI00479834 |
| 376 kDa protein | IPI00479143 |
| 39 kDa protein | IPI00070070 |
| 39 kDa protein | IPI00479497 |
| 47 kDa protein | IPI00479602 |
| 48 kDa protein | IPI00414747 |
| 65 kDa protein | IPI00414018 |
| 66 kDa protein | IPI00479085 |
| 67 kDa protein | IPI00332849 |
| 71 kDa protein | IPI00477128 |
| 73 kDa protein | IPI00412783 |
| 82 kDa protein | IPI00478238 |
| 84 kDa protein | IPI00412853 |
| 90 kDa protein | IPI00478692 |
| 97 kDa protein | IPI00472544 |
| 99 kDa protein | IPI00414260 |
| ABC transporter ABCA7 | IPI00293895 |
| Acetoacetyl-CoA synthetase | IPI00217272 |
| ACSL6 protein | IPI00384110 |
| Actin, alpha cardiac | IPI00023006 |
| Actin, aortic smooth muscle | IPI00008603 |
| Activating receptor PILRbeta | IPI00186781 |
| ADAM 10 precursor | IPI00013897 |
| ADAMTS-1 precursor | IPI00005908 |
| Adapter-related protein complex 1 gamma 1 subunit | IPI00479353 |
| Adipsin/complement factor D precursor | IPI00165972 |
| Adlican | IPI00012347 |
| ADM precursor | IPI00017968 |
| A-gamma globin | IPI00220706 |

FIG. 7A

| Protein Name | IPI Address |
|---|---|
| Agrin precursor | IPI00374563 |
| ALMS1 protein | IPI00178743 |
| AlphA 1 type XIII collAgen isoform 3 | IPI00375409 |
| AlphA 3 type VI collAgen isoform 4 precursor | IPI00072918 |
| Alpha tachykinin 3 variant 2 | IPI00431183 |
| Alpha-1,3-mannosyl-glycoprotein 2-beta-Nacetylglucosaminyltransferase | IPI00000138 |
| Alpha-1-acid glycoprotein 1 precursor | IPI00022429 |
| Alpha-fetoprotein precursor | IPI00022443 |
| Alpha-ketoglutarate dehydrogenase complex dihydrolipoyl succinyltransferase | IPI00033034 |
| Alu subfamily SQ sequence contamination warning entry | IPI00023543 |
| Aminomethyltransferase, mitochondrial precursor | IPI00299300 |
| Angiopoietin-related protein 2 precursor | IPI00007800 |
| Angiotensin I converting enzyme, isoform 3 | IPI00178017 |
| Ankyrin repeat and SOCS box protein 2 | IPI00216028 |
| Ankyrin repeat domain protein 9 | IPI00073421 |
| Antigen MLAA-20 | IPI00447178 |
| APG7L protein | IPI00479911 |
| Apolipoprotein B-100 precursor | IPI00022229 |
| Apolipoprotein F precursor | IPI00480119 |
| ARHGAP8 protein | IPI00472223 |
| AspArtAte AminotrAnsferAse 1 | IPI00219029 |
| ATP-binding cassette, sub-family A (ABC1), member 1 | IPI00477917 |
| ATP-binding cassette, sub-family A, member 1 | IPI00293460 |
| ATP-dependent RNA helicase DDX24 | IPI00006987 |
| AtriAl/embryonic AlkAli myosin light chAin | IPI00384992 |
| Autosomal highly conserved protein | IPI00008285 |
| AXL receptor tyrosine kinase, isoform 1 | IPI00296992 |
| BA231F10.1 | IPI00472399 |
| Bactericidal/permeability-increasing protein-like 3 precursor | IPI00414328 |
| Beta-1,4 N-acetylgalactosaminyltransferase | IPI00025473 |
| Beta-hexosaminidase alpha chain precursor | IPI00027851 |
| Beta-neoendorphin-dynorphin precursor | IPI00000832 |
| BMP and activin membrane-bound inhibitor homolog precursor | IPI00011899 |
| Bone morphogenetic protein 15 precursor | IPI00001485 |
| Bone specific CMF608 | IPI00183913 |
| Brain protein | IPI00292304 |
| Brain-derived neurotrophic factor precursor | IPI00012058 |
| Brain-specific angiogenesis inhibitor 1 precursor | IPI00022333 |
| Brain-specific angiogenesis inhibitor 3 precursor | IPI00028448 |

FIG. 7B

| Protein Name | IPI Address |
|---|---|
| Bromodomain protein CELTIX1 | IPI00001707 |
| Bullous pemphigoid antigen 1 isoform 1 | IPI00074148 |
| Bullous pemphigoid antigen 1 isoform 1eB precursor | IPI00142768 |
| C17orf28 protein | IPI00247634 |
| C1D protein | IPI00007322 |
| C1orf40 protein | IPI00304374 |
| C21orf258 protein | IPI00374082 |
| C9orf86 protein | IPI00186586 |
| Cadherin 11, type 2, isoform 1 preproprotein | IPI00386476 |
| Cadherin-22 precursor | IPI00000436 |
| Calcitonin gene-related peptide I precursor | IPI00027855 |
| CalCium binding protein Cab45 preCursor | IPI00009794 |
| Calcium/calmodulin-dependent protein kinase II delta, isoform 1 | IPI00172636 |
| Calmin | IPI00101942 |
| Calmodulin 2 | IPI00411575 |
| Calreticulin precursor | IPI00020599 |
| Calsyntenin-3 precursor | IPI00396423 |
| CANT1 protein | IPI00103175 |
| Cappuccino protein homolog | IPI00020002 |
| Cathepsin F precursor | IPI00002816 |
| Cathepsin L precursor | IPI00012887 |
| Cathepsin S precursor | IPI00299150 |
| CatSper4 | IPI00398709 |
| Cell recognition protein CASPR4 | IPI00216250 |
| Cell surface glycoprotein MUC18 precursor | IPI00016334 |
| Centrosome protein Cep63 | IPI00060568 |
| Centrosome-associated protein 350 | IPI00103595 |
| Cerebellin 3 precursor | IPI00402157 |
| Chemokine (C-X-C motif) ligand 16 | IPI00004946 |
| Chondroitin sulfate proteoglycan 5-III | IPI00434467 |
| Chromosome 10 open reading frame 88 | IPI00296845 |
| Chromosome 6 open reading frame 152 | IPI00334013 |
| Chromosome 9 open reading frame 140 | IPI00328702 |
| Chronic myelogenous leukemia tumor antigen 66 | IPI00306398 |
| Coagulation factor X precursor | IPI00019576 |
| Coagulation factor XII precursor | IPI00019581 |
| Cohesin subunit SA-1 | IPI00025158 |
| Coiled-coil domain containing protein 9 | IPI00177642 |
| Collagen alpha 1 | IPI00019090 |
| Collagen alpha 1(III) chain precursor | IPI00021033 |

FIG. 7C

| Protein Name | IPI Address |
|---|---|
| Collagen alpha 1(XV) chain precursor | IPI00295414 |
| Complement C1q tumor necrosis factor-related protein 4 precursor | IPI00011094 |
| Component of oligomeric golgi complex 6 | IPI00398963 |
| CSRV314 | IPI00432626 |
| Cystatin M precursor | IPI00019954 |
| Cytochrome P450 1A1 | IPI00218839 |
| Cytokine-like protein C17 precursor | IPI00032876 |
| DEAH (Asp-Glu-Ala-His) box polypeptide 29 | IPI00217413 |
| Delta globin | IPI00473011 |
| Dermatopontin precursor | IPI00292130 |
| Dermcidin precursor | IPI00027547 |
| Dermokine-beta | IPI00454602 |
| Dipeptidyl peptidase-like protein 2 | IPI00464986 |
| Dipeptidyl-peptidase II precursor | IPI00296141 |
| DJ1003J2.3.1 | IPI00171382 |
| DJ1042K10.2.2 | IPI00023854 |
| DJ1119A7.3 | IPI00003697 |
| DJ153G14.2 | IPI00181864 |
| DJ68D18.1.2 | IPI00300020 |
| DJ788L20.2 | IPI00100250 |
| DJ977L11.1 | IPI00478622 |
| DKFZp434L142 protein | IPI00165044 |
| DKFZP564O243 protein | IPI00042514 |
| DNA cytosine methyltransferase 3 alpha, isoform a | IPI00329216 |
| DNA excision repair protein ERCC-6 | IPI00414779 |
| DNA-directed RNA polymerase I largest subunit | IPI00031960 |
| DNA-repair protein XRCC2 | IPI00306229 |
| DRIM protein | IPI00004970 |
| Dyskerin | IPI00221394 |
| Endothelin 3, isoform 2 preproprotein | IPI00410367 |
| Ephrin A1 isoform b prEcursor | IPI00377015 |
| Ephrin receptor EphB3 | IPI00376360 |
| Epsilon globin | IPI00217471 |
| ErythrocytE mEmbranE protEin band 4.2 | IPI00028120 |
| Estrogen receptor binding protein | IPI00290410 |
| Exostosin-like 3 | IPI00015135 |
| F1Fo-ATP synthase complex Fo membrane domain g subunit | IPI00385203 |
| FAM31B protein | IPI00059795 |
| Fanconi anemia group E protein | IPI00030252 |
| Fas apoptotic inhibitory molecule 2 | IPI00017569 |

FIG. 7D

| Protein Name | IPI Address |
|---|---|
| FCGR3A protein | IPI00218834 |
| Fibromodulin | IPI00292732 |
| FLJ00006 protein | IPI00396282 |
| FLJ00172 protein | IPI00291755 |
| FLJ00179 protein | IPI00411980 |
| FLJ00199 protein | IPI00291731 |
| FLJ00239 protein | IPI00152731 |
| FLJ00332 protein | IPI00216811 |
| FLJ11029 protein | IPI00305822 |
| FLJ34512 protein | IPI00216820 |
| Follistatin-related protein 1 precursor | IPI00029723 |
| Formin 2 | IPI00021176 |
| Formin-binding protein 17 | IPI00102670 |
| Frizzled-related protein precursor | IPI00294650 |
| Full-length cDNA 5-PRIME end of clone CS0DJ009YL13 of T cells | IPI00384016 |
| Full-length cDNA clone CS0DM007YO13 of Fetal liver of Homo sapiens | IPI00007199 |
| FXYD6 | IPI00004367 |
| FYVE and coiled-coil domain containing 1 | IPI00001580 |
| G protein-coupled sphingolipid receptor | IPI00015343 |
| G4 protein | IPI00099521 |
| GAJ | IPI00029810 |
| Gamma tachykinin 3 variant 2 | IPI00479258 |
| Gamma-synuclein | IPI00297714 |
| Gelsolin precursor | IPI00026314 |
| Glutaminyl-peptide cyclotransferase precursor | IPI00003919 |
| Glutaredoxin (thioltransferase) | IPI00219025 |
| Glyceraldehyde-3-phosphate dehydroGenase | IPI00219018 |
| Glycerol kinase, isoform a | IPI00419934 |
| Golgi apparatus protein 1 | IPI00414717 |
| GolGin-67 isoform a | IPI00016475 |
| Grb10 interacting GYF protein 1 | IPI00428657 |
| Grb10 interacting GYF protein 2 | IPI00418687 |
| Gremlin | IPI00298476 |
| Guanylin precursor | IPI00026926 |
| HBB protein | IPI00470375 |
| Heat sHock 10kDa protein 1 (cHaperonin 10) | IPI00220362 |
| HEJ1 | IPI00045223 |
| Hematopoietic PBX-interacting protein | IPI00332106 |
| Hemoglobin beta | IPI00218816 |
| Hepatocellular carcinoma associated protein TB6 | IPI00293898 |

FIG. 7E

| Protein Name | IPI Address |
|---|---|
| Heterogeneous nuclear ribonucleoprotein L isoform b | IPI00465225 |
| HEXIM1 protein | IPI00007941 |
| Hexokinase, type II | IPI00102864 |
| HGF activator like protein | IPI00041065 |
| HGS_RE408 | IPI00290826 |
| HIV TAT specific factor 1 | IPI00013788 |
| HRPE773 | IPI00060800 |
| HSPC009 | IPI00022277 |
| HSPC098 | IPI00000627 |
| Hus1+-like protein | IPI00004712 |
| Hypothetical protein | IPI00032525 |
| Hypothetical protein | IPI00103241 |
| Hypothetical protein | IPI00217740 |
| Hypothetical protein | IPI00328892 |
| Hypothetical protein | IPI00329547 |
| Hypothetical protein | IPI00333324 |
| Hypothetical protein | IPI00382748 |
| Hypothetical protein | IPI00386433 |
| Hypothetical protein | IPI00386604 |
| Hypothetical protein | IPI00386986 |
| Hypothetical protein | IPI00409639 |
| Hypothetical protein | IPI00419333 |
| Hypothetical protein | IPI00432512 |
| Hypothetical protein | IPI00448792 |
| Hypothetical protein | IPI00465230 |
| Hypothetical protein | IPI00470620 |
| Hypothetical protein | IPI00478227 |
| Hypothetical protein | IPI00384931 |
| Hypothetical protein | IPI00419345 |
| Hypothetical protein | IPI00430806 |
| Hypothetical protein | IPI00470772 |
| Hypothetical protein DKFZp434A2017 | IPI00295380 |
| Hypothetical protein DKFZp434C011 | IPI00152946 |
| Hypothetical protein DKFZP434J0113 | IPI00217802 |
| Hypothetical protein DKFZp434K1421 | IPI00030274 |
| Hypothetical protein DKFZp434P097 | IPI00011232 |
| Hypothetical protein DKFZp434P1219 | IPI00396169 |
| Hypothetical protein DKFZp547D2210 | IPI00217787 |
| Hypothetical protein DKFZp547N1615 | IPI00028864 |
| Hypothetical protein DKFZp586K2123 | IPI00411596 |

FIG. 7F

| Protein Name | IPI Address |
|---|---|
| Hypothetical protein DKFZp666G229 | IPI00470388 |
| Hypothetical protein DKFZp686A06175 | IPI00478616 |
| Hypothetical protein DKFZp686C086 | IPI00472977 |
| Hypothetical protein DKFZp686C195 | IPI00426054 |
| Hypothetical protein DKFZp686D0623 | IPI00470584 |
| Hypothetical protein DKFZp686D0880 | IPI00464979 |
| Hypothetical protein DKFZp686G09165 | IPI00470464 |
| Hypothetical protein DKFZp686H14204 | IPI00384909 |
| Hypothetical protein DKFZp686H22230 | IPI00470804 |
| Hypothetical protein DKFZp686L13193 | IPI00418334 |
| Hypothetical protein DKFZp686N18114 | IPI00171323 |
| Hypothetical protein DKFZp686O0186 | IPI00384977 |
| Hypothetical protein DKFZp761D171 | IPI00385612 |
| Hypothetical protein DKFZp761F0118 | IPI00384202 |
| Hypothetical protein DKFZp761G128 | IPI00413016 |
| Hypothetical protein DKFZp761M0817 | IPI00182757 |
| Hypothetical protein DKFZp781A0122 | IPI00470805 |
| Hypothetical protein FLJ10650 | IPI00018805 |
| Hypothetical protein FLJ10871 | IPI00290514 |
| Hypothetical protein FLJ10955 | IPI00395775 |
| Hypothetical protein FLJ12133 | IPI00153050 |
| Hypothetical protein FLJ12666 | IPI00002373 |
| Hypothetical protein FLJ13110 | IPI00009673 |
| Hypothetical protein FLJ13409 | IPI00336000 |
| Hypothetical protein FLJ13459 | IPI00303852 |
| Hypothetical protein FLJ13782 | IPI00016576 |
| Hypothetical protein FLJ13813 | IPI00030385 |
| Hypothetical protein FLJ14456 | IPI00165528 |
| Hypothetical protein FLJ14494 | IPI00304069 |
| Hypothetical protein FLJ14714 | IPI00395424 |
| Hypothetical protein FLJ16032 | IPI00442338 |
| Hypothetical protein FLJ16127 | IPI00442326 |
| Hypothetical protein FLJ16417 | IPI00465100 |
| Hypothetical protein FLJ20055 | IPI00165009 |
| Hypothetical protein FLJ21011 | IPI00329662 |
| Hypothetical protein FLJ21156 | IPI00456642 |
| Hypothetical protein FLJ21415 | IPI00015479 |
| Hypothetical protein FLJ21816 | IPI00172559 |
| Hypothetical protein FLJ22474 | IPI00003052 |
| Hypothetical protein FLJ23420 | IPI00419535 |

FIG. 7G

| Protein Name | IPI Address |
| --- | --- |
| Hypothetical protein FLJ25224 | IPI00060969 |
| Hypothetical protein FLJ25690 | IPI00167196 |
| Hypothetical protein FLJ30356 | IPI00059639 |
| Hypothetical protein FLJ31401 | IPI00043428 |
| Hypothetical protein FLJ32363 | IPI00374273 |
| Hypothetical protein FLJ32451 | IPI00065491 |
| Hypothetical protein FLJ32800 | IPI00065349 |
| Hypothetical protein FLJ32842 | IPI00480036 |
| Hypothetical protein FLJ34512 | IPI00413989 |
| Hypothetical protein FLJ34922 | IPI00171044 |
| Hypothetical protein FLJ38419 | IPI00167575 |
| Hypothetical protein FLJ38522 | IPI00384796 |
| Hypothetical protein FLJ39374 | IPI00167490 |
| Hypothetical protein FLJ39963 | IPI00179405 |
| Hypothetical protein FLJ40941 | IPI00167233 |
| Hypothetical protein FLJ41598 | IPI00419164 |
| Hypothetical protein FLJ42730 | IPI00446159 |
| Hypothetical protein FLJ43795 | IPI00445546 |
| Hypothetical protein FLJ44006 | IPI00418993 |
| Hypothetical protein FLJ44069 | IPI00445212 |
| Hypothetical protein FLJ44161 | IPI00445366 |
| Hypothetical protein FLJ44241 | IPI00465179 |
| Hypothetical protein FLJ44324 | IPI00445227 |
| Hypothetical protein FLJ45140 | IPI00444823 |
| Hypothetical protein FLJ45264 | IPI00444644 |
| Hypothetical protein FLJ45525 | IPI00299571 |
| Hypothetical protein FLJ45715 | IPI00444259 |
| Hypothetical protein FLJ45736 | IPI00444240 |
| Hypothetical protein FLJ46550 | IPI00443682 |
| Hypothetical protein FLJ46675 | IPI00479983 |
| Hypothetical protein FLJ46747 | IPI00443445 |
| Hypothetical protein FLJ90005 | IPI00477479 |
| Hypothetical protein FLJ90091 | IPI00328520 |
| Hypothetical protein FLJ90551 | IPI00181556 |
| Hypothetical protein FLJ90661 | IPI00168352 |
| Hypothetical protein LOC113174 | IPI00304935 |
| Hypothetical protein LOC122618 | IPI00060310 |
| Hypothetical protein LOC90624 | IPI00329321 |
| Hypothetical protein MGC26885 | IPI00216887 |
| Hypothetical protein MGC29784 | IPI00166131 |

FIG. 7H

| Protein Name | IPI Address |
|---|---|
| Hypothetical protein PIK3CG | IPI00292690 |
| Hypothetical protein PSEC0200 | IPI00166392 |
| Hypothetical protein PSEC0250 | IPI00410487 |
| ICBP90 binding protein 1 | IPI00465273 |
| Ig heavy chain V-II region SESS precursor | IPI00385557 |
| Ig heavy chain V-III region BUT | IPI00382481 |
| Ig heavy chain V-III region GA | IPI00382483 |
| Ig heavy chain V-III region WAS | IPI00382493 |
| Ig kappa chain V-I region BAN | IPI00385555 |
| Ig kappa chain V-I region HK102 precursor | IPI00478600 |
| Ig kappa chain V-III region VG precursor | IPI00419453 |
| Ig kappa chain V-III region VH precursor | IPI00024138 |
| Ig kappa chain V-IV region B17 precursor | IPI00386133 |
| Ig lambda chain V-III region SH | IPI00382436 |
| Ig lambda chain V-IV region Hil | IPI00382440 |
| IL-17RC | IPI00303074 |
| Immunoglobulin-like domain protein MGC33530 precursor | IPI00290411 |
| Import inner membrane translocase subunit TIM44, mitochondrial precursor | IPI00306516 |
| Importin 9 | IPI00185146 |
| Inhibin beta A chain precursor | IPI00028670 |
| Inositol polyphosphate-5-phosphatase F | IPI00383580 |
| Insulin receptor tyrosine kinase substrate | IPI00179326 |
| Insulin-like growth factor IB precursor | IPI00433029 |
| Insulinoma-glucagonoma protein 20 splice variant 2 | IPI00292094 |
| Integral membrane protein 2B | IPI00031821 |
| Inter-alpha trypsin Inhibitor heavy chain precursor 5 Isoform 2 | IPI00451977 |
| Inter-alpha-trypsin inhibitor heavy chain H2 precursor | IPI00305461 |
| Intercellular adhesion molecule-5 precursor | IPI00290456 |
| Interleukin 17 receptor C, isoform 3 | IPI00013761 |
| Interleukin-1 receptor-associated kinase-like 2 | IPI00304986 |
| IQ motif containing E | IPI00419922 |
| Isocitrate dehydrogenase [NAD] subunit alpha, mitochondrial precursor | IPI00030702 |
| Isocitrate dehydrogenase [NADP] cytoplasmic | IPI00027223 |
| Kainate receptor subunit KA2a | IPI00103335 |
| KARCA1 protein | IPI00168703 |
| Kelch/ankyrin repeat containing cyclin A1 interacting protein | IPI00449308 |
| Keratin b20 | IPI00431749 |
| KHSRP protein | IPI00479786 |
| KIAA0300 protein | IPI00329826 |

FIG. 71

| Protein Name | IPI Address |
|---|---|
| KIAA0323 protein | IPI00307649 |
| KIAA0351 protein | IPI00329517 |
| KIAA0372 protein | IPI00005634 |
| KIAA0443 protein | IPI00060549 |
| KIAA0477 protein | IPI00337544 |
| KIAA0523 protein | IPI00479532 |
| KIAA0663 protein | IPI00384636 |
| KIAA1185 protein | IPI00170935 |
| KIAA1204 protein | IPI00297288 |
| KIAA1265 protein | IPI00008085 |
| KIAA1274 protein | IPI00297212 |
| KIAA1384 protein | IPI00418195 |
| KIAA1450 protein | IPI00001790 |
| KIAA1604 protein | IPI00177381 |
| KIAA1640 protein | IPI00288939 |
| KIAA1730 protein | IPI00155199 |
| KIAA1840 protein | IPI00101923 |
| KIAA1946 | IPI00396166 |
| KSS splice variant b | IPI00375393 |
| Laminin alpha-1 chain precursor | IPI00375294 |
| Laminin gamma-1 chain precursor | IPI00298281 |
| LAR | IPI00107831 |
| Latent transforming growth factor beta binding protein 1 isoform LTBP-1L | IPI00410152 |
| Latent transforming growth factor beta binding protein, isoform 1L precursor | IPI00220249 |
| Leukemia-associated protein with a CXXC domain | IPI00303112 |
| Leukocyte receptor cluster (LRC) member 1 | IPI00100947 |
| Line-1 repeat mRNA with 2 open reading frames | IPI00477474 |
| Lipopolysaccharide-binding protein precursor | IPI00032311 |
| Liprin-alpha 2 | IPI00289271 |
| LOC374654 protein | IPI00394856 |
| LP2209 | IPI00428724 |
| L-plastin | IPI00010471 |
| LTLL9335 | IPI00432693 |
| Lysosomal-associated multitransmembrane protein | IPI00013827 |
| Macrophage colony stimulating factor I receptor precursor | IPI00011218 |
| Major prion protein precursor | IPI00022284 |
| Mammalian ependymin related protein 1 | IPI00259102 |
| Mannosidase, alpha, class 1B, member 1 | IPI00383856 |
| Mannosyl-oligosaccharide 1,2-alpha-mannosidase IC | IPI00299669 |

FIG. 7J

| Protein Name | IPI Address |
| --- | --- |
| MAP-kinase activating death domain-containing protein isoform a | IPI00107844 |
| Matrin 3 | IPI00017297 |
| McKusick-Kaufman/Bardet-Biedl syndromes putative chaperonin | IPI00014939 |
| MDM1 protein | IPI00178639 |
| Megakaryocyte-associated tyrosine-protein kinase | IPI00000868 |
| Melanoma derived growth regulatory protein precursor | IPI00003448 |
| Metabotropic glutamate receptor 3 precursor | IPI00478165 |
| Metalloproteinase inhibitor 1 precursor | IPI00032292 |
| Metallothionein-III | IPI00016666 |
| MGAT3 protein | IPI00020406 |
| MIC2L1 isoform E3-E4 | IPI00177578 |
| Microfibrillar-associated protein 5 precursor | IPI00012832 |
| Microsomal signal peptidase 18 kDa subunit | IPI00104128 |
| Microtubule-associated protein 1B isoforM 2 | IPI00374770 |
| Middle-chain acyl-CoA synthetase1 | IPI00059184 |
| MinichroMosoMe Maintenance protein 10 isoforM 1 | IPI00375915 |
| Mitochondrial ribosomal protein L48 | IPI00295066 |
| Mitogen-activated protein kinase kinase kinase 12 | IPI00006775 |
| Mitotic kinesin-related protein | IPI00044751 |
| Molybdenum cofactor synthesis protein 2 small subunit | IPI00002968 |
| Monocarboxylate transporter 3 | IPI00296004 |
| MOP-4 | IPI00023647 |
| Mosaic serine protease | IPI00012505 |
| Mothers against decapentaplegic homolog 4 | IPI00013404 |
| MSFL2541 | IPI00399139 |
| Mu-crystallin homolog | IPI00000949 |
| Muellerian inhibiting factor precursor | IPI00008577 |
| Multi-functional protein MFP | IPI00479309 |
| Multiple inositol polyphosphate phosphatase | IPI00293748 |
| Muscle-cadherin precursor | IPI00024048 |
| Muscle-type acylphosphatase 2 | IPI00216461 |
| Myelin associated glycoprotein isoforM b precursor | IPI00375253 |
| Myelin P0 protein precursor | IPI00106596 |
| Myelin protein zero | IPI00334017 |
| Myosin If | IPI00218638 |
| Myosin-reactive immunoglobulin heavy chain variable region | IPI00384395 |
| Myosin-reactive immunoglobulin kappa chain variable region | IPI00384401 |
| N-acetyltransferase 5 isoform b | IPI00375482 |
| NDST2 protein | IPI00103042 |
| Nebulin-related anchoring protein | IPI00478974 |

FIG. 7K

| Protein Name | IPI Address |
|---|---|
| Nectin-like protein 3 | IPI00293836 |
| NEFL protein | IPI00237671 |
| Neural cell adhesion molecule 1 | IPI00185362 |
| Neural proliferation differentiation and control protein-1 precursor | IPI00299699 |
| Neurexin 1-beta precursor | IPI00428511 |
| Neurexophilin 4 precursor | IPI00293723 |
| Neuritin | IPI00470625 |
| Neuroendocrine convertase 2 precursor | IPI00029131 |
| Neurogenic locus notch homolog protein 2 precursor | IPI00297655 |
| Neurogenin 3 | IPI00025789 |
| Neurotrypsin precursor | IPI00011063 |
| NICE-4 protein | IPI00005416 |
| NIPA1 protein | IPI00477060 |
| Nyctalopin precursor | IPI00072576 |
| Olfactory receptor 51Q1 | IPI00386384 |
| Optic atrOphy 1 isOfOrm 4 | IPI00107749 |
| Optineurin isoform 1 | IPI00304189 |
| Ornithine decarboxylase antizyme 2 | IPI00028937 |
| Orthopedia | IPI00029796 |
| Osteomodulin precursor | IPI00020990 |
| OTTHUMP00000021593 | IPI00374531 |
| OTTHUMP00000021980 | IPI00337642 |
| OTTHUMP00000031659 | IPI00337350 |
| OTTHUMP00000042410 | IPI00477417 |
| Oxidored-nitro domain-containing protein | IPI00154774 |
| Oxytocin-neurophysin 1 precursor | IPI00000144 |
| Paired-like homeobox protein PEPP-1 | IPI00169348 |
| PCPB protein | IPI00329775 |
| Peptidyl-prolyl cis-trans isomerase C | IPI00024129 |
| Peroxiredoxin 2 | IPI00027350 |
| Phosphatidylinositol transfer protein, cytoplasmic 1, isoform b | IPI00063187 |
| PHYHD1 protein | IPI00413674 |
| PKY protein kinase | IPI00099522 |
| PLC-zeta | IPI00172666 |
| Pleiotrophin precursor | IPI00412264 |
| PNAS-138 | IPI00382460 |
| Podocalyxin-like protein | IPI00419595 |
| Polymeric-immunoglobulin receptor precursor | IPI00004573 |
| Potassium voltage-gated channel subfamily C member 1 | IPI00010174 |
| Potassium voltage-gated channel subfamily KQT member 3 | IPI00012857 |

FIG. 7L

| Protein Name | IPI Address |
|---|---|
| Potassium/sodium hyperpolarization-activated cyclic nucleotide-gated channel 2 | IPI00218946 |
| PPIB protein | IPI00419262 |
| PR domain containing 10 isoform 1 | IPI00398772 |
| PREDICTED: C219-reactive peptide | IPI00374065 |
| PREDICTED: chromosome 14 open reading frame 125 | IPI00329192 |
| PREDICTED: chromosome 20 open reading frame 82 | IPI00291076 |
| PREDICTED: hypothetical protein LOC150368 | IPI00297381 |
| PREDICTED: hypothetical protein XP_211408 | IPI00376174 |
| PREDICTED: hypothetical protein XP_373555 | IPI00398397 |
| PREDICTED: hypothetical protein XP_373915 | IPI00374797 |
| PREDICTED: hypothetical protein XP_373979 | IPI00398691 |
| PREDICTED: hypothetical protein XP_374010 | IPI00397039 |
| PREDICTED: hypothetical protein XP_374046 | IPI00397059 |
| PREDICTED: hypothetical protein XP_374095 | IPI00397090 |
| PREDICTED: hypothetical protein XP_374333 | IPI00375094 |
| PREDICTED: hypothetical protein XP_378700 | IPI00401559 |
| PREDICTED: hypothetical protein XP_379029 | IPI00456790 |
| PREDICTED: hypothetical protein XP_379306 | IPI00402509 |
| PREDICTED: hypothetical protein XP_498568 | IPI00456125 |
| PREDICTED: hypothetical protein XP_499091 | IPI00454686 |
| PREDICTED: hypothetical protein XP_499305 | IPI00464965 |
| PREDICTED: KIAA0367 protein | IPI00004557 |
| PREDICTED: KIAA0527 protein | IPI00297224 |
| PREDICTED: KIAA0819 protein | IPI00016356 |
| PREDICTED: KIAA1337 protein | IPI00002283 |
| PREDICTED: KIAA1543 | IPI00176702 |
| PREDICTED: KIAA1856 protein | IPI00186448 |
| PREDICTED: odz, odd Oz/ten-m homolog 2 | IPI00182194 |
| PREDICTED: odz, odd Oz/ten-m homolog 3 | IPI00398020 |
| PREDICTED: similar to 28 kDa heat- and acid-stable phosphoprotein (PDGF-associated prot | IPI00376589 |
| PREDICTED: similar to 40S ribosomal protein S16 | IPI00397701 |
| PREDICTED: similar to 60S ribosomal protein L23a | IPI00051652 |
| PREDICTED: similar to Adrenoleukodystrophy protein (ALDP) | IPI00397198 |
| PREDICTED: similar to anaphase promoting complex subunit 1 | IPI00472098 |
| PREDICTED: similar to asparagine synthetase | IPI00399031 |
| PREDICTED: similar to CCR4-NOT transcription complex, subunit 6like | IPI00455253 |
| PREDICTED: similar to CG3047-PA | IPI00376412 |

FIG. 7M

| Protein Name | IPI Address |
|---|---|
| PREDICTED: similar to Chloride intracellular channel protein 4 (Intracellular chloride | IPI00455949 |
| PREDICTED: similar to DEAD/H (Asp-Glu-Ala-Asp/His) box polypeptide 11 | IPI00398943 |
| PREDICTED: similar to Fatty acid-binding protein, epidermal (EFABP) (Psoriasis-associa | IPI00398985 |
| PREDICTED: similar to germ and embryonic stem cell enriched protein STELLA | IPI00402063 |
| PREDICTED: similar to Glutathione S-transferase Mu 5 (GSTM5-5) (GST class-Mu 5) | IPI00454856 |
| PREDICTED: similar to golgin-67 isoform c | IPI00472363 |
| PREDICTED: similar to heat shock 10kDa protein 1 (chaperonin 10) | IPI00455469 |
| PREDICTED: similar to Histidine-rich glycoprotein precursor (Histidine-proline rich gly | IPI00454879 |
| PREDICTED: similar to hypothetical protein A830023L05 | IPI00455633 |
| PREDICTED: similar to Hypothetical protein BC005730 | IPI00252950 |
| PREDICTED: similar to matrilin 2 precursor | IPI00145674 |
| PREDICTED: similar to melanoma antigen, family A, 10 | IPI00455972 |
| PREDICTED: similar to pre-mRNA splicing SR protein related (68.2 kD) (rsr-1) | IPI00402573 |
| PREDICTED: similar to Ribosome biogenesis protein BMS1 homolog | IPI00253009 |
| PREDICTED: similar to RIKEN cDNA 4930539E08 | IPI00398117 |
| PREDICTED: similar to SURF6 protein | IPI00455997 |
| PREDICTED: similar to tumor necrosis factor, alpha-induced protein 2 | IPI00073442 |
| PREDICTED: similar to ZNF43 protein | IPI00455390 |
| PREDICTED: similar to zonadhesin | IPI00457064 |
| PREDICTED: zinc finger protein 469 | IPI00084684 |
| Pregnancy-specific beta-1-glycoprotein 8 precursor | IPI00334256 |
| PRO1787 | IPI00032189 |
| Profilin 2 isoform a | IPI00219468 |
| Profilin-3 | IPI00235167 |
| Progesterone recePtor membrane comPonent 1 | IPI00220739 |
| Progesterone-induced blocking factor 1 | IPI00472584 |
| Prolargin precursor | IPI00020987 |
| Proline-rich protein 4 precursor | IPI00027019 |
| ProlylcarboxyPeptidase isoform 2 | IPI00399307 |
| Prostate tumor overexpressed gene 1 | IPI00010118 |
| Prostatic binding Protein | IPI00219446 |
| Protease inhibitor H | IPI00297040 |
| Protein C20orf98 | IPI00017231 |
| Protein FAM38A | IPI00006093 |

FIG. 7N

| Protein Name | IPI Address |
|---|---|
| Protein PRO1854 | IPI00006005 |
| Protein tyrosine Phosphatase domain containing 1 Protein isoform 1 | IPI00376989 |
| Protein tyrosine phosphatase, non-receptor type 14 | IPI00477830 |
| Protein-L-isoaspartate (D-aspartate) O-methyltransferase | IPI00411680 |
| Protein-tyrosine sulfotransferase 1 | IPI00030106 |
| Protocadherin 1 isoform 2 Precursor | IPI00176458 |
| Protocadherin Fat 2 precursor | IPI00302641 |
| P-selectin glycoprotein ligand 1 precursor | IPI00029591 |
| PSMC3 protein | IPI00018398 |
| PSST739 | IPI00394870 |
| PTPL1-associated RhoGAP | IPI00152011 |
| Purkinje cell protein 4 | IPI00010148 |
| Putative 4 repeat voltage-gated ion channel | IPI00217996 |
| Putative acyl-CoA thioester hydrolase CGI-16 | IPI00220710 |
| Putative alpha-mannosidase C1orf22 | IPI00009410 |
| Putative secreted ligand | IPI00003834 |
| Putative secretory protein | IPI00027806 |
| Pyruvate kinase 3 isoform 1 | IPI00479186 |
| QVSK201 | IPI00465325 |
| RAS p21 protein activator 3 | IPI00383401 |
| Ras-related protein Rap-2b | IPI00018364 |
| Receptor-interacting serine/threonine-protein kinase 2 | IPI00021917 |
| Replication protein A 70 kDa DNA-binding subunit | IPI00020127 |
| Retbindin | IPI00027765 |
| RGD, leucine-rich repeat, tropomodulin and proline-rich containing protein | IPI00456628 |
| Rho guanine nucleotide exchange factor 1 isoform 1 | IPI00395605 |
| Rho/rac-interacting citron kinase | IPI00022465 |
| Rho/rac guanine nucleotide exchange factor (GEF) 2 | IPI00412782 |
| Rho-GTPase activating protein 10 | IPI00169307 |
| Rho-GTPase-activating protein 5 | IPI00013988 |
| Ribonuclease 4 precursor | IPI00029699 |
| Ribosomal protein L39 | IPI00219162 |
| Ribosomal protein L3-like | IPI00219335 |
| Ribosomal protein L7 | IPI00030179 |
| Ribosome biogenesis protein BMS1 homolog | IPI00006099 |
| RNA-binding protein 5 | IPI00005036 |
| Rotatin | IPI00414117 |
| SAA1 protein | IPI00452748 |
| Salvador homolog 1 protein | IPI00301738 |
| Sarco/endoplaSmic reticulum Ca2+ -ATPase isoform d | IPI00218442 |

FIG. 70

| Protein Name | IPI Address |
|---|---|
| SAYY8238 | IPI00432771 |
| SCMH1 protein | IPI00187110 |
| Selenoprotein P precursor | IPI00029061 |
| SEMA3B protein | IPI00448569 |
| Serine protease HTRA1 precursor | IPI00003176 |
| Serine protease inhibitor, Kazal type, 5 | IPI00299453 |
| Serine/threonine-protein kinase H1 | IPI00007810 |
| Seven transmembrane helix receptor | IPI00376212 |
| SH3 domain-binding glutamic acid-rich-like protein | IPI00025318 |
| SH3-domain GRB2-like 1 | IPI00019169 |
| Sia-alpha-2,3-Gal-beta-1,4-GlcNAc-R:alpha 2,8-sialyltransferase | IPI00026285 |
| Similar to ecotropic viral integration site 5; Neuroblastoma stage 4S gene | IPI00060473 |
| Similar to expressed sequence AI593442 | IPI00217781 |
| Similar to phospholipase C, beta 3 | IPI00181283 |
| Similar to portion of neuronal pentraxin i NPX1 or NP1 | IPI00059308 |
| Similar to protein kinase C substrate | IPI00382750 |
| SLAP | IPI00432472 |
| SLC5A12 protein | IPI00383383 |
| Small intestine SPAK-like kinase | IPI00457335 |
| SNC66 protein | IPI00383164 |
| Sodium/potassium-transporting ATPase alpha-2 chain precursor | IPI00003021 |
| Sortilin precursor | IPI00217882 |
| Spir-2 protein | IPI00162208 |
| Splice Isoform 1 Of Activating signal cointegrator 1 complex subunit 3 | IPI00430472 |
| Splice Isoform 1 Of ADAMTS-16 precursor | IPI00386697 |
| Splice Isoform 1 Of ADAMTS-2 precursor | IPI00030757 |
| Splice Isoform 1 Of Adapter-related protein complex 3 beta 1 subunit | IPI00021129 |
| Splice Isoform 1 Of Adapter-related protein complex 3 delta 1 subunit | IPI00411453 |
| Splice Isoform 1 Of Aquaporin 4 | IPI00022799 |
| Splice Isoform 1 Of Bone morphogenetic protein 1 precursor | IPI00009054 |
| Splice Isoform 1 Of Calcium/calmodulin-dependent protein kinase type II alpha chain | IPI00098624 |
| Splice Isoform 1 Of CCG1-interacting factor B | IPI00063827 |
| Splice Isoform 1 Of Collagen alpha 2(VI) chain precursor | IPI00304840 |
| Splice Isoform 1 Of COP9 signalosome complex subunit 1 | IPI00479323 |
| Splice Isoform 1 Of Cullin homolog 4B | IPI00477156 |
| Splice Isoform 1 Of Cyclic-AMP-dependent transcription factor ATF-6 beta | IPI00004084 |
| Splice Isoform 1 Of Desmoplakin | IPI00013933 |

FIG. 7P

| Protein Name | IPI Address |
|---|---|
| Splice Isoform 1 Of Double-stranded RNA-specific adenosine deaminase | IPI00394665 |
| Splice Isoform 1 Of Dynein intermediate chain 1, cytosolic | IPI00022461 |
| Splice Isoform 1 Of Ecto-ADP-ribosyltransferase 3 precursor | IPI00013682 |
| Splice Isoform 1 Of Endothelin-3 precursor | IPI00025365 |
| Splice Isoform 1 Of ERC protein 1 | IPI00216719 |
| Splice Isoform 1 Of Gamma-tubulin complex component 6 | IPI00045491 |
| Splice Isoform 1 Of Glutaryl-CoA dehydrogenase, mitochondrial precursor | IPI00024317 |
| Splice Isoform 1 Of HpaII tiny fragments locus 9c protein | IPI00337307 |
| Splice Isoform 1 Of Inositol 1,4,5-trisphosphate receptor type 2 | IPI00031545 |
| Splice Isoform 1 Of IQ calmodulin-binding motif containing protein 1 | IPI00014255 |
| Splice Isoform 1 Of Lysosomal trafficking regulator | IPI00017094 |
| Splice Isoform 1 Of Neuroligin 1 precursor | IPI00307328 |
| Splice Isoform 1 Of Neuropilin-1 precursor | IPI00299594 |
| Splice Isoform 1 Of Osteopontin precursor | IPI00021000 |
| Splice Isoform 1 Of p130Cas-associated protein | IPI00479643 |
| Splice Isoform 1 Of Partitioning defective-6 homolog alpha | IPI00027217 |
| Splice Isoform 1 Of Pleckstrin homology domain containing family C member 1 | IPI00000856 |
| Splice Isoform 1 Of Polycystic kidney and hepatic disease 1 precursor | IPI00293274 |
| Splice Isoform 1 Of Protachykinin 1 precursor | IPI00023571 |
| Splice Isoform 1 Of Protein C21orf70 | IPI00027898 |
| Splice Isoform 1 Of Putative polypeptide N-acetylgalactosaminyltransferase-like protein | IPI00166613 |
| Splice Isoform 1 Of Receptor-type tyrosine-protein phosphatase delta precursor | IPI00011642 |
| Splice Isoform 1 Of Rotavirus 'X' associated non-structural protein | IPI00099131 |
| Splice Isoform 1 Of Serine/threonine-protein kinase RIPK4 | IPI00025714 |
| Splice Isoform 1 Of SET binding factor 1 | IPI00029446 |
| Splice Isoform 1 Of Short transient receptor potential channel 6 | IPI00031683 |
| Splice Isoform 1 Of Sodium/potassium-transporting ATPase alpha-1 chain precursor | IPI00006482 |
| Splice Isoform 1 Of Spectrin beta chain, brain 3 | IPI00018829 |
| Splice Isoform 1 Of Telomerase-binding protein EST1A | IPI00015793 |
| Splice Isoform 1 Of Tetratricopeptide repeat protein 7A | IPI00397195 |
| Splice Isoform 1 Of Transcription factor E2-alpha | IPI00013929 |
| Splice Isoform 1 Of Trans-Golgi network integral membrane protein 2 precursor | IPI00012545 |
| Splice Isoform 1 Of Tubby-like protein 4 | IPI00024994 |
| Splice Isoform 1 Of Ubiquitin carboxyl-terminal hydrolase 33 | IPI00236901 |

FIG. 7Q

| Protein Name | IPI Address |
|---|---|
| Splice Isoform 1 Of Ubiquitin-conjugating enzyme E2 variant 1 | IPI00019599 |
| Splice Isoform 1 Of UPF0338 protein NG5 | IPI00043810 |
| Splice Isoform 1 Of Vacuolar protein sorting 18 | IPI00001985 |
| Splice Isoform 1 Of Voltage-dependent N-type calcium channel alpha1B subunit | IPI00025477 |
| Splice Isoform 1 Of Zinc finger DHHC domain containing protein 13 | IPI00410663 |
| Splice Isoform 10 Of Integrin alpha-7 precursor | IPI00216421 |
| Splice Isoform 11 Of Integrin alpha-7 precursor | IPI00216422 |
| Splice Isoform 2 Of ADAMTS-16 precursor | IPI00186114 |
| Splice Isoform 2 Of ADAMTS-2 precursor | IPI00012366 |
| Splice Isoform 2 Of Amphiphysin | IPI00220791 |
| Splice Isoform 2 Of Angiogenic factor VG5Q | IPI00106911 |
| Splice Isoform 2 Of Apolipoprotein L1 precursor | IPI00186903 |
| Splice Isoform 2 Of Arfaptin 1 | IPI00216520 |
| Splice Isoform 2 Of Basigin precursor | IPI00019906 |
| Splice Isoform 2 Of Bone morphogenetic protein 1 precursor | IPI00014021 |
| Splice Isoform 2 Of Bromodomain adjacent to zinc finger domain protein 1A | IPI00383565 |
| Splice Isoform 2 Of Cadherin-11 precursor | IPI00293539 |
| Splice Isoform 2 Of Calcium/calmodulin-dependent protein kinase type II alpha chain | IPI00215715 |
| Splice Isoform 2 Of Canalicular multispecific organic anion transporter 2 | IPI00251066 |
| Splice Isoform 2 Of CCR4-NOT transcription complex subunit 4 | IPI00410682 |
| Splice Isoform 2 Of Collagen alpha 2(VI) chain precursor | IPI00220613 |
| Splice Isoform 2 Of Collagen alpha 3(VI) chain precursor | IPI00220701 |
| Splice Isoform 2 Of Complement factor H precursor | IPI00218999 |
| Splice Isoform 2 Of Cullin homolog 1 | IPI00334426 |
| Splice Isoform 2 Of Development and differentiation-enhancing factor 2 | IPI00409613 |
| Splice Isoform 2 Of EGF-containing fibulin-like extracellular matrix protein 1 precurso | IPI00220813 |
| Splice Isoform 2 Of Endothelin-3 precursor | IPI00220210 |
| Splice Isoform 2 Of Ephrin type-A receptor 5 precursor | IPI00215945 |
| Splice Isoform 2 Of Glutaryl-CoA dehydrogenase, mitochondrial precursor | IPI00218112 |
| Splice Isoform 2 Of HLA class I histocompatibility antigen, Cw-16 alpha chain precursor | IPI00472035 |
| Splice Isoform 2 Of ICOS ligand precursor | IPI00414888 |
| Splice Isoform 2 Of Insulin receptor precursor | IPI00220325 |
| Splice Isoform 2 Of Integrin alpha-7 precursor | IPI00220748 |

FIG. 7R

| Protein Name | IPI Address |
|---|---|
| Splice Isoform 2 Of Interleukin-12 receptor beta-2 chain precursor | IPI00438856 |
| Splice Isoform 2 Of Interleukin-18 binding protein precursor | IPI00220525 |
| Splice Isoform 2 Of MAGUK p55 subfamily member 2 | IPI00218271 |
| Splice Isoform 2 Of MAM domain-containing glycosylphosphatidylinositol anchor protein 1 | IPI00410349 |
| Splice Isoform 2 Of Metabotropic glutamate receptor 8 precursor | IPI00396012 |
| Splice Isoform 2 Of Mitochondrial dicarboxylate carrier | IPI00217277 |
| Splice Isoform 2 Of Myosin Va | IPI00100956 |
| Splice Isoform 2 Of Myosin VIIa | IPI00215753 |
| Splice Isoform 2 Of N-acetylmuramoyl-L-alanine amidase precursor | IPI00394992 |
| Splice Isoform 2 Of Neural cell adhesion molecule 1, 120 kDa isoform precursor | IPI00220737 |
| Splice Isoform 2 Of NTF2-related export protein 2 | IPI00221003 |
| Splice Isoform 2 Of Oral-facial-digital syndrome 1 protein | IPI00221364 |
| Splice Isoform 2 Of Pleckstrin homology domain containing family C member 1 | IPI00383500 |
| Splice Isoform 2 Of Protachykinin 1 precursor | IPI00219086 |
| Splice Isoform 2 Of Protein-L-isoaspartate | IPI00024989 |
| Splice Isoform 2 Of Putative polypeptide N-acetylgalactosaminyltransferase-like protein | IPI00456715 |
| Splice Isoform 2 Of Retinoic acid receptor responder protein 1 | IPI00410377 |
| Splice Isoform 2 Of Roundabout homolog 2 precursor | IPI00420043 |
| Splice Isoform 2 Of Secretory carrier-associated membrane protein 1 | IPI00067352 |
| Splice Isoform 2 Of Sentrin-specific protease 6 | IPI00332748 |
| Splice Isoform 2 Of Sodium/potassium/calcium exchanger 2 precursor | IPI00218809 |
| Splice Isoform 2 Of Solute carrier family 26 member 6 | IPI00218923 |
| Splice Isoform 2 Of Stromal cell-derived factor 1 precursor | IPI00216304 |
| Splice Isoform 2 Of T-cell surface glycoprotein E2 precursor | IPI00220117 |
| Splice Isoform 2 Of Trans-Golgi network integral membrane protein 2 precursor | IPI00297543 |
| Splice Isoform 2 Of Ubiquilin 1 | IPI00071180 |
| Splice Isoform 2 Of UDP-N-acetylglucosamine--peptide N-acetylglucosaminyltransferase 11 | IPI00219856 |
| Splice Isoform 2 Of Voltage-dependent N-type calcium channel alpha1B subunit | IPI00220431 |
| Splice Isoform 3 Of ADAMTS-9 precursor | IPI00386763 |
| Splice Isoform 3 Of Adapter-related protein complex 3 delta 1 subunit | IPI00413686 |
| Splice Isoform 3 Of Apoptotic protease activating factor 1 | IPI00217461 |
| Splice Isoform 3 Of Bone morphogenetic protein 1 precursor | IPI00218040 |
| Splice Isoform 3 Of Calcium/calmodulin-dependent protein kinase type II beta chain | IPI00219165 |

FIG. 7S

| Protein Name | IPI Address |
|---|---|
| Splice Isoform 3 Of Collagen alpha 2(VI) chain precursor | IPI00073454 |
| Splice Isoform 3 Of Dachshund homolog 2 | IPI00402353 |
| Splice Isoform 3 Of Latrophilin 3 precursor | IPI00410312 |
| Splice Isoform 3 Of Myosin XVIIIA | IPI00477329 |
| Splice Isoform 3 Of Osteopontin precursor | IPI00218875 |
| Splice Isoform 3 Of Receptor-type tyrosine-protein phosphatase delta precursor | IPI00219860 |
| Splice Isoform 3 Of Reelin precursor | IPI00298066 |
| Splice Isoform 3 Of Seizure 6-like protein precursor | IPI00220333 |
| Splice Isoform 3 Of Signal-regulatory protein beta-2 precursor | IPI00218601 |
| Splice Isoform 3 Of Solute carrier family 12 member 2 | IPI00220844 |
| Splice Isoform 3 Of Triggering receptor expressed on myeloid cells 2 precursor | IPI00384361 |
| Splice Isoform 3 Of Tuftelin | IPI00218512 |
| Splice Isoform 3 Of Ubiquitin carboxyl-terminal hydrolase 6 | IPI00423565 |
| Splice Isoform 3 Of Versican core protein precursor | IPI00215629 |
| Splice Isoform 4 Of Integrin alpha-7 precursor | IPI00220750 |
| Splice Isoform 4 Of Peptidyl-glycine alpha-amidating monooxygenase precursor | IPI00219043 |
| Splice Isoform 4 Of Receptor-type tyrosine-protein phosphatase S precursor | IPI00332273 |
| Splice Isoform 5 Of Chordin precursor | IPI00221163 |
| Splice Isoform 5 Of Neuronal cell adhesion molecule precursor | IPI00333781 |
| Splice Isoform 5 Of Receptor-type tyrosine-protein phosphatase S precursor | IPI00299590 |
| Splice Isoform 6 Of Fibronectin precursor | IPI00339226 |
| Splice Isoform 6 Of Myelin-oligodendrocyte glycoprotein precursor | IPI00219666 |
| Splice Isoform 7 Of Calcium/calmodulin-dependent protein kinase type II beta chain | IPI00183066 |
| SRPK2 protein | IPI00413888 |
| ST6GalII protein | IPI00063048 |
| Stem cell growth factor precursor | IPI00033466 |
| Stromelysin-3 precursor | IPI00306778 |
| Superoxide dismutase [Mn], mitochondrial precursor | IPI00022314 |
| SWI/SNF-related matrix-associated actin-dependent regulator of chromatin a1 isoform b | IPI00376861 |
| Synaptotagmin VII | IPI00012902 |
| Synaptotagmin-1 | IPI00009439 |
| Synaptotagmin-4 | IPI00022735 |
| Synphilin 1 | IPI00002293 |
| T1 protein | IPI00181881 |

FIG. 7T

| Protein Name | IPI Address |
|---|---|
| TAGLN protein | IPI00216138 |
| TAR RNA loop binding protein | IPI00298447 |
| TCN2 protein | IPI00386630 |
| Testis-specific BRDT protein | IPI00410355 |
| THAP domain protein 2 | IPI00027774 |
| Tpr | IPI00022970 |
| Transcription elongation regulator 1 | IPI00247871 |
| Transcription factor SL1 | IPI00385907 |
| Transcription factor SOX-7 | IPI00027779 |
| Transcription initiation factor IIE, alpha subunit | IPI00019977 |
| Transcriptional activator SRCAP | IPI00009101 |
| Transmembrane 7 superfamily member 1 | IPI00019017 |
| Transmembrane protein 16B | IPI00033553 |
| TRAP/Mediator complex component TRAP25 | IPI00063213 |
| TRIF-related adapter molecule | IPI00329281 |
| TriosephosphaTe isomerase 1 | IPI00465028 |
| Tripeptidyl-peptidase I precursor | IPI00298237 |
| tRNA-splicing endonuclease subunit SEN15 | IPI00450071 |
| Tropomyosin 3 | IPI00479615 |
| Trypsinogen C | IPI00169276 |
| TSLC1-like 2 | IPI00176427 |
| Tumor necrosis factor receptor superfamily member 19L precursor | IPI00064377 |
| Tyrosine phosphatase zeta polypeptide 2 HTPZP2 | IPI00472466 |
| Tyrosine-protein kinase CSK | IPI00013212 |
| Ubiquitin carboxyl-terminal hydrolase 24 | IPI00398505 |
| Ubiquitin carboxyl-terminal hydrolase isozyme L1 | IPI00018352 |
| Ubiquitin-like protein fUbi and ribosomal protein S30 precUrsor | IPI00019770 |
| UDP-Gal:betaGlcNAc beta 1,4- galactosyltransferase 1, membrane-bound form | IPI00215767 |
| Uncharacterized hematopoietic stem/progenitor cells protein MDS031 | IPI00020512 |
| Unnamed secretory protein | IPI00216914 |
| UTP14, U3 small nucleolar ribonucleoprotein, homolog A | IPI00107113 |
| Utrophin | IPI00009329 |
| Vesicular integral-membrane protein VIP36 precursor | IPI00009950 |
| Vitamin K epoxide reductase complex, subunit 1-like 1 | IPI00166079 |
| Voltage-dependent calcium channel gamma-6 subunit | IPI00011072 |
| WD repeat membrane protein | IPI00396243 |
| Werner helicase interacting protein, isoform 2 | IPI00102997 |
| XA protein | IPI00383520 |
| Zinc finger FYVE domain containing protein 28 | IPI00288918 |
| Zinc finger protein | IPI00399361 |

FIG. 7U

| Protein Name | IPI Address |
|---|---|
| Zinc finger protein 577 | IPI00013397 |
| Zinc finger protein 95 homolog | IPI00032316 |
| ZNF627 protein | IPI00029023 |

FIG. 7V

SEQUENCE LISTING

<160> NUMBER OF SEQ ID NOS: 1353

<210> SEQ ID NO 1
<211> LENGTH: 24
<212> TYPE: PRT
<213> ORGANISM: H. sapiens

<400> SEQUENCE: 1

Ala Glu Pro Pro Lys Ala Pro Glu Gln Glu Gln Ala Ala Pro Gly Pro
1               5                   10                  15

Ala Ala Gly Gly Glu Ala Pro Lys
            20

<210> SEQ ID NO 2
<211> LENGTH: 7
<212> TYPE: PRT
<213> ORGANISM: H. sapiens

<400> SEQUENCE: 2

Glu Ala Asp Val Val Ala Arg
1               5

<210> SEQ ID NO 3
<211> LENGTH: 10
<212> TYPE: PRT
<213> ORGANISM: H. sapiens

<400> SEQUENCE: 3

Glu Lys Pro Asp Gln Asp Ala Glu Gly Lys
1               5                   10

<210> SEQ ID NO 4
<211> LENGTH: 14
<212> TYPE: PRT
<213> ORGANISM: H. sapiens

<400> SEQUENCE: 4

Glu Ser Glu Pro Gln Ala Ala Ala Glu Pro Ala Glu Ala Lys
1               5                   10

<210> SEQ ID NO 5
<211> LENGTH: 5
<212> TYPE: PRT
<213> ORGANISM: H. sapiens

<400> SEQUENCE: 5

Ala Ala Pro Met Lys
1               5

<210> SEQ ID NO 6
<211> LENGTH: 11
<212> TYPE: PRT
<213> ORGANISM: H. sapiens

<400> SEQUENCE: 6

Gly Gln Gly Gly Leu Ala Tyr Pro Gly Val Arg
1               5                   10

```
<210> SEQ ID NO 7
<211> LENGTH: 12
<212> TYPE: PRT
<213> ORGANISM: H. sapiens

<400> SEQUENCE: 7

Ile Asp Thr Ser Cys Val Cys Thr Leu Thr Ile Lys
1               5                   10

<210> SEQ ID NO 8
<211> LENGTH: 13
<212> TYPE: PRT
<213> ORGANISM: H. sapiens

<400> SEQUENCE: 8

Asn Tyr Leu Asp Ala Ala Asn Met Ser Met Arg Val Arg
1               5                   10

<210> SEQ ID NO 9
<211> LENGTH: 10
<212> TYPE: PRT
<213> ORGANISM: H. sapiens

<400> SEQUENCE: 9

Glu Leu Pro Gly Glu Thr Leu Glu Ser Lys
1               5                   10

<210> SEQ ID NO 10
<211> LENGTH: 23
<212> TYPE: PRT
<213> ORGANISM: H. sapiens

<400> SEQUENCE: 10

Glu Ser Leu Asp Pro Val Gln Glu Pro Gly Gly Gln Ala Glu Ala Asp
1               5                   10                  15

Gly Asp Val Pro Gly Pro Arg
            20

<210> SEQ ID NO 11
<211> LENGTH: 10
<212> TYPE: PRT
<213> ORGANISM: H. sapiens

<400> SEQUENCE: 11

Gly Glu Ala Glu Gly Gln Ala Glu Ala Lys
1               5                   10

<210> SEQ ID NO 12
<211> LENGTH: 17
<212> TYPE: PRT
<213> ORGANISM: H. sapiens

<400> SEQUENCE: 12

Gly Glu Ala Gly Gly Gln Ala Glu Ala Glu Gly Asp Ala Pro Gly Pro
1               5                   10                  15

Arg

<210> SEQ ID NO 13
<211> LENGTH: 10
<212> TYPE: PRT
<213> ORGANISM: H. sapiens

<400> SEQUENCE: 13

Gly Glu Ala Gly Gly Gln Ala Glu Ala Arg
```

```
<210> SEQ ID NO 14
<211> LENGTH: 20
<212> TYPE: PRT
<213> ORGANISM: H. sapiens

<400> SEQUENCE: 14

His Val Glu Pro Gly Glu Pro Leu Ala Pro Ser Pro Gln Glu Pro Gln
 1               5                  10                  15

Ala Val Gly Arg
        20

<210> SEQ ID NO 15
<211> LENGTH: 18
<212> TYPE: PRT
<213> ORGANISM: H. sapiens

<400> SEQUENCE: 15

Asn Thr Gln Asn Asp Phe Glu Val His Ile Val Gln Val Glu Asn Asp
 1               5                  10                  15

Glu Ile

<210> SEQ ID NO 16
<211> LENGTH: 10
<212> TYPE: PRT
<213> ORGANISM: H. sapiens

<400> SEQUENCE: 16

Gln Glu Thr Gln Glu Ala Pro Gly Pro Arg
 1               5                  10

<210> SEQ ID NO 17
<211> LENGTH: 24
<212> TYPE: PRT
<213> ORGANISM: H. sapiens

<400> SEQUENCE: 17

Arg Glu Ser Leu Asp Pro Val Gln Glu Pro Gly Gly Gln Ala Glu Ala
 1               5                  10                  15

Asp Gly Asp Val Pro Gly Pro Arg
        20

<210> SEQ ID NO 18
<211> LENGTH: 10
<212> TYPE: PRT
<213> ORGANISM: H. sapiens

<400> SEQUENCE: 18

Thr Glu Val Gln Leu Glu His Leu Ser Arg
 1               5                  10

<210> SEQ ID NO 19
<211> LENGTH: 24
<212> TYPE: PRT
<213> ORGANISM: H. sapiens

<400> SEQUENCE: 19

Ala Glu Gly Asn Asn Gln Ala Pro Gly Glu Glu Glu Glu Glu Glu Glu
 1               5                  10                  15

Glu Ala Thr Asn Thr His Pro Pro
        20
```

```
<210> SEQ ID NO 20
<211> LENGTH: 9
<212> TYPE: PRT
<213> ORGANISM: H. sapiens

<400> SEQUENCE: 20

Glu Ala Val Glu Glu Pro Ser Ser Lys
 1               5

<210> SEQ ID NO 21
<211> LENGTH: 15
<212> TYPE: PRT
<213> ORGANISM: H. sapiens

<400> SEQUENCE: 21

Glu Glu Glu Glu Glu Met Ala Val Val Pro Gln Gly Leu Phe Arg
 1               5                  10                  15

<210> SEQ ID NO 22
<211> LENGTH: 11
<212> TYPE: PRT
<213> ORGANISM: H. sapiens

<400> SEQUENCE: 22

Glu Leu Gln Asp Leu Ala Leu Gln Gly Ala Lys
 1               5                  10

<210> SEQ ID NO 23
<211> LENGTH: 6
<212> TYPE: PRT
<213> ORGANISM: H. sapiens

<400> SEQUENCE: 23

Glu Trp Glu Asp Ser Lys
 1               5

<210> SEQ ID NO 24
<211> LENGTH: 24
<212> TYPE: PRT
<213> ORGANISM: H. sapiens

<400> SEQUENCE: 24

Gly Glu Gln Glu His Ser Gln Gln Lys Glu Glu Glu Glu Met Ala
 1               5                  10                  15

Val Val Pro Gln Gly Leu Phe Arg
                20

<210> SEQ ID NO 25
<211> LENGTH: 11
<212> TYPE: PRT
<213> ORGANISM: H. sapiens

<400> SEQUENCE: 25

Gly Leu Ser Ala Glu Pro Gly Trp Gln Ala Lys
 1               5                  10

<210> SEQ ID NO 26
<211> LENGTH: 6
<212> TYPE: PRT
<213> ORGANISM: H. sapiens

<400> SEQUENCE: 26

Gly Tyr Pro Glu Glu Lys
 1               5
```

```
<210> SEQ ID NO 27
<211> LENGTH: 6
<212> TYPE: PRT
<213> ORGANISM: H. sapiens

<400> SEQUENCE: 27

His Gln Asn Leu Leu Lys
 1               5

<210> SEQ ID NO 28
<211> LENGTH: 6
<212> TYPE: PRT
<213> ORGANISM: H. sapiens

<400> SEQUENCE: 28

Ile Leu Ser Ile Leu Arg
 1               5

<210> SEQ ID NO 29
<211> LENGTH: 23
<212> TYPE: PRT
<213> ORGANISM: H. sapiens

<400> SEQUENCE: 29

Ser Glu Ala Leu Ala Val Asp Gly Ala Gly Lys Pro Gly Ala Glu Glu
 1               5                  10                  15

Ala Gln Asp Pro Glu Gly Lys
                20

<210> SEQ ID NO 30
<211> LENGTH: 21
<212> TYPE: PRT
<213> ORGANISM: H. sapiens

<400> SEQUENCE: 30

Ser Gly Glu Ala Thr Asp Gly Ala Arg Pro Gln Ala Leu Pro Glu Pro
 1               5                  10                  15

Met Gln Glu Ser Lys
                20

<210> SEQ ID NO 31
<211> LENGTH: 10
<212> TYPE: PRT
<213> ORGANISM: H. sapiens

<400> SEQUENCE: 31

Ser Gly Glu Leu Glu Gln Glu Glu Glu Arg
 1               5                  10

<210> SEQ ID NO 32
<211> LENGTH: 9
<212> TYPE: PRT
<213> ORGANISM: H. sapiens

<400> SEQUENCE: 32

Val Ala His Gln Leu Gln Ala Leu Arg
 1               5

<210> SEQ ID NO 33
<211> LENGTH: 20
<212> TYPE: PRT
<213> ORGANISM: H. sapiens
```

-continued

```
<400> SEQUENCE: 33

Tyr Pro Gly Pro Gln Ala Glu Gly Asp Ser Glu Gly Leu Ser Gln Gly
1               5                   10                  15

Leu Val Asp Arg
            20

<210> SEQ ID NO 34
<211> LENGTH: 22
<212> TYPE: PRT
<213> ORGANISM: H. sapiens

<400> SEQUENCE: 34

Tyr Pro Gly Pro Gln Ala Glu Gly Asp Ser Glu Gly Leu Ser Gln Gly
1               5                   10                  15

Leu Val Asp Arg Glu Lys
            20

<210> SEQ ID NO 35
<211> LENGTH: 11
<212> TYPE: PRT
<213> ORGANISM: H. sapiens

<400> SEQUENCE: 35

Ala Asp Gln Thr Val Leu Thr Glu Asp Glu Lys
1               5                   10

<210> SEQ ID NO 36
<211> LENGTH: 12
<212> TYPE: PRT
<213> ORGANISM: H. sapiens

<400> SEQUENCE: 36

Ala Asp Gln Thr Val Leu Thr Glu Asp Glu Lys Lys
1               5                   10

<210> SEQ ID NO 37
<211> LENGTH: 13
<212> TYPE: PRT
<213> ORGANISM: H. sapiens

<400> SEQUENCE: 37

Ala Ser Glu Glu Glu Pro Glu Tyr Gly Glu Glu Ile Lys
1               5                   10

<210> SEQ ID NO 38
<211> LENGTH: 8
<212> TYPE: PRT
<213> ORGANISM: H. sapiens

<400> SEQUENCE: 38

Ala Tyr Phe Met Ser Asp Thr Arg
1               5

<210> SEQ ID NO 39
<211> LENGTH: 12
<212> TYPE: PRT
<213> ORGANISM: H. sapiens

<400> SEQUENCE: 39

Cys Ile Ile Glu Val Leu Ser Asn Ala Leu Ser Lys
1               5                   10

<210> SEQ ID NO 40
```

```
<211> LENGTH: 11
<212> TYPE: PRT
<213> ORGANISM: H. sapiens

<400> SEQUENCE: 40

Asp Lys Glu Thr Thr Glu Asn Glu Asn Thr Lys
1               5                   10

<210> SEQ ID NO 41
<211> LENGTH: 14
<212> TYPE: PRT
<213> ORGANISM: H. sapiens

<400> SEQUENCE: 41

Asp Pro Ala Asp Ala Ser Glu Ala His Glu Ser Ser Ser Arg
1               5                   10

<210> SEQ ID NO 42
<211> LENGTH: 13
<212> TYPE: PRT
<213> ORGANISM: H. sapiens

<400> SEQUENCE: 42

Glu Asp Glu Glu Glu Glu Gly Glu Asn Tyr Gln Lys
1               5                   10

<210> SEQ ID NO 43
<211> LENGTH: 17
<212> TYPE: PRT
<213> ORGANISM: H. sapiens

<400> SEQUENCE: 43

Glu Leu Asp Arg Asn Tyr Leu Asn Tyr Gly Glu Glu Gly Ala Pro Gly
1               5                   10                  15

Lys

<210> SEQ ID NO 44
<211> LENGTH: 14
<212> TYPE: PRT
<213> ORGANISM: H. sapiens

<400> SEQUENCE: 44

Glu Leu Glu Asn Leu Ala Ala Met Asp Leu Glu Leu Gln Lys
1               5                   10

<210> SEQ ID NO 45
<211> LENGTH: 16
<212> TYPE: PRT
<213> ORGANISM: H. sapiens

<400> SEQUENCE: 45

Gly Glu Ala Gly Ala Pro Gly Glu Glu Asp Ile Gln Gly Pro Thr Lys
1               5                   10                  15

<210> SEQ ID NO 46
<211> LENGTH: 6
<212> TYPE: PRT
<213> ORGANISM: H. sapiens

<400> SEQUENCE: 46

Gly Leu Glu Pro Gly Lys
1               5

<210> SEQ ID NO 47
```

```
<211> LENGTH: 15
<212> TYPE: PRT
<213> ORGANISM: H. sapiens

<400> SEQUENCE: 47

Gly Tyr Pro Gly Val Gln Ala Pro Glu Asp Leu Glu Trp Glu Arg
 1               5                  10                  15

<210> SEQ ID NO 48
<211> LENGTH: 16
<212> TYPE: PRT
<213> ORGANISM: H. sapiens

<400> SEQUENCE: 48

His Leu Glu Glu Pro Gly Glu Thr Gln Asn Ala Phe Leu Asn Glu Arg
 1               5                  10                  15

<210> SEQ ID NO 49
<211> LENGTH: 15
<212> TYPE: PRT
<213> ORGANISM: H. sapiens

<400> SEQUENCE: 49

Lys Glu Leu Glu Asn Leu Ala Ala Met Asp Leu Glu Leu Gln Lys
 1               5                  10                  15

<210> SEQ ID NO 50
<211> LENGTH: 13
<212> TYPE: PRT
<213> ORGANISM: H. sapiens

<400> SEQUENCE: 50

Met Ala His Gly Tyr Gly Glu Glu Ser Glu Glu Glu Arg
 1               5                  10

<210> SEQ ID NO 51
<211> LENGTH: 9
<212> TYPE: PRT
<213> ORGANISM: H. sapiens

<400> SEQUENCE: 51

Asn His Asn Glu Gly Met Val Thr Arg
 1               5

<210> SEQ ID NO 52
<211> LENGTH: 13
<212> TYPE: PRT
<213> ORGANISM: H. sapiens

<400> SEQUENCE: 52

Asn Tyr Leu Asn Tyr Gly Glu Glu Gly Ala Pro Gly Lys
 1               5                  10

<210> SEQ ID NO 53
<211> LENGTH: 9
<212> TYPE: PRT
<213> ORGANISM: H. sapiens

<400> SEQUENCE: 53

Asn Tyr Pro Ser Leu Glu Leu Asp Lys
 1               5

<210> SEQ ID NO 54
<211> LENGTH: 6
<212> TYPE: PRT
```

<213> ORGANISM: H. sapiens

<400> SEQUENCE: 54

Gln Ala Ser Ala Ile Lys
1               5

<210> SEQ ID NO 55
<211> LENGTH: 16
<212> TYPE: PRT
<213> ORGANISM: H. sapiens

<400> SEQUENCE: 55

Ser Gln Arg Glu Asp Glu Glu Glu Glu Gly Glu Asn Tyr Gln Lys
1               5                   10                  15

<210> SEQ ID NO 56
<211> LENGTH: 11
<212> TYPE: PRT
<213> ORGANISM: H. sapiens

<400> SEQUENCE: 56

Ser Ser Ala Pro Pro Ile Thr Pro Glu Cys Arg
1               5                   10

<210> SEQ ID NO 57
<211> LENGTH: 20
<212> TYPE: PRT
<213> ORGANISM: H. sapiens

<400> SEQUENCE: 57

Ser Ser Gln Glu Ser Gly Glu Glu Ala Gly Ser Gln Glu Asn His Pro
1               5                   10                  15

Gln Glu Ser Lys
            20

<210> SEQ ID NO 58
<211> LENGTH: 12
<212> TYPE: PRT
<213> ORGANISM: H. sapiens

<400> SEQUENCE: 58

Ser Ser Gln Gly Gly Ser Leu Pro Ser Glu Glu Lys
1               5                   10

<210> SEQ ID NO 59
<211> LENGTH: 11
<212> TYPE: PRT
<213> ORGANISM: H. sapiens

<400> SEQUENCE: 59

Val Ala Gln Leu Asp Gln Leu Leu His Tyr Arg
1               5                   10

<210> SEQ ID NO 60
<211> LENGTH: 8
<212> TYPE: PRT
<213> ORGANISM: H. sapiens

<400> SEQUENCE: 60

Val Gln Glu Asn Gln Met Asp Lys
1               5

<210> SEQ ID NO 61
<211> LENGTH: 9

```
<212> TYPE: PRT
<213> ORGANISM: H. sapiens

<400> SEQUENCE: 61

Trp Ala Glu Gly Gly His Ser Arg
 1               5

<210> SEQ ID NO 62
<211> LENGTH: 11
<212> TYPE: PRT
<213> ORGANISM: H. sapiens

<400> SEQUENCE: 62

Trp Gln Gln Gln Gly Asp Leu Gln Asp Thr Lys
 1               5                  10

<210> SEQ ID NO 63
<211> LENGTH: 9
<212> TYPE: PRT
<213> ORGANISM: H. sapiens

<400> SEQUENCE: 63

Ala Val Tyr Leu Pro Asn Cys Asp Arg
 1               5

<210> SEQ ID NO 64
<211> LENGTH: 8
<212> TYPE: PRT
<213> ORGANISM: H. sapiens

<400> SEQUENCE: 64

Gly Ile Cys Trp Cys Val Asp Lys
 1               5

<210> SEQ ID NO 65
<211> LENGTH: 7
<212> TYPE: PRT
<213> ORGANISM: H. sapiens

<400> SEQUENCE: 65

Gly Val Cys Leu Asn Glu Lys
 1               5

<210> SEQ ID NO 66
<211> LENGTH: 10
<212> TYPE: PRT
<213> ORGANISM: H. sapiens

<400> SEQUENCE: 66

His Met Glu Ala Ser Leu Gln Glu Leu Lys
 1               5                  10

<210> SEQ ID NO 67
<211> LENGTH: 9
<212> TYPE: PRT
<213> ORGANISM: H. sapiens

<400> SEQUENCE: 67

Gln Glu Ser Glu Gln Gly Pro Cys Arg
 1               5

<210> SEQ ID NO 68
<211> LENGTH: 22
<212> TYPE: PRT
<213> ORGANISM: H. sapiens
```

-continued

```
<400> SEQUENCE: 68

Asp Cys Ser Gln Glu Asp Asn Asn Val Glu Gly Leu Ala His Leu Met
1               5                   10                  15

Met Gly Asp Gln Gly Lys
            20

<210> SEQ ID NO 69
<211> LENGTH: 18
<212> TYPE: PRT
<213> ORGANISM: H. sapiens

<400> SEQUENCE: 69

Asp Met Thr Val Phe Ser Gly Leu Phe Val Gly Gly Leu Pro Pro Glu
1               5                   10                  15

Leu Arg

<210> SEQ ID NO 70
<211> LENGTH: 11
<212> TYPE: PRT
<213> ORGANISM: H. sapiens

<400> SEQUENCE: 70

Glu Pro Tyr Pro Gly Ser Ala Glu Val Ile Arg
1               5                   10

<210> SEQ ID NO 71
<211> LENGTH: 8
<212> TYPE: PRT
<213> ORGANISM: H. sapiens

<400> SEQUENCE: 71

Met Gly Thr Ala Leu Leu Gln Arg
1               5

<210> SEQ ID NO 72
<211> LENGTH: 12
<212> TYPE: PRT
<213> ORGANISM: H. sapiens

<400> SEQUENCE: 72

Asn Gly Asp Ile Asp Tyr Cys Glu Leu Asn Ala Arg
1               5                   10

<210> SEQ ID NO 73
<211> LENGTH: 6
<212> TYPE: PRT
<213> ORGANISM: H. sapiens

<400> SEQUENCE: 73

Asn Asn Gly Met Cys Arg
1               5

<210> SEQ ID NO 74
<211> LENGTH: 5
<212> TYPE: PRT
<213> ORGANISM: H. sapiens

<400> SEQUENCE: 74

Gln Gly Asp Pro Lys
1               5

<210> SEQ ID NO 75
```

```
<211> LENGTH: 13
<212> TYPE: PRT
<213> ORGANISM: H. sapiens

<400> SEQUENCE: 75

Thr Leu Gln Arg Asn Gly Leu Met Leu His Thr Gly Lys
1               5                   10

<210> SEQ ID NO 76
<211> LENGTH: 8
<212> TYPE: PRT
<213> ORGANISM: H. sapiens

<400> SEQUENCE: 76

Phe Gln Leu Thr Phe Pro Leu Arg
1               5

<210> SEQ ID NO 77
<211> LENGTH: 6
<212> TYPE: PRT
<213> ORGANISM: H. sapiens

<400> SEQUENCE: 77

Ile Asp Glu Leu Glu Arg
1               5

<210> SEQ ID NO 78
<211> LENGTH: 9
<212> TYPE: PRT
<213> ORGANISM: H. sapiens

<400> SEQUENCE: 78

Leu Glu Asn Leu Glu Gln Tyr Ser Arg
1               5

<210> SEQ ID NO 79
<211> LENGTH: 14
<212> TYPE: PRT
<213> ORGANISM: H. sapiens

<400> SEQUENCE: 79

Gln Pro Gly Ser Gly Lys Asn Thr Met Gly Asp Leu Ser Arg
1               5                   10

<210> SEQ ID NO 80
<211> LENGTH: 18
<212> TYPE: PRT
<213> ORGANISM: H. sapiens

<400> SEQUENCE: 80

Thr Pro Ala Ala Glu Thr Leu Ser Gln Leu Gly Gln Thr Leu Gln Ser
1               5                   10                  15

Leu Lys

<210> SEQ ID NO 81
<211> LENGTH: 8
<212> TYPE: PRT
<213> ORGANISM: H. sapiens

<400> SEQUENCE: 81

Val Asn Thr Leu Glu Glu Gly Lys
1               5

<210> SEQ ID NO 82
```

```
<211> LENGTH: 7
<212> TYPE: PRT
<213> ORGANISM: H. sapiens

<400> SEQUENCE: 82

Trp Thr Phe Glu Ala Cys Arg
1               5

<210> SEQ ID NO 83
<211> LENGTH: 12
<212> TYPE: PRT
<213> ORGANISM: H. sapiens

<400> SEQUENCE: 83

Ala Asp Gln Asp Thr Ile Arg Glu Leu Thr Gly Lys
1               5                   10

<210> SEQ ID NO 84
<211> LENGTH: 22
<212> TYPE: PRT
<213> ORGANISM: H. sapiens

<400> SEQUENCE: 84

Asp Thr Met Ala Asp Gly Pro Trp Asp Ser Pro Ala Leu Ile Leu Glu
1               5                   10                  15

Leu Glu Asp Ala Val Arg
            20

<210> SEQ ID NO 85
<211> LENGTH: 14
<212> TYPE: PRT
<213> ORGANISM: H. sapiens

<400> SEQUENCE: 85

Glu Glu Leu Leu Leu Leu Gln Ser Thr Ala Glu Gln Leu Arg
1               5                   10

<210> SEQ ID NO 86
<211> LENGTH: 8
<212> TYPE: PRT
<213> ORGANISM: H. sapiens

<400> SEQUENCE: 86

Glu Leu Asp Val Leu Gln Gly Arg
1               5

<210> SEQ ID NO 87
<211> LENGTH: 5
<212> TYPE: PRT
<213> ORGANISM: H. sapiens

<400> SEQUENCE: 87

Glu Leu Thr Gly Lys
1               5

<210> SEQ ID NO 88
<211> LENGTH: 9
<212> TYPE: PRT
<213> ORGANISM: H. sapiens

<400> SEQUENCE: 88

Gly Leu Gln Gly Ala Gly Pro Arg Arg
1               5
```

```
<210> SEQ ID NO 89
<211> LENGTH: 10
<212> TYPE: PRT
<213> ORGANISM: H. sapiens

<400> SEQUENCE: 89

Ile Asp Arg Leu Glu Glu Leu Pro Ala Arg
1               5                   10

<210> SEQ ID NO 90
<211> LENGTH: 6
<212> TYPE: PRT
<213> ORGANISM: H. sapiens

<400> SEQUENCE: 90

Ile Ser Ile Pro Ile Arg
1               5

<210> SEQ ID NO 91
<211> LENGTH: 7
<212> TYPE: PRT
<213> ORGANISM: H. sapiens

<400> SEQUENCE: 91

Leu Glu Glu Leu Pro Ala Arg
1               5

<210> SEQ ID NO 92
<211> LENGTH: 10
<212> TYPE: PRT
<213> ORGANISM: H. sapiens

<400> SEQUENCE: 92

Leu Val Glu Ala Phe Gly Gly Ala Thr Lys
1               5                   10

<210> SEQ ID NO 93
<211> LENGTH: 17
<212> TYPE: PRT
<213> ORGANISM: H. sapiens

<400> SEQUENCE: 93

Met Asp Gln Leu Glu Gly Gln Leu Leu Ala Gln Val Leu Ala Leu Glu
1               5                   10                  15

Lys

<210> SEQ ID NO 94
<211> LENGTH: 15
<212> TYPE: PRT
<213> ORGANISM: H. sapiens

<400> SEQUENCE: 94

Gln Arg Gln Glu Val Glu Lys Glu Leu Asp Val Leu Gln Gly Arg
1               5                   10                  15

<210> SEQ ID NO 95
<211> LENGTH: 9
<212> TYPE: PRT
<213> ORGANISM: H. sapiens

<400> SEQUENCE: 95

Gln Thr Ala Leu Gln Gln Glu Ala Arg
1               5
```

```
<210> SEQ ID NO 96
<211> LENGTH: 11
<212> TYPE: PRT
<213> ORGANISM: H. sapiens

<400> SEQUENCE: 96

Gln Thr Ala Leu Gln Gln Glu Ala Arg Ile Arg
 1               5                  10

<210> SEQ ID NO 97
<211> LENGTH: 8
<212> TYPE: PRT
<213> ORGANISM: H. sapiens

<400> SEQUENCE: 97

Val Ala Leu Ser His Ser Ser Arg
 1               5

<210> SEQ ID NO 98
<211> LENGTH: 18
<212> TYPE: PRT
<213> ORGANISM: H. sapiens

<400> SEQUENCE: 98

Glu Ile Thr Val Ala Thr Gly Gly Phe Ile Tyr Thr Gly Glu Val Val
 1               5                  10                  15

His Arg

<210> SEQ ID NO 99
<211> LENGTH: 8
<212> TYPE: PRT
<213> ORGANISM: H. sapiens

<400> SEQUENCE: 99

Ile Gln Gln Ile Pro Asn Val Arg
 1               5

<210> SEQ ID NO 100
<211> LENGTH: 6
<212> TYPE: PRT
<213> ORGANISM: H. sapiens

<400> SEQUENCE: 100

Gly Arg Arg Ala Leu Arg
 1               5

<210> SEQ ID NO 101
<211> LENGTH: 6
<212> TYPE: PRT
<213> ORGANISM: H. sapiens

<400> SEQUENCE: 101

His Pro Thr Met Leu Lys
 1               5

<210> SEQ ID NO 102
<211> LENGTH: 7
<212> TYPE: PRT
<213> ORGANISM: H. sapiens

<400> SEQUENCE: 102

Met Ala Val Glu Tyr Asp Arg
 1               5
```

```
<210> SEQ ID NO 103
<211> LENGTH: 7
<212> TYPE: PRT
<213> ORGANISM: H. sapiens

<400> SEQUENCE: 103

Met Ser Pro Ala Val Arg Arg
1               5

<210> SEQ ID NO 104
<211> LENGTH: 16
<212> TYPE: PRT
<213> ORGANISM: H. sapiens

<400> SEQUENCE: 104

Met Ser Pro Trp Ala Ser Gly Gly His Phe Met Asn Thr Ala Glu Arg
1               5                   10                  15

<210> SEQ ID NO 105
<211> LENGTH: 21
<212> TYPE: PRT
<213> ORGANISM: H. sapiens

<400> SEQUENCE: 105

Ser Leu Ala Gly Pro Ala Gly Ala Ala Pro Ala Pro Gly Leu Gly Ala
1               5                   10                  15

Ala Ala Ala Ala Pro
            20

<210> SEQ ID NO 106
<211> LENGTH: 13
<212> TYPE: PRT
<213> ORGANISM: H. sapiens

<400> SEQUENCE: 106

Thr Gly Ala Gly Pro Gly Arg Gly Gly Leu Arg Ala Arg
1               5                   10

<210> SEQ ID NO 107
<211> LENGTH: 9
<212> TYPE: PRT
<213> ORGANISM: H. sapiens

<400> SEQUENCE: 107

Cys Asp Glu Pro Ile Leu Ser Asn Arg
1               5

<210> SEQ ID NO 108
<211> LENGTH: 14
<212> TYPE: PRT
<213> ORGANISM: H. sapiens

<400> SEQUENCE: 108

Leu Tyr Thr Leu Val Leu Thr Asp Pro Asp Ala Pro Ser Arg
1               5                   10

<210> SEQ ID NO 109
<211> LENGTH: 23
<212> TYPE: PRT
<213> ORGANISM: H. sapiens

<400> SEQUENCE: 109

Ala Ala Gln Leu Arg Pro Ile Ser Leu Pro Gly Val Ser Ser Thr Glu
1               5                   10                  15
```

Asp Leu Gln Asp Leu Phe Arg
            20

<210> SEQ ID NO 110
<211> LENGTH: 11
<212> TYPE: PRT
<213> ORGANISM: H. sapiens

<400> SEQUENCE: 110

Phe Ser Gln Phe Leu Gly Asp Pro Val Glu Lys
1               5                   10

<210> SEQ ID NO 111
<211> LENGTH: 21
<212> TYPE: PRT
<213> ORGANISM: H. sapiens

<400> SEQUENCE: 111

Leu Thr Tyr Gln Glu Ile Trp Thr Ser Leu Gly Ser Ala Met Pro Glu
1               5                   10                  15

Pro Glu Ser Leu Arg
            20

<210> SEQ ID NO 112
<211> LENGTH: 9
<212> TYPE: PRT
<213> ORGANISM: H. sapiens

<400> SEQUENCE: 112

Gln Ser Leu Asp Gln Val Thr Asn Arg
1               5

<210> SEQ ID NO 113
<211> LENGTH: 8
<212> TYPE: PRT
<213> ORGANISM: H. sapiens

<400> SEQUENCE: 113

Thr Gly Gln Asp Val Asp Gly Lys
1               5

<210> SEQ ID NO 114
<211> LENGTH: 7
<212> TYPE: PRT
<213> ORGANISM: H. sapiens

<400> SEQUENCE: 114

Tyr Ser Phe Leu Glu Leu Arg
1               5

<210> SEQ ID NO 115
<211> LENGTH: 9
<212> TYPE: PRT
<213> ORGANISM: H. sapiens

<400> SEQUENCE: 115

Asp Arg Phe Val Asn Asp Tyr Asp Lys
1               5

<210> SEQ ID NO 116
<211> LENGTH: 8
<212> TYPE: PRT
<213> ORGANISM: H. sapiens

<400> SEQUENCE: 116

```
Leu Gly His Glu Glu Gln Gln Lys
 1               5

<210> SEQ ID NO 117
<211> LENGTH: 19
<212> TYPE: PRT
<213> ORGANISM: H. sapiens

<400> SEQUENCE: 117

Val Ile Asp Phe Asp Glu Asn Thr Ala Leu Asp Asp Ala Glu Glu Glu
 1               5                  10                  15

Ser Phe Arg

<210> SEQ ID NO 118
<211> LENGTH: 11
<212> TYPE: PRT
<213> ORGANISM: H. sapiens

<400> SEQUENCE: 118

Ala Asp Gln Thr Val Leu Thr Glu Asp Glu Lys
 1               5                  10

<210> SEQ ID NO 119
<211> LENGTH: 13
<212> TYPE: PRT
<213> ORGANISM: H. sapiens

<400> SEQUENCE: 119

Ala Ser Glu Glu Glu Pro Glu Tyr Gly Glu Glu Ile Lys
 1               5                  10

<210> SEQ ID NO 120
<211> LENGTH: 8
<212> TYPE: PRT
<213> ORGANISM: H. sapiens

<400> SEQUENCE: 120

Ala Tyr Phe Met Ser Asp Thr Arg
 1               5

<210> SEQ ID NO 121
<211> LENGTH: 8
<212> TYPE: PRT
<213> ORGANISM: H. sapiens

<400> SEQUENCE: 121

Gly Glu Asp Ser Ser Glu Glu Lys
 1               5

<210> SEQ ID NO 122
<211> LENGTH: 6
<212> TYPE: PRT
<213> ORGANISM: H. sapiens

<400> SEQUENCE: 122

Gly Leu Glu Pro Gly Lys
 1               5

<210> SEQ ID NO 123
<211> LENGTH: 6
<212> TYPE: PRT
<213> ORGANISM: H. sapiens

<400> SEQUENCE: 123
```

```
Gly Ser Glu Glu Tyr Arg
1               5
```

<210> SEQ ID NO 124
<211> LENGTH: 7
<212> TYPE: PRT
<213> ORGANISM: H. sapiens

<400> SEQUENCE: 124

```
His Pro Gln Gly Ala Trp Lys
1               5
```

<210> SEQ ID NO 125
<211> LENGTH: 7
<212> TYPE: PRT
<213> ORGANISM: H. sapiens

<400> SEQUENCE: 125

```
Lys Glu Glu Leu Val Ala Arg
1               5
```

<210> SEQ ID NO 126
<211> LENGTH: 9
<212> TYPE: PRT
<213> ORGANISM: H. sapiens

<400> SEQUENCE: 126

```
Asn His Asn Glu Gly Met Val Thr Arg
1               5
```

<210> SEQ ID NO 127
<211> LENGTH: 13
<212> TYPE: PRT
<213> ORGANISM: H. sapiens

<400> SEQUENCE: 127

```
Asn Tyr Leu Asn Tyr Gly Glu Glu Gly Ala Pro Gly Lys
1               5                   10
```

<210> SEQ ID NO 128
<211> LENGTH: 9
<212> TYPE: PRT
<213> ORGANISM: H. sapiens

<400> SEQUENCE: 128

```
Asn Tyr Pro Ser Leu Glu Leu Asp Lys
1               5
```

<210> SEQ ID NO 129
<211> LENGTH: 6
<212> TYPE: PRT
<213> ORGANISM: H. sapiens

<400> SEQUENCE: 129

```
Gln Ala Ser Ala Ile Lys
1               5
```

<210> SEQ ID NO 130
<211> LENGTH: 11
<212> TYPE: PRT
<213> ORGANISM: H. sapiens

<400> SEQUENCE: 130

```
Ser Ser Ala Pro Pro Ile Thr Pro Glu Cys Arg
```

```
            1               5                   10
```

<210> SEQ ID NO 131
<211> LENGTH: 12
<212> TYPE: PRT
<213> ORGANISM: H. sapiens

<400> SEQUENCE: 131

```
Ser Ser Gln Gly Gly Ser Leu Pro Ser Glu Glu Lys
 1               5                   10
```

<210> SEQ ID NO 132
<211> LENGTH: 6
<212> TYPE: PRT
<213> ORGANISM: H. sapiens

<400> SEQUENCE: 132

```
Thr Arg His Ser Glu Lys
 1               5
```

<210> SEQ ID NO 133
<211> LENGTH: 11
<212> TYPE: PRT
<213> ORGANISM: H. sapiens

<400> SEQUENCE: 133

```
Val Ala Gln Leu Asp Gln Leu Leu His Tyr Arg
 1               5                   10
```

<210> SEQ ID NO 134
<211> LENGTH: 8
<212> TYPE: PRT
<213> ORGANISM: H. sapiens

<400> SEQUENCE: 134

```
Val Gln Glu Asn Gln Met Asp Lys
 1               5
```

<210> SEQ ID NO 135
<211> LENGTH: 9
<212> TYPE: PRT
<213> ORGANISM: H. sapiens

<400> SEQUENCE: 135

```
Trp Ala Glu Gly Gly Gly His Ser Arg
 1               5
```

<210> SEQ ID NO 136
<211> LENGTH: 11
<212> TYPE: PRT
<213> ORGANISM: H. sapiens

<400> SEQUENCE: 136

```
Trp Gln Gln Gln Gly Asp Leu Gln Asp Thr Lys
 1               5                   10
```

<210> SEQ ID NO 137
<211> LENGTH: 5
<212> TYPE: PRT
<213> ORGANISM: H. sapiens

<400> SEQUENCE: 137

```
Ala Ile Thr Glu Lys
 1               5
```

```
<210> SEQ ID NO 138
<211> LENGTH: 5
<212> TYPE: PRT
<213> ORGANISM: H. sapiens

<400> SEQUENCE: 138

Ala Val Phe Asp Lys
1               5

<210> SEQ ID NO 139
<211> LENGTH: 5
<212> TYPE: PRT
<213> ORGANISM: H. sapiens

<400> SEQUENCE: 139

Asp Phe Ile Asn Lys
1               5

<210> SEQ ID NO 140
<211> LENGTH: 19
<212> TYPE: PRT
<213> ORGANISM: H. sapiens

<400> SEQUENCE: 140

Glu Leu Ser Ala Glu Arg Pro Leu Asn Glu Gln Ile Ala Glu Ala Glu
1               5                   10                  15

Glu Asp Lys

<210> SEQ ID NO 141
<211> LENGTH: 21
<212> TYPE: PRT
<213> ORGANISM: H. sapiens

<400> SEQUENCE: 141

Glu Leu Ser Ala Glu Arg Pro Leu Asn Glu Gln Ile Ala Glu Ala Glu
1               5                   10                  15

Glu Asp Lys Ile Lys
            20

<210> SEQ ID NO 142
<211> LENGTH: 6
<212> TYPE: PRT
<213> ORGANISM: H. sapiens

<400> SEQUENCE: 142

Glu Tyr Gly Ser Leu Lys
1               5

<210> SEQ ID NO 143
<211> LENGTH: 24
<212> TYPE: PRT
<213> ORGANISM: H. sapiens

<400> SEQUENCE: 143

Phe Gln Asp Asp Pro Asp Gly Leu His Gln Leu Asp Gly Thr Pro Leu
1               5                   10                  15

Thr Ala Glu Asp Ile Val His Lys
            20

<210> SEQ ID NO 144
<211> LENGTH: 10
<212> TYPE: PRT
<213> ORGANISM: H. sapiens
```

-continued

<400> SEQUENCE: 144

Gly Asn Lys Glu Asp Tyr Asp Leu Ser Lys
1               5                   10

<210> SEQ ID NO 145
<211> LENGTH: 7
<212> TYPE: PRT
<213> ORGANISM: H. sapiens

<400> SEQUENCE: 145

Ile Tyr Glu Glu Asn Asp Arg
1               5

<210> SEQ ID NO 146
<211> LENGTH: 10
<212> TYPE: PRT
<213> ORGANISM: H. sapiens

<400> SEQUENCE: 146

Lys Leu Ile Asp Asp Tyr Asp Ser Thr Lys
1               5                   10

<210> SEQ ID NO 147
<211> LENGTH: 9
<212> TYPE: PRT
<213> ORGANISM: H. sapiens

<400> SEQUENCE: 147

Leu Ile Asp Asp Tyr Asp Ser Thr Lys
1               5

<210> SEQ ID NO 148
<211> LENGTH: 6
<212> TYPE: PRT
<213> ORGANISM: H. sapiens

<400> SEQUENCE: 148

Asn Ile Glu Trp Leu Lys
1               5

<210> SEQ ID NO 149
<211> LENGTH: 25
<212> TYPE: PRT
<213> ORGANISM: H. sapiens

<400> SEQUENCE: 149

Tyr Gly Thr Ile Ser Pro Glu Glu Gly Val Ser Tyr Leu Glu Asn Leu
1               5                   10                  15

Asp Glu Met Ile Ala Leu Gln Thr Lys
            20                  25

<210> SEQ ID NO 150
<211> LENGTH: 6
<212> TYPE: PRT
<213> ORGANISM: H. sapiens

<400> SEQUENCE: 150

Glu Leu Glu Ala Phe Arg
1               5

<210> SEQ ID NO 151
<211> LENGTH: 8
<212> TYPE: PRT

```
<213> ORGANISM: H. sapiens

<400> SEQUENCE: 151

Phe Phe Gln Tyr Asp Thr Trp Lys
1               5

<210> SEQ ID NO 152
<211> LENGTH: 5
<212> TYPE: PRT
<213> ORGANISM: H. sapiens

<400> SEQUENCE: 152

Gly Phe Tyr Phe Arg
1               5

<210> SEQ ID NO 153
<211> LENGTH: 6
<212> TYPE: PRT
<213> ORGANISM: H. sapiens

<400> SEQUENCE: 153

Gly His Val Leu Ala Lys
1               5

<210> SEQ ID NO 154
<211> LENGTH: 9
<212> TYPE: PRT
<213> ORGANISM: H. sapiens

<400> SEQUENCE: 154

Gly Ile Val Glu Glu Cys Cys Phe Arg
1               5

<210> SEQ ID NO 155
<211> LENGTH: 7
<212> TYPE: PRT
<213> ORGANISM: H. sapiens

<400> SEQUENCE: 155

Gly Leu Pro Ala Leu Leu Arg
1               5

<210> SEQ ID NO 156
<211> LENGTH: 16
<212> TYPE: PRT
<213> ORGANISM: H. sapiens

<400> SEQUENCE: 156

Ser Cys Asp Leu Ala Leu Leu Glu Thr Tyr Cys Ala Thr Pro Ala Lys
1               5                   10                  15

<210> SEQ ID NO 157
<211> LENGTH: 5
<212> TYPE: PRT
<213> ORGANISM: H. sapiens

<400> SEQUENCE: 157

Tyr Pro Val Gly Lys
1               5

<210> SEQ ID NO 158
<211> LENGTH: 9
<212> TYPE: PRT
<213> ORGANISM: H. sapiens
```

```
<400> SEQUENCE: 158

Phe Tyr Phe Glu Asn Leu Leu Ala Lys
 1               5

<210> SEQ ID NO 159
<211> LENGTH: 11
<212> TYPE: PRT
<213> ORGANISM: H. sapiens

<400> SEQUENCE: 159

Gly Ala Ile Leu Thr Thr Met Leu Ala Thr Arg
 1               5                  10

<210> SEQ ID NO 160
<211> LENGTH: 12
<212> TYPE: PRT
<213> ORGANISM: H. sapiens

<400> SEQUENCE: 160

Phe Asp Glu Leu Asp Met Ser Pro Gly Asp Pro Lys
 1               5                  10

<210> SEQ ID NO 161
<211> LENGTH: 13
<212> TYPE: PRT
<213> ORGANISM: H. sapiens

<400> SEQUENCE: 161

Gly Gly His Gly Gln Gln Asp Leu Phe Arg Val Leu Lys
 1               5                  10

<210> SEQ ID NO 162
<211> LENGTH: 7
<212> TYPE: PRT
<213> ORGANISM: H. sapiens

<400> SEQUENCE: 162

Gly Ile Pro Pro Ser Leu Arg
 1               5

<210> SEQ ID NO 163
<211> LENGTH: 7
<212> TYPE: PRT
<213> ORGANISM: H. sapiens

<400> SEQUENCE: 163

Leu Arg Ser Leu Ser Pro Lys
 1               5

<210> SEQ ID NO 164
<211> LENGTH: 9
<212> TYPE: PRT
<213> ORGANISM: H. sapiens

<400> SEQUENCE: 164

Tyr Leu Pro Gly Tyr Tyr Ser Glu Lys
 1               5

<210> SEQ ID NO 165
<211> LENGTH: 11
<212> TYPE: PRT
<213> ORGANISM: H. sapiens

<400> SEQUENCE: 165
```

```
Asp Ile Gln Gly Ser Leu Gln Asp Ile Phe Lys
1               5                   10
```

<210> SEQ ID NO 166
<211> LENGTH: 16
<212> TYPE: PRT
<213> ORGANISM: H. sapiens

<400> SEQUENCE: 166

```
Gly Ile Phe Arg Ile Asn Glu Asn Thr Gly Ser Val Ser Val Thr Arg
1               5                   10                  15
```

<210> SEQ ID NO 167
<211> LENGTH: 7
<212> TYPE: PRT
<213> ORGANISM: H. sapiens

<400> SEQUENCE: 167

```
Thr Leu Phe Val His Ala Arg
1               5
```

<210> SEQ ID NO 168
<211> LENGTH: 16
<212> TYPE: PRT
<213> ORGANISM: H. sapiens

<400> SEQUENCE: 168

```
Thr Pro His Ala Glu Asp Met Ala Glu Leu Val Ile Val Gly Gly Lys
1               5                   10                  15
```

<210> SEQ ID NO 169
<211> LENGTH: 10
<212> TYPE: PRT
<213> ORGANISM: H. sapiens

<400> SEQUENCE: 169

```
Val Asp Cys Asn Ala Ala Gly Ala Leu Arg
1               5                   10
```

<210> SEQ ID NO 170
<211> LENGTH: 11
<212> TYPE: PRT
<213> ORGANISM: H. sapiens

<400> SEQUENCE: 170

```
Val Asn Ser Asp Gly Gly Leu Val Ala Leu Arg
1               5                   10
```

<210> SEQ ID NO 171
<211> LENGTH: 9
<212> TYPE: PRT
<213> ORGANISM: H. sapiens

<400> SEQUENCE: 171

```
Tyr Glu Val Ser Ser Pro Tyr Phe Lys
1               5
```

<210> SEQ ID NO 172
<211> LENGTH: 7
<212> TYPE: PRT
<213> ORGANISM: H. sapiens

<400> SEQUENCE: 172

```
Ile Leu Ile Glu Asp Trp Lys
1               5
```

```
<210> SEQ ID NO 173
<211> LENGTH: 11
<212> TYPE: PRT
<213> ORGANISM: H. sapiens

<400> SEQUENCE: 173

Thr Val Lys Glu Glu Ala Glu Lys Pro Glu Arg
 1               5                  10

<210> SEQ ID NO 174
<211> LENGTH: 6
<212> TYPE: PRT
<213> ORGANISM: H. sapiens

<400> SEQUENCE: 174

Ala Glu Met Glu Glu Lys
 1               5

<210> SEQ ID NO 175
<211> LENGTH: 7
<212> TYPE: PRT
<213> ORGANISM: H. sapiens

<400> SEQUENCE: 175

Ala Gln Glu Ile Tyr Glu Lys
 1               5

<210> SEQ ID NO 176
<211> LENGTH: 8
<212> TYPE: PRT
<213> ORGANISM: H. sapiens

<400> SEQUENCE: 176

Asp Leu Val Glu Met Glu Gln Lys
 1               5

<210> SEQ ID NO 177
<211> LENGTH: 7
<212> TYPE: PRT
<213> ORGANISM: H. sapiens

<400> SEQUENCE: 177

Asp Val Gln Leu Gln Gln Lys
 1               5

<210> SEQ ID NO 178
<211> LENGTH: 17
<212> TYPE: PRT
<213> ORGANISM: H. sapiens

<400> SEQUENCE: 178

Glu Ala Leu Lys Glu Asn Lys Ser Leu Gln Glu Glu Leu Ser Leu Ala
 1               5                  10                  15

Arg

<210> SEQ ID NO 179
<211> LENGTH: 20
<212> TYPE: PRT
<213> ORGANISM: H. sapiens

<400> SEQUENCE: 179

Glu Glu Asp Val Ser Tyr Leu Ser Gly Gln Leu Ser Glu Lys Glu Ala
 1               5                  10                  15
```

```
Ala Leu Thr Lys
        20

<210> SEQ ID NO 180
<211> LENGTH: 24
<212> TYPE: PRT
<213> ORGANISM: H. sapiens

<400> SEQUENCE: 180

Glu Ile Lys Glu Leu Glu Asn Leu Leu Ser Gln Glu Glu Glu Glu Asn
1               5                   10                  15

Ile Val Leu Glu Glu Glu Asn Lys
        20

<210> SEQ ID NO 181
<211> LENGTH: 5
<212> TYPE: PRT
<213> ORGANISM: H. sapiens

<400> SEQUENCE: 181

Glu Leu Leu Gln Arg
1               5

<210> SEQ ID NO 182
<211> LENGTH: 10
<212> TYPE: PRT
<213> ORGANISM: H. sapiens

<400> SEQUENCE: 182

Glu Leu Leu Ser Gln Leu Glu Glu Thr Arg
1               5                   10

<210> SEQ ID NO 183
<211> LENGTH: 16
<212> TYPE: PRT
<213> ORGANISM: H. sapiens

<400> SEQUENCE: 183

Glu Met Lys Gln Met Glu Gly Glu Gly Ile Ala Pro Ile Lys Met Lys
1               5                   10                  15

<210> SEQ ID NO 184
<211> LENGTH: 10
<212> TYPE: PRT
<213> ORGANISM: H. sapiens

<400> SEQUENCE: 184

Glu Asn Glu Asn Ile Gly Asp Gln Leu Arg
1               5                   10

<210> SEQ ID NO 185
<211> LENGTH: 10
<212> TYPE: PRT
<213> ORGANISM: H. sapiens

<400> SEQUENCE: 185

Glu Asn Leu Ala Gln Ala Val Glu His Arg
1               5                   10

<210> SEQ ID NO 186
<211> LENGTH: 6
<212> TYPE: PRT
<213> ORGANISM: H. sapiens
```

```
<400> SEQUENCE: 186

Leu Asp Glu Leu Gln Lys
1               5

<210> SEQ ID NO 187
<211> LENGTH: 6
<212> TYPE: PRT
<213> ORGANISM: H. sapiens

<400> SEQUENCE: 187

Leu Leu Met Val Thr Lys
1               5

<210> SEQ ID NO 188
<211> LENGTH: 9
<212> TYPE: PRT
<213> ORGANISM: H. sapiens

<400> SEQUENCE: 188

Asn Glu Thr Glu Thr Ala Glu Glu Arg
1               5

<210> SEQ ID NO 189
<211> LENGTH: 5
<212> TYPE: PRT
<213> ORGANISM: H. sapiens

<400> SEQUENCE: 189

Gln Asp Gly Asp Lys
1               5

<210> SEQ ID NO 190
<211> LENGTH: 11
<212> TYPE: PRT
<213> ORGANISM: H. sapiens

<400> SEQUENCE: 190

Ser Met Ser Ser Leu Gln Asn Asp Arg Asp Arg
1               5                   10

<210> SEQ ID NO 191
<211> LENGTH: 13
<212> TYPE: PRT
<213> ORGANISM: H. sapiens

<400> SEQUENCE: 191

Ser Ser Lys Ile Ala Glu Ser Thr Glu Trp Gln Glu Lys
1               5                   10

<210> SEQ ID NO 192
<211> LENGTH: 8
<212> TYPE: PRT
<213> ORGANISM: H. sapiens

<400> SEQUENCE: 192

Ser Ser Trp Glu Ile His Glu Arg
1               5

<210> SEQ ID NO 193
<211> LENGTH: 9
<212> TYPE: PRT
<213> ORGANISM: H. sapiens

<400> SEQUENCE: 193
```

-continued

Ala Gln Pro Gly Trp Gly Ser Pro Arg
1               5

<210> SEQ ID NO 194
<211> LENGTH: 14
<212> TYPE: PRT
<213> ORGANISM: H. sapiens

<400> SEQUENCE: 194

Glu Gln Asp Ala Pro Val Ala Gly Leu Gln Pro Val Glu Arg
1               5                   10

<210> SEQ ID NO 195
<211> LENGTH: 13
<212> TYPE: PRT
<213> ORGANISM: H. sapiens

<400> SEQUENCE: 195

Arg Pro Gly Gly Ser Tyr Pro Ala Ala Ala Ala Ala Lys
1               5                   10

<210> SEQ ID NO 196
<211> LENGTH: 12
<212> TYPE: PRT
<213> ORGANISM: H. sapiens

<400> SEQUENCE: 196

Ser Thr Pro Leu Gly Gln Gln Gln Pro Ala Pro Arg
1               5                   10

<210> SEQ ID NO 197
<211> LENGTH: 10
<212> TYPE: PRT
<213> ORGANISM: H. sapiens

<400> SEQUENCE: 197

Tyr Glu Pro Ala Gly Gly Asp Ala Asn Arg
1               5                   10

<210> SEQ ID NO 198
<211> LENGTH: 7
<212> TYPE: PRT
<213> ORGANISM: H. sapiens

<400> SEQUENCE: 198

Leu Ala Leu Phe Pro Asp Lys
1               5

<210> SEQ ID NO 199
<211> LENGTH: 7
<212> TYPE: PRT
<213> ORGANISM: H. sapiens

<400> SEQUENCE: 199

Ser Ala Trp Cys Glu Ala Lys
1               5

<210> SEQ ID NO 200
<211> LENGTH: 11
<212> TYPE: PRT
<213> ORGANISM: H. sapiens

<400> SEQUENCE: 200

Ala Asn Thr Pro Asp Ser Asp Ile Thr Glu Lys
1               5                   10

```
<210> SEQ ID NO 201
<211> LENGTH: 15
<212> TYPE: PRT
<213> ORGANISM: H. sapiens

<400> SEQUENCE: 201

His Gly Leu Asn Gly Ile Leu Ala Asp Glu Met Gly Leu Gly Lys
 1               5                  10                  15

<210> SEQ ID NO 202
<211> LENGTH: 7
<212> TYPE: PRT
<213> ORGANISM: H. sapiens

<400> SEQUENCE: 202

Asn Leu Phe Asn Leu Asp Arg
 1               5

<210> SEQ ID NO 203
<211> LENGTH: 8
<212> TYPE: PRT
<213> ORGANISM: H. sapiens

<400> SEQUENCE: 203

Gln Glu Leu Arg Glu Val Leu Lys
 1               5

<210> SEQ ID NO 204
<211> LENGTH: 12
<212> TYPE: PRT
<213> ORGANISM: H. sapiens

<400> SEQUENCE: 204

Ser Ala Asp Glu Gln Ser Ile Tyr Glu Lys Glu Arg
 1               5                  10

<210> SEQ ID NO 205
<211> LENGTH: 7
<212> TYPE: PRT
<213> ORGANISM: H. sapiens

<400> SEQUENCE: 205

Ser Leu Phe Arg Arg Leu Lys
 1               5

<210> SEQ ID NO 206
<211> LENGTH: 20
<212> TYPE: PRT
<213> ORGANISM: H. sapiens

<400> SEQUENCE: 206

Val Phe Ala Glu Asp Gln Asp Met Gln Tyr Ala Ser Gln Ser Glu Val
 1               5                  10                  15

Pro Asn Gly Lys
            20

<210> SEQ ID NO 207
<211> LENGTH: 12
<212> TYPE: PRT
<213> ORGANISM: H. sapiens

<400> SEQUENCE: 207

Tyr Gln His Leu Met Thr Ile Asn Ala Asn Asn Arg
```

-continued

```
<210> SEQ ID NO 208
<211> LENGTH: 15
<212> TYPE: PRT
<213> ORGANISM: H. sapiens

<400> SEQUENCE: 208

Ala Glu Asp His Phe Ser Val Ile Asp Phe Asn Gln Asn Ile Arg
 1               5                  10                  15

<210> SEQ ID NO 209
<211> LENGTH: 13
<212> TYPE: PRT
<213> ORGANISM: H. sapiens

<400> SEQUENCE: 209

Ala His Gly Leu Ile Gly Gln Phe Met Gln Glu Pro Lys
 1               5                  10

<210> SEQ ID NO 210
<211> LENGTH: 13
<212> TYPE: PRT
<213> ORGANISM: H. sapiens

<400> SEQUENCE: 210

Ala His Val Ser Phe Lys Pro Thr Val Ala Gln Gln Arg
 1               5                  10

<210> SEQ ID NO 211
<211> LENGTH: 8
<212> TYPE: PRT
<213> ORGANISM: H. sapiens

<400> SEQUENCE: 211

Phe Gln Leu Val Ala Glu Asn Arg
 1               5

<210> SEQ ID NO 212
<211> LENGTH: 11
<212> TYPE: PRT
<213> ORGANISM: H. sapiens

<400> SEQUENCE: 212

Phe Tyr Asn Gln Val Ser Thr Pro Leu Leu Arg
 1               5                  10

<210> SEQ ID NO 213
<211> LENGTH: 15
<212> TYPE: PRT
<213> ORGANISM: H. sapiens

<400> SEQUENCE: 213

Ile Gln Pro Ser Gly Gly Thr Asn Ile Asn Glu Ala Leu Leu Arg
 1               5                  10                  15

<210> SEQ ID NO 214
<211> LENGTH: 12
<212> TYPE: PRT
<213> ORGANISM: H. sapiens

<400> SEQUENCE: 214

Ile Tyr Gly Asn Gln Asp Thr Ser Ser Gln Leu Lys
 1               5                  10
```

```
<210> SEQ ID NO 215
<211> LENGTH: 9
<212> TYPE: PRT
<213> ORGANISM: H. sapiens

<400> SEQUENCE: 215

Ser Leu Ala Pro Thr Ala Ala Ala Lys
1               5

<210> SEQ ID NO 216
<211> LENGTH: 10
<212> TYPE: PRT
<213> ORGANISM: H. sapiens

<400> SEQUENCE: 216

Ser Ser Ala Leu Asp Met Glu Asn Phe Arg
1               5                   10

<210> SEQ ID NO 217
<211> LENGTH: 4
<212> TYPE: PRT
<213> ORGANISM: H. sapiens

<400> SEQUENCE: 217

Tyr Ile Glu Lys
1

<210> SEQ ID NO 218
<211> LENGTH: 14
<212> TYPE: PRT
<213> ORGANISM: H. sapiens

<400> SEQUENCE: 218

Glu Gln Leu Gly Glu Phe Tyr Glu Ala Leu Asp Cys Leu Arg
1               5                   10

<210> SEQ ID NO 219
<211> LENGTH: 7
<212> TYPE: PRT
<213> ORGANISM: H. sapiens

<400> SEQUENCE: 219

Lys Gln Glu Glu Gly Glu Ser
1               5

<210> SEQ ID NO 220
<211> LENGTH: 8
<212> TYPE: PRT
<213> ORGANISM: H. sapiens

<400> SEQUENCE: 220

Thr Glu Asp Thr Ile Phe Leu Arg
1               5

<210> SEQ ID NO 221
<211> LENGTH: 9
<212> TYPE: PRT
<213> ORGANISM: H. sapiens

<400> SEQUENCE: 221

Trp Phe Tyr Ile Ala Ser Ala Phe Arg
1               5

<210> SEQ ID NO 222
```

```
<211> LENGTH: 5
<212> TYPE: PRT
<213> ORGANISM: H. sapiens

<400> SEQUENCE: 222

Asp Leu Met Glu Lys
1               5

<210> SEQ ID NO 223
<211> LENGTH: 20
<212> TYPE: PRT
<213> ORGANISM: H. sapiens

<400> SEQUENCE: 223

Glu Pro Cys Val Glu Ser Leu Val Ser Gln Tyr Phe Gln Thr Val Thr
1               5                   10                  15

Asp Tyr Gly Lys
            20

<210> SEQ ID NO 224
<211> LENGTH: 8
<212> TYPE: PRT
<213> ORGANISM: H. sapiens

<400> SEQUENCE: 224

Glu Gln Leu Thr Pro Leu Ile Lys
1               5

<210> SEQ ID NO 225
<211> LENGTH: 10
<212> TYPE: PRT
<213> ORGANISM: H. sapiens

<400> SEQUENCE: 225

Ser Lys Glu Gln Leu Thr Pro Leu Ile Lys
1               5                   10

<210> SEQ ID NO 226
<211> LENGTH: 9
<212> TYPE: PRT
<213> ORGANISM: H. sapiens

<400> SEQUENCE: 226

Ser Pro Glu Leu Gln Ala Glu Ala Lys
1               5

<210> SEQ ID NO 227
<211> LENGTH: 5
<212> TYPE: PRT
<213> ORGANISM: H. sapiens

<400> SEQUENCE: 227

Ser Tyr Phe Glu Lys
1               5

<210> SEQ ID NO 228
<211> LENGTH: 11
<212> TYPE: PRT
<213> ORGANISM: H. sapiens

<400> SEQUENCE: 228

Val Lys Ser Pro Glu Leu Gln Ala Glu Ala Lys
1               5                   10
```

```
<210> SEQ ID NO 229
<211> LENGTH: 9
<212> TYPE: PRT
<213> ORGANISM: H. sapiens

<400> SEQUENCE: 229

Glu Phe Gly Asn Thr Leu Glu Asp Lys
 1               5

<210> SEQ ID NO 230
<211> LENGTH: 9
<212> TYPE: PRT
<213> ORGANISM: H. sapiens

<400> SEQUENCE: 230

Glu Trp Phe Ser Glu Thr Phe Gln Lys
 1               5

<210> SEQ ID NO 231
<211> LENGTH: 11
<212> TYPE: PRT
<213> ORGANISM: H. sapiens

<400> SEQUENCE: 231

Leu Lys Glu Phe Gly Asn Thr Leu Glu Asp Lys
 1               5                  10

<210> SEQ ID NO 232
<211> LENGTH: 7
<212> TYPE: PRT
<213> ORGANISM: H. sapiens

<400> SEQUENCE: 232

Gln Ser Glu Leu Ser Ala Lys
 1               5

<210> SEQ ID NO 233
<211> LENGTH: 14
<212> TYPE: PRT
<213> ORGANISM: H. sapiens

<400> SEQUENCE: 233

Cys Pro Asn Pro Pro Val Gln Glu Asn Phe Asp Val Asn Lys
 1               5                  10

<210> SEQ ID NO 234
<211> LENGTH: 9
<212> TYPE: PRT
<213> ORGANISM: H. sapiens

<400> SEQUENCE: 234

Ile Lys Val Leu Asn Gln Glu Leu Arg
 1               5

<210> SEQ ID NO 235
<211> LENGTH: 11
<212> TYPE: PRT
<213> ORGANISM: H. sapiens

<400> SEQUENCE: 235

Met Thr Val Thr Asp Gln Val Asn Cys Pro Lys
 1               5                  10

<210> SEQ ID NO 236
<211> LENGTH: 11
```

```
<212> TYPE: PRT
<213> ORGANISM: H. sapiens

<400> SEQUENCE: 236

Asn Ile Leu Thr Ser Asn Asn Ile Asp Val Lys
 1               5                  10

<210> SEQ ID NO 237
<211> LENGTH: 13
<212> TYPE: PRT
<213> ORGANISM: H. sapiens

<400> SEQUENCE: 237

Asn Pro Asn Leu Pro Pro Glu Thr Val Asp Ser Leu Lys
 1               5                  10

<210> SEQ ID NO 238
<211> LENGTH: 7
<212> TYPE: PRT
<213> ORGANISM: H. sapiens

<400> SEQUENCE: 238

Val Leu Asn Gln Glu Leu Arg
 1               5

<210> SEQ ID NO 239
<211> LENGTH: 6
<212> TYPE: PRT
<213> ORGANISM: H. sapiens

<400> SEQUENCE: 239

Trp Tyr Glu Ile Glu Lys
 1               5

<210> SEQ ID NO 240
<211> LENGTH: 15
<212> TYPE: PRT
<213> ORGANISM: H. sapiens

<400> SEQUENCE: 240

Ala Ala Thr Val Gly Ser Leu Ala Gly Gln Pro Leu Gln Glu Arg
 1               5                  10                  15

<210> SEQ ID NO 241
<211> LENGTH: 8
<212> TYPE: PRT
<213> ORGANISM: H. sapiens

<400> SEQUENCE: 241

Ala Leu Met Asp Glu Thr Met Lys
 1               5

<210> SEQ ID NO 242
<211> LENGTH: 7
<212> TYPE: PRT
<213> ORGANISM: H. sapiens

<400> SEQUENCE: 242

Ala Gln Ala Trp Gly Glu Arg
 1               5

<210> SEQ ID NO 243
<211> LENGTH: 7
<212> TYPE: PRT
<213> ORGANISM: H. sapiens
```

```
<400> SEQUENCE: 243

Asp Ala Asp Asp Leu Gln Lys
1               5

<210> SEQ ID NO 244
<211> LENGTH: 7
<212> TYPE: PRT
<213> ORGANISM: H. sapiens

<400> SEQUENCE: 244

Asp Arg Leu Asp Glu Val Lys
1               5

<210> SEQ ID NO 245
<211> LENGTH: 11
<212> TYPE: PRT
<213> ORGANISM: H. sapiens

<400> SEQUENCE: 245

Glu Gly Ala Glu Arg Gly Leu Ser Ala Ile Arg
1               5                   10

<210> SEQ ID NO 246
<211> LENGTH: 8
<212> TYPE: PRT
<213> ORGANISM: H. sapiens

<400> SEQUENCE: 246

Glu Leu Gln Ala Ala Gln Ala Arg
1               5

<210> SEQ ID NO 247
<211> LENGTH: 7
<212> TYPE: PRT
<213> ORGANISM: H. sapiens

<400> SEQUENCE: 247

Glu Gln Val Ala Glu Val Arg
1               5

<210> SEQ ID NO 248
<211> LENGTH: 6
<212> TYPE: PRT
<213> ORGANISM: H. sapiens

<400> SEQUENCE: 248

Phe Trp Asp Tyr Leu Arg
1               5

<210> SEQ ID NO 249
<211> LENGTH: 6
<212> TYPE: PRT
<213> ORGANISM: H. sapiens

<400> SEQUENCE: 249

Leu Ala Ser His Leu Arg
1               5

<210> SEQ ID NO 250
<211> LENGTH: 9
<212> TYPE: PRT
<213> ORGANISM: H. sapiens

<400> SEQUENCE: 250
```

Leu Glu Glu Gln Ala Gln Gln Ile Arg
1               5

<210> SEQ ID NO 251
<211> LENGTH: 11
<212> TYPE: PRT
<213> ORGANISM: H. sapiens

<400> SEQUENCE: 251

Leu Gly Ala Asp Met Glu Asp Val Cys Gly Arg
1               5                   10

<210> SEQ ID NO 252
<211> LENGTH: 9
<212> TYPE: PRT
<213> ORGANISM: H. sapiens

<400> SEQUENCE: 252

Leu Gly Pro Leu Val Glu Gln Gly Arg
1               5

<210> SEQ ID NO 253
<211> LENGTH: 9
<212> TYPE: PRT
<213> ORGANISM: H. sapiens

<400> SEQUENCE: 253

Leu Gln Ala Glu Ala Phe Gln Ala Arg
1               5

<210> SEQ ID NO 254
<211> LENGTH: 10
<212> TYPE: PRT
<213> ORGANISM: H. sapiens

<400> SEQUENCE: 254

Gln Gln Thr Glu Trp Gln Ser Gly Gln Arg
1               5                   10

<210> SEQ ID NO 255
<211> LENGTH: 8
<212> TYPE: PRT
<213> ORGANISM: H. sapiens

<400> SEQUENCE: 255

Gln Trp Ala Gly Leu Val Glu Lys
1               5

<210> SEQ ID NO 256
<211> LENGTH: 15
<212> TYPE: PRT
<213> ORGANISM: H. sapiens

<400> SEQUENCE: 256

Ser Glu Leu Glu Glu Gln Leu Thr Pro Val Ala Glu Glu Thr Arg
1               5                   10                  15

<210> SEQ ID NO 257
<211> LENGTH: 12
<212> TYPE: PRT
<213> ORGANISM: H. sapiens

<400> SEQUENCE: 257

Ser Trp Phe Glu Pro Leu Val Glu Asp Met Gln Arg

-continued

<210> SEQ ID NO 258
<211> LENGTH: 14
<212> TYPE: PRT
<213> ORGANISM: H. sapiens

<400> SEQUENCE: 258

Val Glu Gln Ala Val Glu Thr Glu Pro Glu Pro Glu Leu Arg
1               5                   10

<210> SEQ ID NO 259
<211> LENGTH: 7
<212> TYPE: PRT
<213> ORGANISM: H. sapiens

<400> SEQUENCE: 259

Trp Glu Leu Ala Leu Gly Arg
1               5

<210> SEQ ID NO 260
<211> LENGTH: 9
<212> TYPE: PRT
<213> ORGANISM: H. sapiens

<400> SEQUENCE: 260

Ala Thr Val Val Tyr Gln Gly Glu Arg
1               5

<210> SEQ ID NO 261
<211> LENGTH: 10
<212> TYPE: PRT
<213> ORGANISM: H. sapiens

<400> SEQUENCE: 261

Lys Ala Thr Val Val Tyr Gln Gly Glu Arg
1               5                   10

<210> SEQ ID NO 262
<211> LENGTH: 6
<212> TYPE: PRT
<213> ORGANISM: H. sapiens

<400> SEQUENCE: 262

Val Ser Phe Phe Cys Lys
1               5

<210> SEQ ID NO 263
<211> LENGTH: 15
<212> TYPE: PRT
<213> ORGANISM: H. sapiens

<400> SEQUENCE: 263

Gly Glu Ala Gly Ala Ala Gly Pro Ala Gly Pro Ala Gly Pro Arg
1               5                   10                  15

<210> SEQ ID NO 264
<211> LENGTH: 18
<212> TYPE: PRT
<213> ORGANISM: H. sapiens

<400> SEQUENCE: 264

Gly Glu Thr Gly Pro Ser Gly Pro Val Gly Pro Ala Gly Ala Val Gly
1               5                   10                  15

Pro Arg

<210> SEQ ID NO 265
<211> LENGTH: 11
<212> TYPE: PRT
<213> ORGANISM: H. sapiens

<400> SEQUENCE: 265

Gly Pro Ala Gly Pro Ser Gly Pro Ala Gly Lys
1               5                   10

<210> SEQ ID NO 266
<211> LENGTH: 9
<212> TYPE: PRT
<213> ORGANISM: H. sapiens

<400> SEQUENCE: 266

Gly Val Val Gly Pro Gln Gly Ala Arg
1               5

<210> SEQ ID NO 267
<211> LENGTH: 6
<212> TYPE: PRT
<213> ORGANISM: H. sapiens

<400> SEQUENCE: 267

Leu Leu Leu Leu Pro Arg
1               5

<210> SEQ ID NO 268
<211> LENGTH: 14
<212> TYPE: PRT
<213> ORGANISM: H. sapiens

<400> SEQUENCE: 268

Thr Gln Ser Ser Leu Val Pro Ala Leu Thr Asp Phe Val Arg
1               5                   10

<210> SEQ ID NO 269
<211> LENGTH: 9
<212> TYPE: PRT
<213> ORGANISM: H. sapiens

<400> SEQUENCE: 269

Asp Leu Ser Glu Asn Asn Asp Gln Arg
1               5

<210> SEQ ID NO 270
<211> LENGTH: 20
<212> TYPE: PRT
<213> ORGANISM: H. sapiens

<400> SEQUENCE: 270

Asp Gln Leu Val Ile Pro Asp Gly Gln Glu Glu Gln Glu Ala Ala
1               5                   10                  15
Gly Glu Gly Arg
            20

<210> SEQ ID NO 271
<211> LENGTH: 9
<212> TYPE: PRT
<213> ORGANISM: H. sapiens

<400> SEQUENCE: 271

Asp Thr Ile Asn Leu Leu Asp Gln Arg
1               5

<210> SEQ ID NO 272
<211> LENGTH: 15
<212> TYPE: PRT
<213> ORGANISM: H. sapiens

<400> SEQUENCE: 272

Glu Glu Thr Asn Glu Ile Gln Val Val Asn Glu Glu Pro Gln Arg
1               5                   10                  15

<210> SEQ ID NO 273
<211> LENGTH: 12
<212> TYPE: PRT
<213> ORGANISM: H. sapiens

<400> SEQUENCE: 273

Glu Gln Val Val Glu Asp Arg Pro Val Gly Gly Arg
1               5                   10

<210> SEQ ID NO 274
<211> LENGTH: 17
<212> TYPE: PRT
<213> ORGANISM: H. sapiens

<400> SEQUENCE: 274

Gly Phe Gly Gly Ala Gly Glu Leu Gly Gln Thr Pro Gln Val Gln Ala
1               5                   10                  15

Ala

<210> SEQ ID NO 275
<211> LENGTH: 22
<212> TYPE: PRT
<213> ORGANISM: H. sapiens

<400> SEQUENCE: 275

Gly Phe Gly Gly Ala Gly Glu Leu Gly Gln Thr Pro Gln Val Gln Ala
1               5                   10                  15

Ala Leu Ser Val Ser Gln
            20

<210> SEQ ID NO 276
<211> LENGTH: 7
<212> TYPE: PRT
<213> ORGANISM: H. sapiens

<400> SEQUENCE: 276

Leu Pro Gln Glu Pro Gly Arg
1               5

<210> SEQ ID NO 277
<211> LENGTH: 15
<212> TYPE: PRT
<213> ORGANISM: H. sapiens

<400> SEQUENCE: 277

Leu Ser Val Ser Gln Glu Asn Pro Glu Met Glu Gly Pro Glu Arg
1               5                   10                  15

<210> SEQ ID NO 278
<211> LENGTH: 11
<212> TYPE: PRT
<213> ORGANISM: H. sapiens

```
<400> SEQUENCE: 278

Met Gly Leu Gly Asn Gly Arg Arg Ser Met Lys
1               5                   10

<210> SEQ ID NO 279
<211> LENGTH: 11
<212> TYPE: PRT
<213> ORGANISM: H. sapiens

<400> SEQUENCE: 279

Asn Ile Asp Val Phe Asn Val Glu Asp Gln Lys
1               5                   10

<210> SEQ ID NO 280
<211> LENGTH: 12
<212> TYPE: PRT
<213> ORGANISM: H. sapiens

<400> SEQUENCE: 280

Asn Ile Asp Val Phe Asn Val Glu Asp Gln Lys Arg
1               5                   10

<210> SEQ ID NO 281
<211> LENGTH: 21
<212> TYPE: PRT
<213> ORGANISM: H. sapiens

<400> SEQUENCE: 281

Asn Gln Thr Asn Leu Glu Arg Lys Phe Ser Tyr Asp Leu Ser Gln Cys
1               5                   10                  15

Ile Asn Gln Met Lys
            20

<210> SEQ ID NO 282
<211> LENGTH: 12
<212> TYPE: PRT
<213> ORGANISM: H. sapiens

<400> SEQUENCE: 282

Gln Gln Leu Gln Ala Leu Ser Glu Pro Gln Pro Arg
1               5                   10

<210> SEQ ID NO 283
<211> LENGTH: 12
<212> TYPE: PRT
<213> ORGANISM: H. sapiens

<400> SEQUENCE: 283

Arg Asp Thr Ile Asn Leu Leu Asp Gln Arg Glu Lys
1               5                   10

<210> SEQ ID NO 284
<211> LENGTH: 16
<212> TYPE: PRT
<213> ORGANISM: H. sapiens

<400> SEQUENCE: 284

Asp Lys Asp Ser Pro Glu Thr Glu Glu Asn Pro Ala Pro Glu Pro Arg
1               5                   10                  15

<210> SEQ ID NO 285
<211> LENGTH: 19
<212> TYPE: PRT
```

-continued

<213> ORGANISM: H. sapiens

<400> SEQUENCE: 285

Ser Ala Thr Glu Pro Gly Pro Pro Gly Tyr Ser Val Ser Pro Ala Val
1               5                   10                  15

Pro Gly Arg

<210> SEQ ID NO 286
<211> LENGTH: 11
<212> TYPE: PRT
<213> ORGANISM: H. sapiens

<400> SEQUENCE: 286

Ser Pro Gly Leu Pro Ile Arg Ser Ala Arg Arg
1               5                   10

<210> SEQ ID NO 287
<211> LENGTH: 11
<212> TYPE: PRT
<213> ORGANISM: H. sapiens

<400> SEQUENCE: 287

Ala Gly Leu Ala Lys Pro Pro Ala Ala Ala Lys
1               5                   10

<210> SEQ ID NO 288
<211> LENGTH: 9
<212> TYPE: PRT
<213> ORGANISM: H. sapiens

<400> SEQUENCE: 288

Asp Gln Ala Ala Ala Leu Val Pro Lys
1               5

<210> SEQ ID NO 289
<211> LENGTH: 15
<212> TYPE: PRT
<213> ORGANISM: H. sapiens

<400> SEQUENCE: 289

Met Trp Ile Gln Gln Leu Leu Gly Leu Ser Ser Met Ser Ile Arg
1               5                   10                  15

<210> SEQ ID NO 290
<211> LENGTH: 22
<212> TYPE: PRT
<213> ORGANISM: H. sapiens

<400> SEQUENCE: 290

Ser Ser Pro Ser Leu Ala Ser Ser Ser Ser Ser Ser Ser Ala Val
1               5                   10                  15

Ala Gly Gly Ala Pro Glu
            20

<210> SEQ ID NO 291
<211> LENGTH: 12
<212> TYPE: PRT
<213> ORGANISM: H. sapiens

<400> SEQUENCE: 291

Asp Ile Gln Gln Thr Leu Thr Gln Asn Met Glu Arg
1               5                   10

<210> SEQ ID NO 292
<211> LENGTH: 5
<212> TYPE: PRT
<213> ORGANISM: H. sapiens

<400> SEQUENCE: 292

Leu Glu Ala Leu Lys
 1               5

<210> SEQ ID NO 293
<211> LENGTH: 13
<212> TYPE: PRT
<213> ORGANISM: H. sapiens

<400> SEQUENCE: 293

Arg Pro Pro Arg Pro Gly Thr Asn Gly Trp Ser Arg Arg
 1               5                  10

<210> SEQ ID NO 294
<211> LENGTH: 12
<212> TYPE: PRT
<213> ORGANISM: H. sapiens

<400> SEQUENCE: 294

Ser Ser Thr Gln Met Thr Trp Gly Ala Leu Phe Arg
 1               5                  10

<210> SEQ ID NO 295
<211> LENGTH: 9
<212> TYPE: PRT
<213> ORGANISM: H. sapiens

<400> SEQUENCE: 295

Trp Asn Gly Met Ser Arg Leu Glu Lys
 1               5

<210> SEQ ID NO 296
<211> LENGTH: 7
<212> TYPE: PRT
<213> ORGANISM: H. sapiens

<400> SEQUENCE: 296

Leu Thr Val Ser Trp Leu Lys
 1               5

<210> SEQ ID NO 297
<211> LENGTH: 11
<212> TYPE: PRT
<213> ORGANISM: H. sapiens

<400> SEQUENCE: 297

Asn Leu Ile Leu Ala Pro Gly Glu Asp Gly Arg
 1               5                  10

<210> SEQ ID NO 298
<211> LENGTH: 14
<212> TYPE: PRT
<213> ORGANISM: H. sapiens

<400> SEQUENCE: 298

Thr Ser Gly Ala Pro Pro Glu Ser Asn Pro Gly Asp Val Lys
 1               5                  10

<210> SEQ ID NO 299
<211> LENGTH: 18

-continued

```
<212> TYPE: PRT
<213> ORGANISM: H. sapiens

<400> SEQUENCE: 299

Val Ile Ala Ile Asn Glu Val Gly Ser Ser His Pro Ser Leu Pro Ser
1               5                   10                  15

Glu Arg

<210> SEQ ID NO 300
<211> LENGTH: 15
<212> TYPE: PRT
<213> ORGANISM: H. sapiens

<400> SEQUENCE: 300

Tyr Val Val Gly Gln Thr Pro Val Tyr Val Pro Tyr Glu Ile Arg
1               5                   10                  15

<210> SEQ ID NO 301
<211> LENGTH: 9
<212> TYPE: PRT
<213> ORGANISM: H. sapiens

<400> SEQUENCE: 301

Ala Glu Ala Pro Ala Leu Phe Ser Arg
1               5

<210> SEQ ID NO 302
<211> LENGTH: 10
<212> TYPE: PRT
<213> ORGANISM: H. sapiens

<400> SEQUENCE: 302

Ala Glu Asp Ser Pro Glu Gly Tyr Glu Lys
1               5                   10

<210> SEQ ID NO 303
<211> LENGTH: 8
<212> TYPE: PRT
<213> ORGANISM: H. sapiens

<400> SEQUENCE: 303

Asp Thr Ala Glu Leu Pro Ala Arg
1               5

<210> SEQ ID NO 304
<211> LENGTH: 17
<212> TYPE: PRT
<213> ORGANISM: H. sapiens

<400> SEQUENCE: 304

Gly Glu Lys Pro Ala Ser Pro Ala Val Gln Pro Asp Ala Ala Leu Gln
1               5                   10                  15

Arg

<210> SEQ ID NO 305
<211> LENGTH: 10
<212> TYPE: PRT
<213> ORGANISM: H. sapiens

<400> SEQUENCE: 305

Lys Thr Met Glu Gly Pro Val Glu Gly Arg
1               5                   10
```

```
<210> SEQ ID NO 306
<211> LENGTH: 18
<212> TYPE: PRT
<213> ORGANISM: H. sapiens

<400> SEQUENCE: 306

Lys Thr Met Glu Gly Pro Val Glu Gly Arg Asp Thr Ala Glu Leu Pro
 1               5                  10                  15
Ala Arg

<210> SEQ ID NO 307
<211> LENGTH: 13
<212> TYPE: PRT
<213> ORGANISM: H. sapiens

<400> SEQUENCE: 307

Leu Ala Ala Val Leu Ala Gly Tyr Gly Val Glu Leu Arg
 1               5                  10

<210> SEQ ID NO 308
<211> LENGTH: 9
<212> TYPE: PRT
<213> ORGANISM: H. sapiens

<400> SEQUENCE: 308

Leu Pro Glu Gln Gly Ser Ser Ser Arg
 1               5

<210> SEQ ID NO 309
<211> LENGTH: 13
<212> TYPE: PRT
<213> ORGANISM: H. sapiens

<400> SEQUENCE: 309

Asn Pro Gly Gly Val Val Asn Val Gly Ala Asp Ile Lys
 1               5                  10

<210> SEQ ID NO 310
<211> LENGTH: 19
<212> TYPE: PRT
<213> ORGANISM: H. sapiens

<400> SEQUENCE: 310

Ser Glu Leu Glu Ala Gln Thr Gly Leu Gln Ile Leu Gln Thr Gly Val
 1               5                  10                  15
Gly Gln Arg

<210> SEQ ID NO 311
<211> LENGTH: 9
<212> TYPE: PRT
<213> ORGANISM: H. sapiens

<400> SEQUENCE: 311

Thr Met Glu Gly Pro Val Glu Gly Arg
 1               5

<210> SEQ ID NO 312
<211> LENGTH: 11
<212> TYPE: PRT
<213> ORGANISM: H. sapiens

<400> SEQUENCE: 312

Cys Phe Glu Thr Val Tyr Asp Gly Tyr Ser Lys
 1               5                  10
```

```
<210> SEQ ID NO 313
<211> LENGTH: 7
<212> TYPE: PRT
<213> ORGANISM: H. sapiens

<400> SEQUENCE: 313

Thr Tyr Tyr Thr Pro Thr Arg
1               5

<210> SEQ ID NO 314
<211> LENGTH: 12
<212> TYPE: PRT
<213> ORGANISM: H. sapiens

<400> SEQUENCE: 314

Glu Arg Pro Trp Gly Ala Ala Asp Gly Leu Ser Arg
1               5                   10

<210> SEQ ID NO 315
<211> LENGTH: 9
<212> TYPE: PRT
<213> ORGANISM: H. sapiens

<400> SEQUENCE: 315

Ile Tyr Ser Phe Gly Leu Gly Gly Arg
1               5

<210> SEQ ID NO 316
<211> LENGTH: 13
<212> TYPE: PRT
<213> ORGANISM: H. sapiens

<400> SEQUENCE: 316

Leu Asp Ala Pro Pro Pro Ala Ala Pro Leu Pro Arg
1               5                   10

<210> SEQ ID NO 317
<211> LENGTH: 11
<212> TYPE: PRT
<213> ORGANISM: H. sapiens

<400> SEQUENCE: 317

Leu Arg Lys Ser Ser Val Cys Gln Asn Gly Arg
1               5                   10

<210> SEQ ID NO 318
<211> LENGTH: 9
<212> TYPE: PRT
<213> ORGANISM: H. sapiens

<400> SEQUENCE: 318

Cys Phe Leu Ala Phe Thr Gln Thr Lys
1               5

<210> SEQ ID NO 319
<211> LENGTH: 12
<212> TYPE: PRT
<213> ORGANISM: H. sapiens

<400> SEQUENCE: 319

Asp Gln Leu Pro Tyr Ile Cys Gln Phe Gly Ile Val
1               5                   10
```

```
<210> SEQ ID NO 320
<211> LENGTH: 11
<212> TYPE: PRT
<213> ORGANISM: H. sapiens

<400> SEQUENCE: 320

Glu Gln Gln Ala Leu Gln Thr Val Cys Leu Lys
1               5                   10

<210> SEQ ID NO 321
<211> LENGTH: 21
<212> TYPE: PRT
<213> ORGANISM: H. sapiens

<400> SEQUENCE: 321

Gly Gly Thr Leu Ser Thr Pro Gln Thr Gly Ser Glu Asn Asp Ala Leu
1               5                   10                  15

Tyr Glu Tyr Leu Arg
            20

<210> SEQ ID NO 322
<211> LENGTH: 6
<212> TYPE: PRT
<213> ORGANISM: H. sapiens

<400> SEQUENCE: 322

Lys Ile Val Asn Ala Lys
1               5

<210> SEQ ID NO 323
<211> LENGTH: 12
<212> TYPE: PRT
<213> ORGANISM: H. sapiens

<400> SEQUENCE: 323

Leu Asp Thr Leu Ala Gln Glu Val Ala Leu Leu Lys
1               5                   10

<210> SEQ ID NO 324
<211> LENGTH: 6
<212> TYPE: PRT
<213> ORGANISM: H. sapiens

<400> SEQUENCE: 324

Met Phe Glu Glu Leu Lys
1               5

<210> SEQ ID NO 325
<211> LENGTH: 14
<212> TYPE: PRT
<213> ORGANISM: H. sapiens

<400> SEQUENCE: 325

Asn Trp Glu Thr Glu Ile Thr Ala Gln Pro Asp Gly Gly Lys
1               5                   10

<210> SEQ ID NO 326
<211> LENGTH: 12
<212> TYPE: PRT
<213> ORGANISM: H. sapiens

<400> SEQUENCE: 326

Thr Phe His Glu Ala Ser Glu Asp Cys Ile Ser Arg
1               5                   10
```

```
<210> SEQ ID NO 327
<211> LENGTH: 4
<212> TYPE: PRT
<213> ORGANISM: H. sapiens

<400> SEQUENCE: 327

Trp Phe Asp Lys
 1

<210> SEQ ID NO 328
<211> LENGTH: 14
<212> TYPE: PRT
<213> ORGANISM: H. sapiens

<400> SEQUENCE: 328

Ala Ala Met Val Gly Met Leu Ala Asn Phe Leu Gly Phe Arg
 1               5                  10

<210> SEQ ID NO 329
<211> LENGTH: 12
<212> TYPE: PRT
<213> ORGANISM: H. sapiens

<400> SEQUENCE: 329

Ala Leu Gln Asp Gln Leu Val Leu Val Ala Ala Lys
 1               5                  10

<210> SEQ ID NO 330
<211> LENGTH: 12
<212> TYPE: PRT
<213> ORGANISM: H. sapiens

<400> SEQUENCE: 330

Asp Pro Thr Phe Ile Pro Ala Pro Ile Gln Ala Lys
 1               5                  10

<210> SEQ ID NO 331
<211> LENGTH: 9
<212> TYPE: PRT
<213> ORGANISM: H. sapiens

<400> SEQUENCE: 331

Phe Met Gln Ala Val Thr Gly Trp Lys
 1               5

<210> SEQ ID NO 332
<211> LENGTH: 8
<212> TYPE: PRT
<213> ORGANISM: H. sapiens

<400> SEQUENCE: 332

Leu Asp Thr Glu Asp Lys Leu Arg
 1               5

<210> SEQ ID NO 333
<211> LENGTH: 17
<212> TYPE: PRT
<213> ORGANISM: H. sapiens

<400> SEQUENCE: 333

Gln Pro Phe Val Gln Gly Leu Ala Leu Tyr Thr Pro Val Val Leu Pro
 1               5                  10                  15

Arg
```

```
<210> SEQ ID NO 334
<211> LENGTH: 13
<212> TYPE: PRT
<213> ORGANISM: H. sapiens

<400> SEQUENCE: 334

Ser Leu Asp Phe Thr Glu Leu Asp Val Ala Ala Glu Lys
1               5                   10

<210> SEQ ID NO 335
<211> LENGTH: 7
<212> TYPE: PRT
<213> ORGANISM: H. sapiens

<400> SEQUENCE: 335

Thr Ser Pro Val Asp Glu Lys
1               5

<210> SEQ ID NO 336
<211> LENGTH: 8
<212> TYPE: PRT
<213> ORGANISM: H. sapiens

<400> SEQUENCE: 336

Val Ala Asn Pro Leu Ser Thr Ala
1               5

<210> SEQ ID NO 337
<211> LENGTH: 17
<212> TYPE: PRT
<213> ORGANISM: H. sapiens

<400> SEQUENCE: 337

Val Leu Ser Ala Leu Gln Ala Val Gln Gly Leu Leu Val Ala Gln Gly
1               5                   10                  15

Arg

<210> SEQ ID NO 338
<211> LENGTH: 18
<212> TYPE: PRT
<213> ORGANISM: H. sapiens

<400> SEQUENCE: 338

Ala Ala Val Pro Ser Gly Ala Ser Thr Gly Ile Tyr Glu Ala Leu Glu
1               5                   10                  15

Leu Arg

<210> SEQ ID NO 339
<211> LENGTH: 13
<212> TYPE: PRT
<213> ORGANISM: H. sapiens

<400> SEQUENCE: 339

Gly Asn Pro Thr Val Glu Val Asp Leu Tyr Thr Ala Lys
1               5                   10

<210> SEQ ID NO 340
<211> LENGTH: 16
<212> TYPE: PRT
<213> ORGANISM: H. sapiens

<400> SEQUENCE: 340

Tyr Ile Thr Gly Asp Gln Leu Gly Ala Leu Tyr Gln Asp Phe Val Arg
```

```
                1               5                  10                 15
```

<210> SEQ ID NO 341
<211> LENGTH: 18
<212> TYPE: PRT
<213> ORGANISM: H. sapiens

<400> SEQUENCE: 341

```
Ala Ala Val Pro Ser Gly Ala Ser Thr Gly Ile Tyr Glu Ala Leu Glu
 1               5                  10                  15

Leu Arg
```

<210> SEQ ID NO 342
<211> LENGTH: 13
<212> TYPE: PRT
<213> ORGANISM: H. sapiens

<400> SEQUENCE: 342

```
Gly Asn Pro Thr Val Glu Val Asp Leu Phe Thr Ser Lys
 1               5                  10
```

<210> SEQ ID NO 343
<211> LENGTH: 14
<212> TYPE: PRT
<213> ORGANISM: H. sapiens

<400> SEQUENCE: 343

```
Val Val Ile Gly Met Asp Val Ala Ala Ser Glu Phe Phe Arg
 1               5                  10
```

<210> SEQ ID NO 344
<211> LENGTH: 20
<212> TYPE: PRT
<213> ORGANISM: H. sapiens

<400> SEQUENCE: 344

```
Ala Val Ile His Pro Asp Tyr Asp Ala Ala Ser His Asp Gln Asp Ile
 1               5                  10                  15

Met Leu Leu Arg
             20
```

<210> SEQ ID NO 345
<211> LENGTH: 18
<212> TYPE: PRT
<213> ORGANISM: H. sapiens

<400> SEQUENCE: 345

```
Asp Ser Cys Gln Gly Asp Ser Gly Gly Pro Leu Val Cys Gly Asp His
 1               5                  10                  15

Leu Arg
```

<210> SEQ ID NO 346
<211> LENGTH: 11
<212> TYPE: PRT
<213> ORGANISM: H. sapiens

<400> SEQUENCE: 346

```
Glu Lys Pro Gly Val Tyr Thr Asn Val Cys Arg
 1               5                  10
```

<210> SEQ ID NO 347
<211> LENGTH: 11
<212> TYPE: PRT

```
<213> ORGANISM: H. sapiens

<400> SEQUENCE: 347

Glu Ser Ser Gln Glu Gln Ser Ser Val Val Arg
1               5                   10

<210> SEQ ID NO 348
<211> LENGTH: 13
<212> TYPE: PRT
<213> ORGANISM: H. sapiens

<400> SEQUENCE: 348

Gly Leu Val Ser Trp Gly Asn Ile Pro Cys Gly Ser Lys
1               5                   10

<210> SEQ ID NO 349
<211> LENGTH: 10
<212> TYPE: PRT
<213> ORGANISM: H. sapiens

<400> SEQUENCE: 349

Lys Pro Asn Leu Gln Val Phe Leu Gly Lys
1               5                   10

<210> SEQ ID NO 350
<211> LENGTH: 12
<212> TYPE: PRT
<213> ORGANISM: H. sapiens

<400> SEQUENCE: 350

Leu Ser Glu Leu Ile Gln Pro Leu Pro Leu Glu Arg
1               5                   10

<210> SEQ ID NO 351
<211> LENGTH: 9
<212> TYPE: PRT
<213> ORGANISM: H. sapiens

<400> SEQUENCE: 351

Leu Val His Gly Gly Pro Cys Asp Lys
1               5

<210> SEQ ID NO 352
<211> LENGTH: 20
<212> TYPE: PRT
<213> ORGANISM: H. sapiens

<400> SEQUENCE: 352

Thr Ala Asp Gly Asp Phe Pro Asp Thr Ile Gln Cys Ala Tyr Ile His
1               5                   10                  15

Leu Val Ser Arg
            20

<210> SEQ ID NO 353
<211> LENGTH: 7
<212> TYPE: PRT
<213> ORGANISM: H. sapiens

<400> SEQUENCE: 353

Tyr Thr Asn Trp Ile Gln Lys
1               5

<210> SEQ ID NO 354
<211> LENGTH: 12
```

```
-continued

<212> TYPE: PRT
<213> ORGANISM: H. sapiens

<400> SEQUENCE: 354

Ile Thr Thr Thr Ser Pro Trp Met Phe Pro Ser Arg
1               5                   10

<210> SEQ ID NO 355
<211> LENGTH: 11
<212> TYPE: PRT
<213> ORGANISM: H. sapiens

<400> SEQUENCE: 355

Leu Glu Pro Gly Gln Gln Glu Tyr Tyr Arg
1               5                   10

<210> SEQ ID NO 356
<211> LENGTH: 14
<212> TYPE: PRT
<213> ORGANISM: H. sapiens

<400> SEQUENCE: 356

Ser Ser Gly Leu Val Ser Asn Ala Pro Gly Val Gln Ile Arg
1               5                   10

<210> SEQ ID NO 357
<211> LENGTH: 11
<212> TYPE: PRT
<213> ORGANISM: H. sapiens

<400> SEQUENCE: 357

Ser Thr Glu Leu Cys Gly Leu Trp Gln Gly Arg
1               5                   10

<210> SEQ ID NO 358
<211> LENGTH: 21
<212> TYPE: PRT
<213> ORGANISM: H. sapiens

<400> SEQUENCE: 358

Ala Ala Asp His Asp Val Gly Ser Glu Leu Pro Pro Glu Gly Val Leu
1               5                   10                  15

Gly Ala Leu Leu Arg
            20

<210> SEQ ID NO 359
<211> LENGTH: 12
<212> TYPE: PRT
<213> ORGANISM: H. sapiens

<400> SEQUENCE: 359

Ala Glu Ala Gln Glu Ala Glu Asp Gln Gln Ala Arg
1               5                   10

<210> SEQ ID NO 360
<211> LENGTH: 10
<212> TYPE: PRT
<213> ORGANISM: H. sapiens

<400> SEQUENCE: 360

Ala Gly Ser Pro Leu Leu Trp Gly Pro Arg
1               5                   10

<210> SEQ ID NO 361
```

```
<211> LENGTH: 10
<212> TYPE: PRT
<213> ORGANISM: H. sapiens

<400> SEQUENCE: 361

Ala Leu Ala His Leu Leu Glu Ala Glu Arg
1               5                   10

<210> SEQ ID NO 362
<211> LENGTH: 14
<212> TYPE: PRT
<213> ORGANISM: H. sapiens

<400> SEQUENCE: 362

Ala Arg Ala Glu Ala Gln Glu Ala Glu Asp Gln Gln Ala Arg
1               5                   10

<210> SEQ ID NO 363
<211> LENGTH: 12
<212> TYPE: PRT
<213> ORGANISM: H. sapiens

<400> SEQUENCE: 363

Gly Glu Ala Ala Gly Ala Val Gln Glu Leu Ala Arg
1               5                   10

<210> SEQ ID NO 364
<211> LENGTH: 15
<212> TYPE: PRT
<213> ORGANISM: H. sapiens

<400> SEQUENCE: 364

Ile Leu Ala Gly Ser Ala Asp Ser Glu Gly Val Ala Ala Pro Arg
1               5                   10                  15

<210> SEQ ID NO 365
<211> LENGTH: 16
<212> TYPE: PRT
<213> ORGANISM: H. sapiens

<400> SEQUENCE: 365

Ile Leu Ala Gly Ser Ala Asp Ser Glu Gly Val Ala Ala Pro Arg Arg
1               5                   10                  15

<210> SEQ ID NO 366
<211> LENGTH: 11
<212> TYPE: PRT
<213> ORGANISM: H. sapiens

<400> SEQUENCE: 366

Leu Glu Thr Pro Ala Pro Gln Val Pro Ala Arg
1               5                   10

<210> SEQ ID NO 367
<211> LENGTH: 11
<212> TYPE: PRT
<213> ORGANISM: H. sapiens

<400> SEQUENCE: 367

Met Ala Gly Ser Pro Leu Leu Trp Gly Pro Arg
1               5                   10

<210> SEQ ID NO 368
<211> LENGTH: 21
<212> TYPE: PRT
```

-continued

<213> ORGANISM: H. sapiens

<400> SEQUENCE: 368

Asn Ser Asp Pro Ala Leu Gly Leu Asp Asp Pro Asp Ala Pro Ala
1               5                   10                  15

Ala Gln Leu Ala Arg
            20

<210> SEQ ID NO 369
<211> LENGTH: 7
<212> TYPE: PRT
<213> ORGANISM: H. sapiens

<400> SEQUENCE: 369

Val Leu Ala Gln Leu Leu Arg
1               5

<210> SEQ ID NO 370
<211> LENGTH: 6
<212> TYPE: PRT
<213> ORGANISM: H. sapiens

<400> SEQUENCE: 370

Val Trp Gly Ala Pro Arg
1               5

<210> SEQ ID NO 371
<211> LENGTH: 6
<212> TYPE: PRT
<213> ORGANISM: H. sapiens

<400> SEQUENCE: 371

Ala Val Cys Val Leu Lys
1               5

<210> SEQ ID NO 372
<211> LENGTH: 14
<212> TYPE: PRT
<213> ORGANISM: H. sapiens

<400> SEQUENCE: 372

Gly Asp Gly Pro Val Gln Gly Ile Ile Asn Phe Glu Gln Lys
1               5                   10

<210> SEQ ID NO 373
<211> LENGTH: 8
<212> TYPE: PRT
<213> ORGANISM: H. sapiens

<400> SEQUENCE: 373

Gly Gly Asn Glu Glu Ser Thr Lys
1               5

<210> SEQ ID NO 374
<211> LENGTH: 10
<212> TYPE: PRT
<213> ORGANISM: H. sapiens

<400> SEQUENCE: 374

Leu Ala Cys Gly Val Ile Gly Ile Ala Gln
1               5                   10

<210> SEQ ID NO 375
<211> LENGTH: 6

```
<212> TYPE: PRT
<213> ORGANISM: H. sapiens

<400> SEQUENCE: 375

Val Trp Gly Ser Ile Lys
  1               5

<210> SEQ ID NO 376
<211> LENGTH: 6
<212> TYPE: PRT
<213> ORGANISM: H. sapiens

<400> SEQUENCE: 376

Phe Lys Ala Ile Glu Lys
  1               5

<210> SEQ ID NO 377
<211> LENGTH: 12
<212> TYPE: PRT
<213> ORGANISM: H. sapiens

<400> SEQUENCE: 377

Tyr Leu Val Leu Asp Cys Val Pro Glu Glu Arg Arg
  1               5                  10

<210> SEQ ID NO 378
<211> LENGTH: 18
<212> TYPE: PRT
<213> ORGANISM: H. sapiens

<400> SEQUENCE: 378

Glu Val Leu Thr Gly Asn Asp Glu Val Ile Gly Gln Val Leu Ser Thr
  1               5                  10                  15

Leu Lys

<210> SEQ ID NO 379
<211> LENGTH: 14
<212> TYPE: PRT
<213> ORGANISM: H. sapiens

<400> SEQUENCE: 379

Leu Gly Ala Ser Pro Leu His Val Asp Leu Ala Thr Leu Arg
  1               5                  10

<210> SEQ ID NO 380
<211> LENGTH: 13
<212> TYPE: PRT
<213> ORGANISM: H. sapiens

<400> SEQUENCE: 380

Leu Pro Tyr Thr Ala Ser Ser Gly Leu Met Ala Pro Arg
  1               5                  10

<210> SEQ ID NO 381
<211> LENGTH: 16
<212> TYPE: PRT
<213> ORGANISM: H. sapiens

<400> SEQUENCE: 381

Leu Ser Ile Glu Asp Phe Thr Ala Tyr Gly Gly Val Phe Gly Asn Lys
  1               5                  10                  15

<210> SEQ ID NO 382
<211> LENGTH: 15
```

-continued

<212> TYPE: PRT
<213> ORGANISM: H. sapiens

<400> SEQUENCE: 382

Met Met Ala Ala Met Ala Thr Ala Arg Val Arg Met Gly Pro Arg
1               5                   10                  15

<210> SEQ ID NO 383
<211> LENGTH: 9
<212> TYPE: PRT
<213> ORGANISM: H. sapiens

<400> SEQUENCE: 383

Asn Val Leu Leu Phe Leu Gln Asp Lys
1               5

<210> SEQ ID NO 384
<211> LENGTH: 17
<212> TYPE: PRT
<213> ORGANISM: H. sapiens

<400> SEQUENCE: 384

Ser Glu Asp Val Pro Tyr Thr Ala Ala Leu Thr Ala Val Arg Pro Ser
1               5                   10                  15

Arg

<210> SEQ ID NO 385
<211> LENGTH: 11
<212> TYPE: PRT
<213> ORGANISM: H. sapiens

<400> SEQUENCE: 385

Gly Val Ile Ser Asn Ser Gly Gly Pro Val Arg
1               5                   10

<210> SEQ ID NO 386
<211> LENGTH: 10
<212> TYPE: PRT
<213> ORGANISM: H. sapiens

<400> SEQUENCE: 386

Thr Phe Glu Ile Ser Asp Ile Gly Ala Lys
1               5                   10

<210> SEQ ID NO 387
<211> LENGTH: 7
<212> TYPE: PRT
<213> ORGANISM: H. sapiens

<400> SEQUENCE: 387

Val Tyr Ser Leu Pro Gly Arg
1               5

<210> SEQ ID NO 388
<211> LENGTH: 9
<212> TYPE: PRT
<213> ORGANISM: H. sapiens

<400> SEQUENCE: 388

Trp Ser Ala Ser Phe Thr Val Thr Lys
1               5

<210> SEQ ID NO 389
<211> LENGTH: 11

-continued

```
<212> TYPE: PRT
<213> ORGANISM: H. sapiens

<400> SEQUENCE: 389

Glu Arg Ser Lys Pro Val His Glu Leu Asn Arg
1               5                   10

<210> SEQ ID NO 390
<211> LENGTH: 11
<212> TYPE: PRT
<213> ORGANISM: H. sapiens

<400> SEQUENCE: 390

Asn Ala Asn Thr Phe Ile Ser Pro Gln Gln Arg
1               5                   10

<210> SEQ ID NO 391
<211> LENGTH: 9
<212> TYPE: PRT
<213> ORGANISM: H. sapiens

<400> SEQUENCE: 391

Leu Cys Gly Gly Gly Ile Gln Glu Arg
1               5

<210> SEQ ID NO 392
<211> LENGTH: 17
<212> TYPE: PRT
<213> ORGANISM: H. sapiens

<400> SEQUENCE: 392

Ser Glu Gln Leu Lys Glu Glu Ser Gly Glu Gln Phe Pro Gly Cys
1               5                   10                  15

Arg

<210> SEQ ID NO 393
<211> LENGTH: 8
<212> TYPE: PRT
<213> ORGANISM: H. sapiens

<400> SEQUENCE: 393

Ser Ser Gln Phe Thr Ser Cys Lys
1               5

<210> SEQ ID NO 394
<211> LENGTH: 8
<212> TYPE: PRT
<213> ORGANISM: H. sapiens

<400> SEQUENCE: 394

Val Val Ile Glu Arg Ile Ala Arg
1               5

<210> SEQ ID NO 395
<211> LENGTH: 14
<212> TYPE: PRT
<213> ORGANISM: H. sapiens

<400> SEQUENCE: 395

Glu Gln Leu Gly Glu Phe Tyr Glu Ala Leu Asp Cys Leu Arg
1               5                   10

<210> SEQ ID NO 396
<211> LENGTH: 7
```

```
<212> TYPE: PRT
<213> ORGANISM: H. sapiens

<400> SEQUENCE: 396

Lys Gln Glu Glu Gly Glu Ser
1               5

<210> SEQ ID NO 397
<211> LENGTH: 6
<212> TYPE: PRT
<213> ORGANISM: H. sapiens

<400> SEQUENCE: 397

Asn Glu Glu Tyr Asn Lys
1               5

<210> SEQ ID NO 398
<211> LENGTH: 15
<212> TYPE: PRT
<213> ORGANISM: H. sapiens

<400> SEQUENCE: 398

Asn Trp Gly Leu Ser Val Tyr Ala Asp Lys Pro Glu Thr Thr Lys
1               5                   10                  15

<210> SEQ ID NO 399
<211> LENGTH: 9
<212> TYPE: PRT
<213> ORGANISM: H. sapiens

<400> SEQUENCE: 399

Ser Asp Val Val Tyr Thr Asp Trp Lys
1               5

<210> SEQ ID NO 400
<211> LENGTH: 8
<212> TYPE: PRT
<213> ORGANISM: H. sapiens

<400> SEQUENCE: 400

Thr Glu Asp Thr Ile Phe Leu Arg
1               5

<210> SEQ ID NO 401
<211> LENGTH: 12
<212> TYPE: PRT
<213> ORGANISM: H. sapiens

<400> SEQUENCE: 401

Thr Tyr Met Leu Ala Phe Asp Val Asn Asp Glu Lys
1               5                   10

<210> SEQ ID NO 402
<211> LENGTH: 9
<212> TYPE: PRT
<213> ORGANISM: H. sapiens

<400> SEQUENCE: 402

Trp Phe Tyr Ile Ala Ser Ala Phe Arg
1               5

<210> SEQ ID NO 403
<211> LENGTH: 15
<212> TYPE: PRT
<213> ORGANISM: H. sapiens
```

-continued

<400> SEQUENCE: 403

Tyr Val Gly Gly Gln Glu His Phe Ala His Leu Leu Ile Leu Arg
1               5                   10                  15

<210> SEQ ID NO 404
<211> LENGTH: 12
<212> TYPE: PRT
<213> ORGANISM: H. sapiens

<400> SEQUENCE: 404

Ala Phe Ile Gln Leu Trp Ala Phe Asp Ala Val Lys
1               5                   10

<210> SEQ ID NO 405
<211> LENGTH: 8
<212> TYPE: PRT
<213> ORGANISM: H. sapiens

<400> SEQUENCE: 405

Glu Thr Leu Leu Gln Asp Phe Arg
1               5

<210> SEQ ID NO 406
<211> LENGTH: 15
<212> TYPE: PRT
<213> ORGANISM: H. sapiens

<400> SEQUENCE: 406

Glu Tyr Cys Gly Val Pro Gly Asp Gly Asp Glu Glu Leu Leu Arg
1               5                   10                  15

<210> SEQ ID NO 407
<211> LENGTH: 5
<212> TYPE: PRT
<213> ORGANISM: H. sapiens

<400> SEQUENCE: 407

Phe Tyr Ser Glu Lys
1               5

<210> SEQ ID NO 408
<211> LENGTH: 17
<212> TYPE: PRT
<213> ORGANISM: H. sapiens

<400> SEQUENCE: 408

Gly Glu Cys Val Pro Gly Glu Gln Glu Pro Glu Pro Ile Leu Ile Pro
1               5                   10                  15

Arg

<210> SEQ ID NO 409
<211> LENGTH: 18
<212> TYPE: PRT
<213> ORGANISM: H. sapiens

<400> SEQUENCE: 409

Gly Pro Cys Arg Ala Phe Ile Gln Leu Trp Ala Phe Asp Ala Val Lys
1               5                   10                  15

Gly Lys

<210> SEQ ID NO 410
<211> LENGTH: 11

```
<212> TYPE: PRT
<213> ORGANISM: H. sapiens

<400> SEQUENCE: 410

Thr Val Ala Ala Cys Asn Leu Pro Ile Val Arg
1               5                   10

<210> SEQ ID NO 411
<211> LENGTH: 19
<212> TYPE: PRT
<213> ORGANISM: H. sapiens

<400> SEQUENCE: 411

Val Val Ala Gln Gly Val Gly Ile Pro Glu Asp Ser Ile Phe Thr Met
1               5                   10                  15

Ala Asp Arg

<210> SEQ ID NO 412
<211> LENGTH: 8
<212> TYPE: PRT
<213> ORGANISM: H. sapiens

<400> SEQUENCE: 412

Asp Phe His Ile Asn Leu Phe Arg
1               5

<210> SEQ ID NO 413
<211> LENGTH: 12
<212> TYPE: PRT
<213> ORGANISM: H. sapiens

<400> SEQUENCE: 413

Gln His Leu Gly Asp Val Leu Asn Phe Leu Pro Leu
1               5                   10

<210> SEQ ID NO 414
<211> LENGTH: 8
<212> TYPE: PRT
<213> ORGANISM: H. sapiens

<400> SEQUENCE: 414

Ala Leu Ser Gln Glu Ile Thr Arg
1               5

<210> SEQ ID NO 415
<211> LENGTH: 16
<212> TYPE: PRT
<213> ORGANISM: H. sapiens

<400> SEQUENCE: 415

Asp Phe Asn Leu Leu Gln Val Ser Glu Pro Ser Glu Pro Cys Val Arg
1               5                   10                  15

<210> SEQ ID NO 416
<211> LENGTH: 14
<212> TYPE: PRT
<213> ORGANISM: H. sapiens

<400> SEQUENCE: 416

Ala His Tyr Gly Gly Phe Thr Val Gln Asn Glu Ala Asn Lys
1               5                   10

<210> SEQ ID NO 417
<211> LENGTH: 10
```

```
<212> TYPE: PRT
<213> ORGANISM: H. sapiens

<400> SEQUENCE: 417

Glu Asp Gly Gly Gly Trp Trp Tyr Asn Arg
1               5                   10

<210> SEQ ID NO 418
<211> LENGTH: 19
<212> TYPE: PRT
<213> ORGANISM: H. sapiens

<400> SEQUENCE: 418

Glu Glu Ala Pro Ser Leu Arg Pro Ala Pro Pro Ile Ser Gly Gly
1               5                   10                  15

Gly Tyr Arg

<210> SEQ ID NO 419
<211> LENGTH: 7
<212> TYPE: PRT
<213> ORGANISM: H. sapiens

<400> SEQUENCE: 419

Gly Ser Trp Tyr Ser Met Arg
1               5

<210> SEQ ID NO 420
<211> LENGTH: 21
<212> TYPE: PRT
<213> ORGANISM: H. sapiens

<400> SEQUENCE: 420

Lys Gly Gly Glu Thr Ser Glu Met Tyr Leu Ile Gln Pro Asp Ser Ser
1               5                   10                  15

Val Lys Pro Tyr Arg
            20

<210> SEQ ID NO 421
<211> LENGTH: 6
<212> TYPE: PRT
<213> ORGANISM: H. sapiens

<400> SEQUENCE: 421

Lys Trp Asp Pro Tyr Lys
1               5

<210> SEQ ID NO 422
<211> LENGTH: 14
<212> TYPE: PRT
<213> ORGANISM: H. sapiens

<400> SEQUENCE: 422

Met Gly Pro Thr Glu Leu Leu Ile Glu Met Glu Asp Trp Lys
1               5                   10

<210> SEQ ID NO 423
<211> LENGTH: 9
<212> TYPE: PRT
<213> ORGANISM: H. sapiens

<400> SEQUENCE: 423

Gln Asp Gly Ser Val Asp Phe Gly Arg
1               5
```

-continued

```
<210> SEQ ID NO 424
<211> LENGTH: 13
<212> TYPE: PRT
<213> ORGANISM: H. sapiens

<400> SEQUENCE: 424

Gln Gly Phe Gly Asn Val Ala Thr Asn Thr Asp Gly Lys
1               5                   10

<210> SEQ ID NO 425
<211> LENGTH: 7
<212> TYPE: PRT
<213> ORGANISM: H. sapiens

<400> SEQUENCE: 425

Ser Ile Leu Glu Asn Leu Arg
1               5

<210> SEQ ID NO 426
<211> LENGTH: 7
<212> TYPE: PRT
<213> ORGANISM: H. sapiens

<400> SEQUENCE: 426

Tyr Gln Ile Ser Val Asn Lys
1               5

<210> SEQ ID NO 427
<211> LENGTH: 13
<212> TYPE: PRT
<213> ORGANISM: H. sapiens

<400> SEQUENCE: 427

Tyr Tyr Trp Gly Gly Gln Tyr Thr Trp Asp Met Ala Lys
1               5                   10

<210> SEQ ID NO 428
<211> LENGTH: 9
<212> TYPE: PRT
<213> ORGANISM: H. sapiens

<400> SEQUENCE: 428

Ala Gln Thr Asp Arg Glu Asp Leu Arg
1               5

<210> SEQ ID NO 429
<211> LENGTH: 9
<212> TYPE: PRT
<213> ORGANISM: H. sapiens

<400> SEQUENCE: 429

Phe Asp Ser Asp Ala Ala Ser Pro Arg
1               5

<210> SEQ ID NO 430
<211> LENGTH: 13
<212> TYPE: PRT
<213> ORGANISM: H. sapiens

<400> SEQUENCE: 430

Leu Leu Arg Gly Tyr His Gln Asp Ala Tyr Asp Gly Lys
1               5                   10

<210> SEQ ID NO 431
```

```
<211> LENGTH: 17
<212> TYPE: PRT
<213> ORGANISM: H. sapiens

<400> SEQUENCE: 431

Tyr Thr Cys His Val Gln His Glu Gly Leu Pro Lys Pro Leu Thr Leu
 1               5                  10                  15

Arg

<210> SEQ ID NO 432
<211> LENGTH: 9
<212> TYPE: PRT
<213> ORGANISM: H. sapiens

<400> SEQUENCE: 432

Phe Asp Asn Asp Ala Ala Ser Pro Arg
 1               5

<210> SEQ ID NO 433
<211> LENGTH: 14
<212> TYPE: PRT
<213> ORGANISM: H. sapiens

<400> SEQUENCE: 433

Phe Ile Ser Val Gly Tyr Val Asp Asp Thr Gln Phe Val Arg
 1               5                  10

<210> SEQ ID NO 434
<211> LENGTH: 7
<212> TYPE: PRT
<213> ORGANISM: H. sapiens

<400> SEQUENCE: 434

Val Asn Leu Arg Thr Leu Arg
 1               5

<210> SEQ ID NO 435
<211> LENGTH: 13
<212> TYPE: PRT
<213> ORGANISM: H. sapiens

<400> SEQUENCE: 435

Trp Ala Ala Val Val Val Pro Ser Gly Glu Glu Gln Arg
 1               5                  10

<210> SEQ ID NO 436
<211> LENGTH: 4
<212> TYPE: PRT
<213> ORGANISM: H. sapiens

<400> SEQUENCE: 436

Tyr Leu Glu Lys
 1

<210> SEQ ID NO 437
<211> LENGTH: 7
<212> TYPE: PRT
<213> ORGANISM: H. sapiens

<400> SEQUENCE: 437

Lys Pro Gly Ser Ser Val Lys
 1               5

<210> SEQ ID NO 438
```

```
<211> LENGTH: 12
<212> TYPE: PRT
<213> ORGANISM: H. sapiens

<400> SEQUENCE: 438

Gln Ala Pro Gly Gln Gly Leu Glu Trp Met Gly Arg
 1               5                  10

<210> SEQ ID NO 439
<211> LENGTH: 10
<212> TYPE: PRT
<213> ORGANISM: H. sapiens

<400> SEQUENCE: 439

Glu Leu Gly Gln Met Asn Leu Thr Glu Arg
 1               5                  10

<210> SEQ ID NO 440
<211> LENGTH: 8
<212> TYPE: PRT
<213> ORGANISM: H. sapiens

<400> SEQUENCE: 440

Glu Val Glu Glu Glu Met Glu Lys
 1               5

<210> SEQ ID NO 441
<211> LENGTH: 7
<212> TYPE: PRT
<213> ORGANISM: H. sapiens

<400> SEQUENCE: 441

Phe Gly Glu Ile Tyr Glu Lys
 1               5

<210> SEQ ID NO 442
<211> LENGTH: 16
<212> TYPE: PRT
<213> ORGANISM: H. sapiens

<400> SEQUENCE: 442

Phe Lys Asn Glu Val Asn Thr Leu Glu Glu Phe Leu Ala Leu Lys
 1               5                  10                  15

<210> SEQ ID NO 443
<211> LENGTH: 11
<212> TYPE: PRT
<213> ORGANISM: H. sapiens

<400> SEQUENCE: 443

Lys Met Asn Ser Glu Phe His Ser Ala Ala Lys
 1               5                  10

<210> SEQ ID NO 444
<211> LENGTH: 12
<212> TYPE: PRT
<213> ORGANISM: H. sapiens

<400> SEQUENCE: 444

Leu Glu Asp Leu Gly Glu Leu His Arg Ala Ala Arg
 1               5                  10

<210> SEQ ID NO 445
<211> LENGTH: 6
<212> TYPE: PRT
```

```
<213> ORGANISM: H. sapiens

<400> SEQUENCE: 445

Leu Leu Ile Glu Glu Arg
1               5

<210> SEQ ID NO 446
<211> LENGTH: 10
<212> TYPE: PRT
<213> ORGANISM: H. sapiens

<400> SEQUENCE: 446

Asn Met Leu Glu Arg Gly Glu Gly Glu Arg
1               5                   10

<210> SEQ ID NO 447
<211> LENGTH: 18
<212> TYPE: PRT
<213> ORGANISM: H. sapiens

<400> SEQUENCE: 447

Gln Met Glu Asn Met Val Ser Val Leu Gln Asn Glu Leu Ser Glu Thr
1               5                   10                  15

Lys Lys

<210> SEQ ID NO 448
<211> LENGTH: 9
<212> TYPE: PRT
<213> ORGANISM: H. sapiens

<400> SEQUENCE: 448

Arg Asn Ala Asp Met Leu Tyr Asn Lys
1               5

<210> SEQ ID NO 449
<211> LENGTH: 21
<212> TYPE: PRT
<213> ORGANISM: H. sapiens

<400> SEQUENCE: 449

Ser Gly Asp Val Pro Gly Val Glu His Val Leu Ala Pro Gly Asp Thr
1               5                   10                  15

Gly Val Asp Lys Arg
            20

<210> SEQ ID NO 450
<211> LENGTH: 5
<212> TYPE: PRT
<213> ORGANISM: H. sapiens

<400> SEQUENCE: 450

Ser Tyr Met Glu Arg
1               5

<210> SEQ ID NO 451
<211> LENGTH: 13
<212> TYPE: PRT
<213> ORGANISM: H. sapiens

<400> SEQUENCE: 451

Thr Ser Gln Glu Pro Glu Met Ala Lys Asp Cys Asp Arg
1               5                   10
```

<210> SEQ ID NO 452
<211> LENGTH: 12
<212> TYPE: PRT
<213> ORGANISM: H. sapiens

<400> SEQUENCE: 452

Asp Ile Ala Pro Thr Leu Thr Leu Tyr Val Gly Lys
1               5                   10

<210> SEQ ID NO 453
<211> LENGTH: 7
<212> TYPE: PRT
<213> ORGANISM: H. sapiens

<400> SEQUENCE: 453

Asp Tyr Ala Glu Val Gly Arg
1               5

<210> SEQ ID NO 454
<211> LENGTH: 21
<212> TYPE: PRT
<213> ORGANISM: H. sapiens

<400> SEQUENCE: 454

Asp Tyr Ala Glu Val Gly Arg Val Gly Tyr Val Ser Gly Trp Gly Arg
1               5                   10                  15

Asn Ala Asn Phe Lys
            20

<210> SEQ ID NO 455
<211> LENGTH: 6
<212> TYPE: PRT
<213> ORGANISM: H. sapiens

<400> SEQUENCE: 455

Phe Thr Asp His Leu Lys
1               5

<210> SEQ ID NO 456
<211> LENGTH: 8
<212> TYPE: PRT
<213> ORGANISM: H. sapiens

<400> SEQUENCE: 456

Gly Ser Phe Pro Trp Gln Ala Lys
1               5

<210> SEQ ID NO 457
<211> LENGTH: 10
<212> TYPE: PRT
<213> ORGANISM: H. sapiens

<400> SEQUENCE: 457

His Tyr Glu Gly Ser Thr Val Pro Glu Lys
1               5                   10

<210> SEQ ID NO 458
<211> LENGTH: 11
<212> TYPE: PRT
<213> ORGANISM: H. sapiens

<400> SEQUENCE: 458

His Tyr Glu Gly Ser Thr Val Pro Glu Lys Lys
1               5                   10

```
<210> SEQ ID NO 459
<211> LENGTH: 9
<212> TYPE: PRT
<213> ORGANISM: H. sapiens

<400> SEQUENCE: 459

Ile Leu Gly Gly His Leu Asp Ala Lys
1               5

<210> SEQ ID NO 460
<211> LENGTH: 12
<212> TYPE: PRT
<213> ORGANISM: H. sapiens

<400> SEQUENCE: 460

Leu Pro Glu Cys Glu Ala Val Cys Gly Lys Pro Lys
1               5                   10

<210> SEQ ID NO 461
<211> LENGTH: 8
<212> TYPE: PRT
<213> ORGANISM: H. sapiens

<400> SEQUENCE: 461

Asn Pro Ala Asn Pro Val Gln Arg
1               5

<210> SEQ ID NO 462
<211> LENGTH: 8
<212> TYPE: PRT
<213> ORGANISM: H. sapiens

<400> SEQUENCE: 462

Asn Pro Ala Asn Pro Val Gln Arg
1               5

<210> SEQ ID NO 463
<211> LENGTH: 7
<212> TYPE: PRT
<213> ORGANISM: H. sapiens

<400> SEQUENCE: 463

Gln Leu Val Glu Ile Glu Lys
1               5

<210> SEQ ID NO 464
<211> LENGTH: 5
<212> TYPE: PRT
<213> ORGANISM: H. sapiens

<400> SEQUENCE: 464

Gln Trp Ile Asn Lys
1               5

<210> SEQ ID NO 465
<211> LENGTH: 20
<212> TYPE: PRT
<213> ORGANISM: H. sapiens

<400> SEQUENCE: 465

Ser Pro Val Gly Val Gln Pro Ile Leu Asn Glu His Thr Phe Cys Ala
1               5                   10                  15

Gly Met Ser Lys
            20
```

<210> SEQ ID NO 466
<211> LENGTH: 12
<212> TYPE: PRT
<213> ORGANISM: H. sapiens

<400> SEQUENCE: 466

Thr Glu Gly Asp Gly Val Tyr Thr Leu Asn Asp Lys
 1               5                  10

<210> SEQ ID NO 467
<211> LENGTH: 13
<212> TYPE: PRT
<213> ORGANISM: H. sapiens

<400> SEQUENCE: 467

Thr Glu Gly Asp Gly Val Tyr Thr Leu Asn Asn Glu Lys
 1               5                  10

<210> SEQ ID NO 468
<211> LENGTH: 9
<212> TYPE: PRT
<213> ORGANISM: H. sapiens

<400> SEQUENCE: 468

Val Gly Tyr Val Ser Gly Trp Gly Arg
 1               5

<210> SEQ ID NO 469
<211> LENGTH: 10
<212> TYPE: PRT
<213> ORGANISM: H. sapiens

<400> SEQUENCE: 469

Val Thr Ser Ile Gln Asp Trp Val Gln Lys
 1               5                  10

<210> SEQ ID NO 470
<211> LENGTH: 4
<212> TYPE: PRT
<213> ORGANISM: H. sapiens

<400> SEQUENCE: 470

Tyr Gln Cys Lys
 1

<210> SEQ ID NO 471
<211> LENGTH: 14
<212> TYPE: PRT
<213> ORGANISM: H. sapiens

<400> SEQUENCE: 471

Tyr Val Met Leu Pro Val Ala Asp Gln Asp Gln Cys Ile Arg
 1               5                  10

<210> SEQ ID NO 472
<211> LENGTH: 17
<212> TYPE: PRT
<213> ORGANISM: H. sapiens

<400> SEQUENCE: 472

Asp Leu Gly Leu Ala Ala Asp Leu Pro Gly Gly Ala Glu Gly Ala Ala
 1               5                  10                  15

Ala

```
<210> SEQ ID NO 473
<211> LENGTH: 13
<212> TYPE: PRT
<213> ORGANISM: H. sapiens

<400> SEQUENCE: 473

Asp Leu Gly Pro His Ala Glu Gly Gln Leu Ala Pro Arg
 1               5                  10

<210> SEQ ID NO 474
<211> LENGTH: 11
<212> TYPE: PRT
<213> ORGANISM: H. sapiens

<400> SEQUENCE: 474

Gly Gly Glu Asp Ala Ala Val Gln Glu Pro Arg
 1               5                  10

<210> SEQ ID NO 475
<211> LENGTH: 7
<212> TYPE: PRT
<213> ORGANISM: H. sapiens

<400> SEQUENCE: 475

Gln Pro Gln Ala Val Leu Arg
 1               5

<210> SEQ ID NO 476
<211> LENGTH: 14
<212> TYPE: PRT
<213> ORGANISM: H. sapiens

<400> SEQUENCE: 476

Ala Ser Trp Glu Gly His Trp Ser Pro Ala Pro Ser Ser Arg
 1               5                  10

<210> SEQ ID NO 477
<211> LENGTH: 8
<212> TYPE: PRT
<213> ORGANISM: H. sapiens

<400> SEQUENCE: 477

Lys Ile His Glu Glu Glu Val Arg
 1               5

<210> SEQ ID NO 478
<211> LENGTH: 11
<212> TYPE: PRT
<213> ORGANISM: H. sapiens

<400> SEQUENCE: 478

Leu Ala Leu Asp Ile Glu Ile Ala Thr Tyr Arg
 1               5                  10

<210> SEQ ID NO 479
<211> LENGTH: 12
<212> TYPE: PRT
<213> ORGANISM: H. sapiens

<400> SEQUENCE: 479

Asn Ala Val Met Arg Leu Cys Phe Leu Lys Ala Arg
 1               5                  10
```

```
<210> SEQ ID NO 480
<211> LENGTH: 9
<212> TYPE: PRT
<213> ORGANISM: H. sapiens

<400> SEQUENCE: 480

Asn Phe Glu Ile Asp Thr Glu Gly Lys
 1               5

<210> SEQ ID NO 481
<211> LENGTH: 14
<212> TYPE: PRT
<213> ORGANISM: H. sapiens

<400> SEQUENCE: 481

Asn Phe Glu Ile Asp Thr Glu Gly Lys Asn Ala Val Met Arg
 1               5                  10

<210> SEQ ID NO 482
<211> LENGTH: 6
<212> TYPE: PRT
<213> ORGANISM: H. sapiens

<400> SEQUENCE: 482

Gln Leu Cys Gln Glu Lys
 1               5

<210> SEQ ID NO 483
<211> LENGTH: 10
<212> TYPE: PRT
<213> ORGANISM: H. sapiens

<400> SEQUENCE: 483

Gly Ala Val Glu Ala Pro Gly Thr Pro Lys
 1               5                  10

<210> SEQ ID NO 484
<211> LENGTH: 20
<212> TYPE: PRT
<213> ORGANISM: H. sapiens

<400> SEQUENCE: 484

Gly Phe Pro Arg Pro Leu Glu Asn Ser Glu Ile Pro Met Ile Pro Gly
 1               5                  10                  15

Ala His Pro Lys
            20

<210> SEQ ID NO 485
<211> LENGTH: 18
<212> TYPE: PRT
<213> ORGANISM: H. sapiens

<400> SEQUENCE: 485

Gly Ser Val Gly Ser Glu Pro Gln Ala Phe Asp Val Phe Pro Glu Asn
 1               5                  10                  15

Pro Arg

<210> SEQ ID NO 486
<211> LENGTH: 8
<212> TYPE: PRT
<213> ORGANISM: H. sapiens

<400> SEQUENCE: 486

Gln Ala Asp Leu Pro Asp Ala Lys
```

```
                   1               5

<210> SEQ ID NO 487
<211> LENGTH: 10
<212> TYPE: PRT
<213> ORGANISM: H. sapiens

<400> SEQUENCE: 487

Arg Gly Leu Ile Arg Val Thr Thr Gln Arg
  1               5                  10

<210> SEQ ID NO 488
<211> LENGTH: 14
<212> TYPE: PRT
<213> ORGANISM: H. sapiens

<400> SEQUENCE: 488

Ser Leu Pro Pro Ala Glu Glu Leu Pro Val Glu Thr Pro Lys
  1               5                  10

<210> SEQ ID NO 489
<211> LENGTH: 13
<212> TYPE: PRT
<213> ORGANISM: H. sapiens

<400> SEQUENCE: 489

Ala Asn Ser Val Phe Glu Asp Leu Ser Val Thr Leu Arg
  1               5                  10

<210> SEQ ID NO 490
<211> LENGTH: 8
<212> TYPE: PRT
<213> ORGANISM: H. sapiens

<400> SEQUENCE: 490

Ser Phe Asp Thr Ser Leu Ile Arg
  1               5

<210> SEQ ID NO 491
<211> LENGTH: 12
<212> TYPE: PRT
<213> ORGANISM: H. sapiens

<400> SEQUENCE: 491

Ala Ala Ile Ser Gly Glu Asn Ala Gly Leu Val Arg
  1               5                  10

<210> SEQ ID NO 492
<211> LENGTH: 18
<212> TYPE: PRT
<213> ORGANISM: H. sapiens

<400> SEQUENCE: 492

Phe Ala His Tyr Val Val Thr Ser Gln Val Val Asn Thr Ala Asn Glu
  1               5                  10                  15

Ala Arg

<210> SEQ ID NO 493
<211> LENGTH: 19
<212> TYPE: PRT
<213> ORGANISM: H. sapiens

<400> SEQUENCE: 493

Gly Ser Leu Val Gln Ala Ser Glu Ala Asn Leu Gln Ala Ala Gln Asp
```

-continued

```
                  1               5                  10                 15

Phe Val Arg

<210> SEQ ID NO 494
<211> LENGTH: 13
<212> TYPE: PRT
<213> ORGANISM: H. sapiens

<400> SEQUENCE: 494

Gln Tyr Tyr Glu Gly Ser Glu Ile Val Val Ala Gly Arg
 1               5                  10

<210> SEQ ID NO 495
<211> LENGTH: 13
<212> TYPE: PRT
<213> ORGANISM: H. sapiens

<400> SEQUENCE: 495

Ala Pro Ala Ser Gly Gly Val Ser Ser Pro Leu Val Arg
 1               5                  10

<210> SEQ ID NO 496
<211> LENGTH: 13
<212> TYPE: PRT
<213> ORGANISM: H. sapiens

<400> SEQUENCE: 496

Ala Ser Val Ser Gly Ser Met Pro Met Pro Leu Pro Arg
 1               5                  10

<210> SEQ ID NO 497
<211> LENGTH: 19
<212> TYPE: PRT
<213> ORGANISM: H. sapiens

<400> SEQUENCE: 497

Phe Leu Glu Gly Leu Ser Glu Ala Val Thr Thr Lys Met Gly Arg Ile
 1               5                  10                 15

Phe Leu Lys

<210> SEQ ID NO 498
<211> LENGTH: 14
<212> TYPE: PRT
<213> ORGANISM: H. sapiens

<400> SEQUENCE: 498

Met Ala Thr Ala Pro Ile Arg Ala Ser Ala Ser Gly Ala Arg
 1               5                  10

<210> SEQ ID NO 499
<211> LENGTH: 21
<212> TYPE: PRT
<213> ORGANISM: H. sapiens

<400> SEQUENCE: 499

Val Thr Ser Thr Ser Gln Met Met Pro Thr Ala Ser Gly Asp Met Cys
 1               5                  10                 15

Thr Leu Pro Val Arg
             20

<210> SEQ ID NO 500
<211> LENGTH: 4
<212> TYPE: PRT
```

<213> ORGANISM: H. sapiens

<400> SEQUENCE: 500

Glu His Glu Lys
 1

<210> SEQ ID NO 501
<211> LENGTH: 13
<212> TYPE: PRT
<213> ORGANISM: H. sapiens

<400> SEQUENCE: 501

Glu His Leu Thr Ser Glu Ala Ala Ser Gly Asn His Arg
 1               5                  10

<210> SEQ ID NO 502
<211> LENGTH: 6
<212> TYPE: PRT
<213> ORGANISM: H. sapiens

<400> SEQUENCE: 502

Glu Leu Glu Ala Met Arg
 1               5

<210> SEQ ID NO 503
<211> LENGTH: 11
<212> TYPE: PRT
<213> ORGANISM: H. sapiens

<400> SEQUENCE: 503

Ile Gln Gln Glu Gln Arg Ile Leu Leu Asp Lys
 1               5                  10

<210> SEQ ID NO 504
<211> LENGTH: 7
<212> TYPE: PRT
<213> ORGANISM: H. sapiens

<400> SEQUENCE: 504

Lys Glu Leu Glu Ala Met Arg
 1               5

<210> SEQ ID NO 505
<211> LENGTH: 5
<212> TYPE: PRT
<213> ORGANISM: H. sapiens

<400> SEQUENCE: 505

Leu Glu Met Glu Lys
 1               5

<210> SEQ ID NO 506
<211> LENGTH: 7
<212> TYPE: PRT
<213> ORGANISM: H. sapiens

<400> SEQUENCE: 506

Leu Met Lys Ala Ala Glu Arg
 1               5

<210> SEQ ID NO 507
<211> LENGTH: 12
<212> TYPE: PRT
<213> ORGANISM: H. sapiens

<400> SEQUENCE: 507

Asn Leu Thr His Met Gln Asp Glu Val Asn Val Lys
1               5                   10

<210> SEQ ID NO 508
<211> LENGTH: 10
<212> TYPE: PRT
<213> ORGANISM: H. sapiens

<400> SEQUENCE: 508

Ser Leu Asn Gly Thr Ile Glu Asn Leu Lys
1               5                   10

<210> SEQ ID NO 509
<211> LENGTH: 9
<212> TYPE: PRT
<213> ORGANISM: H. sapiens

<400> SEQUENCE: 509

Thr Asn Arg Glu Leu Leu Asp Val Lys
1               5

<210> SEQ ID NO 510
<211> LENGTH: 13
<212> TYPE: PRT
<213> ORGANISM: H. sapiens

<400> SEQUENCE: 510

Ala Gly Pro Glu Leu Leu Pro Gln Gln Gly Gly Gly Arg
1               5                   10

<210> SEQ ID NO 511
<211> LENGTH: 20
<212> TYPE: PRT
<213> ORGANISM: H. sapiens

<400> SEQUENCE: 511

Ala Gln Met Cys Pro Gly Lys Ala Pro Arg Gly Leu His Val Val Thr
1               5                   10                  15

Thr Asp Gly Arg
            20

<210> SEQ ID NO 512
<211> LENGTH: 14
<212> TYPE: PRT
<213> ORGANISM: H. sapiens

<400> SEQUENCE: 512

Ala Val Ala Ser Gln Trp Pro Glu Glu Leu Ala Ser Ala Arg
1               5                   10

<210> SEQ ID NO 513
<211> LENGTH: 17
<212> TYPE: PRT
<213> ORGANISM: H. sapiens

<400> SEQUENCE: 513

Gly Gly Glu Met Gln Val Glu Ala Gly Gly Thr Ser Pro Ala Gly Glu
1               5                   10                  15

Arg

<210> SEQ ID NO 514
<211> LENGTH: 18

-continued

```
<212> TYPE: PRT
<213> ORGANISM: H. sapiens

<400> SEQUENCE: 514

Gly Gly Glu Met Gln Val Glu Ala Gly Gly Thr Ser Pro Ala Gly Glu
1               5                   10                  15

Arg Arg

<210> SEQ ID NO 515
<211> LENGTH: 7
<212> TYPE: PRT
<213> ORGANISM: H. sapiens

<400> SEQUENCE: 515

Gly Ile Pro Ala Pro Ala Lys
1               5

<210> SEQ ID NO 516
<211> LENGTH: 10
<212> TYPE: PRT
<213> ORGANISM: H. sapiens

<400> SEQUENCE: 516

Gly Leu His Val Val Thr Thr Asp Gly Arg
1               5                   10

<210> SEQ ID NO 517
<211> LENGTH: 7
<212> TYPE: PRT
<213> ORGANISM: H. sapiens

<400> SEQUENCE: 517

Val Leu Leu Ser Ile Leu Arg
1               5

<210> SEQ ID NO 518
<211> LENGTH: 14
<212> TYPE: PRT
<213> ORGANISM: H. sapiens

<400> SEQUENCE: 518

Ser Ser Val Ser Asp Tyr Val Asn Tyr Asp Ile Ile Val Arg
1               5                   10

<210> SEQ ID NO 519
<211> LENGTH: 9
<212> TYPE: PRT
<213> ORGANISM: H. sapiens

<400> SEQUENCE: 519

Asp Asp Val Leu Leu Leu Glu Thr Arg
1               5

<210> SEQ ID NO 520
<211> LENGTH: 8
<212> TYPE: PRT
<213> ORGANISM: H. sapiens

<400> SEQUENCE: 520

Asp Phe Ser Thr Ser Ile Pro Lys
1               5

<210> SEQ ID NO 521
<211> LENGTH: 11
```

```
<212> TYPE: PRT
<213> ORGANISM: H. sapiens

<400> SEQUENCE: 521

Gly Gly Glu Ala Ala Glu Ala Glu Ala Glu Lys
 1               5                  10

<210> SEQ ID NO 522
<211> LENGTH: 14
<212> TYPE: PRT
<213> ORGANISM: H. sapiens

<400> SEQUENCE: 522

Leu Glu Asp Glu Ile Asp Phe Leu Ala Gln Glu Leu Ala Arg
 1               5                  10

<210> SEQ ID NO 523
<211> LENGTH: 11
<212> TYPE: PRT
<213> ORGANISM: H. sapiens

<400> SEQUENCE: 523

Asp Gly Thr Leu Leu Leu Glu Gly Gly Gly Arg
 1               5                  10

<210> SEQ ID NO 524
<211> LENGTH: 10
<212> TYPE: PRT
<213> ORGANISM: H. sapiens

<400> SEQUENCE: 524

Ser Leu Gln Leu Glu Glu Leu Leu Ala Arg
 1               5                  10

<210> SEQ ID NO 525
<211> LENGTH: 13
<212> TYPE: PRT
<213> ORGANISM: H. sapiens

<400> SEQUENCE: 525

Glu Glu Leu Pro Glu Pro Phe Glu His Leu Leu Gln Arg
 1               5                  10

<210> SEQ ID NO 526
<211> LENGTH: 9
<212> TYPE: PRT
<213> ORGANISM: H. sapiens

<400> SEQUENCE: 526

Ile Val Leu Asn Gly Ile Asp Leu Lys
 1               5

<210> SEQ ID NO 527
<211> LENGTH: 7
<212> TYPE: PRT
<213> ORGANISM: H. sapiens

<400> SEQUENCE: 527

Gly Ala Glu Phe Leu Leu Arg
 1               5

<210> SEQ ID NO 528
<211> LENGTH: 9
<212> TYPE: PRT
<213> ORGANISM: H. sapiens
```

```
<400> SEQUENCE: 528

Gly Glu Ala Gly Leu Asp Gly Ala Lys
1               5

<210> SEQ ID NO 529
<211> LENGTH: 13
<212> TYPE: PRT
<213> ORGANISM: H. sapiens

<400> SEQUENCE: 529

Ile Glu Asn Ile Asp His Leu Gly Phe Phe Ile Tyr Arg
1               5                   10

<210> SEQ ID NO 530
<211> LENGTH: 16
<212> TYPE: PRT
<213> ORGANISM: H. sapiens

<400> SEQUENCE: 530

Ser Tyr Glu Leu Pro Asp Gly Gln Val Ile Thr Ile Gly Asn Glu Arg
1               5                   10                  15

<210> SEQ ID NO 531
<211> LENGTH: 6
<212> TYPE: PRT
<213> ORGANISM: H. sapiens

<400> SEQUENCE: 531

Thr Gln Ile Asp Asp Arg
1               5

<210> SEQ ID NO 532
<211> LENGTH: 6
<212> TYPE: PRT
<213> ORGANISM: H. sapiens

<400> SEQUENCE: 532

Leu Phe Ala Glu Glu Lys
1               5

<210> SEQ ID NO 533
<211> LENGTH: 20
<212> TYPE: PRT
<213> ORGANISM: H. sapiens

<400> SEQUENCE: 533

Phe Phe Gly His Gly Ala Glu Asp Ser Leu Ala Asp Gln Ala Ala Asn
1               5                   10                  15

Glu Trp Gly Arg
            20

<210> SEQ ID NO 534
<211> LENGTH: 6
<212> TYPE: PRT
<213> ORGANISM: H. sapiens

<400> SEQUENCE: 534

Leu Gln Asp Met Glu Lys
1               5

<210> SEQ ID NO 535
<211> LENGTH: 6
<212> TYPE: PRT
```

<213> ORGANISM: H. sapiens

<400> SEQUENCE: 535

Val Ile Leu Ala Ile Arg
1               5

<210> SEQ ID NO 536
<211> LENGTH: 8
<212> TYPE: PRT
<213> ORGANISM: H. sapiens

<400> SEQUENCE: 536

Glu Ile Ile Ser Glu Val Gln Arg
1               5

<210> SEQ ID NO 537
<211> LENGTH: 6
<212> TYPE: PRT
<213> ORGANISM: H. sapiens

<400> SEQUENCE: 537

Ala Tyr Leu Ser Ala Lys
1               5

<210> SEQ ID NO 538
<211> LENGTH: 13
<212> TYPE: PRT
<213> ORGANISM: H. sapiens

<400> SEQUENCE: 538

Ile Asn Ser Cys Pro Leu Ser Leu Ser Trp Gly Lys Arg
1               5                   10

<210> SEQ ID NO 539
<211> LENGTH: 10
<212> TYPE: PRT
<213> ORGANISM: H. sapiens

<400> SEQUENCE: 539

Asp Thr Ser Leu Phe Ser Asp Glu Phe Lys
1               5                   10

<210> SEQ ID NO 540
<211> LENGTH: 8
<212> TYPE: PRT
<213> ORGANISM: H. sapiens

<400> SEQUENCE: 540

Trp Ala Leu Gly Gln Val Phe Arg
1               5

<210> SEQ ID NO 541
<211> LENGTH: 8
<212> TYPE: PRT
<213> ORGANISM: H. sapiens

<400> SEQUENCE: 541

Val Ile Ile Phe Gly Met Gly Lys
1               5

<210> SEQ ID NO 542
<211> LENGTH: 6
<212> TYPE: PRT
<213> ORGANISM: H. sapiens

<400> SEQUENCE: 542

Ser Ile Thr Asn Pro Arg
1               5

<210> SEQ ID NO 543
<211> LENGTH: 7
<212> TYPE: PRT
<213> ORGANISM: H. sapiens

<400> SEQUENCE: 543

Phe Leu Pro Leu Phe Asp Arg
1               5

<210> SEQ ID NO 544
<211> LENGTH: 8
<212> TYPE: PRT
<213> ORGANISM: H. sapiens

<400> SEQUENCE: 544

Lys Ser Asp Phe Phe Ile Asn Lys
1               5

<210> SEQ ID NO 545
<211> LENGTH: 8
<212> TYPE: PRT
<213> ORGANISM: H. sapiens

<400> SEQUENCE: 545

Asn Lys Pro Gly Val Tyr Thr Lys
1               5

<210> SEQ ID NO 546
<211> LENGTH: 8
<212> TYPE: PRT
<213> ORGANISM: H. sapiens

<400> SEQUENCE: 546

Val Ile Phe Gly Leu Phe Gly Lys
1               5

<210> SEQ ID NO 547
<211> LENGTH: 6
<212> TYPE: PRT
<213> ORGANISM: H. sapiens

<400> SEQUENCE: 547

Val Thr Asp Leu Met Arg
1               5

<210> SEQ ID NO 548
<211> LENGTH: 9
<212> TYPE: PRT
<213> ORGANISM: H. sapiens

<400> SEQUENCE: 548

Leu Glu Ala Glu Gly Met Arg Gly Arg
1               5

<210> SEQ ID NO 549
<211> LENGTH: 6
<212> TYPE: PRT
<213> ORGANISM: H. sapiens

<400> SEQUENCE: 549

Glu Leu Glu Glu Arg Arg
1               5

<210> SEQ ID NO 550
<211> LENGTH: 9
<212> TYPE: PRT
<213> ORGANISM: H. sapiens

<400> SEQUENCE: 550

Arg Asn Ile Ser His Ile Pro Glu Arg
1               5

<210> SEQ ID NO 551
<211> LENGTH: 10
<212> TYPE: PRT
<213> ORGANISM: H. sapiens

<400> SEQUENCE: 551

Glu Gly Ser Asp Leu Ser Val Val Glu Arg
1               5                   10

<210> SEQ ID NO 552
<211> LENGTH: 14
<212> TYPE: PRT
<213> ORGANISM: H. sapiens

<400> SEQUENCE: 552

Glu Ala Glu Ala Trp Ala Lys Pro Gly Ala Ala Ala Arg Arg
1               5                   10

<210> SEQ ID NO 553
<211> LENGTH: 9
<212> TYPE: PRT
<213> ORGANISM: H. sapiens

<400> SEQUENCE: 553

Gly Ser Gly Glu Gln Gln Ile Met Arg
1               5

<210> SEQ ID NO 554
<211> LENGTH: 6
<212> TYPE: PRT
<213> ORGANISM: H. sapiens

<400> SEQUENCE: 554

Asn Thr Met Ala Met Lys
1               5

<210> SEQ ID NO 555
<211> LENGTH: 14
<212> TYPE: PRT
<213> ORGANISM: H. sapiens

<400> SEQUENCE: 555

Gly Glu Tyr Asp Leu Val Ser Ala Tyr Glu Val Asp His Arg
1               5                   10

<210> SEQ ID NO 556
<211> LENGTH: 8
<212> TYPE: PRT
<213> ORGANISM: H. sapiens

<400> SEQUENCE: 556

Leu Gln Leu Ser Glu Thr Asn Arg
1               5

```
<210> SEQ ID NO 557
<211> LENGTH: 6
<212> TYPE: PRT
<213> ORGANISM: H. sapiens

<400> SEQUENCE: 557

Thr Gln Leu Asp Asp Arg
1               5

<210> SEQ ID NO 558
<211> LENGTH: 14
<212> TYPE: PRT
<213> ORGANISM: H. sapiens

<400> SEQUENCE: 558

Ile Val Glu Pro Tyr Val Thr Phe Gly Phe Pro Asn Pro Lys
1               5                   10

<210> SEQ ID NO 559
<211> LENGTH: 20
<212> TYPE: PRT
<213> ORGANISM: H. sapiens

<400> SEQUENCE: 559

Leu Gly Glu His Asn Ile Glu Val Leu Glu Gly Asn Glu Gln Phe Ile
1               5                   10                  15

Asn Ala Ala Lys
            20

<210> SEQ ID NO 560
<211> LENGTH: 8
<212> TYPE: PRT
<213> ORGANISM: H. sapiens

<400> SEQUENCE: 560

Glu Arg Val Thr Ala Leu Val Arg
1               5

<210> SEQ ID NO 561
<211> LENGTH: 9
<212> TYPE: PRT
<213> ORGANISM: H. sapiens

<400> SEQUENCE: 561

Asp Leu Thr Leu Leu Ile Thr Glu Arg
1               5

<210> SEQ ID NO 562
<211> LENGTH: 9
<212> TYPE: PRT
<213> ORGANISM: H. sapiens

<400> SEQUENCE: 562

Leu Gln Glu Ala Ala Glu Ile Val Lys
1               5

<210> SEQ ID NO 563
<211> LENGTH: 9
<212> TYPE: PRT
<213> ORGANISM: H. sapiens

<400> SEQUENCE: 563

Gly Leu Ala Ala Ala Ala Gly Gly Arg
```

```
                              1               5

<210> SEQ ID NO 564
<211> LENGTH: 6
<212> TYPE: PRT
<213> ORGANISM: H. sapiens

<400> SEQUENCE: 564

Asp Leu Leu Leu Glu Lys
  1               5

<210> SEQ ID NO 565
<211> LENGTH: 7
<212> TYPE: PRT
<213> ORGANISM: H. sapiens

<400> SEQUENCE: 565

Ala Ala His Ala Gly Glu Arg
  1               5

<210> SEQ ID NO 566
<211> LENGTH: 11
<212> TYPE: PRT
<213> ORGANISM: H. sapiens

<400> SEQUENCE: 566

Thr Asp Gln Glu Val Leu Gly Glu Leu Val Arg
  1               5                  10

<210> SEQ ID NO 567
<211> LENGTH: 7
<212> TYPE: PRT
<213> ORGANISM: H. sapiens

<400> SEQUENCE: 567

Glu Ala Asp Val Val Ala Arg
  1               5

<210> SEQ ID NO 568
<211> LENGTH: 10
<212> TYPE: PRT
<213> ORGANISM: H. sapiens

<400> SEQUENCE: 568

Asp Gly Gly Glu Leu Pro Asp Pro Asp Arg
  1               5                  10

<210> SEQ ID NO 569
<211> LENGTH: 11
<212> TYPE: PRT
<213> ORGANISM: H. sapiens

<400> SEQUENCE: 569

Glu Gln Ile Val Ala Gln Tyr Pro Ser Leu Lys
  1               5                  10

<210> SEQ ID NO 570
<211> LENGTH: 23
<212> TYPE: PRT
<213> ORGANISM: H. sapiens

<400> SEQUENCE: 570

Ala Pro Ala Lys Pro Pro Gly Ser Gly Leu Asp Leu Ala Asp Ala Leu
  1               5                  10                  15
```

Asp Asp Gln Asp Asp Gly Arg
            20

<210> SEQ ID NO 571
<211> LENGTH: 9
<212> TYPE: PRT
<213> ORGANISM: H. sapiens

<400> SEQUENCE: 571

Asp Ala Glu Glu Asp Met Pro Gln Arg
1               5

<210> SEQ ID NO 572
<211> LENGTH: 13
<212> TYPE: PRT
<213> ORGANISM: H. sapiens

<400> SEQUENCE: 572

Ser Asp Asp Ser Val Ile Gln Leu Leu Asn Pro Asn Arg
1               5                   10

<210> SEQ ID NO 573
<211> LENGTH: 13
<212> TYPE: PRT
<213> ORGANISM: H. sapiens

<400> SEQUENCE: 573

Trp Leu Cys Val Val Gly Gly Trp Asp Gly Ser Arg Arg
1               5                   10

<210> SEQ ID NO 574
<211> LENGTH: 13
<212> TYPE: PRT
<213> ORGANISM: H. sapiens

<400> SEQUENCE: 574

Trp Leu Cys Val Val Gly Gly Trp Asp Gly Ser Arg Arg
1               5                   10

<210> SEQ ID NO 575
<211> LENGTH: 6
<212> TYPE: PRT
<213> ORGANISM: H. sapiens

<400> SEQUENCE: 575

Leu His Leu Val Ser Arg
1               5

<210> SEQ ID NO 576
<211> LENGTH: 6
<212> TYPE: PRT
<213> ORGANISM: H. sapiens

<400> SEQUENCE: 576

Tyr Gly Glu Glu Ile Lys
1               5

<210> SEQ ID NO 577
<211> LENGTH: 7
<212> TYPE: PRT
<213> ORGANISM: H. sapiens

<400> SEQUENCE: 577

Val Leu Glu Ala Ile Leu Arg
1               5

```
<210> SEQ ID NO 578
<211> LENGTH: 16
<212> TYPE: PRT
<213> ORGANISM: H. sapiens

<400> SEQUENCE: 578

Thr Phe Ala Ser Pro Asn Ala Ser Gly Ser Gly Asn Thr Gly Ala Arg
 1               5                  10                  15

<210> SEQ ID NO 579
<211> LENGTH: 19
<212> TYPE: PRT
<213> ORGANISM: H. sapiens

<400> SEQUENCE: 579

Ala Ala Leu Glu Gly Phe Leu Ala Ala Leu Gln Ala Asp Pro Pro Gln
 1               5                  10                  15

Ala Glu Arg

<210> SEQ ID NO 580
<211> LENGTH: 9
<212> TYPE: PRT
<213> ORGANISM: H. sapiens

<400> SEQUENCE: 580

Asp Asp Thr Pro Met Thr Leu Pro Lys
 1               5

<210> SEQ ID NO 581
<211> LENGTH: 12
<212> TYPE: PRT
<213> ORGANISM: H. sapiens

<400> SEQUENCE: 581

Asp Glu Leu Ala Pro Ala Gly Thr Gly Val Ser Arg
 1               5                  10

<210> SEQ ID NO 582
<211> LENGTH: 10
<212> TYPE: PRT
<213> ORGANISM: H. sapiens

<400> SEQUENCE: 582

Glu Trp Ala Met Ala Asp Asn Gln Ser Lys
 1               5                  10

<210> SEQ ID NO 583
<211> LENGTH: 6
<212> TYPE: PRT
<213> ORGANISM: H. sapiens

<400> SEQUENCE: 583

Phe Leu His Gln Glu Arg
 1               5

<210> SEQ ID NO 584
<211> LENGTH: 9
<212> TYPE: PRT
<213> ORGANISM: H. sapiens

<400> SEQUENCE: 584

Gly Gly Leu Gln Pro Pro Asp Ser Lys
 1               5
```

```
<210> SEQ ID NO 585
<211> LENGTH: 12
<212> TYPE: PRT
<213> ORGANISM: H. sapiens

<400> SEQUENCE: 585

Gly Ser Thr Glu Gln Asp Ala Ala Ser Pro Glu Lys
 1               5                  10

<210> SEQ ID NO 586
<211> LENGTH: 14
<212> TYPE: PRT
<213> ORGANISM: H. sapiens

<400> SEQUENCE: 586

Gly Ser Thr Glu Gln Asp Ala Ala Ser Pro Glu Lys Glu Lys
 1               5                  10

<210> SEQ ID NO 587
<211> LENGTH: 8
<212> TYPE: PRT
<213> ORGANISM: H. sapiens

<400> SEQUENCE: 587

Leu Val Glu Thr His Ala Thr Arg
 1               5

<210> SEQ ID NO 588
<211> LENGTH: 9
<212> TYPE: PRT
<213> ORGANISM: H. sapiens

<400> SEQUENCE: 588

Met Asp Gln Cys Glu Ser Ser Thr Arg
 1               5

<210> SEQ ID NO 589
<211> LENGTH: 9
<212> TYPE: PRT
<213> ORGANISM: H. sapiens

<400> SEQUENCE: 589

Met Asn Pro Leu Glu Gln Tyr Glu Arg
 1               5

<210> SEQ ID NO 590
<211> LENGTH: 10
<212> TYPE: PRT
<213> ORGANISM: H. sapiens

<400> SEQUENCE: 590

Gln Met Tyr Pro Glu Leu Gln Ile Ala Arg
 1               5                  10

<210> SEQ ID NO 591
<211> LENGTH: 12
<212> TYPE: PRT
<213> ORGANISM: H. sapiens

<400> SEQUENCE: 591

Val Glu Gln Ala Thr Gln Ala Ile Pro Met Glu Arg
 1               5                  10
```

```
<210> SEQ ID NO 592
<211> LENGTH: 9
<212> TYPE: PRT
<213> ORGANISM: H. sapiens

<400> SEQUENCE: 592

Val Ile Ala Leu Ile Asn Asp Gln Arg
1               5

<210> SEQ ID NO 593
<211> LENGTH: 6
<212> TYPE: PRT
<213> ORGANISM: H. sapiens

<400> SEQUENCE: 593

Val Leu Glu Tyr Cys Arg
1               5

<210> SEQ ID NO 594
<211> LENGTH: 6
<212> TYPE: PRT
<213> ORGANISM: H. sapiens

<400> SEQUENCE: 594

Val Leu Leu Ala Leu Arg
1               5

<210> SEQ ID NO 595
<211> LENGTH: 7
<212> TYPE: PRT
<213> ORGANISM: H. sapiens

<400> SEQUENCE: 595

Trp Glu Pro Asp Pro Gln Arg
1               5

<210> SEQ ID NO 596
<211> LENGTH: 10
<212> TYPE: PRT
<213> ORGANISM: H. sapiens

<400> SEQUENCE: 596

Glu Leu Pro Gly Glu Thr Leu Glu Ser Lys
1               5                   10

<210> SEQ ID NO 597
<211> LENGTH: 20
<212> TYPE: PRT
<213> ORGANISM: H. sapiens

<400> SEQUENCE: 597

Glu Ser Leu Asp Pro Val Gln Glu Pro Gly Gly Gln Ala Glu Ala Asp
1               5                   10                  15

Gly Asp Val Pro
            20

<210> SEQ ID NO 598
<211> LENGTH: 10
<212> TYPE: PRT
<213> ORGANISM: H. sapiens

<400> SEQUENCE: 598

Gly Glu Ala Glu Gly Gln Ala Glu Ala Lys
1               5                   10
```

```
<210> SEQ ID NO 599
<211> LENGTH: 17
<212> TYPE: PRT
<213> ORGANISM: H. sapiens

<400> SEQUENCE: 599

Gly Glu Ala Gly Gly Gln Ala Glu Ala Glu Gly Asp Ala Pro Gly Pro
 1               5                  10                  15

Arg

<210> SEQ ID NO 600
<211> LENGTH: 10
<212> TYPE: PRT
<213> ORGANISM: H. sapiens

<400> SEQUENCE: 600

Gly Glu Ala Gly Gly Gln Ala Glu Ala Arg
 1               5                  10

<210> SEQ ID NO 601
<211> LENGTH: 20
<212> TYPE: PRT
<213> ORGANISM: H. sapiens

<400> SEQUENCE: 601

His Val Glu Pro Gly Glu Pro Leu Ala Pro Ser Pro Gln Glu Pro Gln
 1               5                  10                  15

Ala Val Gly Arg
            20

<210> SEQ ID NO 602
<211> LENGTH: 18
<212> TYPE: PRT
<213> ORGANISM: H. sapiens

<400> SEQUENCE: 602

Asn Thr Gln Asn Asp Phe Glu Val His Ile Val Gln Val Glu Asn Asp
 1               5                  10                  15

Glu Ile

<210> SEQ ID NO 603
<211> LENGTH: 10
<212> TYPE: PRT
<213> ORGANISM: H. sapiens

<400> SEQUENCE: 603

Gln Glu Thr Gln Glu Ala Pro Gly Pro Arg
 1               5                  10

<210> SEQ ID NO 604
<211> LENGTH: 20
<212> TYPE: PRT
<213> ORGANISM: H. sapiens

<400> SEQUENCE: 604

Arg Glu Ser Leu Asp Pro Val Gln Glu Pro Gly Gly Gln Ala Glu Ala
 1               5                  10                  15

Asp Gly Asp Val
            20

<210> SEQ ID NO 605
<211> LENGTH: 10
```

```
<212> TYPE: PRT
<213> ORGANISM: H. sapiens

<400> SEQUENCE: 605

Thr Glu Val Gln Leu Glu His Leu Ser Arg
1               5                   10

<210> SEQ ID NO 606
<211> LENGTH: 11
<212> TYPE: PRT
<213> ORGANISM: H. sapiens

<400> SEQUENCE: 606

Ala Asp Gln Thr Val Leu Thr Glu Asp Glu Lys
1               5                   10

<210> SEQ ID NO 607
<211> LENGTH: 12
<212> TYPE: PRT
<213> ORGANISM: H. sapiens

<400> SEQUENCE: 607

Ala Asp Gln Thr Val Leu Thr Glu Asp Glu Lys Lys
1               5                   10

<210> SEQ ID NO 608
<211> LENGTH: 13
<212> TYPE: PRT
<213> ORGANISM: H. sapiens

<400> SEQUENCE: 608

Ala Ser Glu Glu Glu Pro Glu Tyr Gly Glu Glu Ile Lys
1               5                   10

<210> SEQ ID NO 609
<211> LENGTH: 8
<212> TYPE: PRT
<213> ORGANISM: H. sapiens

<400> SEQUENCE: 609

Ala Tyr Phe Met Ser Asp Thr Arg
1               5

<210> SEQ ID NO 610
<211> LENGTH: 12
<212> TYPE: PRT
<213> ORGANISM: H. sapiens

<400> SEQUENCE: 610

Cys Ile Ile Glu Val Leu Ser Asn Ala Leu Ser Lys
1               5                   10

<210> SEQ ID NO 611
<211> LENGTH: 11
<212> TYPE: PRT
<213> ORGANISM: H. sapiens

<400> SEQUENCE: 611

Asp Lys Glu Thr Thr Glu Asn Glu Asn Thr Lys
1               5                   10

<210> SEQ ID NO 612
<211> LENGTH: 14
<212> TYPE: PRT
<213> ORGANISM: H. sapiens
```

-continued

```
<400> SEQUENCE: 612

Asp Pro Ala Asp Ala Ser Glu Ala His Glu Ser Ser Ser Arg
1               5                   10

<210> SEQ ID NO 613
<211> LENGTH: 13
<212> TYPE: PRT
<213> ORGANISM: H. sapiens

<400> SEQUENCE: 613

Glu Asp Glu Glu Glu Glu Glu Gly Glu Asn Tyr Gln Lys
1               5                   10

<210> SEQ ID NO 614
<211> LENGTH: 17
<212> TYPE: PRT
<213> ORGANISM: H. sapiens

<400> SEQUENCE: 614

Glu Leu Asp Arg Asn Tyr Leu Asn Tyr Gly Glu Glu Gly Ala Pro Gly
1               5                   10                  15

Lys

<210> SEQ ID NO 615
<211> LENGTH: 14
<212> TYPE: PRT
<213> ORGANISM: H. sapiens

<400> SEQUENCE: 615

Glu Leu Glu Asn Leu Ala Ala Met Asp Leu Glu Leu Gln Lys
1               5                   10

<210> SEQ ID NO 616
<211> LENGTH: 16
<212> TYPE: PRT
<213> ORGANISM: H. sapiens

<400> SEQUENCE: 616

Gly Glu Ala Gly Ala Pro Gly Glu Glu Asp Ile Gln Gly Pro Thr Lys
1               5                   10                  15

<210> SEQ ID NO 617
<211> LENGTH: 6
<212> TYPE: PRT
<213> ORGANISM: H. sapiens

<400> SEQUENCE: 617

Gly Leu Glu Pro Gly Lys
1               5

<210> SEQ ID NO 618
<211> LENGTH: 15
<212> TYPE: PRT
<213> ORGANISM: H. sapiens

<400> SEQUENCE: 618

Gly Tyr Pro Gly Val Gln Ala Pro Glu Asp Leu Glu Trp Glu Arg
1               5                   10                  15

<210> SEQ ID NO 619
<211> LENGTH: 16
<212> TYPE: PRT
<213> ORGANISM: H. sapiens
```

<400> SEQUENCE: 619

His Leu Glu Glu Pro Gly Glu Thr Gln Asn Ala Phe Leu Asn Glu Arg
1               5                   10                  15

<210> SEQ ID NO 620
<211> LENGTH: 15
<212> TYPE: PRT
<213> ORGANISM: H. sapiens

<400> SEQUENCE: 620

Lys Glu Leu Glu Asn Leu Ala Ala Met Asp Leu Glu Leu Gln Lys
1               5                   10                  15

<210> SEQ ID NO 621
<211> LENGTH: 13
<212> TYPE: PRT
<213> ORGANISM: H. sapiens

<400> SEQUENCE: 621

Met Ala His Gly Tyr Gly Glu Glu Ser Glu Glu Glu Arg
1               5                   10

<210> SEQ ID NO 622
<211> LENGTH: 9
<212> TYPE: PRT
<213> ORGANISM: H. sapiens

<400> SEQUENCE: 622

Asn His Asn Glu Gly Met Val Thr Arg
1               5

<210> SEQ ID NO 623
<211> LENGTH: 13
<212> TYPE: PRT
<213> ORGANISM: H. sapiens

<400> SEQUENCE: 623

Asn Tyr Leu Asn Tyr Gly Glu Glu Gly Ala Pro Gly Lys
1               5                   10

<210> SEQ ID NO 624
<211> LENGTH: 9
<212> TYPE: PRT
<213> ORGANISM: H. sapiens

<400> SEQUENCE: 624

Asn Tyr Pro Ser Leu Glu Leu Asp Lys
1               5

<210> SEQ ID NO 625
<211> LENGTH: 6
<212> TYPE: PRT
<213> ORGANISM: H. sapiens

<400> SEQUENCE: 625

Gln Ala Ser Ala Ile Lys
1               5

<210> SEQ ID NO 626
<211> LENGTH: 16
<212> TYPE: PRT
<213> ORGANISM: H. sapiens

<400> SEQUENCE: 626

Ser Gln Arg Glu Asp Glu Glu Glu Glu Gly Glu Asn Tyr Gln Lys
1               5                   10                  15

<210> SEQ ID NO 627
<211> LENGTH: 11
<212> TYPE: PRT
<213> ORGANISM: H. sapiens

<400> SEQUENCE: 627

Ser Ser Ala Pro Pro Ile Thr Pro Glu Cys Arg
1               5                   10

<210> SEQ ID NO 628
<211> LENGTH: 20
<212> TYPE: PRT
<213> ORGANISM: H. sapiens

<400> SEQUENCE: 628

Ser Ser Gln Glu Ser Gly Glu Glu Ala Gly Ser Gln Glu Asn His Pro
1               5                   10                  15

Gln Glu Ser Lys
            20

<210> SEQ ID NO 629
<211> LENGTH: 12
<212> TYPE: PRT
<213> ORGANISM: H. sapiens

<400> SEQUENCE: 629

Ser Ser Gln Gly Gly Ser Leu Pro Ser Glu Glu Lys
1               5                   10

<210> SEQ ID NO 630
<211> LENGTH: 11
<212> TYPE: PRT
<213> ORGANISM: H. sapiens

<400> SEQUENCE: 630

Val Ala Gln Leu Asp Gln Leu Leu His Tyr Arg
1               5                   10

<210> SEQ ID NO 631
<211> LENGTH: 8
<212> TYPE: PRT
<213> ORGANISM: H. sapiens

<400> SEQUENCE: 631

Val Gln Glu Asn Gln Met Asp Lys
1               5

<210> SEQ ID NO 632
<211> LENGTH: 9
<212> TYPE: PRT
<213> ORGANISM: H. sapiens

<400> SEQUENCE: 632

Trp Ala Glu Gly Gly Gly His Ser Arg
1               5

<210> SEQ ID NO 633
<211> LENGTH: 11
<212> TYPE: PRT
<213> ORGANISM: H. sapiens

-continued

```
<400> SEQUENCE: 633

Trp Gln Gln Gln Gly Asp Leu Gln Asp Thr Lys
1               5                   10

<210> SEQ ID NO 634
<211> LENGTH: 15
<212> TYPE: PRT
<213> ORGANISM: H. sapiens

<400> SEQUENCE: 634

Ala Pro Gly Gly Gly Gly Ala Asn Leu Lys Gly Asp Arg Ser Arg
1               5                   10                  15

<210> SEQ ID NO 635
<211> LENGTH: 18
<212> TYPE: PRT
<213> ORGANISM: H. sapiens

<400> SEQUENCE: 635

Thr Pro Pro Ala Glu Glu Leu Ala Glu Pro Gln Ala Ala Gly Gly
1               5                   10                  15

Gln Lys

<210> SEQ ID NO 636
<211> LENGTH: 8
<212> TYPE: PRT
<213> ORGANISM: H. sapiens

<400> SEQUENCE: 636

Cys Cys Lys Val Cys Pro Gly Lys
1               5

<210> SEQ ID NO 637
<211> LENGTH: 11
<212> TYPE: PRT
<213> ORGANISM: H. sapiens

<400> SEQUENCE: 637

Glu Glu Leu Pro Gly Gln Ser Phe Asp Asn Lys
1               5                   10

<210> SEQ ID NO 638
<211> LENGTH: 16
<212> TYPE: PRT
<213> ORGANISM: H. sapiens

<400> SEQUENCE: 638

Gly Asp Gly Glu Leu Ser Trp Glu His Ser Asp Gly Asp Ile Phe Arg
1               5                   10                  15

<210> SEQ ID NO 639
<211> LENGTH: 18
<212> TYPE: PRT
<213> ORGANISM: H. sapiens

<400> SEQUENCE: 639

Leu Thr Cys Ala Phe Pro Val Ser Val Pro Asp Ser Cys Cys Arg Val
1               5                   10                  15

Cys Arg

<210> SEQ ID NO 640
<211> LENGTH: 9
<212> TYPE: PRT
```

```
<213> ORGANISM: H. sapiens

<400> SEQUENCE: 640

Val Leu Tyr Leu Glu Arg Ser Glu Lys
 1               5

<210> SEQ ID NO 641
<211> LENGTH: 4
<212> TYPE: PRT
<213> ORGANISM: H. sapiens

<400> SEQUENCE: 641

Tyr Pro Cys Lys
 1

<210> SEQ ID NO 642
<211> LENGTH: 9
<212> TYPE: PRT
<213> ORGANISM: H. sapiens

<400> SEQUENCE: 642

Ala Val Tyr Leu Pro Asn Cys Asp Arg
 1               5

<210> SEQ ID NO 643
<211> LENGTH: 8
<212> TYPE: PRT
<213> ORGANISM: H. sapiens

<400> SEQUENCE: 643

Gly Ile Cys Trp Cys Val Asp Lys
 1               5

<210> SEQ ID NO 644
<211> LENGTH: 7
<212> TYPE: PRT
<213> ORGANISM: H. sapiens

<400> SEQUENCE: 644

Gly Val Cys Leu Asn Glu Lys
 1               5

<210> SEQ ID NO 645
<211> LENGTH: 10
<212> TYPE: PRT
<213> ORGANISM: H. sapiens

<400> SEQUENCE: 645

His Met Glu Ala Ser Leu Gln Glu Leu Lys
 1               5                  10

<210> SEQ ID NO 646
<211> LENGTH: 9
<212> TYPE: PRT
<213> ORGANISM: H. sapiens

<400> SEQUENCE: 646

Gln Glu Ser Glu Gln Gly Pro Cys Arg
 1               5

<210> SEQ ID NO 647
<211> LENGTH: 22
<212> TYPE: PRT
<213> ORGANISM: H. sapiens
```

```
<400> SEQUENCE: 647

Asp Cys Ser Gln Glu Asp Asn Asn Val Glu Gly Leu Ala His Leu Met
1               5                   10                  15

Met Gly Asp Gln Gly Lys
            20

<210> SEQ ID NO 648
<211> LENGTH: 18
<212> TYPE: PRT
<213> ORGANISM: H. sapiens

<400> SEQUENCE: 648

Asp Met Thr Val Phe Ser Gly Leu Phe Val Gly Gly Leu Pro Pro Glu
1               5                   10                  15

Leu Arg

<210> SEQ ID NO 649
<211> LENGTH: 11
<212> TYPE: PRT
<213> ORGANISM: H. sapiens

<400> SEQUENCE: 649

Glu Pro Tyr Pro Gly Ser Ala Glu Val Ile Arg
1               5                   10

<210> SEQ ID NO 650
<211> LENGTH: 8
<212> TYPE: PRT
<213> ORGANISM: H. sapiens

<400> SEQUENCE: 650

Met Gly Thr Ala Leu Leu Gln Arg
1               5

<210> SEQ ID NO 651
<211> LENGTH: 12
<212> TYPE: PRT
<213> ORGANISM: H. sapiens

<400> SEQUENCE: 651

Asn Gly Asp Ile Asp Tyr Cys Glu Leu Asn Ala Arg
1               5                   10

<210> SEQ ID NO 652
<211> LENGTH: 6
<212> TYPE: PRT
<213> ORGANISM: H. sapiens

<400> SEQUENCE: 652

Asn Asn Gly Met Cys Arg
1               5

<210> SEQ ID NO 653
<211> LENGTH: 5
<212> TYPE: PRT
<213> ORGANISM: H. sapiens

<400> SEQUENCE: 653

Gln Gly Asp Pro Lys
1               5

<210> SEQ ID NO 654
<211> LENGTH: 13
```

```
<212> TYPE: PRT
<213> ORGANISM: H. sapiens

<400> SEQUENCE: 654

Thr Leu Gln Arg Asn Gly Leu Met Leu His Thr Gly Lys
 1               5                  10

<210> SEQ ID NO 655
<211> LENGTH: 8
<212> TYPE: PRT
<213> ORGANISM: H. sapiens

<400> SEQUENCE: 655

Glu Ser Gln Ala Tyr Tyr Gln Arg
 1               5

<210> SEQ ID NO 656
<211> LENGTH: 10
<212> TYPE: PRT
<213> ORGANISM: H. sapiens

<400> SEQUENCE: 656

Gly Glu Asn Phe Thr Glu Thr Asp Val Lys
 1               5                  10

<210> SEQ ID NO 657
<211> LENGTH: 9
<212> TYPE: PRT
<213> ORGANISM: H. sapiens

<400> SEQUENCE: 657

Gln His Thr Val Thr Thr Thr Thr Lys
 1               5

<210> SEQ ID NO 658
<211> LENGTH: 12
<212> TYPE: PRT
<213> ORGANISM: H. sapiens

<400> SEQUENCE: 658

Val Val Glu Gln Met Cys Ile Thr Gln Tyr Glu Arg
 1               5                  10

<210> SEQ ID NO 659
<211> LENGTH: 11
<212> TYPE: PRT
<213> ORGANISM: H. sapiens

<400> SEQUENCE: 659

Tyr Pro Gly Gln Gly Ser Pro Gly Gly Asn Arg
 1               5                  10

<210> SEQ ID NO 660
<211> LENGTH: 14
<212> TYPE: PRT
<213> ORGANISM: H. sapiens

<400> SEQUENCE: 660

Ala Lys Pro Ser Ala Pro Val Val Ser Gly Pro Ala Ala Arg
 1               5                  10

<210> SEQ ID NO 661
<211> LENGTH: 7
<212> TYPE: PRT
<213> ORGANISM: H. sapiens
```

```
<400> SEQUENCE: 661

Glu Leu Ile Tyr Asn Gln Lys
 1               5

<210> SEQ ID NO 662
<211> LENGTH: 9
<212> TYPE: PRT
<213> ORGANISM: H. sapiens

<400> SEQUENCE: 662

Gly Ser Pro Asp Asp Val Glu Phe Lys
 1               5

<210> SEQ ID NO 663
<211> LENGTH: 10
<212> TYPE: PRT
<213> ORGANISM: H. sapiens

<400> SEQUENCE: 663

Met Glu Pro Ala Gly Pro Ala Pro Gly Arg
 1               5                  10

<210> SEQ ID NO 664
<211> LENGTH: 13
<212> TYPE: PRT
<213> ORGANISM: H. sapiens

<400> SEQUENCE: 664

Ser Val Leu Val Ala Ala Gly Glu Thr Ala Thr Leu Arg
 1               5                  10

<210> SEQ ID NO 665
<211> LENGTH: 11
<212> TYPE: PRT
<213> ORGANISM: H. sapiens

<400> SEQUENCE: 665

Thr Glu Thr Ala Ser Thr Val Thr Glu Asn Lys
 1               5                  10

<210> SEQ ID NO 666
<211> LENGTH: 13
<212> TYPE: PRT
<213> ORGANISM: H. sapiens

<400> SEQUENCE: 666

Val Pro Pro Thr Leu Glu Val Thr Gln Gln Pro Val Arg
 1               5                  10

<210> SEQ ID NO 667
<211> LENGTH: 11
<212> TYPE: PRT
<213> ORGANISM: H. sapiens

<400> SEQUENCE: 667

Met Glu Tyr Ala Leu Asn Met Leu Leu Gln Arg
 1               5                  10

<210> SEQ ID NO 668
<211> LENGTH: 13
<212> TYPE: PRT
<213> ORGANISM: H. sapiens

<400> SEQUENCE: 668
```

Asn Pro Glu Asp Arg Pro Ser Leu Asp Asp Ile Ile Arg
1               5                   10

<210> SEQ ID NO 669
<211> LENGTH: 8
<212> TYPE: PRT
<213> ORGANISM: H. sapiens

<400> SEQUENCE: 669

Gln Gln Ile Gly Asp Ala Ile Arg
1               5

<210> SEQ ID NO 670
<211> LENGTH: 8
<212> TYPE: PRT
<213> ORGANISM: H. sapiens

<400> SEQUENCE: 670

Glu Asp Ala Leu Pro Gly Gln Lys
1               5

<210> SEQ ID NO 671
<211> LENGTH: 6
<212> TYPE: PRT
<213> ORGANISM: H. sapiens

<400> SEQUENCE: 671

Gly Gly Val Val Leu Lys
1               5

<210> SEQ ID NO 672
<211> LENGTH: 8
<212> TYPE: PRT
<213> ORGANISM: H. sapiens

<400> SEQUENCE: 672

Leu Leu Asp Ala Tyr Phe Ala Arg
1               5

<210> SEQ ID NO 673
<211> LENGTH: 13
<212> TYPE: PRT
<213> ORGANISM: H. sapiens

<400> SEQUENCE: 673

Ser Val Ala Asn Asp Glu Leu His Val Met Met Gln Arg
1               5                   10

<210> SEQ ID NO 674
<211> LENGTH: 16
<212> TYPE: PRT
<213> ORGANISM: H. sapiens

<400> SEQUENCE: 674

Cys Leu Val Gly Glu Phe Val Ser Asp Ala Leu Leu Val Pro Asp Lys
1               5                   10                  15

<210> SEQ ID NO 675
<211> LENGTH: 12
<212> TYPE: PRT
<213> ORGANISM: H. sapiens

<400> SEQUENCE: 675

Leu Val Phe Phe Ala Glu Asp Val Gly Ser Asn Lys

```
                1               5                   10
```

<210> SEQ ID NO 676
<211> LENGTH: 10
<212> TYPE: PRT
<213> ORGANISM: H. sapiens

<400> SEQUENCE: 676

```
Thr His Pro His Phe Val Ile Pro Tyr Arg
1               5                   10
```

<210> SEQ ID NO 677
<211> LENGTH: 6
<212> TYPE: PRT
<213> ORGANISM: H. sapiens

<400> SEQUENCE: 677

```
Ala Glu Met Glu Glu Lys
1               5
```

<210> SEQ ID NO 678
<211> LENGTH: 7
<212> TYPE: PRT
<213> ORGANISM: H. sapiens

<400> SEQUENCE: 678

```
Ala Gln Glu Ile Tyr Glu Lys
1               5
```

<210> SEQ ID NO 679
<211> LENGTH: 8
<212> TYPE: PRT
<213> ORGANISM: H. sapiens

<400> SEQUENCE: 679

```
Asp Leu Val Glu Met Glu Gln Lys
1               5
```

<210> SEQ ID NO 680
<211> LENGTH: 7
<212> TYPE: PRT
<213> ORGANISM: H. sapiens

<400> SEQUENCE: 680

```
Asp Val Gln Leu Gln Gln Lys
1               5
```

<210> SEQ ID NO 681
<211> LENGTH: 17
<212> TYPE: PRT
<213> ORGANISM: H. sapiens

<400> SEQUENCE: 681

```
Glu Ala Leu Lys Glu Asn Lys Ser Leu Gln Glu Glu Leu Ser Leu Ala
1               5                   10                  15

Arg
```

<210> SEQ ID NO 682
<211> LENGTH: 20
<212> TYPE: PRT
<213> ORGANISM: H. sapiens

<400> SEQUENCE: 682

```
Glu Glu Asp Val Ser Tyr Leu Ser Gly Gln Leu Ser Glu Lys Glu Ala
1               5                   10                  15
```

-continued

```
                1               5                  10                  15

Ala Leu Thr Lys
            20

<210> SEQ ID NO 683
<211> LENGTH: 24
<212> TYPE: PRT
<213> ORGANISM: H. sapiens

<400> SEQUENCE: 683

Glu Ile Lys Glu Leu Glu Asn Leu Leu Ser Gln Glu Glu Glu Glu Asn
1               5                  10                  15

Ile Val Leu Glu Glu Glu Asn Lys
            20

<210> SEQ ID NO 684
<211> LENGTH: 5
<212> TYPE: PRT
<213> ORGANISM: H. sapiens

<400> SEQUENCE: 684

Glu Leu Leu Gln Arg
1               5

<210> SEQ ID NO 685
<211> LENGTH: 10
<212> TYPE: PRT
<213> ORGANISM: H. sapiens

<400> SEQUENCE: 685

Glu Leu Leu Ser Gln Leu Glu Glu Thr Arg
1               5                  10

<210> SEQ ID NO 686
<211> LENGTH: 16
<212> TYPE: PRT
<213> ORGANISM: H. sapiens

<400> SEQUENCE: 686

Glu Met Lys Gln Met Glu Gly Glu Gly Ile Ala Pro Ile Lys Met Lys
1               5                  10                  15

<210> SEQ ID NO 687
<211> LENGTH: 10
<212> TYPE: PRT
<213> ORGANISM: H. sapiens

<400> SEQUENCE: 687

Glu Asn Glu Asn Ile Gly Asp Gln Leu Arg
1               5                  10

<210> SEQ ID NO 688
<211> LENGTH: 10
<212> TYPE: PRT
<213> ORGANISM: H. sapiens

<400> SEQUENCE: 688

Glu Asn Leu Ala Gln Ala Val Glu His Arg
1               5                  10

<210> SEQ ID NO 689
<211> LENGTH: 6
<212> TYPE: PRT
<213> ORGANISM: H. sapiens
```

```
<400> SEQUENCE: 689

Leu Asp Glu Leu Gln Lys
 1               5

<210> SEQ ID NO 690
<211> LENGTH: 6
<212> TYPE: PRT
<213> ORGANISM: H. sapiens

<400> SEQUENCE: 690

Leu Leu Met Val Thr Lys
 1               5

<210> SEQ ID NO 691
<211> LENGTH: 9
<212> TYPE: PRT
<213> ORGANISM: H. sapiens

<400> SEQUENCE: 691

Asn Glu Thr Glu Thr Ala Glu Glu Arg
 1               5

<210> SEQ ID NO 692
<211> LENGTH: 5
<212> TYPE: PRT
<213> ORGANISM: H. sapiens

<400> SEQUENCE: 692

Gln Asp Gly Asp Lys
 1               5

<210> SEQ ID NO 693
<211> LENGTH: 11
<212> TYPE: PRT
<213> ORGANISM: H. sapiens

<400> SEQUENCE: 693

Ser Met Ser Ser Leu Gln Asn Asp Arg Asp Arg
 1               5                  10

<210> SEQ ID NO 694
<211> LENGTH: 13
<212> TYPE: PRT
<213> ORGANISM: H. sapiens

<400> SEQUENCE: 694

Ser Ser Lys Ile Ala Glu Ser Thr Glu Trp Gln Glu Lys
 1               5                  10

<210> SEQ ID NO 695
<211> LENGTH: 8
<212> TYPE: PRT
<213> ORGANISM: H. sapiens

<400> SEQUENCE: 695

Ser Ser Trp Glu Ile His Glu Arg
 1               5

<210> SEQ ID NO 696
<211> LENGTH: 11
<212> TYPE: PRT
<213> ORGANISM: H. sapiens

<400> SEQUENCE: 696
```

```
Asp Leu Gln Glu Ala Asp Leu Asp Leu Leu Arg
 1               5                   10

<210> SEQ ID NO 697
<211> LENGTH: 7
<212> TYPE: PRT
<213> ORGANISM: H. sapiens

<400> SEQUENCE: 697

Leu Gly Met Thr Asn Ser His
 1               5

<210> SEQ ID NO 698
<211> LENGTH: 14
<212> TYPE: PRT
<213> ORGANISM: H. sapiens

<400> SEQUENCE: 698

Glu Gln Leu Gly Glu Phe Tyr Glu Ala Leu Asp Cys Leu Arg
 1               5                   10

<210> SEQ ID NO 699
<211> LENGTH: 7
<212> TYPE: PRT
<213> ORGANISM: H. sapiens

<400> SEQUENCE: 699

Lys Gln Glu Glu Gly Glu Ser
 1               5

<210> SEQ ID NO 700
<211> LENGTH: 8
<212> TYPE: PRT
<213> ORGANISM: H. sapiens

<400> SEQUENCE: 700

Thr Glu Asp Thr Ile Phe Leu Arg
 1               5

<210> SEQ ID NO 701
<211> LENGTH: 9
<212> TYPE: PRT
<213> ORGANISM: H. sapiens

<400> SEQUENCE: 701

Trp Phe Tyr Ile Ala Ser Ala Phe Arg
 1               5

<210> SEQ ID NO 702
<211> LENGTH: 5
<212> TYPE: PRT
<213> ORGANISM: H. sapiens

<400> SEQUENCE: 702

Asp Leu Met Glu Lys
 1               5

<210> SEQ ID NO 703
<211> LENGTH: 20
<212> TYPE: PRT
<213> ORGANISM: H. sapiens

<400> SEQUENCE: 703

Glu Pro Cys Val Glu Ser Leu Val Ser Gln Tyr Phe Gln Thr Val Thr
```

```
                1               5                  10                  15

Asp Tyr Gly Lys
            20

<210> SEQ ID NO 704
<211> LENGTH: 8
<212> TYPE: PRT
<213> ORGANISM: H. sapiens

<400> SEQUENCE: 704

Glu Gln Leu Thr Pro Leu Ile Lys
1               5

<210> SEQ ID NO 705
<211> LENGTH: 10
<212> TYPE: PRT
<213> ORGANISM: H. sapiens

<400> SEQUENCE: 705

Ser Lys Glu Gln Leu Thr Pro Leu Ile Lys
1               5                   10

<210> SEQ ID NO 706
<211> LENGTH: 9
<212> TYPE: PRT
<213> ORGANISM: H. sapiens

<400> SEQUENCE: 706

Ser Pro Glu Leu Gln Ala Glu Ala Lys
1               5

<210> SEQ ID NO 707
<211> LENGTH: 5
<212> TYPE: PRT
<213> ORGANISM: H. sapiens

<400> SEQUENCE: 707

Ser Tyr Phe Glu Lys
1               5

<210> SEQ ID NO 708
<211> LENGTH: 11
<212> TYPE: PRT
<213> ORGANISM: H. sapiens

<400> SEQUENCE: 708

Val Lys Ser Pro Glu Leu Gln Ala Glu Ala Lys
1               5                   10

<210> SEQ ID NO 709
<211> LENGTH: 9
<212> TYPE: PRT
<213> ORGANISM: H. sapiens

<400> SEQUENCE: 709

Glu Phe Gly Asn Thr Leu Glu Asp Lys
1               5

<210> SEQ ID NO 710
<211> LENGTH: 9
<212> TYPE: PRT
<213> ORGANISM: H. sapiens

<400> SEQUENCE: 710
```

```
Glu Trp Phe Ser Glu Thr Phe Gln Lys
 1               5
```

<210> SEQ ID NO 711
<211> LENGTH: 11
<212> TYPE: PRT
<213> ORGANISM: H. sapiens

<400> SEQUENCE: 711

```
Leu Lys Glu Phe Gly Asn Thr Leu Glu Asp Lys
 1               5                  10
```

<210> SEQ ID NO 712
<211> LENGTH: 7
<212> TYPE: PRT
<213> ORGANISM: H. sapiens

<400> SEQUENCE: 712

```
Gln Ser Glu Leu Ser Ala Lys
 1               5
```

<210> SEQ ID NO 713
<211> LENGTH: 16
<212> TYPE: PRT
<213> ORGANISM: H. sapiens

<400> SEQUENCE: 713

```
Asp Ala Leu Ser Ser Val Gln Glu Ser Gln Val Ala Gln Gln Ala Arg
 1               5                  10                  15
```

<210> SEQ ID NO 714
<211> LENGTH: 7
<212> TYPE: PRT
<213> ORGANISM: H. sapiens

<400> SEQUENCE: 714

```
Asp Tyr Trp Ser Thr Val Lys
 1               5
```

<210> SEQ ID NO 715
<211> LENGTH: 11
<212> TYPE: PRT
<213> ORGANISM: H. sapiens

<400> SEQUENCE: 715

```
Gly Trp Val Thr Asp Gly Phe Ser Ser Leu Lys
 1               5                  10
```

<210> SEQ ID NO 716
<211> LENGTH: 9
<212> TYPE: PRT
<213> ORGANISM: H. sapiens

<400> SEQUENCE: 716

```
Ala Thr Val Val Tyr Gln Gly Glu Arg
 1               5
```

<210> SEQ ID NO 717
<211> LENGTH: 10
<212> TYPE: PRT
<213> ORGANISM: H. sapiens

<400> SEQUENCE: 717

```
Lys Ala Thr Val Val Tyr Gln Gly Glu Arg
 1               5                  10
```

<210> SEQ ID NO 718
<211> LENGTH: 6
<212> TYPE: PRT
<213> ORGANISM: H. sapiens

<400> SEQUENCE: 718

Val Ser Phe Phe Cys Lys
1               5

<210> SEQ ID NO 719
<211> LENGTH: 7
<212> TYPE: PRT
<213> ORGANISM: H. sapiens

<400> SEQUENCE: 719

Ala Phe Leu Leu Thr Pro Arg
1               5

<210> SEQ ID NO 720
<211> LENGTH: 6
<212> TYPE: PRT
<213> ORGANISM: H. sapiens

<400> SEQUENCE: 720

Cys Val Glu Glu Phe Lys
1               5

<210> SEQ ID NO 721
<211> LENGTH: 6
<212> TYPE: PRT
<213> ORGANISM: H. sapiens

<400> SEQUENCE: 721

Phe Leu Leu Tyr Asn Arg
1               5

<210> SEQ ID NO 722
<211> LENGTH: 13
<212> TYPE: PRT
<213> ORGANISM: H. sapiens

<400> SEQUENCE: 722

Trp Ile Tyr His Leu Thr Glu Gly Ser Thr Asp Leu Arg
1               5                   10

<210> SEQ ID NO 723
<211> LENGTH: 6
<212> TYPE: PRT
<213> ORGANISM: H. sapiens

<400> SEQUENCE: 723

Cys Glu Glu Leu Glu Lys
1               5

<210> SEQ ID NO 724
<211> LENGTH: 7
<212> TYPE: PRT
<213> ORGANISM: H. sapiens

<400> SEQUENCE: 724

Glu Thr Ile Glu Glu Leu Arg
1               5

```
<210> SEQ ID NO 725
<211> LENGTH: 9
<212> TYPE: PRT
<213> ORGANISM: H. sapiens

<400> SEQUENCE: 725

Lys Asn Glu Leu Glu Thr Glu Asn Arg
1               5

<210> SEQ ID NO 726
<211> LENGTH: 13
<212> TYPE: PRT
<213> ORGANISM: H. sapiens

<400> SEQUENCE: 726

Leu Ala Ser Thr Gly Ser Gly Gln Ser Phe Leu Ala Arg
1               5                   10

<210> SEQ ID NO 727
<211> LENGTH: 7
<212> TYPE: PRT
<213> ORGANISM: H. sapiens

<400> SEQUENCE: 727

Leu Glu Glu His Leu Glu Lys
1               5

<210> SEQ ID NO 728
<211> LENGTH: 7
<212> TYPE: PRT
<213> ORGANISM: H. sapiens

<400> SEQUENCE: 728

Leu Phe His Ser Leu Glu Lys
1               5

<210> SEQ ID NO 729
<211> LENGTH: 16
<212> TYPE: PRT
<213> ORGANISM: H. sapiens

<400> SEQUENCE: 729

Leu Asn Gln Ser Asp Ser Ile Glu Asp Pro Asn Ser Pro Ala Gly Arg
1               5                   10                  15

<210> SEQ ID NO 730
<211> LENGTH: 13
<212> TYPE: PRT
<213> ORGANISM: H. sapiens

<400> SEQUENCE: 730

Met Leu Lys Leu Asn Gln Glu Gly Ser Asp Asn Glu Lys
1               5                   10

<210> SEQ ID NO 731
<211> LENGTH: 7
<212> TYPE: PRT
<213> ORGANISM: H. sapiens

<400> SEQUENCE: 731

Thr Glu Arg Asp Ser Leu Lys
1               5

<210> SEQ ID NO 732
<211> LENGTH: 4
```

```
<212> TYPE: PRT
<213> ORGANISM: H. sapiens

<400> SEQUENCE: 732

Tyr Leu Glu Lys
  1

<210> SEQ ID NO 733
<211> LENGTH: 11
<212> TYPE: PRT
<213> ORGANISM: H. sapiens

<400> SEQUENCE: 733

Ala Gly Leu Ala Lys Pro Pro Ala Ala Ala Lys
  1               5                  10

<210> SEQ ID NO 734
<211> LENGTH: 9
<212> TYPE: PRT
<213> ORGANISM: H. sapiens

<400> SEQUENCE: 734

Asp Gln Ala Ala Ala Leu Val Pro Lys
  1               5

<210> SEQ ID NO 735
<211> LENGTH: 15
<212> TYPE: PRT
<213> ORGANISM: H. sapiens

<400> SEQUENCE: 735

Met Trp Ile Gln Gln Leu Leu Gly Leu Ser Ser Met Ser Ile Arg
  1               5                  10                  15

<210> SEQ ID NO 736
<211> LENGTH: 23
<212> TYPE: PRT
<213> ORGANISM: H. sapiens

<400> SEQUENCE: 736

Ser Ser Pro Ser Leu Ala Ser Ser Ser Ser Ser Ser Ala Val
  1               5                  10                  15

Ala Gly Gly Ala Pro Glu Gln
                 20

<210> SEQ ID NO 737
<211> LENGTH: 14
<212> TYPE: PRT
<213> ORGANISM: H. sapiens

<400> SEQUENCE: 737

Gly His Gln Asp Leu Asp Pro Asp Asn Glu Gly Glu Leu Arg
  1               5                  10

<210> SEQ ID NO 738
<211> LENGTH: 8
<212> TYPE: PRT
<213> ORGANISM: H. sapiens

<400> SEQUENCE: 738

Leu Ser Phe Phe Gly Leu Glu Lys
  1               5

<210> SEQ ID NO 739
```

```
<211> LENGTH: 7
<212> TYPE: PRT
<213> ORGANISM: H. sapiens

<400> SEQUENCE: 739

Ala Lys Gln Asp Met Ala Arg
1               5

<210> SEQ ID NO 740
<211> LENGTH: 11
<212> TYPE: PRT
<213> ORGANISM: H. sapiens

<400> SEQUENCE: 740

Leu Ala Leu Asp Ile Glu Ile Ala Thr Tyr Arg
1               5                   10

<210> SEQ ID NO 741
<211> LENGTH: 13
<212> TYPE: PRT
<213> ORGANISM: H. sapiens

<400> SEQUENCE: 741

Leu Glu Ser Gly Met Gln Asn Met Ser Ile His Thr Lys
1               5                   10

<210> SEQ ID NO 742
<211> LENGTH: 9
<212> TYPE: PRT
<213> ORGANISM: H. sapiens

<400> SEQUENCE: 742

Gln Leu Glu Thr Leu Gly Gln Glu Lys
1               5

<210> SEQ ID NO 743
<211> LENGTH: 19
<212> TYPE: PRT
<213> ORGANISM: H. sapiens

<400> SEQUENCE: 743

Thr Ala Arg Ser Asn Met Asp Asn Met Phe Glu Ser Tyr Ile Asn Asn
1               5                   10                  15

Leu Arg Arg

<210> SEQ ID NO 744
<211> LENGTH: 7
<212> TYPE: PRT
<213> ORGANISM: H. sapiens

<400> SEQUENCE: 744

Val Ser Thr Ser Gly Pro Arg
1               5

<210> SEQ ID NO 745
<211> LENGTH: 10
<212> TYPE: PRT
<213> ORGANISM: H. sapiens

<400> SEQUENCE: 745

Phe Ser Gly Thr Trp Tyr Ala Met Ala Lys
1               5                   10

<210> SEQ ID NO 746
```

```
<211> LENGTH: 22
<212> TYPE: PRT
<213> ORGANISM: H. sapiens

<400> SEQUENCE: 746

Gly Asn Asp Asp His Trp Ile Val Asp Thr Asp Tyr Asp Thr Tyr Ala
1               5                   10                  15

Val Gln Tyr Ser Cys Arg
            20

<210> SEQ ID NO 747
<211> LENGTH: 18
<212> TYPE: PRT
<213> ORGANISM: H. sapiens

<400> SEQUENCE: 747

Leu Leu Asn Leu Asp Gly Thr Cys Ala Asp Ser Tyr Ser Phe Val Phe
1               5                   10                  15

Ser Arg

<210> SEQ ID NO 748
<211> LENGTH: 8
<212> TYPE: PRT
<213> ORGANISM: H. sapiens

<400> SEQUENCE: 748

Gln Glu Glu Leu Cys Leu Ala Arg
1               5

<210> SEQ ID NO 749
<211> LENGTH: 7
<212> TYPE: PRT
<213> ORGANISM: H. sapiens

<400> SEQUENCE: 749

Val Lys Glu Asn Phe Asp Lys
1               5

<210> SEQ ID NO 750
<211> LENGTH: 10
<212> TYPE: PRT
<213> ORGANISM: H. sapiens

<400> SEQUENCE: 750

Tyr Trp Gly Val Ala Ser Phe Leu Gln Lys
1               5                   10

<210> SEQ ID NO 751
<211> LENGTH: 14
<212> TYPE: PRT
<213> ORGANISM: H. sapiens

<400> SEQUENCE: 751

Glu Glu Ile Asn Ala Leu Val Gln Glu Leu Gly Phe Tyr Arg
1               5                   10

<210> SEQ ID NO 752
<211> LENGTH: 14
<212> TYPE: PRT
<213> ORGANISM: H. sapiens

<400> SEQUENCE: 752

His Leu Pro Gly Ala Asp Pro Glu Leu Val Leu Leu Gly Arg
1               5                   10
```

<210> SEQ ID NO 753
<211> LENGTH: 12
<212> TYPE: PRT
<213> ORGANISM: H. sapiens

<400> SEQUENCE: 753

Ala Leu Tyr Leu Gln Tyr Thr Asp Glu Thr Phe Arg
1               5                   10

<210> SEQ ID NO 754
<211> LENGTH: 14
<212> TYPE: PRT
<213> ORGANISM: H. sapiens

<400> SEQUENCE: 754

Asp Ile Ala Ser Gly Leu Ile Gly Pro Leu Ile Ile Cys Lys
1               5                   10

<210> SEQ ID NO 755
<211> LENGTH: 11
<212> TYPE: PRT
<213> ORGANISM: H. sapiens

<400> SEQUENCE: 755

Asp Ile Phe Thr Gly Leu Ile Gly Pro Met Lys
1               5                   10

<210> SEQ ID NO 756
<211> LENGTH: 14
<212> TYPE: PRT
<213> ORGANISM: H. sapiens

<400> SEQUENCE: 756

Asp Leu Tyr Ser Gly Leu Ile Gly Pro Leu Ile Val Cys Arg
1               5                   10

<210> SEQ ID NO 757
<211> LENGTH: 7
<212> TYPE: PRT
<213> ORGANISM: H. sapiens

<400> SEQUENCE: 757

Asp Ser Leu Asp Lys Glu Lys
1               5

<210> SEQ ID NO 758
<211> LENGTH: 10
<212> TYPE: PRT
<213> ORGANISM: H. sapiens

<400> SEQUENCE: 758

Glu Tyr Thr Asp Ala Ser Phe Thr Asn Arg
1               5                   10

<210> SEQ ID NO 759
<211> LENGTH: 13
<212> TYPE: PRT
<213> ORGANISM: H. sapiens

<400> SEQUENCE: 759

Gly Ala Tyr Pro Leu Ser Ile Glu Pro Ile Gly Val Arg
1               5                   10

<210> SEQ ID NO 760
<211> LENGTH: 8
<212> TYPE: PRT
<213> ORGANISM: H. sapiens

<400> SEQUENCE: 760

Gly Glu Phe Tyr Ile Gly Ser Lys
 1               5

<210> SEQ ID NO 761
<211> LENGTH: 23
<212> TYPE: PRT
<213> ORGANISM: H. sapiens

<400> SEQUENCE: 761

Gly Pro Glu Glu Glu His Leu Gly Ile Leu Gly Pro Val Ile Trp Ala
 1               5                  10                  15

Glu Val Gly Asp Thr Ile Arg
            20

<210> SEQ ID NO 762
<211> LENGTH: 23
<212> TYPE: PRT
<213> ORGANISM: H. sapiens

<400> SEQUENCE: 762

Gly Val Tyr Ser Ser Asp Val Phe Asp Ile Phe Pro Gly Thr Tyr Gln
 1               5                  10                  15

Thr Leu Glu Met Phe Pro Arg
            20

<210> SEQ ID NO 763
<211> LENGTH: 6
<212> TYPE: PRT
<213> ORGANISM: H. sapiens

<400> SEQUENCE: 763

Ile Gly Gly Ser Tyr Lys
 1               5

<210> SEQ ID NO 764
<211> LENGTH: 10
<212> TYPE: PRT
<213> ORGANISM: H. sapiens

<400> SEQUENCE: 764

Ile Tyr His Ser His Ile Asp Ala Pro Lys
 1               5                  10

<210> SEQ ID NO 765
<211> LENGTH: 21
<212> TYPE: PRT
<213> ORGANISM: H. sapiens

<400> SEQUENCE: 765

Lys Ala Glu Glu Glu His Leu Gly Ile Leu Gly Pro Gln Leu His Ala
 1               5                  10                  15

Asp Val Gly Asp Lys
            20

<210> SEQ ID NO 766
<211> LENGTH: 19
<212> TYPE: PRT
<213> ORGANISM: H. sapiens

```
<400> SEQUENCE: 766

Leu Ile Ser Val Asp Thr Glu His Ser Asn Ile Tyr Leu Gln Asn Gly
 1               5                  10                  15

Pro Asp Arg

<210> SEQ ID NO 767
<211> LENGTH: 21
<212> TYPE: PRT
<213> ORGANISM: H. sapiens

<400> SEQUENCE: 767

Met Tyr Tyr Ser Ala Val Asp Pro Thr Lys Asp Ile Phe Thr Gly Leu
 1               5                  10                  15

Ile Gly Pro Met Lys
            20

<210> SEQ ID NO 768
<211> LENGTH: 16
<212> TYPE: PRT
<213> ORGANISM: H. sapiens

<400> SEQUENCE: 768

Asn Asn Glu Gly Thr Tyr Tyr Ser Pro Asn Tyr Asn Pro Gln Ser Arg
 1               5                  10                  15

<210> SEQ ID NO 769
<211> LENGTH: 12
<212> TYPE: PRT
<213> ORGANISM: H. sapiens

<400> SEQUENCE: 769

Gln Ser Glu Asp Ser Thr Phe Tyr Leu Gly Glu Arg
 1               5                  10

<210> SEQ ID NO 770
<211> LENGTH: 8
<212> TYPE: PRT
<213> ORGANISM: H. sapiens

<400> SEQUENCE: 770

Gln Tyr Thr Asp Ser Thr Phe Arg
 1               5

<210> SEQ ID NO 771
<211> LENGTH: 17
<212> TYPE: PRT
<213> ORGANISM: H. sapiens

<400> SEQUENCE: 771

Thr Thr Ile Glu Lys Pro Val Trp Leu Gly Phe Leu Gly Pro Ile Ile
 1               5                  10                  15

Lys

<210> SEQ ID NO 772
<211> LENGTH: 8
<212> TYPE: PRT
<213> ORGANISM: H. sapiens

<400> SEQUENCE: 772

Thr Tyr Ser Asp His Pro Glu Lys
 1               5
```

```
<210> SEQ ID NO 773
<211> LENGTH: 13
<212> TYPE: PRT
<213> ORGANISM: H. sapiens

<400> SEQUENCE: 773

Val Asp Lys Asp Asn Glu Asp Phe Gln Glu Ser Asn Arg
 1               5                  10

<210> SEQ ID NO 774
<211> LENGTH: 13
<212> TYPE: PRT
<213> ORGANISM: H. sapiens

<400> SEQUENCE: 774

Val Asn Lys Asp Asp Glu Glu Phe Ile Glu Ser Asn Lys
 1               5                  10

<210> SEQ ID NO 775
<211> LENGTH: 6
<212> TYPE: PRT
<213> ORGANISM: H. sapiens

<400> SEQUENCE: 775

Val Thr Phe His Asn Lys
 1               5

<210> SEQ ID NO 776
<211> LENGTH: 6
<212> TYPE: PRT
<213> ORGANISM: H. sapiens

<400> SEQUENCE: 776

Val Tyr Val His Leu Lys
 1               5

<210> SEQ ID NO 777
<211> LENGTH: 11
<212> TYPE: PRT
<213> ORGANISM: H. sapiens

<400> SEQUENCE: 777

Ala Leu Asp Phe Ala Val Gly Glu Tyr Asn Lys
 1               5                  10

<210> SEQ ID NO 778
<211> LENGTH: 6
<212> TYPE: PRT
<213> ORGANISM: H. sapiens

<400> SEQUENCE: 778

Ala Leu Gln Val Val Arg
 1               5

<210> SEQ ID NO 779
<211> LENGTH: 9
<212> TYPE: PRT
<213> ORGANISM: H. sapiens

<400> SEQUENCE: 779

Ala Ser Asn Asp Met Tyr His Ser Arg
 1               5

<210> SEQ ID NO 780
```

```
<211> LENGTH: 17
<212> TYPE: PRT
<213> ORGANISM: H. sapiens

<400> SEQUENCE: 780

Lys Gln Ile Val Ala Gly Val Asn Tyr Phe Leu Asp Val Glu Leu Gly
1               5                   10                  15
Arg

<210> SEQ ID NO 781
<211> LENGTH: 16
<212> TYPE: PRT
<213> ORGANISM: H. sapiens

<400> SEQUENCE: 781

Leu Val Gly Gly Pro Met Asp Ala Ser Val Glu Glu Glu Gly Val Arg
1               5                   10                  15

<210> SEQ ID NO 782
<211> LENGTH: 17
<212> TYPE: PRT
<213> ORGANISM: H. sapiens

<400> SEQUENCE: 782

Leu Val Gly Gly Pro Met Asp Ala Ser Val Glu Glu Glu Gly Val Arg
1               5                   10                  15
Arg

<210> SEQ ID NO 783
<211> LENGTH: 16
<212> TYPE: PRT
<213> ORGANISM: H. sapiens

<400> SEQUENCE: 783

Gln Ile Val Ala Gly Val Asn Tyr Phe Leu Asp Val Glu Leu Gly Arg
1               5                   10                  15

<210> SEQ ID NO 784
<211> LENGTH: 6
<212> TYPE: PRT
<213> ORGANISM: H. sapiens

<400> SEQUENCE: 784

Ser Thr Cys Gln Asp Ala
1               5

<210> SEQ ID NO 785
<211> LENGTH: 17
<212> TYPE: PRT
<213> ORGANISM: H. sapiens

<400> SEQUENCE: 785

Thr Gln Pro Asn Leu Asp Asn Cys Pro Phe His Asp Gln Pro His Leu
1               5                   10                  15
Lys

<210> SEQ ID NO 786
<211> LENGTH: 8
<212> TYPE: PRT
<213> ORGANISM: H. sapiens

<400> SEQUENCE: 786

Lys Ser Asp Phe Phe Ile Asn Lys
```

<210> SEQ ID NO 787
<211> LENGTH: 7
<212> TYPE: PRT
<213> ORGANISM: H. sapiens

<400> SEQUENCE: 787

Leu Ile Trp Phe Ser Asp Lys
1               5

<210> SEQ ID NO 788
<211> LENGTH: 9
<212> TYPE: PRT
<213> ORGANISM: H. sapiens

<400> SEQUENCE: 788

Met Gly Gln Ile Ile Gln Tyr Asp Lys
1               5

<210> SEQ ID NO 789
<211> LENGTH: 20
<212> TYPE: PRT
<213> ORGANISM: H. sapiens

<400> SEQUENCE: 789

Ala Val Ile His Pro Asp Tyr Asp Ala Ala Ser His Asp Gln Asp Ile
1               5                   10                  15

Met Leu Leu Arg
            20

<210> SEQ ID NO 790
<211> LENGTH: 18
<212> TYPE: PRT
<213> ORGANISM: H. sapiens

<400> SEQUENCE: 790

Asp Ser Cys Gln Gly Asp Ser Gly Gly Pro Leu Val Cys Gly Asp His
1               5                   10                  15

Leu Arg

<210> SEQ ID NO 791
<211> LENGTH: 11
<212> TYPE: PRT
<213> ORGANISM: H. sapiens

<400> SEQUENCE: 791

Glu Lys Pro Gly Val Tyr Thr Asn Val Cys Arg
1               5                   10

<210> SEQ ID NO 792
<211> LENGTH: 11
<212> TYPE: PRT
<213> ORGANISM: H. sapiens

<400> SEQUENCE: 792

Glu Ser Ser Gln Glu Gln Ser Ser Val Val Arg
1               5                   10

<210> SEQ ID NO 793
<211> LENGTH: 13
<212> TYPE: PRT
<213> ORGANISM: H. sapiens

```
<400> SEQUENCE: 793

Gly Leu Val Ser Trp Gly Asn Ile Pro Cys Gly Ser Lys
 1               5                  10

<210> SEQ ID NO 794
<211> LENGTH: 10
<212> TYPE: PRT
<213> ORGANISM: H. sapiens

<400> SEQUENCE: 794

Lys Pro Asn Leu Gln Val Phe Leu Gly Lys
 1               5                  10

<210> SEQ ID NO 795
<211> LENGTH: 12
<212> TYPE: PRT
<213> ORGANISM: H. sapiens

<400> SEQUENCE: 795

Leu Ser Glu Leu Ile Gln Pro Leu Pro Leu Glu Arg
 1               5                  10

<210> SEQ ID NO 796
<211> LENGTH: 9
<212> TYPE: PRT
<213> ORGANISM: H. sapiens

<400> SEQUENCE: 796

Leu Val His Gly Gly Pro Cys Asp Lys
 1               5

<210> SEQ ID NO 797
<211> LENGTH: 20
<212> TYPE: PRT
<213> ORGANISM: H. sapiens

<400> SEQUENCE: 797

Thr Ala Asp Gly Asp Phe Pro Asp Thr Ile Gln Cys Ala Tyr Ile His
 1               5                  10                  15

Leu Val Ser Arg
            20

<210> SEQ ID NO 798
<211> LENGTH: 7
<212> TYPE: PRT
<213> ORGANISM: H. sapiens

<400> SEQUENCE: 798

Tyr Thr Asn Trp Ile Gln Lys
 1               5

<210> SEQ ID NO 799
<211> LENGTH: 20
<212> TYPE: PRT
<213> ORGANISM: H. sapiens

<400> SEQUENCE: 799

Ala Leu Ser Lys His Gln Asp Phe Asn Ser Ala Val Gln Leu Val Glu
 1               5                  10                  15

Asn Phe Cys Arg
            20

<210> SEQ ID NO 800
```

```
<211> LENGTH: 10
<212> TYPE: PRT
<213> ORGANISM: H. sapiens

<400> SEQUENCE: 800

Glu Leu Leu Glu Ser Tyr Ile Asp Gly Arg
1               5                   10

<210> SEQ ID NO 801
<211> LENGTH: 6
<212> TYPE: PRT
<213> ORGANISM: H. sapiens

<400> SEQUENCE: 801

Ile Ser Met Leu Glu Lys
1               5

<210> SEQ ID NO 802
<211> LENGTH: 20
<212> TYPE: PRT
<213> ORGANISM: H. sapiens

<400> SEQUENCE: 802

Ile Val Glu Gly Ser Asp Ala Glu Ile Gly Met Ser Pro Trp Gln Val
1               5                   10                  15

Met Leu Phe Arg
            20

<210> SEQ ID NO 803
<211> LENGTH: 10
<212> TYPE: PRT
<213> ORGANISM: H. sapiens

<400> SEQUENCE: 803

Asn Phe Thr Glu Asn Asp Leu Leu Val Arg
1               5                   10

<210> SEQ ID NO 804
<211> LENGTH: 19
<212> TYPE: PRT
<213> ORGANISM: H. sapiens

<400> SEQUENCE: 804

Ser Glu Gly Ser Ser Val Asn Leu Ser Pro Pro Leu Glu Gln Cys Val
1               5                   10                  15

Pro Asp Arg

<210> SEQ ID NO 805
<211> LENGTH: 13
<212> TYPE: PRT
<213> ORGANISM: H. sapiens

<400> SEQUENCE: 805

Thr Ala Thr Ser Glu Tyr Gln Thr Phe Phe Asn Pro Arg
1               5                   10

<210> SEQ ID NO 806
<211> LENGTH: 7
<212> TYPE: PRT
<213> ORGANISM: H. sapiens

<400> SEQUENCE: 806

Val Ile Asp Gln Phe Gly Glu
1               5
```

<210> SEQ ID NO 807
<211> LENGTH: 9
<212> TYPE: PRT
<213> ORGANISM: H. sapiens

<400> SEQUENCE: 807

Tyr Gly Phe Tyr Thr His Val Phe Arg
1               5

<210> SEQ ID NO 808
<211> LENGTH: 9
<212> TYPE: PRT
<213> ORGANISM: H. sapiens

<400> SEQUENCE: 808

Gly Asp Tyr Pro Leu Glu Ala Val Arg
1               5

<210> SEQ ID NO 809
<211> LENGTH: 11
<212> TYPE: PRT
<213> ORGANISM: H. sapiens

<400> SEQUENCE: 809

Leu Asp Ile Asp Ser Pro Pro Ile Thr Ala Arg
1               5                   10

<210> SEQ ID NO 810
<211> LENGTH: 7
<212> TYPE: PRT
<213> ORGANISM: H. sapiens

<400> SEQUENCE: 810

Leu Phe Glu Glu Leu Val Arg
1               5

<210> SEQ ID NO 811
<211> LENGTH: 11
<212> TYPE: PRT
<213> ORGANISM: H. sapiens

<400> SEQUENCE: 811

Glu Glu Ile Val Tyr Leu Pro Cys Ile Tyr Arg
1               5                   10

<210> SEQ ID NO 812
<211> LENGTH: 18
<212> TYPE: PRT
<213> ORGANISM: H. sapiens

<400> SEQUENCE: 812

Asn Thr Gly Thr Glu Ala Pro Asp Tyr Leu Ala Thr Val Asp Val Asp
1               5                   10                  15

Pro Lys

<210> SEQ ID NO 813
<211> LENGTH: 13
<212> TYPE: PRT
<213> ORGANISM: H. sapiens

<400> SEQUENCE: 813

Glu Asp Phe Thr Ser Leu Ser Leu Val Leu Tyr Ser Arg
1               5                   10

```
<210> SEQ ID NO 814
<211> LENGTH: 7
<212> TYPE: PRT
<213> ORGANISM: H. sapiens

<400> SEQUENCE: 814

Glu Phe Ser His Leu Gly Lys
  1               5

<210> SEQ ID NO 815
<211> LENGTH: 8
<212> TYPE: PRT
<213> ORGANISM: H. sapiens

<400> SEQUENCE: 815

Glu Leu Pro Glu His Thr Val Lys
  1               5

<210> SEQ ID NO 816
<211> LENGTH: 8
<212> TYPE: PRT
<213> ORGANISM: H. sapiens

<400> SEQUENCE: 816

Glu Leu Ser Ser Phe Ile Asp Lys
  1               5

<210> SEQ ID NO 817
<211> LENGTH: 17
<212> TYPE: PRT
<213> ORGANISM: H. sapiens

<400> SEQUENCE: 817

Gly Gln Glu Leu Cys Ala Asp Tyr Ser Glu Asn Thr Phe Thr Glu Tyr
  1               5                  10                  15

Lys

<210> SEQ ID NO 818
<211> LENGTH: 11
<212> TYPE: PRT
<213> ORGANISM: H. sapiens

<400> SEQUENCE: 818

His Leu Ser Leu Leu Thr Thr Leu Ser Asn Arg
  1               5                  10

<210> SEQ ID NO 819
<211> LENGTH: 22
<212> TYPE: PRT
<213> ORGANISM: H. sapiens

<400> SEQUENCE: 819

His Gln Pro Gln Glu Phe Pro Thr Tyr Val Glu Pro Thr Asn Asp Glu
  1               5                  10                  15

Ile Cys Glu Ala Phe Arg
                 20

<210> SEQ ID NO 820
<211> LENGTH: 15
<212> TYPE: PRT
<213> ORGANISM: H. sapiens

<400> SEQUENCE: 820
```

```
Lys Phe Pro Ser Gly Thr Phe Glu Gln Val Ser Gln Leu Val Lys
 1               5                  10                  15

<210> SEQ ID NO 821
<211> LENGTH: 25
<212> TYPE: PRT
<213> ORGANISM: H. sapiens

<400> SEQUENCE: 821

Leu Ala Gln Lys Val Pro Thr Ala Asp Leu Glu Asp Val Leu Pro Leu
 1               5                  10                  15

Ala Glu Asp Ile Thr Asn Leu Ser Lys
            20                  25

<210> SEQ ID NO 822
<211> LENGTH: 6
<212> TYPE: PRT
<213> ORGANISM: H. sapiens

<400> SEQUENCE: 822

Leu Ser Asn Leu Ile Lys
 1               5

<210> SEQ ID NO 823
<211> LENGTH: 11
<212> TYPE: PRT
<213> ORGANISM: H. sapiens

<400> SEQUENCE: 823

Arg Thr His Leu Pro Glu Val Phe Leu Ser Lys
 1               5                  10

<210> SEQ ID NO 824
<211> LENGTH: 10
<212> TYPE: PRT
<213> ORGANISM: H. sapiens

<400> SEQUENCE: 824

Thr His Leu Pro Glu Val Phe Leu Ser Lys
 1               5                  10

<210> SEQ ID NO 825
<211> LENGTH: 7
<212> TYPE: PRT
<213> ORGANISM: H. sapiens

<400> SEQUENCE: 825

Val Leu Glu Pro Thr Leu Lys
 1               5

<210> SEQ ID NO 826
<211> LENGTH: 11
<212> TYPE: PRT
<213> ORGANISM: H. sapiens

<400> SEQUENCE: 826

Val Met Asp Lys Tyr Thr Phe Glu Leu Ser Arg
 1               5                  10

<210> SEQ ID NO 827
<211> LENGTH: 22
<212> TYPE: PRT
<213> ORGANISM: H. sapiens
```

-continued

```
<400> SEQUENCE: 827

Val Pro Thr Ala Asp Leu Glu Asp Val Leu Pro Leu Ala Glu Asp Ile
1               5                   10                  15

Thr Asn Ile Leu Ser Lys
            20

<210> SEQ ID NO 828
<211> LENGTH: 7
<212> TYPE: PRT
<213> ORGANISM: H. sapiens

<400> SEQUENCE: 828

Tyr Thr Phe Glu Leu Ser Arg
1               5

<210> SEQ ID NO 829
<211> LENGTH: 11
<212> TYPE: PRT
<213> ORGANISM: H. sapiens

<400> SEQUENCE: 829

Gly Val Ile Ser Asn Ser Gly Gly Pro Val Arg
1               5                   10

<210> SEQ ID NO 830
<211> LENGTH: 10
<212> TYPE: PRT
<213> ORGANISM: H. sapiens

<400> SEQUENCE: 830

Thr Phe Glu Ile Ser Asp Ile Gly Ala Lys
1               5                   10

<210> SEQ ID NO 831
<211> LENGTH: 7
<212> TYPE: PRT
<213> ORGANISM: H. sapiens

<400> SEQUENCE: 831

Val Tyr Ser Leu Pro Gly Arg
1               5

<210> SEQ ID NO 832
<211> LENGTH: 9
<212> TYPE: PRT
<213> ORGANISM: H. sapiens

<400> SEQUENCE: 832

Trp Ser Ala Ser Phe Thr Val Thr Lys
1               5

<210> SEQ ID NO 833
<211> LENGTH: 8
<212> TYPE: PRT
<213> ORGANISM: H. sapiens

<400> SEQUENCE: 833

Ala Pro Tyr Pro Asn Tyr Asp Arg
1               5

<210> SEQ ID NO 834
<211> LENGTH: 6
<212> TYPE: PRT
<213> ORGANISM: H. sapiens
```

<400> SEQUENCE: 834

Asp Glu Cys Phe Ala Arg
1               5

<210> SEQ ID NO 835
<211> LENGTH: 9
<212> TYPE: PRT
<213> ORGANISM: H. sapiens

<400> SEQUENCE: 835

Asp Ile Leu Thr Ile Asp Ile Ser Arg
1               5

<210> SEQ ID NO 836
<211> LENGTH: 15
<212> TYPE: PRT
<213> ORGANISM: H. sapiens

<400> SEQUENCE: 836

Glu Val Gly Pro Pro Leu Pro Gln Glu Ala Val Pro Leu Gln Lys
1               5                   10                  15

<210> SEQ ID NO 837
<211> LENGTH: 14
<212> TYPE: PRT
<213> ORGANISM: H. sapiens

<400> SEQUENCE: 837

His Lys His Ile Pro Gly Leu Ile His Asn Met Thr Ala Arg
1               5                   10

<210> SEQ ID NO 838
<211> LENGTH: 10
<212> TYPE: PRT
<213> ORGANISM: H. sapiens

<400> SEQUENCE: 838

Leu Leu Pro Ala Gln Leu Pro Ala Glu Lys
1               5                   10

<210> SEQ ID NO 839
<211> LENGTH: 11
<212> TYPE: PRT
<213> ORGANISM: H. sapiens

<400> SEQUENCE: 839

Leu Thr Phe Ile Asn Asp Leu Cys Gly Pro Arg
1               5                   10

<210> SEQ ID NO 840
<211> LENGTH: 14
<212> TYPE: PRT
<213> ORGANISM: H. sapiens

<400> SEQUENCE: 840

Gln Gly Glu Thr Leu Asn Phe Leu Glu Ile Gly Tyr Ser Arg
1               5                   10

<210> SEQ ID NO 841
<211> LENGTH: 16
<212> TYPE: PRT
<213> ORGANISM: H. sapiens

<400> SEQUENCE: 841

```
Asp Met Ile Gly Arg Cys Phe Val Leu Ser Gln Asp Leu Ala Ile Arg
1               5                   10                  15

<210> SEQ ID NO 842
<211> LENGTH: 16
<212> TYPE: PRT
<213> ORGANISM: H. sapiens

<400> SEQUENCE: 842

Asp Ser Ala Ser Arg Leu Val Pro Glu Val Met Leu Ser Gly Glu Arg
1               5                   10                  15

<210> SEQ ID NO 843
<211> LENGTH: 13
<212> TYPE: PRT
<213> ORGANISM: H. sapiens

<400> SEQUENCE: 843

Glu Leu Glu Pro Pro Glu Gln Gln Glu Pro Gly Glu Arg
1               5                   10

<210> SEQ ID NO 844
<211> LENGTH: 7
<212> TYPE: PRT
<213> ORGANISM: H. sapiens

<400> SEQUENCE: 844

Gly Ala Val Val Ile Leu Arg
1               5

<210> SEQ ID NO 845
<211> LENGTH: 16
<212> TYPE: PRT
<213> ORGANISM: H. sapiens

<400> SEQUENCE: 845

Gly Leu Val Arg Ala Glu Glu Leu Ser Phe Val Ala Gly Ala Pro Arg
1               5                   10                  15

<210> SEQ ID NO 846
<211> LENGTH: 14
<212> TYPE: PRT
<213> ORGANISM: H. sapiens

<400> SEQUENCE: 846

Val Cys Gly Asp Ala Met Phe Gln Leu Gln Glu Asn Val Lys
1               5                   10

<210> SEQ ID NO 847
<211> LENGTH: 13
<212> TYPE: PRT
<213> ORGANISM: H. sapiens

<400> SEQUENCE: 847

Val Asp Gln Ile Leu Glu Thr Arg Asp Met Ile Gly Arg
1               5                   10

<210> SEQ ID NO 848
<211> LENGTH: 6
<212> TYPE: PRT
<213> ORGANISM: H. sapiens

<400> SEQUENCE: 848

Tyr Glu Ala Arg Gln Arg
```

-continued

```
          1               5
```

<210> SEQ ID NO 849
<211> LENGTH: 14
<212> TYPE: PRT
<213> ORGANISM: H. sapiens

<400> SEQUENCE: 849

Glu Gln Leu Gly Glu Phe Tyr Glu Ala Leu Asp Cys Leu Arg
 1               5                  10

<210> SEQ ID NO 850
<211> LENGTH: 9
<212> TYPE: PRT
<213> ORGANISM: H. sapiens

<400> SEQUENCE: 850

Ser Asp Val Val Tyr Thr Asp Trp Lys
 1               5

<210> SEQ ID NO 851
<211> LENGTH: 8
<212> TYPE: PRT
<213> ORGANISM: H. sapiens

<400> SEQUENCE: 851

Thr Glu Asp Thr Ile Phe Leu Arg
 1               5

<210> SEQ ID NO 852
<211> LENGTH: 9
<212> TYPE: PRT
<213> ORGANISM: H. sapiens

<400> SEQUENCE: 852

Trp Phe Tyr Ile Ala Ser Ala Phe Arg
 1               5

<210> SEQ ID NO 853
<211> LENGTH: 14
<212> TYPE: PRT
<213> ORGANISM: H. sapiens

<400> SEQUENCE: 853

Glu Gln Leu Gly Glu Phe Tyr Glu Ala Leu Asp Cys Leu Arg
 1               5                  10

<210> SEQ ID NO 854
<211> LENGTH: 7
<212> TYPE: PRT
<213> ORGANISM: H. sapiens

<400> SEQUENCE: 854

Lys Gln Glu Glu Gly Glu Ser
 1               5

<210> SEQ ID NO 855
<211> LENGTH: 6
<212> TYPE: PRT
<213> ORGANISM: H. sapiens

<400> SEQUENCE: 855

Asn Glu Glu Tyr Asn Lys
 1               5

```
<210> SEQ ID NO 856
<211> LENGTH: 15
<212> TYPE: PRT
<213> ORGANISM: H. sapiens

<400> SEQUENCE: 856

Asn Trp Gly Leu Ser Val Tyr Ala Asp Lys Pro Glu Thr Thr Lys
 1               5                  10                  15

<210> SEQ ID NO 857
<211> LENGTH: 9
<212> TYPE: PRT
<213> ORGANISM: H. sapiens

<400> SEQUENCE: 857

Ser Asp Val Val Tyr Thr Asp Trp Lys
 1               5

<210> SEQ ID NO 858
<211> LENGTH: 8
<212> TYPE: PRT
<213> ORGANISM: H. sapiens

<400> SEQUENCE: 858

Thr Glu Asp Thr Ile Phe Leu Arg
 1               5

<210> SEQ ID NO 859
<211> LENGTH: 12
<212> TYPE: PRT
<213> ORGANISM: H. sapiens

<400> SEQUENCE: 859

Thr Tyr Met Leu Ala Phe Asp Val Asn Asp Glu Lys
 1               5                  10

<210> SEQ ID NO 860
<211> LENGTH: 9
<212> TYPE: PRT
<213> ORGANISM: H. sapiens

<400> SEQUENCE: 860

Trp Phe Tyr Ile Ala Ser Ala Phe Arg
 1               5

<210> SEQ ID NO 861
<211> LENGTH: 15
<212> TYPE: PRT
<213> ORGANISM: H. sapiens

<400> SEQUENCE: 861

Tyr Val Gly Gly Gln Glu His Phe Ala His Leu Leu Ile Leu Arg
 1               5                  10                  15

<210> SEQ ID NO 862
<211> LENGTH: 23
<212> TYPE: PRT
<213> ORGANISM: H. sapiens

<400> SEQUENCE: 862

Ala Pro Ala Lys Pro Pro Gly Ser Gly Leu Asp Leu Ala Asp Ala Leu
 1               5                  10                  15

Asp Asp Gln Asp Asp Gly Arg
                20
```

<210> SEQ ID NO 863
<211> LENGTH: 19
<212> TYPE: PRT
<213> ORGANISM: H. sapiens

<400> SEQUENCE: 863

Ala Pro Ala Asn Thr Leu Gly Asn Asp Phe Asp Leu Ala Asp Ala Leu
 1               5                  10                  15

Asp Asp Arg

<210> SEQ ID NO 864
<211> LENGTH: 16
<212> TYPE: PRT
<213> ORGANISM: H. sapiens

<400> SEQUENCE: 864

Ala Ser Val Asp Ser Gly Ser Ser Glu Glu Gln Gly Gly Ser Ser Arg
 1               5                  10                  15

<210> SEQ ID NO 865
<211> LENGTH: 6
<212> TYPE: PRT
<213> ORGANISM: H. sapiens

<400> SEQUENCE: 865

Leu Phe Ala Glu Glu Lys
 1               5

<210> SEQ ID NO 866
<211> LENGTH: 10
<212> TYPE: PRT
<213> ORGANISM: H. sapiens

<400> SEQUENCE: 866

Glu Leu Gly Gln Met Asn Leu Thr Glu Arg
 1               5                  10

<210> SEQ ID NO 867
<211> LENGTH: 8
<212> TYPE: PRT
<213> ORGANISM: H. sapiens

<400> SEQUENCE: 867

Glu Val Glu Glu Glu Met Glu Lys
 1               5

<210> SEQ ID NO 868
<211> LENGTH: 7
<212> TYPE: PRT
<213> ORGANISM: H. sapiens

<400> SEQUENCE: 868

Phe Gly Glu Ile Tyr Glu Lys
 1               5

<210> SEQ ID NO 869
<211> LENGTH: 16
<212> TYPE: PRT
<213> ORGANISM: H. sapiens

<400> SEQUENCE: 869

Phe Lys Asn Glu Val Asn Thr Leu Glu Glu Glu Phe Leu Ala Leu Lys
 1               5                  10                  15

```
<210> SEQ ID NO 870
<211> LENGTH: 11
<212> TYPE: PRT
<213> ORGANISM: H. sapiens

<400> SEQUENCE: 870

Lys Met Asn Ser Glu Phe His Ser Ala Ala Lys
1               5                   10

<210> SEQ ID NO 871
<211> LENGTH: 12
<212> TYPE: PRT
<213> ORGANISM: H. sapiens

<400> SEQUENCE: 871

Leu Glu Asp Leu Gly Glu Leu His Arg Ala Ala Arg
1               5                   10

<210> SEQ ID NO 872
<211> LENGTH: 6
<212> TYPE: PRT
<213> ORGANISM: H. sapiens

<400> SEQUENCE: 872

Leu Leu Ile Glu Glu Arg
1               5

<210> SEQ ID NO 873
<211> LENGTH: 10
<212> TYPE: PRT
<213> ORGANISM: H. sapiens

<400> SEQUENCE: 873

Asn Met Leu Glu Arg Gly Glu Gly Glu Arg
1               5                   10

<210> SEQ ID NO 874
<211> LENGTH: 18
<212> TYPE: PRT
<213> ORGANISM: H. sapiens

<400> SEQUENCE: 874

Gln Met Glu Asn Met Val Ser Val Leu Gln Asn Glu Leu Ser Glu Thr
1               5                   10                  15

Lys Lys

<210> SEQ ID NO 875
<211> LENGTH: 9
<212> TYPE: PRT
<213> ORGANISM: H. sapiens

<400> SEQUENCE: 875

Arg Asn Ala Asp Met Leu Tyr Asn Lys
1               5

<210> SEQ ID NO 876
<211> LENGTH: 21
<212> TYPE: PRT
<213> ORGANISM: H. sapiens

<400> SEQUENCE: 876

Ser Gly Asp Val Pro Gly Val Glu His Val Leu Ala Pro Gly Asp Thr
1               5                   10                  15
```

-continued

```
Gly Val Asp Lys Arg
            20

<210> SEQ ID NO 877
<211> LENGTH: 5
<212> TYPE: PRT
<213> ORGANISM: H. sapiens

<400> SEQUENCE: 877

Ser Tyr Met Glu Arg
1               5

<210> SEQ ID NO 878
<211> LENGTH: 13
<212> TYPE: PRT
<213> ORGANISM: H. sapiens

<400> SEQUENCE: 878

Thr Ser Gln Glu Pro Glu Met Ala Lys Asp Cys Asp Arg
1               5                   10

<210> SEQ ID NO 879
<211> LENGTH: 14
<212> TYPE: PRT
<213> ORGANISM: H. sapiens

<400> SEQUENCE: 879

Ala Ser Trp Glu Gly His Trp Ser Pro Ala Pro Ser Ser Arg
1               5                   10

<210> SEQ ID NO 880
<211> LENGTH: 8
<212> TYPE: PRT
<213> ORGANISM: H. sapiens

<400> SEQUENCE: 880

Lys Ile His Glu Glu Glu Val Arg
1               5

<210> SEQ ID NO 881
<211> LENGTH: 11
<212> TYPE: PRT
<213> ORGANISM: H. sapiens

<400> SEQUENCE: 881

Leu Ala Leu Asp Ile Glu Ile Ala Thr Tyr Arg
1               5                   10

<210> SEQ ID NO 882
<211> LENGTH: 6
<212> TYPE: PRT
<213> ORGANISM: H. sapiens

<400> SEQUENCE: 882

Ala Ala Ser Gly Pro Lys
1               5

<210> SEQ ID NO 883
<211> LENGTH: 15
<212> TYPE: PRT
<213> ORGANISM: H. sapiens

<400> SEQUENCE: 883

Gly Phe Leu Asn Phe Met Asn Thr Val Leu Val Ala Phe Thr Lys
```

-continued

```
                1               5                  10                  15
```

<210> SEQ ID NO 884
<211> LENGTH: 14
<212> TYPE: PRT
<213> ORGANISM: H. sapiens

<400> SEQUENCE: 884

```
Leu Leu Pro Ile Ser Pro Thr Trp Pro Phe Thr Glu Val Arg
 1               5                  10
```

<210> SEQ ID NO 885
<211> LENGTH: 6
<212> TYPE: PRT
<213> ORGANISM: H. sapiens

<400> SEQUENCE: 885

```
Val Glu Leu Asp Thr Arg
 1               5
```

<210> SEQ ID NO 886
<211> LENGTH: 17
<212> TYPE: PRT
<213> ORGANISM: H. sapiens

<400> SEQUENCE: 886

```
Glu Thr Pro Pro Leu Glu Asp Leu Ala Ala Asn Gln Ser Glu Asp Pro
 1               5                  10                  15

Arg
```

<210> SEQ ID NO 887
<211> LENGTH: 10
<212> TYPE: PRT
<213> ORGANISM: H. sapiens

<400> SEQUENCE: 887

```
Ala Asp Leu Ala Gln Leu Ala Ile Ile Arg
 1               5                  10
```

<210> SEQ ID NO 888
<211> LENGTH: 13
<212> TYPE: PRT
<213> ORGANISM: H. sapiens

<400> SEQUENCE: 888

```
Gly Pro Leu Pro Ala Ala Pro Pro Val Ala Pro Glu Arg
 1               5                  10
```

<210> SEQ ID NO 889
<211> LENGTH: 14
<212> TYPE: PRT
<213> ORGANISM: H. sapiens

<400> SEQUENCE: 889

```
Gly Ser Ser Gly Ser Val Val Val Asp Leu Leu Tyr Trp Arg
 1               5                  10
```

<210> SEQ ID NO 890
<211> LENGTH: 7
<212> TYPE: PRT
<213> ORGANISM: H. sapiens

<400> SEQUENCE: 890

```
Gly Ser Trp Gly Ser Gly Lys
```

```
                           1               5

<210> SEQ ID NO 891
<211> LENGTH: 9
<212> TYPE: PRT
<213> ORGANISM: H. sapiens

<400> SEQUENCE: 891

Gly Glu Ala Gly Leu Asp Gly Ala Lys
 1               5

<210> SEQ ID NO 892
<211> LENGTH: 13
<212> TYPE: PRT
<213> ORGANISM: H. sapiens

<400> SEQUENCE: 892

Gln Asn Thr Ala Asp Ile Leu Gln Asp Leu Thr Gly Arg
 1               5                  10

<210> SEQ ID NO 893
<211> LENGTH: 10
<212> TYPE: PRT
<213> ORGANISM: H. sapiens

<400> SEQUENCE: 893

Leu Ser Ala Glu Ile Leu Arg Leu Glu Lys
 1               5                  10

<210> SEQ ID NO 894
<211> LENGTH: 10
<212> TYPE: PRT
<213> ORGANISM: H. sapiens

<400> SEQUENCE: 894

Asp Pro Gln Ser Thr Glu Leu Ile Pro Arg
 1               5                  10

<210> SEQ ID NO 895
<211> LENGTH: 10
<212> TYPE: PRT
<213> ORGANISM: H. sapiens

<400> SEQUENCE: 895

Ser Leu Gln Leu Glu Glu Leu Leu Ala Arg
 1               5                  10

<210> SEQ ID NO 896
<211> LENGTH: 8
<212> TYPE: PRT
<213> ORGANISM: H. sapiens

<400> SEQUENCE: 896

Tyr Cys Asn Leu Met Met Gln Arg
 1               5

<210> SEQ ID NO 897
<211> LENGTH: 10
<212> TYPE: PRT
<213> ORGANISM: H. sapiens

<400> SEQUENCE: 897

Val Ala Trp Ala Gln Ala Arg Leu Glu Lys
 1               5                  10
```

```
<210> SEQ ID NO 898
<211> LENGTH: 20
<212> TYPE: PRT
<213> ORGANISM: H. sapiens

<400> SEQUENCE: 898

Phe Phe Gly His Gly Ala Glu Asp Ser Leu Ala Asp Gln Ala Ala Asn
1               5                   10                  15

Glu Trp Gly Arg
            20

<210> SEQ ID NO 899
<211> LENGTH: 11
<212> TYPE: PRT
<213> ORGANISM: H. sapiens

<400> SEQUENCE: 899

Ala Ala Asp Gly Ser Leu Asp Thr Gln Pro Lys
1               5                   10

<210> SEQ ID NO 900
<211> LENGTH: 8
<212> TYPE: PRT
<213> ORGANISM: H. sapiens

<400> SEQUENCE: 900

Glu Leu Ile Ala Ala Ala Ser Arg
1               5

<210> SEQ ID NO 901
<211> LENGTH: 14
<212> TYPE: PRT
<213> ORGANISM: H. sapiens

<400> SEQUENCE: 901

Asn Thr Ile Glu Glu Thr Gly Asn Leu Ala Glu Gln Ala Arg
1               5                   10

<210> SEQ ID NO 902
<211> LENGTH: 10
<212> TYPE: PRT
<213> ORGANISM: H. sapiens

<400> SEQUENCE: 902

Ala Gly Gly Ser His Ser Asp Pro Gly Arg
1               5                   10

<210> SEQ ID NO 903
<211> LENGTH: 6
<212> TYPE: PRT
<213> ORGANISM: H. sapiens

<400> SEQUENCE: 903

Asn Thr Met Ala Met Lys
1               5

<210> SEQ ID NO 904
<211> LENGTH: 13
<212> TYPE: PRT
<213> ORGANISM: H. sapiens

<400> SEQUENCE: 904

Glu Leu Glu Pro Pro Glu Gln Gln Glu Pro Gly Glu Arg
1               5                   10
```

```
<210> SEQ ID NO 905
<211> LENGTH: 16
<212> TYPE: PRT
<213> ORGANISM: H. sapiens

<400> SEQUENCE: 905

Leu Leu Ile Tyr Asp Ala Ser Ser Leu Glu Ser Gly Val Pro Ser Arg
 1               5                  10                  15

<210> SEQ ID NO 906
<211> LENGTH: 6
<212> TYPE: PRT
<213> ORGANISM: H. sapiens

<400> SEQUENCE: 906

Glu Leu Glu Glu Arg Arg
 1               5

<210> SEQ ID NO 907
<211> LENGTH: 9
<212> TYPE: PRT
<213> ORGANISM: H. sapiens

<400> SEQUENCE: 907

Leu Gln Glu Ala Ala Glu Ile Val Lys
 1               5

<210> SEQ ID NO 908
<211> LENGTH: 16
<212> TYPE: PRT
<213> ORGANISM: H. sapiens

<400> SEQUENCE: 908

Tyr Phe Ser Thr Thr Glu Asp Tyr Asp His Glu Ile Thr Gly Leu Arg
 1               5                  10                  15

<210> SEQ ID NO 909
<211> LENGTH: 8
<212> TYPE: PRT
<213> ORGANISM: H. sapiens

<400> SEQUENCE: 909

His Gln Cys Ser Ile Asp Leu Lys
 1               5

<210> SEQ ID NO 910
<211> LENGTH: 8
<212> TYPE: PRT
<213> ORGANISM: H. sapiens

<400> SEQUENCE: 910

Met Asp Arg Pro Ser Leu Val Arg
 1               5

<210> SEQ ID NO 911
<211> LENGTH: 14
<212> TYPE: PRT
<213> ORGANISM: H. sapiens

<400> SEQUENCE: 911

Ala Glu Ala Gly Gly Gly Trp Glu Gly Ser Ala Ser Tyr Lys
 1               5                  10
```

```
<210> SEQ ID NO 912
<211> LENGTH: 7
<212> TYPE: PRT
<213> ORGANISM: H. sapiens

<400> SEQUENCE: 912

Thr Ile Glu Glu Leu Ala Arg
 1               5

<210> SEQ ID NO 913
<211> LENGTH: 14
<212> TYPE: PRT
<213> ORGANISM: H. sapiens

<400> SEQUENCE: 913

Ala Ala Leu Gly Glu Ser Gly Glu Gln Ala Asp Gly Pro Lys
 1               5                  10

<210> SEQ ID NO 914
<211> LENGTH: 28
<212> TYPE: PRT
<213> ORGANISM: H. sapiens

<400> SEQUENCE: 914

Asp Leu Leu Gly Gln Gln Pro His Ser Glu Pro Gly Ala Ala Ala Phe
 1               5                  10                  15

Gly Glu Leu Gln Asn Gln Met Pro Gly Pro Ser Lys
            20                  25

<210> SEQ ID NO 915
<211> LENGTH: 29
<212> TYPE: PRT
<213> ORGANISM: H. sapiens

<400> SEQUENCE: 915

Glu Glu Gln Ser Leu Pro Ala Gly Ala Gln Glu Ala Leu Ser Asp Gly
 1               5                  10                  15

Leu Gln Leu Glu Val Gln Pro Ser Glu Glu Glu Ala Arg
            20                  25

<210> SEQ ID NO 916
<211> LENGTH: 19
<212> TYPE: PRT
<213> ORGANISM: H. sapiens

<400> SEQUENCE: 916

His Leu Pro Phe Leu Glu Ala Leu Ser Gln Ala Pro Ala Ser Asp Val
 1               5                  10                  15

Leu Ala Arg

<210> SEQ ID NO 917
<211> LENGTH: 19
<212> TYPE: PRT
<213> ORGANISM: H. sapiens

<400> SEQUENCE: 917

Arg Pro Glu Ala Ser Ser Pro Ala Arg Pro Ser Lys His Ser Val Gly
 1               5                  10                  15

Ser Glu Arg

<210> SEQ ID NO 918
<211> LENGTH: 8
<212> TYPE: PRT
```

<213> ORGANISM: H. sapiens

<400> SEQUENCE: 918

Val Pro Ala Met Asp Phe Tyr Arg
1               5

<210> SEQ ID NO 919
<211> LENGTH: 10
<212> TYPE: PRT
<213> ORGANISM: H. sapiens

<400> SEQUENCE: 919

Tyr Glu Val Ser Pro Val Ala Leu Gln Arg
1               5                   10

<210> SEQ ID NO 920
<211> LENGTH: 24
<212> TYPE: PRT
<213> ORGANISM: H. sapiens

<400> SEQUENCE: 920

Ala Glu Pro Pro Lys Ala Pro Glu Gln Glu Gln Ala Ala Pro Gly Pro
1               5                   10                  15

Ala Ala Gly Gly Glu Ala Pro Lys
            20

<210> SEQ ID NO 921
<211> LENGTH: 7
<212> TYPE: PRT
<213> ORGANISM: H. sapiens

<400> SEQUENCE: 921

Glu Ala Asp Val Val Ala Arg
1               5

<210> SEQ ID NO 922
<211> LENGTH: 10
<212> TYPE: PRT
<213> ORGANISM: H. sapiens

<400> SEQUENCE: 922

Glu Lys Pro Asp Gln Asp Ala Glu Gly Lys
1               5                   10

<210> SEQ ID NO 923
<211> LENGTH: 14
<212> TYPE: PRT
<213> ORGANISM: H. sapiens

<400> SEQUENCE: 923

Glu Ser Glu Pro Gln Ala Ala Ala Glu Pro Ala Glu Ala Lys
1               5                   10

<210> SEQ ID NO 924
<211> LENGTH: 15
<212> TYPE: PRT
<213> ORGANISM: H. sapiens

<400> SEQUENCE: 924

Ala Leu Asp Ile Tyr Ser Ala Val Asp Asp Ala Ser His Glu Lys
1               5                   10                  15

<210> SEQ ID NO 925
<211> LENGTH: 11

-continued

```
<212> TYPE: PRT
<213> ORGANISM: H. sapiens

<400> SEQUENCE: 925

Glu Leu Ile Glu Ala Leu Gln Glu Val Leu Lys
1               5                   10

<210> SEQ ID NO 926
<211> LENGTH: 10
<212> TYPE: PRT
<213> ORGANISM: H. sapiens

<400> SEQUENCE: 926

Gly Thr Ser Cys Asn Ser Phe Leu Leu Lys
1               5                   10

<210> SEQ ID NO 927
<211> LENGTH: 8
<212> TYPE: PRT
<213> ORGANISM: H. sapiens

<400> SEQUENCE: 927

Cys Cys Lys Val Cys Pro Gly Lys
1               5

<210> SEQ ID NO 928
<211> LENGTH: 11
<212> TYPE: PRT
<213> ORGANISM: H. sapiens

<400> SEQUENCE: 928

Glu Glu Leu Pro Gly Gln Ser Phe Asp Asn Lys
1               5                   10

<210> SEQ ID NO 929
<211> LENGTH: 16
<212> TYPE: PRT
<213> ORGANISM: H. sapiens

<400> SEQUENCE: 929

Gly Asp Gly Glu Leu Ser Trp Glu His Ser Asp Gly Asp Ile Phe Arg
1               5                   10                  15

<210> SEQ ID NO 930
<211> LENGTH: 18
<212> TYPE: PRT
<213> ORGANISM: H. sapiens

<400> SEQUENCE: 930

Leu Thr Cys Ala Phe Pro Val Ser Val Pro Asp Ser Cys Cys Arg Val
1               5                   10                  15

Cys Arg

<210> SEQ ID NO 931
<211> LENGTH: 9
<212> TYPE: PRT
<213> ORGANISM: H. sapiens

<400> SEQUENCE: 931

Val Leu Tyr Leu Glu Arg Ser Glu Lys
1               5

<210> SEQ ID NO 932
<211> LENGTH: 4
```

```
<212> TYPE: PRT
<213> ORGANISM: H. sapiens

<400> SEQUENCE: 932

Tyr Pro Cys Lys
 1

<210> SEQ ID NO 933
<211> LENGTH: 8
<212> TYPE: PRT
<213> ORGANISM: H. sapiens

<400> SEQUENCE: 933

Glu Ala Pro Tyr Gly Ala Pro Arg
 1               5

<210> SEQ ID NO 934
<211> LENGTH: 27
<212> TYPE: PRT
<213> ORGANISM: H. sapiens

<400> SEQUENCE: 934

Phe Asp Met Pro Asp Phe Glu Asp Asp Gly Gly Pro Tyr Gly Glu Ser
 1               5                  10                  15

Glu Ala Pro Ala Pro Pro Gly Pro Gly Thr Arg
            20                  25

<210> SEQ ID NO 935
<211> LENGTH: 8
<212> TYPE: PRT
<213> ORGANISM: H. sapiens

<400> SEQUENCE: 935

Gln Gly Pro Val Gly Ser Gly Arg
 1               5

<210> SEQ ID NO 936
<211> LENGTH: 9
<212> TYPE: PRT
<213> ORGANISM: H. sapiens

<400> SEQUENCE: 936

Arg Glu Ala Pro Tyr Gly Ala Pro Arg
 1               5

<210> SEQ ID NO 937
<211> LENGTH: 11
<212> TYPE: PRT
<213> ORGANISM: H. sapiens

<400> SEQUENCE: 937

Ala Gly Ala Ala Gly Ala Leu Pro Ala Gln Arg
 1               5                  10

<210> SEQ ID NO 938
<211> LENGTH: 9
<212> TYPE: PRT
<213> ORGANISM: H. sapiens

<400> SEQUENCE: 938

Ser Ser Asp Gly Leu Gly Val Gly Arg
 1               5

<210> SEQ ID NO 939
```

```
<211> LENGTH: 8
<212> TYPE: PRT
<213> ORGANISM: H. sapiens

<400> SEQUENCE: 939

Phe Gln Leu Thr Phe Pro Leu Arg
1               5

<210> SEQ ID NO 940
<211> LENGTH: 6
<212> TYPE: PRT
<213> ORGANISM: H. sapiens

<400> SEQUENCE: 940

Ile Asp Glu Leu Glu Arg
1               5

<210> SEQ ID NO 941
<211> LENGTH: 9
<212> TYPE: PRT
<213> ORGANISM: H. sapiens

<400> SEQUENCE: 941

Leu Glu Asn Leu Glu Gln Tyr Ser Arg
1               5

<210> SEQ ID NO 942
<211> LENGTH: 14
<212> TYPE: PRT
<213> ORGANISM: H. sapiens

<400> SEQUENCE: 942

Gln Pro Gly Ser Gly Lys Asn Thr Met Gly Asp Leu Ser Arg
1               5                   10

<210> SEQ ID NO 943
<211> LENGTH: 18
<212> TYPE: PRT
<213> ORGANISM: H. sapiens

<400> SEQUENCE: 943

Thr Pro Ala Ala Glu Thr Leu Ser Gln Leu Gly Gln Thr Leu Gln Ser
1               5                   10                  15

Leu Lys

<210> SEQ ID NO 944
<211> LENGTH: 8
<212> TYPE: PRT
<213> ORGANISM: H. sapiens

<400> SEQUENCE: 944

Val Asn Thr Leu Glu Glu Gly Lys
1               5

<210> SEQ ID NO 945
<211> LENGTH: 7
<212> TYPE: PRT
<213> ORGANISM: H. sapiens

<400> SEQUENCE: 945

Trp Thr Phe Glu Ala Cys Arg
1               5

<210> SEQ ID NO 946
```

```
<211> LENGTH: 14
<212> TYPE: PRT
<213> ORGANISM: H. sapiens

<400> SEQUENCE: 946

Ala Val Gly Ala Phe Ser Ala Thr Asp Ser Phe Asp His Lys
 1               5                  10

<210> SEQ ID NO 947
<211> LENGTH: 8
<212> TYPE: PRT
<213> ORGANISM: H. sapiens

<400> SEQUENCE: 947

Phe Phe Gln Met Val Gly Leu Lys
 1               5

<210> SEQ ID NO 948
<211> LENGTH: 7
<212> TYPE: PRT
<213> ORGANISM: H. sapiens

<400> SEQUENCE: 948

Gly Phe Ser Pro Asp Ala Arg
 1               5

<210> SEQ ID NO 949
<211> LENGTH: 13
<212> TYPE: PRT
<213> ORGANISM: H. sapiens

<400> SEQUENCE: 949

Ile Gly Val Asp Glu Phe Ser Thr Leu Val Ala Glu Ser
 1               5                  10

<210> SEQ ID NO 950
<211> LENGTH: 9
<212> TYPE: PRT
<213> ORGANISM: H. sapiens

<400> SEQUENCE: 950

Lys Phe Phe Gln Met Val Gly Leu Lys
 1               5

<210> SEQ ID NO 951
<211> LENGTH: 14
<212> TYPE: PRT
<213> ORGANISM: H. sapiens

<400> SEQUENCE: 951

Ser Gly Phe Ile Glu Glu Asp Glu Leu Gly Phe Ile Leu Lys
 1               5                  10

<210> SEQ ID NO 952
<211> LENGTH: 18
<212> TYPE: PRT
<213> ORGANISM: H. sapiens

<400> SEQUENCE: 952

Glu Ile Thr Val Ala Thr Gly Gly Phe Ile Tyr Thr Gly Glu Val Val
 1               5                  10                  15

His Arg

<210> SEQ ID NO 953
```

```
<211> LENGTH: 8
<212> TYPE: PRT
<213> ORGANISM: H. sapiens

<400> SEQUENCE: 953

Ile Gln Gln Ile Pro Asn Val Arg
 1               5

<210> SEQ ID NO 954
<211> LENGTH: 6
<212> TYPE: PRT
<213> ORGANISM: H. sapiens

<400> SEQUENCE: 954

Gly Arg Arg Ala Leu Arg
 1               5

<210> SEQ ID NO 955
<211> LENGTH: 6
<212> TYPE: PRT
<213> ORGANISM: H. sapiens

<400> SEQUENCE: 955

His Pro Thr Met Leu Lys
 1               5

<210> SEQ ID NO 956
<211> LENGTH: 7
<212> TYPE: PRT
<213> ORGANISM: H. sapiens

<400> SEQUENCE: 956

Met Ala Val Glu Tyr Asp Arg
 1               5

<210> SEQ ID NO 957
<211> LENGTH: 7
<212> TYPE: PRT
<213> ORGANISM: H. sapiens

<400> SEQUENCE: 957

Met Ser Pro Ala Val Arg Arg
 1               5

<210> SEQ ID NO 958
<211> LENGTH: 16
<212> TYPE: PRT
<213> ORGANISM: H. sapiens

<400> SEQUENCE: 958

Met Ser Pro Trp Ala Ser Gly Gly His Phe Met Asn Thr Ala Glu Arg
 1               5                  10                  15

<210> SEQ ID NO 959
<211> LENGTH: 22
<212> TYPE: PRT
<213> ORGANISM: H. sapiens

<400> SEQUENCE: 959

Ser Leu Ala Gly Pro Ala Gly Ala Ala Pro Ala Pro Gly Leu Gly Ala
 1               5                  10                  15

Ala Ala Ala Ala Pro Gly
            20
```

```
<210> SEQ ID NO 960
<211> LENGTH: 13
<212> TYPE: PRT
<213> ORGANISM: H. sapiens

<400> SEQUENCE: 960

Thr Gly Ala Gly Pro Gly Arg Gly Gly Leu Arg Ala Arg
 1               5                  10

<210> SEQ ID NO 961
<211> LENGTH: 16
<212> TYPE: PRT
<213> ORGANISM: H. sapiens

<400> SEQUENCE: 961

Asp Ala Glu Glu Asp Asp Ser Leu Ala Asn Ser Ser Asp Leu Leu Lys
 1               5                  10                  15

<210> SEQ ID NO 962
<211> LENGTH: 9
<212> TYPE: PRT
<213> ORGANISM: H. sapiens

<400> SEQUENCE: 962

Glu Leu Leu Glu Thr Gly Asp Asn Arg
 1               5

<210> SEQ ID NO 963
<211> LENGTH: 19
<212> TYPE: PRT
<213> ORGANISM: H. sapiens

<400> SEQUENCE: 963

Glu Leu Leu Gln Leu Ser Lys Pro Glu Leu Pro Gln Asp Gly Thr Ser
 1               5                  10                  15

Thr Leu Arg

<210> SEQ ID NO 964
<211> LENGTH: 19
<212> TYPE: PRT
<213> ORGANISM: H. sapiens

<400> SEQUENCE: 964

Glu Leu Leu Gln Leu Ser Lys Pro Glu Leu Pro Gln Asp Gly Thr Ser
 1               5                  10                  15

Thr Leu Arg

<210> SEQ ID NO 965
<211> LENGTH: 7
<212> TYPE: PRT
<213> ORGANISM: H. sapiens

<400> SEQUENCE: 965

Glu Val Pro Glu Met Glu Lys
 1               5

<210> SEQ ID NO 966
<211> LENGTH: 16
<212> TYPE: PRT
<213> ORGANISM: H. sapiens

<400> SEQUENCE: 966

Phe Ala Glu Ala Leu Pro Ser Asp Glu Glu Gly Glu Ser Tyr Ser Lys
 1               5                  10                  15
```

<210> SEQ ID NO 967
<211> LENGTH: 6
<212> TYPE: PRT
<213> ORGANISM: H. sapiens

<400> SEQUENCE: 967

Ile Trp Glu Thr Cys Lys
1               5

<210> SEQ ID NO 968
<211> LENGTH: 5
<212> TYPE: PRT
<213> ORGANISM: H. sapiens

<400> SEQUENCE: 968

Leu Pro Ser Leu Lys
1               5

<210> SEQ ID NO 969
<211> LENGTH: 10
<212> TYPE: PRT
<213> ORGANISM: H. sapiens

<400> SEQUENCE: 969

Arg Tyr Gly Gly Phe Met Arg Gly Leu Lys
1               5                   10

<210> SEQ ID NO 970
<211> LENGTH: 14
<212> TYPE: PRT
<213> ORGANISM: H. sapiens

<400> SEQUENCE: 970

Ser Pro Gln Leu Glu Asp Glu Ala Lys Glu Leu Gln Lys Arg
1               5                   10

<210> SEQ ID NO 971
<211> LENGTH: 6
<212> TYPE: PRT
<213> ORGANISM: H. sapiens

<400> SEQUENCE: 971

Tyr Gly Gly Phe Met Lys
1               5

<210> SEQ ID NO 972
<211> LENGTH: 10
<212> TYPE: PRT
<213> ORGANISM: H. sapiens

<400> SEQUENCE: 972

Tyr Gly Gly Phe Met Arg Gly Leu Lys Arg
1               5                   10

<210> SEQ ID NO 973
<211> LENGTH: 14
<212> TYPE: PRT
<213> ORGANISM: H. sapiens

<400> SEQUENCE: 973

Ala Lys Pro Ser Ala Pro Val Val Ser Gly Pro Ala Ala Arg
1               5                   10

<210> SEQ ID NO 974
<211> LENGTH: 16
<212> TYPE: PRT
<213> ORGANISM: H. sapiens

<400> SEQUENCE: 974

Cys Thr Ala Thr Ser Leu Ile Pro Val Gly Pro Ile Gln Trp Phe Arg
1               5                   10                  15

<210> SEQ ID NO 975
<211> LENGTH: 7
<212> TYPE: PRT
<213> ORGANISM: H. sapiens

<400> SEQUENCE: 975

Glu Leu Ile Tyr Asn Gln Lys
1               5

<210> SEQ ID NO 976
<211> LENGTH: 9
<212> TYPE: PRT
<213> ORGANISM: H. sapiens

<400> SEQUENCE: 976

Gly Ser Pro Asp Asp Val Glu Phe Lys
1               5

<210> SEQ ID NO 977
<211> LENGTH: 13
<212> TYPE: PRT
<213> ORGANISM: H. sapiens

<400> SEQUENCE: 977

Ser Val Leu Val Ala Ala Gly Glu Thr Ala Thr Leu Arg
1               5                   10

<210> SEQ ID NO 978
<211> LENGTH: 11
<212> TYPE: PRT
<213> ORGANISM: H. sapiens

<400> SEQUENCE: 978

Thr Glu Thr Ala Ser Thr Val Thr Glu Asn Lys
1               5                   10

<210> SEQ ID NO 979
<211> LENGTH: 13
<212> TYPE: PRT
<213> ORGANISM: H. sapiens

<400> SEQUENCE: 979

Val Pro Pro Thr Leu Glu Val Thr Gln Gln Pro Val Arg
1               5                   10

<210> SEQ ID NO 980
<211> LENGTH: 5
<212> TYPE: PRT
<213> ORGANISM: H. sapiens

<400> SEQUENCE: 980

Leu Glu Leu Gln Arg
1               5

<210> SEQ ID NO 981
<211> LENGTH: 16

-continued

```
<212> TYPE: PRT
<213> ORGANISM: H. sapiens

<400> SEQUENCE: 981

Leu Glu Leu Gln Arg Ser Ala Asn Ser Asn Pro Ala Met Ala Pro Arg
 1               5                  10                  15

<210> SEQ ID NO 982
<211> LENGTH: 5
<212> TYPE: PRT
<213> ORGANISM: H. sapiens

<400> SEQUENCE: 982

Gln Phe Leu Gln Lys
 1               5

<210> SEQ ID NO 983
<211> LENGTH: 11
<212> TYPE: PRT
<213> ORGANISM: H. sapiens

<400> SEQUENCE: 983

Ser Ala Asn Ser Asn Pro Ala Met Ala Pro Arg
 1               5                  10

<210> SEQ ID NO 984
<211> LENGTH: 8
<212> TYPE: PRT
<213> ORGANISM: H. sapiens

<400> SEQUENCE: 984

Ser Leu Ala Ala Ala Ala Gly Lys
 1               5

<210> SEQ ID NO 985
<211> LENGTH: 8
<212> TYPE: PRT
<213> ORGANISM: H. sapiens

<400> SEQUENCE: 985

Glu Asp Ala Leu Pro Gly Gln Lys
 1               5

<210> SEQ ID NO 986
<211> LENGTH: 6
<212> TYPE: PRT
<213> ORGANISM: H. sapiens

<400> SEQUENCE: 986

Gly Gly Val Val Leu Lys
 1               5

<210> SEQ ID NO 987
<211> LENGTH: 15
<212> TYPE: PRT
<213> ORGANISM: H. sapiens

<400> SEQUENCE: 987

Leu Ser Ala Thr Leu Gly Gly Leu Leu Gln Asp His Gly Ser Arg
 1               5                  10                  15

<210> SEQ ID NO 988
<211> LENGTH: 7
<212> TYPE: PRT
<213> ORGANISM: H. sapiens
```

```
<400> SEQUENCE: 988

Leu Tyr Gln Glu Val His Arg
1               5

<210> SEQ ID NO 989
<211> LENGTH: 6
<212> TYPE: PRT
<213> ORGANISM: H. sapiens

<400> SEQUENCE: 989

Ser Gln Thr Tyr Ser Lys
1               5

<210> SEQ ID NO 990
<211> LENGTH: 5
<212> TYPE: PRT
<213> ORGANISM: H. sapiens

<400> SEQUENCE: 990

Val Ala Leu Gln Lys
1               5

<210> SEQ ID NO 991
<211> LENGTH: 8
<212> TYPE: PRT
<213> ORGANISM: H. sapiens

<400> SEQUENCE: 991

Val Pro Ala Met Asp Phe Tyr Arg
1               5

<210> SEQ ID NO 992
<211> LENGTH: 10
<212> TYPE: PRT
<213> ORGANISM: H. sapiens

<400> SEQUENCE: 992

Tyr Glu Val Ser Pro Val Ala Leu Gln Arg
1               5                   10

<210> SEQ ID NO 993
<211> LENGTH: 16
<212> TYPE: PRT
<213> ORGANISM: H. sapiens

<400> SEQUENCE: 993

Asp Met Ile Gly Arg Cys Phe Val Leu Ser Gln Asp Leu Ala Ile Arg
1               5                   10                  15

<210> SEQ ID NO 994
<211> LENGTH: 16
<212> TYPE: PRT
<213> ORGANISM: H. sapiens

<400> SEQUENCE: 994

Asp Ser Ala Ser Arg Leu Val Pro Glu Val Met Leu Ser Gly Glu Arg
1               5                   10                  15

<210> SEQ ID NO 995
<211> LENGTH: 13
<212> TYPE: PRT
<213> ORGANISM: H. sapiens

<400> SEQUENCE: 995
```

```
Glu Leu Glu Pro Pro Glu Gln Gln Pro Gly Glu Arg
 1               5                  10
```

<210> SEQ ID NO 996
<211> LENGTH: 7
<212> TYPE: PRT
<213> ORGANISM: H. sapiens

<400> SEQUENCE: 996

```
Gly Ala Val Val Ile Leu Arg
 1               5
```

<210> SEQ ID NO 997
<211> LENGTH: 16
<212> TYPE: PRT
<213> ORGANISM: H. sapiens

<400> SEQUENCE: 997

```
Gly Leu Val Arg Ala Glu Glu Leu Ser Phe Val Ala Gly Ala Pro Arg
 1               5                  10                  15
```

<210> SEQ ID NO 998
<211> LENGTH: 14
<212> TYPE: PRT
<213> ORGANISM: H. sapiens

<400> SEQUENCE: 998

```
Val Cys Gly Asp Ala Met Phe Gln Leu Gln Glu Asn Val Lys
 1               5                  10
```

<210> SEQ ID NO 999
<211> LENGTH: 13
<212> TYPE: PRT
<213> ORGANISM: H. sapiens

<400> SEQUENCE: 999

```
Val Asp Gln Ile Leu Glu Thr Arg Asp Met Ile Gly Arg
 1               5                  10
```

<210> SEQ ID NO 1000
<211> LENGTH: 6
<212> TYPE: PRT
<213> ORGANISM: H. sapiens

<400> SEQUENCE: 1000

```
Tyr Glu Ala Arg Gln Arg
 1               5
```

<210> SEQ ID NO 1001
<211> LENGTH: 14
<212> TYPE: PRT
<213> ORGANISM: H. sapiens

<400> SEQUENCE: 1001

```
Ala Pro Gly Thr Glu Gly Gln Gln Gln Val His Gly Glu Lys
 1               5                  10
```

<210> SEQ ID NO 1002
<211> LENGTH: 22
<212> TYPE: PRT
<213> ORGANISM: H. sapiens

<400> SEQUENCE: 1002

```
Glu Ala Pro Ala Val Pro Ser Ala Pro Pro Ser Tyr Glu Glu Ala Thr
```

```
                1               5                   10                  15

Ser Gly Glu Gly Met Lys
                20

<210> SEQ ID NO 1003
<211> LENGTH: 6
<212> TYPE: PRT
<213> ORGANISM: H. sapiens

<400> SEQUENCE: 1003

Leu Ser Val Ala Asn Lys
1               5

<210> SEQ ID NO 1004
<211> LENGTH: 6
<212> TYPE: PRT
<213> ORGANISM: H. sapiens

<400> SEQUENCE: 1004

Ile Cys Tyr Val Cys Lys
1               5

<210> SEQ ID NO 1005
<211> LENGTH: 11
<212> TYPE: PRT
<213> ORGANISM: H. sapiens

<400> SEQUENCE: 1005

Glu Gly Gln Ala Val Ala Val Pro Ser Ser Lys
1               5                   10

<210> SEQ ID NO 1006
<211> LENGTH: 9
<212> TYPE: PRT
<213> ORGANISM: H. sapiens

<400> SEQUENCE: 1006

Ala Gln Pro Gly Trp Gly Ser Pro Arg
1               5

<210> SEQ ID NO 1007
<211> LENGTH: 14
<212> TYPE: PRT
<213> ORGANISM: H. sapiens

<400> SEQUENCE: 1007

Glu Gln Asp Ala Pro Val Ala Gly Leu Gln Pro Val Glu Arg
1               5                   10

<210> SEQ ID NO 1008
<211> LENGTH: 13
<212> TYPE: PRT
<213> ORGANISM: H. sapiens

<400> SEQUENCE: 1008

Arg Pro Gly Gly Ser Tyr Pro Ala Ala Ala Ala Lys
1               5                   10

<210> SEQ ID NO 1009
<211> LENGTH: 12
<212> TYPE: PRT
<213> ORGANISM: H. sapiens

<400> SEQUENCE: 1009
```

Ser Thr Pro Leu Gly Gln Gln Pro Ala Pro Arg
1               5                   10

<210> SEQ ID NO 1010
<211> LENGTH: 10
<212> TYPE: PRT
<213> ORGANISM: H. sapiens

<400> SEQUENCE: 1010

Tyr Glu Pro Ala Gly Gly Asp Ala Asn Arg
1               5                   10

<210> SEQ ID NO 1011
<211> LENGTH: 11
<212> TYPE: PRT
<213> ORGANISM: H. sapiens

<400> SEQUENCE: 1011

Ala Asn Thr Pro Asp Ser Asp Ile Thr Glu Lys
1               5                   10

<210> SEQ ID NO 1012
<211> LENGTH: 15
<212> TYPE: PRT
<213> ORGANISM: H. sapiens

<400> SEQUENCE: 1012

His Gly Leu Asn Gly Ile Leu Ala Asp Glu Met Gly Leu Gly Lys
1               5                   10                  15

<210> SEQ ID NO 1013
<211> LENGTH: 7
<212> TYPE: PRT
<213> ORGANISM: H. sapiens

<400> SEQUENCE: 1013

Asn Leu Phe Asn Leu Asp Arg
1               5

<210> SEQ ID NO 1014
<211> LENGTH: 8
<212> TYPE: PRT
<213> ORGANISM: H. sapiens

<400> SEQUENCE: 1014

Gln Glu Leu Arg Glu Val Leu Lys
1               5

<210> SEQ ID NO 1015
<211> LENGTH: 12
<212> TYPE: PRT
<213> ORGANISM: H. sapiens

<400> SEQUENCE: 1015

Ser Ala Asp Glu Gln Ser Ile Tyr Glu Lys Glu Arg
1               5                   10

<210> SEQ ID NO 1016
<211> LENGTH: 7
<212> TYPE: PRT
<213> ORGANISM: H. sapiens

<400> SEQUENCE: 1016

Ser Leu Phe Arg Arg Leu Lys
1               5

```
<210> SEQ ID NO 1017
<211> LENGTH: 20
<212> TYPE: PRT
<213> ORGANISM: H. sapiens

<400> SEQUENCE: 1017

Val Phe Ala Glu Asp Gln Asp Met Gln Tyr Ala Ser Gln Ser Glu Val
1               5                   10                  15
Pro Asn Gly Lys
            20

<210> SEQ ID NO 1018
<211> LENGTH: 12
<212> TYPE: PRT
<213> ORGANISM: H. sapiens

<400> SEQUENCE: 1018

Tyr Gln His Leu Met Thr Ile Asn Ala Asn Asn Arg
1               5                   10

<210> SEQ ID NO 1019
<211> LENGTH: 16
<212> TYPE: PRT
<213> ORGANISM: H. sapiens

<400> SEQUENCE: 1019

Leu Gln Gln Thr Gln Ala Gln Val Asp Glu Val Val Asp Ile Met Arg
1               5                   10                  15

<210> SEQ ID NO 1020
<211> LENGTH: 22
<212> TYPE: PRT
<213> ORGANISM: H. sapiens

<400> SEQUENCE: 1020

Met Met Ile Ile Leu Gly Val Ile Cys Ala Ile Ile Leu Ile Ile Ile
1               5                   10                  15
Ile Val Phe Phe Ser Gly
            20

<210> SEQ ID NO 1021
<211> LENGTH: 16
<212> TYPE: PRT
<213> ORGANISM: H. sapiens

<400> SEQUENCE: 1021

Asp Ala Leu Ser Ser Val Gln Glu Ser Gln Val Ala Gln Gln Ala Arg
1               5                   10                  15

<210> SEQ ID NO 1022
<211> LENGTH: 7
<212> TYPE: PRT
<213> ORGANISM: H. sapiens

<400> SEQUENCE: 1022

Asp Tyr Trp Ser Thr Val Lys
1               5

<210> SEQ ID NO 1023
<211> LENGTH: 11
<212> TYPE: PRT
<213> ORGANISM: H. sapiens
```

-continued

```
<400> SEQUENCE: 1023

Gly Trp Val Thr Asp Gly Phe Ser Ser Leu Lys
1               5                   10

<210> SEQ ID NO 1024
<211> LENGTH: 11
<212> TYPE: PRT
<213> ORGANISM: H. sapiens

<400> SEQUENCE: 1024

Glu Ser Leu Ser Ser Tyr Trp Glu Ser Ala Lys
1               5                   10

<210> SEQ ID NO 1025
<211> LENGTH: 21
<212> TYPE: PRT
<213> ORGANISM: H. sapiens

<400> SEQUENCE: 1025

Ser Thr Ala Ala Met Ser Thr Tyr Thr Gly Ile Phe Thr Asp Gln Val
1               5                   10                  15

Leu Ser Val Leu Lys
            20

<210> SEQ ID NO 1026
<211> LENGTH: 9
<212> TYPE: PRT
<213> ORGANISM: H. sapiens

<400> SEQUENCE: 1026

Thr Ala Ala Gln Asn Leu Tyr Glu Lys
1               5

<210> SEQ ID NO 1027
<211> LENGTH: 9
<212> TYPE: PRT
<213> ORGANISM: H. sapiens

<400> SEQUENCE: 1027

Thr Tyr Leu Pro Ala Val Asp Glu Lys
1               5

<210> SEQ ID NO 1028
<211> LENGTH: 6
<212> TYPE: PRT
<213> ORGANISM: H. sapiens

<400> SEQUENCE: 1028

Leu Leu Leu Leu Pro Arg
1               5

<210> SEQ ID NO 1029
<211> LENGTH: 14
<212> TYPE: PRT
<213> ORGANISM: H. sapiens

<400> SEQUENCE: 1029

Thr Gln Ser Ser Leu Val Pro Ala Leu Thr Asp Phe Val Arg
1               5                   10

<210> SEQ ID NO 1030
<211> LENGTH: 9
<212> TYPE: PRT
<213> ORGANISM: H. sapiens
```

```
<400> SEQUENCE: 1030

Asp Leu Ser Glu Asn Asn Asp Gln Arg
1               5

<210> SEQ ID NO 1031
<211> LENGTH: 20
<212> TYPE: PRT
<213> ORGANISM: H. sapiens

<400> SEQUENCE: 1031

Asp Gln Leu Val Ile Pro Asp Gly Gln Glu Glu Gln Glu Ala Ala
1               5                   10                  15

Gly Glu Gly Arg
            20

<210> SEQ ID NO 1032
<211> LENGTH: 9
<212> TYPE: PRT
<213> ORGANISM: H. sapiens

<400> SEQUENCE: 1032

Asp Thr Ile Asn Leu Leu Asp Gln Arg
1               5

<210> SEQ ID NO 1033
<211> LENGTH: 15
<212> TYPE: PRT
<213> ORGANISM: H. sapiens

<400> SEQUENCE: 1033

Glu Glu Thr Asn Glu Ile Gln Val Val Asn Glu Glu Pro Gln Arg
1               5                   10                  15

<210> SEQ ID NO 1034
<211> LENGTH: 12
<212> TYPE: PRT
<213> ORGANISM: H. sapiens

<400> SEQUENCE: 1034

Glu Gln Val Val Glu Asp Arg Pro Val Gly Gly Arg
1               5                   10

<210> SEQ ID NO 1035
<211> LENGTH: 17
<212> TYPE: PRT
<213> ORGANISM: H. sapiens

<400> SEQUENCE: 1035

Gly Phe Gly Gly Ala Gly Glu Leu Gly Gln Thr Pro Gln Val Gln Ala
1               5                   10                  15

Ala

<210> SEQ ID NO 1036
<211> LENGTH: 24
<212> TYPE: PRT
<213> ORGANISM: H. sapiens

<400> SEQUENCE: 1036

Gly Phe Gly Gly Ala Gly Glu Leu Gly Gln Thr Pro Gln Val Gln Ala
1               5                   10                  15

Ala Leu Ser Val Ser Gln Glu Asn
            20
```

```
<210> SEQ ID NO 1037
<211> LENGTH: 7
<212> TYPE: PRT
<213> ORGANISM: H. sapiens

<400> SEQUENCE: 1037

Leu Pro Gln Glu Pro Gly Arg
 1               5

<210> SEQ ID NO 1038
<211> LENGTH: 15
<212> TYPE: PRT
<213> ORGANISM: H. sapiens

<400> SEQUENCE: 1038

Leu Ser Val Ser Gln Glu Asn Pro Glu Met Glu Gly Pro Glu Arg
 1               5                  10                  15

<210> SEQ ID NO 1039
<211> LENGTH: 11
<212> TYPE: PRT
<213> ORGANISM: H. sapiens

<400> SEQUENCE: 1039

Met Gly Leu Gly Asn Gly Arg Arg Ser Met Lys
 1               5                  10

<210> SEQ ID NO 1040
<211> LENGTH: 11
<212> TYPE: PRT
<213> ORGANISM: H. sapiens

<400> SEQUENCE: 1040

Asn Ile Asp Val Phe Asn Val Glu Asp Gln Lys
 1               5                  10

<210> SEQ ID NO 1041
<211> LENGTH: 12
<212> TYPE: PRT
<213> ORGANISM: H. sapiens

<400> SEQUENCE: 1041

Asn Ile Asp Val Phe Asn Val Glu Asp Gln Lys Arg
 1               5                  10

<210> SEQ ID NO 1042
<211> LENGTH: 21
<212> TYPE: PRT
<213> ORGANISM: H. sapiens

<400> SEQUENCE: 1042

Asn Gln Thr Asn Leu Glu Arg Lys Phe Ser Tyr Asp Leu Ser Gln Cys
 1               5                  10                  15

Ile Asn Gln Met Lys
            20

<210> SEQ ID NO 1043
<211> LENGTH: 12
<212> TYPE: PRT
<213> ORGANISM: H. sapiens

<400> SEQUENCE: 1043

Gln Gln Leu Gln Ala Leu Ser Glu Pro Gln Pro Arg
```

```
                1               5                   10
```

<210> SEQ ID NO 1044
<211> LENGTH: 12
<212> TYPE: PRT
<213> ORGANISM: H. sapiens

<400> SEQUENCE: 1044

```
Arg Asp Thr Ile Asn Leu Leu Asp Gln Arg Glu Lys
 1               5                   10
```

<210> SEQ ID NO 1045
<211> LENGTH: 9
<212> TYPE: PRT
<213> ORGANISM: H. sapiens

<400> SEQUENCE: 1045

```
Asp Tyr Phe Met Pro Cys Pro Gly Arg
 1               5
```

<210> SEQ ID NO 1046
<211> LENGTH: 6
<212> TYPE: PRT
<213> ORGANISM: H. sapiens

<400> SEQUENCE: 1046

```
Glu Leu Ile Ser Glu Arg
 1               5
```

<210> SEQ ID NO 1047
<211> LENGTH: 7
<212> TYPE: PRT
<213> ORGANISM: H. sapiens

<400> SEQUENCE: 1047

```
Leu His Ile Met Ala Gly Arg
 1               5
```

<210> SEQ ID NO 1048
<211> LENGTH: 7
<212> TYPE: PRT
<213> ORGANISM: H. sapiens

<400> SEQUENCE: 1048

```
Leu Trp Trp Leu Asp Leu Lys
 1               5
```

<210> SEQ ID NO 1049
<211> LENGTH: 11
<212> TYPE: PRT
<213> ORGANISM: H. sapiens

<400> SEQUENCE: 1049

```
Asn Phe Pro Ser Pro Val Asp Ala Ala Phe Arg
 1               5                   10
```

<210> SEQ ID NO 1050
<211> LENGTH: 9
<212> TYPE: PRT
<213> ORGANISM: H. sapiens

<400> SEQUENCE: 1050

```
Val Asp Gly Ala Leu Cys Met Glu Lys
 1               5
```

<210> SEQ ID NO 1051
<211> LENGTH: 8
<212> TYPE: PRT
<213> ORGANISM: H. sapiens

<400> SEQUENCE: 1051

Val Trp Val Tyr Pro Pro Glu Lys
 1               5

<210> SEQ ID NO 1052
<211> LENGTH: 11
<212> TYPE: PRT
<213> ORGANISM: H. sapiens

<400> SEQUENCE: 1052

Tyr Tyr Cys Phe Gln Gly Asn Gln Phe Leu Arg
 1               5                  10

<210> SEQ ID NO 1053
<211> LENGTH: 14
<212> TYPE: PRT
<213> ORGANISM: H. sapiens

<400> SEQUENCE: 1053

Gly His Gln Asp Leu Asp Pro Asp Asn Glu Gly Glu Leu Arg
 1               5                  10

<210> SEQ ID NO 1054
<211> LENGTH: 8
<212> TYPE: PRT
<213> ORGANISM: H. sapiens

<400> SEQUENCE: 1054

Leu Ser Phe Phe Gly Leu Glu Lys
 1               5

<210> SEQ ID NO 1055
<211> LENGTH: 12
<212> TYPE: PRT
<213> ORGANISM: H. sapiens

<400> SEQUENCE: 1055

Asp Ile Gln Gln Thr Leu Thr Gln Asn Met Glu Arg
 1               5                  10

<210> SEQ ID NO 1056
<211> LENGTH: 5
<212> TYPE: PRT
<213> ORGANISM: H. sapiens

<400> SEQUENCE: 1056

Leu Glu Ala Leu Lys
 1               5

<210> SEQ ID NO 1057
<211> LENGTH: 13
<212> TYPE: PRT
<213> ORGANISM: H. sapiens

<400> SEQUENCE: 1057

Arg Pro Pro Arg Pro Gly Thr Asn Gly Trp Ser Arg Arg
 1               5                  10

<210> SEQ ID NO 1058

```
<211> LENGTH: 12
<212> TYPE: PRT
<213> ORGANISM: H. sapiens

<400> SEQUENCE: 1058

Ser Ser Thr Gln Met Thr Trp Gly Ala Leu Phe Arg
1               5                   10

<210> SEQ ID NO 1059
<211> LENGTH: 9
<212> TYPE: PRT
<213> ORGANISM: H. sapiens

<400> SEQUENCE: 1059

Trp Asn Gly Met Ser Arg Leu Glu Lys
1               5

<210> SEQ ID NO 1060
<211> LENGTH: 11
<212> TYPE: PRT
<213> ORGANISM: H. sapiens

<400> SEQUENCE: 1060

Ala Glu Glu Glu Glu Leu Ala Arg Pro Pro Arg
1               5                   10

<210> SEQ ID NO 1061
<211> LENGTH: 9
<212> TYPE: PRT
<213> ORGANISM: H. sapiens

<400> SEQUENCE: 1061

Ala Gln Pro Gly Trp Gly Ser Pro Arg
1               5

<210> SEQ ID NO 1062
<211> LENGTH: 8
<212> TYPE: PRT
<213> ORGANISM: H. sapiens

<400> SEQUENCE: 1062

Asp Pro Cys Lys Gly Lys Gly Arg
1               5

<210> SEQ ID NO 1063
<211> LENGTH: 14
<212> TYPE: PRT
<213> ORGANISM: H. sapiens

<400> SEQUENCE: 1063

Glu Gln Asp Ala Pro Val Ala Gly Leu Gln Pro Val Glu Arg
1               5                   10

<210> SEQ ID NO 1064
<211> LENGTH: 11
<212> TYPE: PRT
<213> ORGANISM: H. sapiens

<400> SEQUENCE: 1064

Gly His Ala Pro Cys Ser Ser Val Leu Gly Arg
1               5                   10

<210> SEQ ID NO 1065
<211> LENGTH: 15
<212> TYPE: PRT
```

<213> ORGANISM: H. sapiens

<400> SEQUENCE: 1065

Gly His Arg Thr Thr Tyr Thr Glu Cys Cys Cys Gln Asp Gly Lys
1               5                   10                  15

<210> SEQ ID NO 1066
<211> LENGTH: 16
<212> TYPE: PRT
<213> ORGANISM: H. sapiens

<400> SEQUENCE: 1066

Leu Gly Thr Pro Gln Arg Ser Gly Ala Ala Pro Pro Thr Pro Pro Arg
1               5                   10                  15

<210> SEQ ID NO 1067
<211> LENGTH: 17
<212> TYPE: PRT
<213> ORGANISM: H. sapiens

<400> SEQUENCE: 1067

Ser Pro Asn Leu Arg Arg Ser Ser Ala Ala Gly Glu Gly Thr Leu Ala
1               5                   10                  15

Arg

<210> SEQ ID NO 1068
<211> LENGTH: 14
<212> TYPE: PRT
<213> ORGANISM: H. sapiens

<400> SEQUENCE: 1068

Val Thr Asn Asp Val Cys Ser Glu Pro Leu Arg Gly His Arg
1               5                   10

<210> SEQ ID NO 1069
<211> LENGTH: 6
<212> TYPE: PRT
<213> ORGANISM: H. sapiens

<400> SEQUENCE: 1069

Val Tyr Ser Leu Phe Arg
1               5

<210> SEQ ID NO 1070
<211> LENGTH: 10
<212> TYPE: PRT
<213> ORGANISM: H. sapiens

<400> SEQUENCE: 1070

Tyr Glu Pro Ala Gly Gly Asp Ala Asn Arg
1               5                   10

<210> SEQ ID NO 1071
<211> LENGTH: 23
<212> TYPE: PRT
<213> ORGANISM: H. sapiens

<400> SEQUENCE: 1071

Ala Pro Ala Lys Pro Pro Gly Ser Gly Leu Asp Leu Ala Asp Ala Leu
1               5                   10                  15

Asp Asp Gln Asp Asp Gly Arg
            20

```
<210> SEQ ID NO 1072
<211> LENGTH: 19
<212> TYPE: PRT
<213> ORGANISM: H. sapiens

<400> SEQUENCE: 1072

Ala Pro Ala Asn Thr Leu Gly Asn Asp Phe Asp Leu Ala Asp Ala Leu
 1               5                  10                  15

Asp Asp Arg

<210> SEQ ID NO 1073
<211> LENGTH: 15
<212> TYPE: PRT
<213> ORGANISM: H. sapiens

<400> SEQUENCE: 1073

Asp Leu Glu Asp Ile Val Gly Gly Glu Tyr Lys Pro Asp Lys
 1               5                  10                  15

<210> SEQ ID NO 1074
<211> LENGTH: 6
<212> TYPE: PRT
<213> ORGANISM: H. sapiens

<400> SEQUENCE: 1074

Glu Thr Ser Ser Val Lys
 1               5

<210> SEQ ID NO 1075
<211> LENGTH: 15
<212> TYPE: PRT
<213> ORGANISM: H. sapiens

<400> SEQUENCE: 1075

Gly Glu Asn Leu Glu Ala Val Val Cys Glu Glu Pro Gln Val Lys
 1               5                  10                  15

<210> SEQ ID NO 1076
<211> LENGTH: 7
<212> TYPE: PRT
<213> ORGANISM: H. sapiens

<400> SEQUENCE: 1076

Lys Pro Gly Ile Gly Gly Arg
 1               5

<210> SEQ ID NO 1077
<211> LENGTH: 12
<212> TYPE: PRT
<213> ORGANISM: H. sapiens

<400> SEQUENCE: 1077

Lys Pro Ile Ala Gly Gly Gly Gly Phe Ser Asp Lys
 1               5                  10

<210> SEQ ID NO 1078
<211> LENGTH: 19
<212> TYPE: PRT
<213> ORGANISM: H. sapiens

<400> SEQUENCE: 1078

Tyr Ser Thr Leu His Thr Gln Ser Ala Glu Pro Pro Pro Pro Glu
 1               5                  10                  15

Pro Ala Arg
```

<210> SEQ ID NO 1079
<211> LENGTH: 7
<212> TYPE: PRT
<213> ORGANISM: H. sapiens

<400> SEQUENCE: 1079

Ala Ala Phe Asp Val Cys Lys
1               5

<210> SEQ ID NO 1080
<211> LENGTH: 7
<212> TYPE: PRT
<213> ORGANISM: H. sapiens

<400> SEQUENCE: 1080

Ala Asp Gln Asp Thr Ile Arg
1               5

<210> SEQ ID NO 1081
<211> LENGTH: 12
<212> TYPE: PRT
<213> ORGANISM: H. sapiens

<400> SEQUENCE: 1081

Ala Asp Gln Asp Thr Ile Arg Glu Leu Thr Gly Lys
1               5                   10

<210> SEQ ID NO 1082
<211> LENGTH: 14
<212> TYPE: PRT
<213> ORGANISM: H. sapiens

<400> SEQUENCE: 1082

Glu Glu Leu Leu Leu Leu Gln Ser Thr Ala Glu Gln Leu Arg
1               5                   10

<210> SEQ ID NO 1083
<211> LENGTH: 8
<212> TYPE: PRT
<213> ORGANISM: H. sapiens

<400> SEQUENCE: 1083

Glu Leu Asp Val Leu Gln Gly Arg
1               5

<210> SEQ ID NO 1084
<211> LENGTH: 5
<212> TYPE: PRT
<213> ORGANISM: H. sapiens

<400> SEQUENCE: 1084

Glu Leu Thr Gly Lys
1               5

<210> SEQ ID NO 1085
<211> LENGTH: 9
<212> TYPE: PRT
<213> ORGANISM: H. sapiens

<400> SEQUENCE: 1085

Gly Leu Gln Gly Ala Gly Pro Arg Arg
1               5

```
<210> SEQ ID NO 1086
<211> LENGTH: 11
<212> TYPE: PRT
<213> ORGANISM: H. sapiens

<400> SEQUENCE: 1086

Ile Asp Arg Leu Glu Gln Glu Leu Pro Ala Arg
1               5                   10

<210> SEQ ID NO 1087
<211> LENGTH: 6
<212> TYPE: PRT
<213> ORGANISM: H. sapiens

<400> SEQUENCE: 1087

Ile Ser Ile Pro Ile Arg
1               5

<210> SEQ ID NO 1088
<211> LENGTH: 8
<212> TYPE: PRT
<213> ORGANISM: H. sapiens

<400> SEQUENCE: 1088

Leu Glu Gln Glu Leu Pro Ala Arg
1               5

<210> SEQ ID NO 1089
<211> LENGTH: 10
<212> TYPE: PRT
<213> ORGANISM: H. sapiens

<400> SEQUENCE: 1089

Leu Val Glu Ala Phe Gly Gly Ala Thr Lys
1               5                   10

<210> SEQ ID NO 1090
<211> LENGTH: 17
<212> TYPE: PRT
<213> ORGANISM: H. sapiens

<400> SEQUENCE: 1090

Met Asp Gln Leu Glu Gly Gln Leu Leu Ala Gln Val Leu Ala Leu Glu
1               5                   10                  15

Lys

<210> SEQ ID NO 1091
<211> LENGTH: 15
<212> TYPE: PRT
<213> ORGANISM: H. sapiens

<400> SEQUENCE: 1091

Gln Arg Gln Glu Val Glu Lys Glu Leu Asp Val Leu Gln Gly Arg
1               5                   10                  15

<210> SEQ ID NO 1092
<211> LENGTH: 9
<212> TYPE: PRT
<213> ORGANISM: H. sapiens

<400> SEQUENCE: 1092

Gln Thr Ala Leu Gln Gln Glu Ala Arg
1               5
```

```
<210> SEQ ID NO 1093
<211> LENGTH: 8
<212> TYPE: PRT
<213> ORGANISM: H. sapiens

<400> SEQUENCE: 1093

Val Ala Leu Ser His Ser Ser Arg
1               5

<210> SEQ ID NO 1094
<211> LENGTH: 9
<212> TYPE: PRT
<213> ORGANISM: H. sapiens

<400> SEQUENCE: 1094

Val Ala Gln Leu Pro Leu Ser Leu Lys
1               5

<210> SEQ ID NO 1095
<211> LENGTH: 11
<212> TYPE: PRT
<213> ORGANISM: H. sapiens

<400> SEQUENCE: 1095

Ala Pro Ala Ala His Pro Glu Gly Gln Leu Lys
1               5                   10

<210> SEQ ID NO 1096
<211> LENGTH: 11
<212> TYPE: PRT
<213> ORGANISM: H. sapiens

<400> SEQUENCE: 1096

Asp Leu Glu Leu Leu Ile Gln Thr Ala Thr Arg
1               5                   10

<210> SEQ ID NO 1097
<211> LENGTH: 17
<212> TYPE: PRT
<213> ORGANISM: H. sapiens

<400> SEQUENCE: 1097

Glu Glu Thr Pro Ala Thr Glu Ser Pro Asp Thr Gly Leu Tyr Tyr His
1               5                   10                  15

Arg

<210> SEQ ID NO 1098
<211> LENGTH: 10
<212> TYPE: PRT
<213> ORGANISM: H. sapiens

<400> SEQUENCE: 1098

Glu Met Glu Glu Glu Arg Leu Arg Met Arg
1               5                   10

<210> SEQ ID NO 1099
<211> LENGTH: 7
<212> TYPE: PRT
<213> ORGANISM: H. sapiens

<400> SEQUENCE: 1099

Glu Val Asp Thr Ser Glu Lys
1               5
```

-continued

```
<210> SEQ ID NO 1100
<211> LENGTH: 18
<212> TYPE: PRT
<213> ORGANISM: H. sapiens

<400> SEQUENCE: 1100

Phe His Pro Asp Thr Asp Asp Val Pro Val Pro Ala Pro Ala Gly Asp
1               5                   10                  15
Gln Lys

<210> SEQ ID NO 1101
<211> LENGTH: 5
<212> TYPE: PRT
<213> ORGANISM: H. sapiens

<400> SEQUENCE: 1101

Leu Asp Glu Leu Lys
1               5

<210> SEQ ID NO 1102
<211> LENGTH: 10
<212> TYPE: PRT
<213> ORGANISM: H. sapiens

<400> SEQUENCE: 1102

Leu Pro Glu Val Glu Val Pro Gln His Leu
1               5                   10

<210> SEQ ID NO 1103
<211> LENGTH: 10
<212> TYPE: PRT
<213> ORGANISM: H. sapiens

<400> SEQUENCE: 1103

Leu Gln Ala Ala Asn Ala Glu Asp Ile Lys
1               5                   10

<210> SEQ ID NO 1104
<211> LENGTH: 13
<212> TYPE: PRT
<213> ORGANISM: H. sapiens

<400> SEQUENCE: 1104

Leu Val Thr Leu Glu Glu Phe Leu Ala Ser Thr Gln Arg
1               5                   10

<210> SEQ ID NO 1105
<211> LENGTH: 10
<212> TYPE: PRT
<213> ORGANISM: H. sapiens

<400> SEQUENCE: 1105

Gln Gln Gln Gln Gln Gln Gln Gly His Lys
1               5                   10

<210> SEQ ID NO 1106
<211> LENGTH: 10
<212> TYPE: PRT
<213> ORGANISM: H. sapiens

<400> SEQUENCE: 1106

Tyr Leu Glu Ser Leu Gly Glu Glu Gln Arg
1               5                   10
```

```
<210> SEQ ID NO 1107
<211> LENGTH: 16
<212> TYPE: PRT
<213> ORGANISM: H. sapiens

<400> SEQUENCE: 1107

Tyr Leu Gln Glu Val Ile Asp Val Leu Glu Thr Asp Gly His Phe Arg
1               5                   10                  15

<210> SEQ ID NO 1108
<211> LENGTH: 5
<212> TYPE: PRT
<213> ORGANISM: H. sapiens

<400> SEQUENCE: 1108

Ala Ala Asp Leu Lys
1               5

<210> SEQ ID NO 1109
<211> LENGTH: 6
<212> TYPE: PRT
<213> ORGANISM: H. sapiens

<400> SEQUENCE: 1109

Ala Glu Asp Leu Phe Arg
1               5

<210> SEQ ID NO 1110
<211> LENGTH: 10
<212> TYPE: PRT
<213> ORGANISM: H. sapiens

<400> SEQUENCE: 1110

Ala Leu Ala Ile Gln Asn Trp Val Asp Lys
1               5                   10

<210> SEQ ID NO 1111
<211> LENGTH: 8
<212> TYPE: PRT
<213> ORGANISM: H. sapiens

<400> SEQUENCE: 1111

Ala Tyr Gly Ala Thr Pro Ser Arg
1               5

<210> SEQ ID NO 1112
<211> LENGTH: 7
<212> TYPE: PRT
<213> ORGANISM: H. sapiens

<400> SEQUENCE: 1112

Cys Leu Leu Gln Ser Leu Lys
1               5

<210> SEQ ID NO 1113
<211> LENGTH: 10
<212> TYPE: PRT
<213> ORGANISM: H. sapiens

<400> SEQUENCE: 1113

Asp Ile Val Asn Gln Val Gly Asp Asn Arg
1               5                   10

<210> SEQ ID NO 1114
<211> LENGTH: 11
```

```
<212> TYPE: PRT
<213> ORGANISM: H. sapiens

<400> SEQUENCE: 1114

Gly Thr Thr Leu Leu Ser Ser Glu Val Gln Lys
1               5                   10

<210> SEQ ID NO 1115
<211> LENGTH: 6
<212> TYPE: PRT
<213> ORGANISM: H. sapiens

<400> SEQUENCE: 1115

Ile Asn Asn Met Tyr Arg
1               5

<210> SEQ ID NO 1116
<211> LENGTH: 9
<212> TYPE: PRT
<213> ORGANISM: H. sapiens

<400> SEQUENCE: 1116

Leu Cys Ser Ile Asp Tyr Pro Glu Arg
1               5

<210> SEQ ID NO 1117
<211> LENGTH: 13
<212> TYPE: PRT
<213> ORGANISM: H. sapiens

<400> SEQUENCE: 1117

Leu Met Gly Ile Phe Asp Thr Ser Trp Val Ser Met Lys
1               5                   10

<210> SEQ ID NO 1118
<211> LENGTH: 13
<212> TYPE: PRT
<213> ORGANISM: H. sapiens

<400> SEQUENCE: 1118

Asn Leu Ser Glu Val Val Asn Ser Ile Val Trp Val Arg
1               5                   10

<210> SEQ ID NO 1119
<211> LENGTH: 18
<212> TYPE: PRT
<213> ORGANISM: H. sapiens

<400> SEQUENCE: 1119

Asn Ser Lys Ala Gly Ser Gly Gly Lys Ser Gln Ile Thr Trp Asp Asn
1               5                   10                  15

Pro Lys

<210> SEQ ID NO 1120
<211> LENGTH: 19
<212> TYPE: PRT
<213> ORGANISM: H. sapiens

<400> SEQUENCE: 1120

Asn Tyr Ile Ser Glu Ile Gln Asp Ser Pro Gln Gln Leu Leu Gln Ala
1               5                   10                  15

Phe Leu Lys
```

```
<210> SEQ ID NO 1121
<211> LENGTH: 9
<212> TYPE: PRT
<213> ORGANISM: H. sapiens

<400> SEQUENCE: 1121

Gln Val Phe Ala Pro Met Leu Leu Lys
 1               5

<210> SEQ ID NO 1122
<211> LENGTH: 10
<212> TYPE: PRT
<213> ORGANISM: H. sapiens

<400> SEQUENCE: 1122

Ser Ile Thr Ala Gly Ser Lys Phe Asp Arg
 1               5                  10

<210> SEQ ID NO 1123
<211> LENGTH: 6
<212> TYPE: PRT
<213> ORGANISM: H. sapiens

<400> SEQUENCE: 1123

Val Asp Glu Asp Phe Arg
 1               5

<210> SEQ ID NO 1124
<211> LENGTH: 10
<212> TYPE: PRT
<213> ORGANISM: H. sapiens

<400> SEQUENCE: 1124

Val Glu Glu His Ser Val Met Thr Val Lys
 1               5                  10

<210> SEQ ID NO 1125
<211> LENGTH: 14
<212> TYPE: PRT
<213> ORGANISM: H. sapiens

<400> SEQUENCE: 1125

Val Leu Ser Phe Pro Gly Gly Ser Leu Leu Leu Ala Gly Arg
 1               5                  10

<210> SEQ ID NO 1126
<211> LENGTH: 11
<212> TYPE: PRT
<213> ORGANISM: H. sapiens

<400> SEQUENCE: 1126

Val Val Val Leu Met Asn Ile Asp Leu Leu Arg
 1               5                  10

<210> SEQ ID NO 1127
<211> LENGTH: 12
<212> TYPE: PRT
<213> ORGANISM: H. sapiens

<400> SEQUENCE: 1127

Trp Glu Gly Pro Glu Asp Pro Leu Gln Tyr Leu Arg
 1               5                  10

<210> SEQ ID NO 1128
<211> LENGTH: 17
```

-continued

<212> TYPE: PRT
<213> ORGANISM: H. sapiens

<400> SEQUENCE: 1128

Tyr Val Arg Gly Glu His Leu Ser Pro Asp His Trp Leu Asp Leu Phe
1               5                   10                  15

Arg

<210> SEQ ID NO 1129
<211> LENGTH: 19
<212> TYPE: PRT
<213> ORGANISM: H. sapiens

<400> SEQUENCE: 1129

Ala Ile Gln Asp Gly Thr Ile Val Leu Met Gly Thr Tyr Asp Asp Gly
1               5                   10                  15

Ala Thr Lys

<210> SEQ ID NO 1130
<211> LENGTH: 9
<212> TYPE: PRT
<213> ORGANISM: H. sapiens

<400> SEQUENCE: 1130

Asp Asn Trp Val Phe Cys Gly Gly Lys
1               5

<210> SEQ ID NO 1131
<211> LENGTH: 5
<212> TYPE: PRT
<213> ORGANISM: H. sapiens

<400> SEQUENCE: 1131

His Phe Ala Phe Lys
1               5

<210> SEQ ID NO 1132
<211> LENGTH: 13
<212> TYPE: PRT
<213> ORGANISM: H. sapiens

<400> SEQUENCE: 1132

Ile Cys Leu Glu Asp Asn Val Leu Met Ser Gly Val Lys
1               5                   10

<210> SEQ ID NO 1133
<211> LENGTH: 16
<212> TYPE: PRT
<213> ORGANISM: H. sapiens

<400> SEQUENCE: 1133

Leu Ile Ala Asp Leu Gly Ser Thr Ser Ile Thr Asn Leu Gly Phe Arg
1               5                   10                  15

<210> SEQ ID NO 1134
<211> LENGTH: 12
<212> TYPE: PRT
<213> ORGANISM: H. sapiens

<400> SEQUENCE: 1134

Met Ala Ser Gly Ala Ala Asn Val Val Gly Pro Lys
1               5                   10

```
<210> SEQ ID NO 1135
<211> LENGTH: 11
<212> TYPE: PRT
<213> ORGANISM: H. sapiens

<400> SEQUENCE: 1135

Met Asp Ala Ser Leu Gly Asn Leu Phe Ala Arg
1               5                   10

<210> SEQ ID NO 1136
<211> LENGTH: 8
<212> TYPE: PRT
<213> ORGANISM: H. sapiens

<400> SEQUENCE: 1136

Ser Ala Leu Asp Thr Ala Ala Arg
1               5

<210> SEQ ID NO 1137
<211> LENGTH: 8
<212> TYPE: PRT
<213> ORGANISM: H. sapiens

<400> SEQUENCE: 1137

Ser Pro Phe Glu Gln His Ile Lys
1               5

<210> SEQ ID NO 1138
<211> LENGTH: 8
<212> TYPE: PRT
<213> ORGANISM: H. sapiens

<400> SEQUENCE: 1138

Thr Gly Glu Val Leu Asp Thr Lys
1               5

<210> SEQ ID NO 1139
<211> LENGTH: 12
<212> TYPE: PRT
<213> ORGANISM: H. sapiens

<400> SEQUENCE: 1139

Glu Arg Pro Trp Gly Ala Ala Asp Gly Leu Ser Arg
1               5                   10

<210> SEQ ID NO 1140
<211> LENGTH: 9
<212> TYPE: PRT
<213> ORGANISM: H. sapiens

<400> SEQUENCE: 1140

Ile Tyr Ser Phe Gly Leu Gly Gly Arg
1               5

<210> SEQ ID NO 1141
<211> LENGTH: 13
<212> TYPE: PRT
<213> ORGANISM: H. sapiens

<400> SEQUENCE: 1141

Leu Asp Ala Pro Pro Pro Ala Ala Pro Leu Pro Arg
1               5                   10

<210> SEQ ID NO 1142
<211> LENGTH: 11
```

```
<212> TYPE: PRT
<213> ORGANISM: H. sapiens

<400> SEQUENCE: 1142

Leu Arg Lys Ser Ser Val Cys Gln Asn Gly Arg
1               5                   10

<210> SEQ ID NO 1143
<211> LENGTH: 9
<212> TYPE: PRT
<213> ORGANISM: H. sapiens

<400> SEQUENCE: 1143

Cys Phe Leu Ala Phe Thr Gln Thr Lys
1               5

<210> SEQ ID NO 1144
<211> LENGTH: 12
<212> TYPE: PRT
<213> ORGANISM: H. sapiens

<400> SEQUENCE: 1144

Asp Gln Leu Pro Tyr Ile Cys Gln Phe Gly Ile Val
1               5                   10

<210> SEQ ID NO 1145
<211> LENGTH: 11
<212> TYPE: PRT
<213> ORGANISM: H. sapiens

<400> SEQUENCE: 1145

Glu Gln Gln Ala Leu Gln Thr Val Cys Leu Lys
1               5                   10

<210> SEQ ID NO 1146
<211> LENGTH: 21
<212> TYPE: PRT
<213> ORGANISM: H. sapiens

<400> SEQUENCE: 1146

Gly Gly Thr Leu Ser Thr Pro Gln Thr Gly Ser Glu Asn Asp Ala Leu
1               5                   10                  15

Tyr Glu Tyr Leu Arg
            20

<210> SEQ ID NO 1147
<211> LENGTH: 6
<212> TYPE: PRT
<213> ORGANISM: H. sapiens

<400> SEQUENCE: 1147

Lys Ile Val Asn Ala Lys
1               5

<210> SEQ ID NO 1148
<211> LENGTH: 12
<212> TYPE: PRT
<213> ORGANISM: H. sapiens

<400> SEQUENCE: 1148

Leu Asp Thr Leu Ala Gln Glu Val Ala Leu Leu Lys
1               5                   10

<210> SEQ ID NO 1149
```

```
<211> LENGTH: 6
<212> TYPE: PRT
<213> ORGANISM: H. sapiens

<400> SEQUENCE: 1149

Met Phe Glu Glu Leu Lys
 1               5

<210> SEQ ID NO 1150
<211> LENGTH: 14
<212> TYPE: PRT
<213> ORGANISM: H. sapiens

<400> SEQUENCE: 1150

Asn Trp Glu Thr Glu Ile Thr Ala Gln Pro Asp Gly Gly Lys
 1               5                  10

<210> SEQ ID NO 1151
<211> LENGTH: 12
<212> TYPE: PRT
<213> ORGANISM: H. sapiens

<400> SEQUENCE: 1151

Thr Phe His Glu Ala Ser Glu Asp Cys Ile Ser Arg
 1               5                  10

<210> SEQ ID NO 1152
<211> LENGTH: 4
<212> TYPE: PRT
<213> ORGANISM: H. sapiens

<400> SEQUENCE: 1152

Trp Phe Asp Lys
 1

<210> SEQ ID NO 1153
<211> LENGTH: 13
<212> TYPE: PRT
<213> ORGANISM: H. sapiens

<400> SEQUENCE: 1153

Ala Ala Asp Asp Thr Trp Glu Pro Phe Ala Ser Gly Lys
 1               5                  10

<210> SEQ ID NO 1154
<211> LENGTH: 23
<212> TYPE: PRT
<213> ORGANISM: H. sapiens

<400> SEQUENCE: 1154

Ala Leu Gly Ile Ser Pro Phe His Glu His Ala Glu Val Val Phe Thr
 1               5                  10                  15

Ala Asn Asp Ser Gly Pro Arg
                20

<210> SEQ ID NO 1155
<211> LENGTH: 6
<212> TYPE: PRT
<213> ORGANISM: H. sapiens

<400> SEQUENCE: 1155

Cys Pro Leu Met Val Lys
 1               5
```

```
<210> SEQ ID NO 1156
<211> LENGTH: 5
<212> TYPE: PRT
<213> ORGANISM: H. sapiens

<400> SEQUENCE: 1156

Asp Ser Gly Pro Arg
 1               5

<210> SEQ ID NO 1157
<211> LENGTH: 13
<212> TYPE: PRT
<213> ORGANISM: H. sapiens

<400> SEQUENCE: 1157

Gly Ser Pro Ala Ile Asn Val Ala Val His Val Phe Arg
 1               5                  10

<210> SEQ ID NO 1158
<211> LENGTH: 14
<212> TYPE: PRT
<213> ORGANISM: H. sapiens

<400> SEQUENCE: 1158

Gly Ser Pro Ala Ile Asn Val Ala Val His Val Phe Arg Lys
 1               5                  10

<210> SEQ ID NO 1159
<211> LENGTH: 14
<212> TYPE: PRT
<213> ORGANISM: H. sapiens

<400> SEQUENCE: 1159

Lys Ala Ala Asp Asp Thr Trp Glu Pro Phe Ala Ser Gly Lys
 1               5                  10

<210> SEQ ID NO 1160
<211> LENGTH: 23
<212> TYPE: PRT
<213> ORGANISM: H. sapiens

<400> SEQUENCE: 1160

Arg Tyr Thr Ile Ala Ala Leu Leu Ser Pro Tyr Ser Tyr Ser Thr Thr
 1               5                  10                  15

Ala Val Val Thr Asn Pro Lys
                20

<210> SEQ ID NO 1161
<211> LENGTH: 4
<212> TYPE: PRT
<213> ORGANISM: H. sapiens

<400> SEQUENCE: 1161

Ser Tyr Trp Lys
 1

<210> SEQ ID NO 1162
<211> LENGTH: 22
<212> TYPE: PRT
<213> ORGANISM: H. sapiens

<400> SEQUENCE: 1162

Thr Ser Glu Ser Gly Glu Leu His Gly Leu Thr Thr Glu Glu Glu Phe
 1               5                  10                  15
```

-continued

```
Val Glu Gly Ile Tyr Lys
            20

<210> SEQ ID NO 1163
<211> LENGTH: 6
<212> TYPE: PRT
<213> ORGANISM: H. sapiens

<400> SEQUENCE: 1163

Val Glu Ile Asp Thr Lys
1               5

<210> SEQ ID NO 1164
<211> LENGTH: 6
<212> TYPE: PRT
<213> ORGANISM: H. sapiens

<400> SEQUENCE: 1164

Val Leu Asp Ala Val Arg
1               5

<210> SEQ ID NO 1165
<211> LENGTH: 22
<212> TYPE: PRT
<213> ORGANISM: H. sapiens

<400> SEQUENCE: 1165

Tyr Thr Ile Ala Ala Leu Leu Ser Pro Tyr Ser Tyr Ser Thr Thr Ala
1               5                   10                  15

Val Val Thr Asn Pro Lys
            20

<210> SEQ ID NO 1166
<211> LENGTH: 23
<212> TYPE: PRT
<213> ORGANISM: H. sapiens

<400> SEQUENCE: 1166

Tyr Thr Ile Ala Ala Leu Leu Ser Pro Tyr Ser Tyr Ser Thr Thr Ala
1               5                   10                  15

Val Val Thr Asn Pro Lys Glu
            20

<210> SEQ ID NO 1167
<211> LENGTH: 12
<212> TYPE: PRT
<213> ORGANISM: H. sapiens

<400> SEQUENCE: 1167

Asp Gln Ser Glu Pro Leu Gly Arg Val Leu Ser Arg
1               5                   10

<210> SEQ ID NO 1168
<211> LENGTH: 17
<212> TYPE: PRT
<213> ORGANISM: H. sapiens

<400> SEQUENCE: 1168

Glu Leu Thr Gly Tyr Asn Ala Asp Val Ile Cys Leu Gln Glu Val Asp
1               5                   10                  15

Arg

<210> SEQ ID NO 1169
```

```
<211> LENGTH: 9
<212> TYPE: PRT
<213> ORGANISM: H. sapiens

<400> SEQUENCE: 1169

Leu Pro Gly Ala Arg Ala Ala Leu Arg
 1               5

<210> SEQ ID NO 1170
<211> LENGTH: 6
<212> TYPE: PRT
<213> ORGANISM: H. sapiens

<400> SEQUENCE: 1170

Gln Asn Leu Ile Gln Lys
 1               5

<210> SEQ ID NO 1171
<211> LENGTH: 8
<212> TYPE: PRT
<213> ORGANISM: H. sapiens

<400> SEQUENCE: 1171

Val Ile Arg Thr Ala Val Glu Lys
 1               5

<210> SEQ ID NO 1172
<211> LENGTH: 14
<212> TYPE: PRT
<213> ORGANISM: H. sapiens

<400> SEQUENCE: 1172

Ala Ala Met Val Gly Met Leu Ala Asn Phe Leu Gly Phe Arg
 1               5                  10

<210> SEQ ID NO 1173
<211> LENGTH: 12
<212> TYPE: PRT
<213> ORGANISM: H. sapiens

<400> SEQUENCE: 1173

Ala Leu Gln Asp Gln Leu Val Leu Val Ala Ala Lys
 1               5                  10

<210> SEQ ID NO 1174
<211> LENGTH: 12
<212> TYPE: PRT
<213> ORGANISM: H. sapiens

<400> SEQUENCE: 1174

Asp Pro Thr Phe Ile Pro Ala Pro Ile Gln Ala Lys
 1               5                  10

<210> SEQ ID NO 1175
<211> LENGTH: 9
<212> TYPE: PRT
<213> ORGANISM: H. sapiens

<400> SEQUENCE: 1175

Phe Met Gln Ala Val Thr Gly Trp Lys
 1               5

<210> SEQ ID NO 1176
<211> LENGTH: 8
<212> TYPE: PRT
```

-continued

```
<213> ORGANISM: H. sapiens

<400> SEQUENCE: 1176

Leu Asp Thr Glu Asp Lys Leu Arg
  1               5

<210> SEQ ID NO 1177
<211> LENGTH: 17
<212> TYPE: PRT
<213> ORGANISM: H. sapiens

<400> SEQUENCE: 1177

Gln Pro Phe Val Gln Gly Leu Ala Leu Tyr Thr Pro Val Val Leu Pro
  1               5                  10                  15

Arg

<210> SEQ ID NO 1178
<211> LENGTH: 13
<212> TYPE: PRT
<213> ORGANISM: H. sapiens

<400> SEQUENCE: 1178

Ser Leu Asp Phe Thr Glu Leu Asp Val Ala Ala Glu Lys
  1               5                  10

<210> SEQ ID NO 1179
<211> LENGTH: 7
<212> TYPE: PRT
<213> ORGANISM: H. sapiens

<400> SEQUENCE: 1179

Thr Ser Pro Val Asp Glu Lys
  1               5

<210> SEQ ID NO 1180
<211> LENGTH: 8
<212> TYPE: PRT
<213> ORGANISM: H. sapiens

<400> SEQUENCE: 1180

Val Ala Asn Pro Leu Ser Thr Ala
  1               5

<210> SEQ ID NO 1181
<211> LENGTH: 17
<212> TYPE: PRT
<213> ORGANISM: H. sapiens

<400> SEQUENCE: 1181

Val Leu Ser Ala Leu Gln Ala Val Gln Gly Leu Leu Val Ala Gln Gly
  1               5                  10                  15

Arg

<210> SEQ ID NO 1182
<211> LENGTH: 9
<212> TYPE: PRT
<213> ORGANISM: H. sapiens

<400> SEQUENCE: 1182

Glu Phe Gly Asn Thr Leu Glu Asp Lys
  1               5

<210> SEQ ID NO 1183
```

```
<211> LENGTH: 9
<212> TYPE: PRT
<213> ORGANISM: H. sapiens

<400> SEQUENCE: 1183

Glu Trp Phe Ser Glu Thr Phe Gln Lys
1               5

<210> SEQ ID NO 1184
<211> LENGTH: 11
<212> TYPE: PRT
<213> ORGANISM: H. sapiens

<400> SEQUENCE: 1184

Leu Lys Glu Phe Gly Asn Thr Leu Glu Asp Lys
1               5                   10

<210> SEQ ID NO 1185
<211> LENGTH: 7
<212> TYPE: PRT
<213> ORGANISM: H. sapiens

<400> SEQUENCE: 1185

Gln Ser Glu Leu Ser Ala Lys
1               5

<210> SEQ ID NO 1186
<211> LENGTH: 11
<212> TYPE: PRT
<213> ORGANISM: H. sapiens

<400> SEQUENCE: 1186

Ala Ser Glu Phe Leu Gly Tyr Trp Glu Pro Arg
1               5                   10

<210> SEQ ID NO 1187
<211> LENGTH: 12
<212> TYPE: PRT
<213> ORGANISM: H. sapiens

<400> SEQUENCE: 1187

Glu Phe Asn Pro Leu Val Ile Val Gly Leu Ser Lys
1               5                   10

<210> SEQ ID NO 1188
<211> LENGTH: 18
<212> TYPE: PRT
<213> ORGANISM: H. sapiens

<400> SEQUENCE: 1188

Ala Ala Val Pro Ser Gly Ala Ser Thr Gly Ile Tyr Glu Ala Leu Glu
1               5                   10                  15

Leu Arg

<210> SEQ ID NO 1189
<211> LENGTH: 13
<212> TYPE: PRT
<213> ORGANISM: H. sapiens

<400> SEQUENCE: 1189

Gly Asn Pro Thr Val Glu Val Asp Leu Tyr Thr Ala Lys
1               5                   10

<210> SEQ ID NO 1190
```

```
<211> LENGTH: 16
<212> TYPE: PRT
<213> ORGANISM: H. sapiens

<400> SEQUENCE: 1190

Tyr Ile Thr Gly Asp Gln Leu Gly Ala Leu Tyr Gln Asp Phe Val Arg
1               5                   10                  15

<210> SEQ ID NO 1191
<211> LENGTH: 18
<212> TYPE: PRT
<213> ORGANISM: H. sapiens

<400> SEQUENCE: 1191

Ala Ala Val Pro Ser Gly Ala Ser Thr Gly Ile Tyr Glu Ala Leu Glu
1               5                   10                  15

Leu Arg

<210> SEQ ID NO 1192
<211> LENGTH: 13
<212> TYPE: PRT
<213> ORGANISM: H. sapiens

<400> SEQUENCE: 1192

Gly Asn Pro Thr Val Glu Val Asp Leu Phe Thr Ser Lys
1               5                   10

<210> SEQ ID NO 1193
<211> LENGTH: 14
<212> TYPE: PRT
<213> ORGANISM: H. sapiens

<400> SEQUENCE: 1193

Val Val Ile Gly Met Asp Val Ala Ala Ser Glu Phe Phe Arg
1               5                   10

<210> SEQ ID NO 1194
<211> LENGTH: 6
<212> TYPE: PRT
<213> ORGANISM: H. sapiens

<400> SEQUENCE: 1194

Ala Trp Val Ala Trp Arg
1               5

<210> SEQ ID NO 1195
<211> LENGTH: 12
<212> TYPE: PRT
<213> ORGANISM: H. sapiens

<400> SEQUENCE: 1195

Gly Ile Ser Leu Ala Asn Trp Met Cys Leu Ala Lys
1               5                   10

<210> SEQ ID NO 1196
<211> LENGTH: 12
<212> TYPE: PRT
<213> ORGANISM: H. sapiens

<400> SEQUENCE: 1196

Ser Thr Asp Tyr Gly Ile Phe Gln Ile Asn Ser Arg
1               5                   10

<210> SEQ ID NO 1197
```

-continued

```
<211> LENGTH: 8
<212> TYPE: PRT
<213> ORGANISM: H. sapiens

<400> SEQUENCE: 1197

Glu Ala Glu Asn Gln His Asn Lys
1               5

<210> SEQ ID NO 1198
<211> LENGTH: 22
<212> TYPE: PRT
<213> ORGANISM: H. sapiens

<400> SEQUENCE: 1198

Glu Met Leu Asp Gln Ser Asn Gln Trp Gly Gly Thr Ala Leu Val Val
1               5                   10                  15

Pro Ala Phe Glu Ile Arg
            20

<210> SEQ ID NO 1199
<211> LENGTH: 9
<212> TYPE: PRT
<213> ORGANISM: H. sapiens

<400> SEQUENCE: 1199

Glu Pro Gly Glu Phe Ala Leu Leu Arg
1               5

<210> SEQ ID NO 1200
<211> LENGTH: 6
<212> TYPE: PRT
<213> ORGANISM: H. sapiens

<400> SEQUENCE: 1200

Gln Tyr Gly Phe Asn Arg
1               5

<210> SEQ ID NO 1201
<211> LENGTH: 8
<212> TYPE: PRT
<213> ORGANISM: H. sapiens

<400> SEQUENCE: 1201

Ser Cys Gln Glu Val Phe Asp Lys
1               5

<210> SEQ ID NO 1202
<211> LENGTH: 6
<212> TYPE: PRT
<213> ORGANISM: H. sapiens

<400> SEQUENCE: 1202

Ser Val Asp Gln Val Lys
1               5

<210> SEQ ID NO 1203
<211> LENGTH: 16
<212> TYPE: PRT
<213> ORGANISM: H. sapiens

<400> SEQUENCE: 1203

Thr Ala Leu Ala Ser Gly Gly Val Leu Asp Ala Ser Gly Asp Tyr Arg
1               5                   10                  15
```

```
<210> SEQ ID NO 1204
<211> LENGTH: 19
<212> TYPE: PRT
<213> ORGANISM: H. sapiens

<400> SEQUENCE: 1204

Thr Ala Leu Ala Ser Gly Gly Val Leu Asp Ala Ser Gly Asp Tyr Arg
1               5                   10                  15

Val Tyr Arg

<210> SEQ ID NO 1205
<211> LENGTH: 7
<212> TYPE: PRT
<213> ORGANISM: H. sapiens

<400> SEQUENCE: 1205

Val Pro Thr Phe Asp Glu Arg
1               5

<210> SEQ ID NO 1206
<211> LENGTH: 14
<212> TYPE: PRT
<213> ORGANISM: H. sapiens

<400> SEQUENCE: 1206

Trp Glu Gly Pro Leu Ser Val Ser Val Phe Ala Ala Thr Lys
1               5                   10

<210> SEQ ID NO 1207
<211> LENGTH: 9
<212> TYPE: PRT
<213> ORGANISM: H. sapiens

<400> SEQUENCE: 1207

Tyr Glu Ala Ala Val Pro Asp Pro Arg
1               5

<210> SEQ ID NO 1208
<211> LENGTH: 6
<212> TYPE: PRT
<213> ORGANISM: H. sapiens

<400> SEQUENCE: 1208

Tyr Pro Asn Ser Pro Arg
1               5

<210> SEQ ID NO 1209
<211> LENGTH: 11
<212> TYPE: PRT
<213> ORGANISM: H. sapiens

<400> SEQUENCE: 1209

Asp Ser Asp Ile Ile Glu Asp Val Met Val Lys
1               5                   10

<210> SEQ ID NO 1210
<211> LENGTH: 10
<212> TYPE: PRT
<213> ORGANISM: H. sapiens

<400> SEQUENCE: 1210

Ile Cys Gln Arg Ala Glu Gly Ala Glu Arg
1               5                   10
```

<210> SEQ ID NO 1211
<211> LENGTH: 13
<212> TYPE: PRT
<213> ORGANISM: H. sapiens

<400> SEQUENCE: 1211

Ile Leu Glu Val Val Asn Gln Ile Gln Asp Glu Glu Arg
1               5                   10

<210> SEQ ID NO 1212
<211> LENGTH: 11
<212> TYPE: PRT
<213> ORGANISM: H. sapiens

<400> SEQUENCE: 1212

Trp Tyr Val Asn Leu His Ser Leu Met Asp Arg
1               5                   10

<210> SEQ ID NO 1213
<211> LENGTH: 12
<212> TYPE: PRT
<213> ORGANISM: H. sapiens

<400> SEQUENCE: 1213

Asp Val Glu Met Glu Pro Val Gln Gln Ala Glu Lys
1               5                   10

<210> SEQ ID NO 1214
<211> LENGTH: 7
<212> TYPE: PRT
<213> ORGANISM: H. sapiens

<400> SEQUENCE: 1214

Gly Asn Glu Gly Gln Met Arg
1               5

<210> SEQ ID NO 1215
<211> LENGTH: 14
<212> TYPE: PRT
<213> ORGANISM: H. sapiens

<400> SEQUENCE: 1215

Ile Asn Glu Tyr Gln Arg Lys Ala Glu Gln Glu Asn Glu Lys
1               5                   10

<210> SEQ ID NO 1216
<211> LENGTH: 8
<212> TYPE: PRT
<213> ORGANISM: H. sapiens

<400> SEQUENCE: 1216

Lys Ala Asn Thr Gln Asp Leu Arg
1               5

<210> SEQ ID NO 1217
<211> LENGTH: 6
<212> TYPE: PRT
<213> ORGANISM: H. sapiens

<400> SEQUENCE: 1217

Leu Ser Gln Leu Gln Lys
1               5

<210> SEQ ID NO 1218
<211> LENGTH: 10

<212> TYPE: PRT
<213> ORGANISM: H. sapiens

<400> SEQUENCE: 1218

Asn Asp Gln Trp Ala Trp Glu Thr Leu Arg
1               5                   10

<210> SEQ ID NO 1219
<211> LENGTH: 9
<212> TYPE: PRT
<213> ORGANISM: H. sapiens

<400> SEQUENCE: 1219

Asn Ile Asn Thr Glu Arg Thr Leu Lys
1               5

<210> SEQ ID NO 1220
<211> LENGTH: 10
<212> TYPE: PRT
<213> ORGANISM: H. sapiens

<400> SEQUENCE: 1220

Gln Leu Glu Glu Ala Asn Asp Leu Leu Arg
1               5                   10

<210> SEQ ID NO 1221
<211> LENGTH: 10
<212> TYPE: PRT
<213> ORGANISM: H. sapiens

<400> SEQUENCE: 1221

Ser Gln Gly Gly Asp Gly Tyr Tyr Gly Arg
1               5                   10

<210> SEQ ID NO 1222
<211> LENGTH: 8
<212> TYPE: PRT
<213> ORGANISM: H. sapiens

<400> SEQUENCE: 1222

Val Val Lys Asn Thr Ser Gly Lys
1               5

<210> SEQ ID NO 1223
<211> LENGTH: 5
<212> TYPE: PRT
<213> ORGANISM: H. sapiens

<400> SEQUENCE: 1223

Glu Leu Leu Gln Arg
1               5

<210> SEQ ID NO 1224
<211> LENGTH: 9
<212> TYPE: PRT
<213> ORGANISM: H. sapiens

<400> SEQUENCE: 1224

Phe Glu Cys Gly Ser Val Gly Leu Lys
1               5

<210> SEQ ID NO 1225
<211> LENGTH: 7
<212> TYPE: PRT
<213> ORGANISM: H. sapiens

<400> SEQUENCE: 1225

Gly Glu Met Gly Leu Gln Arg
1               5

<210> SEQ ID NO 1226
<211> LENGTH: 12
<212> TYPE: PRT
<213> ORGANISM: H. sapiens

<400> SEQUENCE: 1226

Ile Arg Asp Leu Ile Ala Ile Glu Arg Ser Ser Arg
1               5                   10

<210> SEQ ID NO 1227
<211> LENGTH: 14
<212> TYPE: PRT
<213> ORGANISM: H. sapiens

<400> SEQUENCE: 1227

Lys Val Glu Thr Asp Trp His Met Val Tyr Leu Ala Arg Lys
1               5                   10

<210> SEQ ID NO 1228
<211> LENGTH: 9
<212> TYPE: PRT
<213> ORGANISM: H. sapiens

<400> SEQUENCE: 1228

Gln Leu Phe Leu Ser Glu Asn Arg Arg
1               5

<210> SEQ ID NO 1229
<211> LENGTH: 15
<212> TYPE: PRT
<213> ORGANISM: H. sapiens

<400> SEQUENCE: 1229

Tyr Val Trp Asp Tyr Thr Glu Leu Gln Arg Thr Leu Ser Leu Lys
1               5                   10                  15

<210> SEQ ID NO 1230
<211> LENGTH: 9
<212> TYPE: PRT
<213> ORGANISM: H. sapiens

<400> SEQUENCE: 1230

Asp Glu Gln Tyr Leu Phe Leu Val Arg
1               5

<210> SEQ ID NO 1231
<211> LENGTH: 10
<212> TYPE: PRT
<213> ORGANISM: H. sapiens

<400> SEQUENCE: 1231

Gly Phe Leu Val Val Gln Gly Asp Pro Arg
1               5                   10

<210> SEQ ID NO 1232
<211> LENGTH: 18
<212> TYPE: PRT
<213> ORGANISM: H. sapiens

<400> SEQUENCE: 1232

```
Ile Ile Thr Glu Asn Asp His Val Leu Leu Phe Trp Lys Ser Leu Ala
1               5                   10                  15

Leu Lys

<210> SEQ ID NO 1233
<211> LENGTH: 8
<212> TYPE: PRT
<213> ORGANISM: H. sapiens

<400> SEQUENCE: 1233

Leu Asn Phe Gly Leu Gly Asn Arg
1               5

<210> SEQ ID NO 1234
<211> LENGTH: 16
<212> TYPE: PRT
<213> ORGANISM: H. sapiens

<400> SEQUENCE: 1234

Thr Asp Leu Gly Asp Ser Pro Leu Ala Phe Glu His Val Met Thr Arg
1               5                   10                  15

<210> SEQ ID NO 1235
<211> LENGTH: 18
<212> TYPE: PRT
<213> ORGANISM: H. sapiens

<400> SEQUENCE: 1235

Thr Pro Glu Gly Leu Pro Asp Ala Pro Arg Asn Leu Gln Leu Ser Leu
1               5                   10                  15

Pro Arg

<210> SEQ ID NO 1236
<211> LENGTH: 19
<212> TYPE: PRT
<213> ORGANISM: H. sapiens

<400> SEQUENCE: 1236

Asp Phe Ser Glu Asp Gln Gly Tyr Pro Asp Pro Asn Pro Cys Pro
1               5                   10                  15

Val Gly Lys

<210> SEQ ID NO 1237
<211> LENGTH: 20
<212> TYPE: PRT
<213> ORGANISM: H. sapiens

<400> SEQUENCE: 1237

Glu Phe Gln Leu His Gln His Leu Phe Asp Pro Glu His Asp Tyr Pro
1               5                   10                  15

Gly Leu Gly Lys
            20

<210> SEQ ID NO 1238
<211> LENGTH: 7
<212> TYPE: PRT
<213> ORGANISM: H. sapiens

<400> SEQUENCE: 1238

Leu Asp Asn Val Val Ala Lys
1               5
```

-continued

<210> SEQ ID NO 1239
<211> LENGTH: 15
<212> TYPE: PRT
<213> ORGANISM: H. sapiens

<400> SEQUENCE: 1239

Leu Leu His Gly Val Met Glu Gln Leu Gly Ile Ala Arg Pro Arg
1               5                   10                  15

<210> SEQ ID NO 1240
<211> LENGTH: 5
<212> TYPE: PRT
<213> ORGANISM: H. sapiens

<400> SEQUENCE: 1240

Leu Leu Tyr Glu Lys
1               5

<210> SEQ ID NO 1241
<211> LENGTH: 10
<212> TYPE: PRT
<213> ORGANISM: H. sapiens

<400> SEQUENCE: 1241

Ser Val Asn Pro Tyr Leu Gln Gly Gln Arg
1               5                   10

<210> SEQ ID NO 1242
<211> LENGTH: 13
<212> TYPE: PRT
<213> ORGANISM: H. sapiens

<400> SEQUENCE: 1242

Ser Val Pro His Phe Ser Asp Glu Asp Lys Asp Pro Glu
1               5                   10

<210> SEQ ID NO 1243
<211> LENGTH: 18
<212> TYPE: PRT
<213> ORGANISM: H. sapiens

<400> SEQUENCE: 1243

Thr Ala Asp Asp Gly Cys Leu Glu Asn Thr Pro Asp Thr Ala Glu Phe
1               5                   10                  15

Ser Arg

<210> SEQ ID NO 1244
<211> LENGTH: 8
<212> TYPE: PRT
<213> ORGANISM: H. sapiens

<400> SEQUENCE: 1244

Val Ser Glu Ala Asp Ile Gln Arg
1               5

<210> SEQ ID NO 1245
<211> LENGTH: 6
<212> TYPE: PRT
<213> ORGANISM: H. sapiens

<400> SEQUENCE: 1245

Gly Trp Glu Cys Thr Lys
1               5

```
<210> SEQ ID NO 1246
<211> LENGTH: 10
<212> TYPE: PRT
<213> ORGANISM: H. sapiens

<400> SEQUENCE: 1246

Ile Val Gly Gln Leu Met Asp Gly Leu Lys
1               5                   10

<210> SEQ ID NO 1247
<211> LENGTH: 19
<212> TYPE: PRT
<213> ORGANISM: H. sapiens

<400> SEQUENCE: 1247

Gln Met Ser Tyr Gly Phe Leu Phe Pro Pro Tyr Leu Ser Ser Ser Pro
1               5                   10                  15

Glu Ala Lys

<210> SEQ ID NO 1248
<211> LENGTH: 11
<212> TYPE: PRT
<213> ORGANISM: H. sapiens

<400> SEQUENCE: 1248

Arg Ile Glu Asp Ile His Leu Leu Val Glu Arg
1               5                   10

<210> SEQ ID NO 1249
<211> LENGTH: 23
<212> TYPE: PRT
<213> ORGANISM: H. sapiens

<400> SEQUENCE: 1249

Thr Glu Phe Leu Ser Asn Tyr Leu Thr Asn Val Asp Asp Ile Thr Leu
1               5                   10                  15

Val Pro Gly Thr Leu Gly Arg
            20

<210> SEQ ID NO 1250
<211> LENGTH: 7
<212> TYPE: PRT
<213> ORGANISM: H. sapiens

<400> SEQUENCE: 1250

Val Trp Asn Tyr Phe Gln Arg
1               5

<210> SEQ ID NO 1251
<211> LENGTH: 7
<212> TYPE: PRT
<213> ORGANISM: H. sapiens

<400> SEQUENCE: 1251

Trp Val Glu Glu Leu Met Lys
1               5

<210> SEQ ID NO 1252
<211> LENGTH: 13
<212> TYPE: PRT
<213> ORGANISM: H. sapiens

<400> SEQUENCE: 1252
```

```
Trp Trp Gly Gly Gln Pro Leu Trp Ile Thr Ala Thr Lys
 1               5                  10
```

<210> SEQ ID NO 1253
<211> LENGTH: 17
<212> TYPE: PRT
<213> ORGANISM: H. sapiens

<400> SEQUENCE: 1253

```
Cys Tyr Ile Leu Glu Asn Asp Thr Val Gln Cys Asp Leu Asp Leu Tyr
 1               5                  10                  15

Lys
```

<210> SEQ ID NO 1254
<211> LENGTH: 9
<212> TYPE: PRT
<213> ORGANISM: H. sapiens

<400> SEQUENCE: 1254

```
Ser Val Ala Ile Glu Val Asp Gly Arg
 1               5
```

<210> SEQ ID NO 1255
<211> LENGTH: 18
<212> TYPE: PRT
<213> ORGANISM: H. sapiens

<400> SEQUENCE: 1255

```
Thr Phe Ala Val Tyr Leu Asn Ser Thr Gly Tyr Arg Thr Ala Phe Phe
 1               5                  10                  15

Gly Lys
```

<210> SEQ ID NO 1256
<211> LENGTH: 11
<212> TYPE: PRT
<213> ORGANISM: H. sapiens

<400> SEQUENCE: 1256

```
Val Asp Ala Gln Glu Glu Asn Phe Leu Pro Lys
 1               5                  10
```

<210> SEQ ID NO 1257
<211> LENGTH: 13
<212> TYPE: PRT
<213> ORGANISM: H. sapiens

<400> SEQUENCE: 1257

```
Val Tyr His Val Gly Leu Gly Asp Ala Ala Gln Pro Arg
 1               5                  10
```

<210> SEQ ID NO 1258
<211> LENGTH: 6
<212> TYPE: PRT
<213> ORGANISM: H. sapiens

<400> SEQUENCE: 1258

```
Ala Val Cys Val Leu Lys
 1               5
```

<210> SEQ ID NO 1259
<211> LENGTH: 14
<212> TYPE: PRT
<213> ORGANISM: H. sapiens

```
<400> SEQUENCE: 1259

Gly Asp Gly Pro Val Gln Gly Ile Ile Asn Phe Glu Gln Lys
1               5                   10

<210> SEQ ID NO 1260
<211> LENGTH: 8
<212> TYPE: PRT
<213> ORGANISM: H. sapiens

<400> SEQUENCE: 1260

Gly Gly Asn Glu Glu Ser Thr Lys
1               5

<210> SEQ ID NO 1261
<211> LENGTH: 10
<212> TYPE: PRT
<213> ORGANISM: H. sapiens

<400> SEQUENCE: 1261

Leu Ala Cys Gly Val Ile Gly Ile Ala Gln
1               5                   10

<210> SEQ ID NO 1262
<211> LENGTH: 6
<212> TYPE: PRT
<213> ORGANISM: H. sapiens

<400> SEQUENCE: 1262

Val Trp Gly Ser Ile Lys
1               5

<210> SEQ ID NO 1263
<211> LENGTH: 6
<212> TYPE: PRT
<213> ORGANISM: H. sapiens

<400> SEQUENCE: 1263

Phe Lys Ala Ile Glu Lys
1               5

<210> SEQ ID NO 1264
<211> LENGTH: 12
<212> TYPE: PRT
<213> ORGANISM: H. sapiens

<400> SEQUENCE: 1264

Tyr Leu Val Leu Asp Cys Val Pro Glu Glu Arg Arg
1               5                   10

<210> SEQ ID NO 1265
<211> LENGTH: 15
<212> TYPE: PRT
<213> ORGANISM: H. sapiens

<400> SEQUENCE: 1265

Asp Leu Pro Glu Thr Leu Asn Glu Leu His Leu Asp His Asn Lys
1               5                   10                  15

<210> SEQ ID NO 1266
<211> LENGTH: 11
<212> TYPE: PRT
<213> ORGANISM: H. sapiens

<400> SEQUENCE: 1266
```

```
Ile Gln Ala Ile Glu Leu Glu Asp Leu Leu Arg
1               5                   10

<210> SEQ ID NO 1267
<211> LENGTH: 14
<212> TYPE: PRT
<213> ORGANISM: H. sapiens

<400> SEQUENCE: 1267

Cys Gly Leu Phe Met Cys Ile Ala Val Asn Leu Cys Gly Lys
1               5                   10

<210> SEQ ID NO 1268
<211> LENGTH: 11
<212> TYPE: PRT
<213> ORGANISM: H. sapiens

<400> SEQUENCE: 1268

Asp Glu Ser Lys Glu Pro Ile Val Glu Val Arg
1               5                   10

<210> SEQ ID NO 1269
<211> LENGTH: 11
<212> TYPE: PRT
<213> ORGANISM: H. sapiens

<400> SEQUENCE: 1269

Phe Phe Leu Cys Gln Val Ala Gly Asp Ala Lys
1               5                   10

<210> SEQ ID NO 1270
<211> LENGTH: 12
<212> TYPE: PRT
<213> ORGANISM: H. sapiens

<400> SEQUENCE: 1270

Gly Leu Gly Glu Ile Ser Ala Ala Ser Glu Phe Lys
1               5                   10

<210> SEQ ID NO 1271
<211> LENGTH: 4
<212> TYPE: PRT
<213> ORGANISM: H. sapiens

<400> SEQUENCE: 1271

Ile Phe Gln Lys
1

<210> SEQ ID NO 1272
<211> LENGTH: 9
<212> TYPE: PRT
<213> ORGANISM: H. sapiens

<400> SEQUENCE: 1272

Gln Asp Asp Gly Gly Ser Pro Ile Arg
1               5

<210> SEQ ID NO 1273
<211> LENGTH: 12
<212> TYPE: PRT
<213> ORGANISM: H. sapiens

<400> SEQUENCE: 1273

Thr Gln Pro Val Gln Gly Glu Pro Ser Ala Pro Lys
1               5                   10
```

<210> SEQ ID NO 1274
<211> LENGTH: 5
<212> TYPE: PRT
<213> ORGANISM: H. sapiens

<400> SEQUENCE: 1274

Val Asn Leu Ile Lys
1               5

<210> SEQ ID NO 1275
<211> LENGTH: 11
<212> TYPE: PRT
<213> ORGANISM: H. sapiens

<400> SEQUENCE: 1275

Asp Ile Gln Gly Ser Leu Gln Asp Ile Phe Lys
1               5                   10

<210> SEQ ID NO 1276
<211> LENGTH: 16
<212> TYPE: PRT
<213> ORGANISM: H. sapiens

<400> SEQUENCE: 1276

Gly Ile Phe Arg Ile Asn Glu Asn Thr Gly Ser Val Ser Val Thr Arg
1               5                   10                  15

<210> SEQ ID NO 1277
<211> LENGTH: 7
<212> TYPE: PRT
<213> ORGANISM: H. sapiens

<400> SEQUENCE: 1277

Thr Leu Phe Val His Ala Arg
1               5

<210> SEQ ID NO 1278
<211> LENGTH: 16
<212> TYPE: PRT
<213> ORGANISM: H. sapiens

<400> SEQUENCE: 1278

Thr Pro His Ala Glu Asp Met Ala Glu Leu Val Ile Val Gly Gly Lys
1               5                   10                  15

<210> SEQ ID NO 1279
<211> LENGTH: 10
<212> TYPE: PRT
<213> ORGANISM: H. sapiens

<400> SEQUENCE: 1279

Val Asp Cys Asn Ala Ala Gly Ala Leu Arg
1               5                   10

<210> SEQ ID NO 1280
<211> LENGTH: 11
<212> TYPE: PRT
<213> ORGANISM: H. sapiens

<400> SEQUENCE: 1280

Val Asn Ser Asp Gly Gly Leu Val Ala Leu Arg
1               5                   10

```
<210> SEQ ID NO 1281
<211> LENGTH: 9
<212> TYPE: PRT
<213> ORGANISM: H. sapiens

<400> SEQUENCE: 1281

Tyr Glu Val Ser Ser Pro Tyr Phe Lys
 1               5

<210> SEQ ID NO 1282
<211> LENGTH: 23
<212> TYPE: PRT
<213> ORGANISM: H. sapiens

<400> SEQUENCE: 1282

Ala Pro Ala Lys Pro Pro Gly Ser Gly Leu Asp Leu Ala Asp Ala Leu
 1               5                  10                  15

Asp Asp Gln Asp Asp Gly Arg
            20

<210> SEQ ID NO 1283
<211> LENGTH: 19
<212> TYPE: PRT
<213> ORGANISM: H. sapiens

<400> SEQUENCE: 1283

Ala Pro Ala Asn Thr Leu Gly Asn Asp Phe Asp Leu Ala Asp Ala Leu
 1               5                  10                  15

Asp Asp Arg

<210> SEQ ID NO 1284
<211> LENGTH: 16
<212> TYPE: PRT
<213> ORGANISM: H. sapiens

<400> SEQUENCE: 1284

Ala Ser Val Asp Ser Gly Ser Ser Glu Glu Gln Gly Gly Ser Ser Arg
 1               5                  10                  15

<210> SEQ ID NO 1285
<211> LENGTH: 6
<212> TYPE: PRT
<213> ORGANISM: H. sapiens

<400> SEQUENCE: 1285

Leu Phe Ala Glu Glu Lys
 1               5

<210> SEQ ID NO 1286
<211> LENGTH: 6
<212> TYPE: PRT
<213> ORGANISM: H. sapiens

<400> SEQUENCE: 1286

Asp Leu Asp Asp Thr Lys
 1               5

<210> SEQ ID NO 1287
<211> LENGTH: 19
<212> TYPE: PRT
<213> ORGANISM: H. sapiens

<400> SEQUENCE: 1287

Asp Leu Asp Asp Thr Lys Met Gln Lys Ser Leu Ser Leu Leu Asp Ala
 1               5                  10                  15
```

-continued

```
                1               5               10              15

Glu Asn Arg

<210> SEQ ID NO 1288
<211> LENGTH: 7
<212> TYPE: PRT
<213> ORGANISM: H. sapiens

<400> SEQUENCE: 1288

Ile Val Met Thr Pro Ser Arg
 1               5

<210> SEQ ID NO 1289
<211> LENGTH: 10
<212> TYPE: PRT
<213> ORGANISM: H. sapiens

<400> SEQUENCE: 1289

Ser Leu Ser Leu Leu Asp Ala Glu Asn Arg
 1               5                   10

<210> SEQ ID NO 1290
<211> LENGTH: 6
<212> TYPE: PRT
<213> ORGANISM: H. sapiens

<400> SEQUENCE: 1290

Thr Asp Gly Arg Met Arg
 1               5

<210> SEQ ID NO 1291
<211> LENGTH: 12
<212> TYPE: PRT
<213> ORGANISM: H. sapiens

<400> SEQUENCE: 1291

Ala Gly Met Leu Val Ser Gly Leu Ala Gly Glu Lys
 1               5                   10

<210> SEQ ID NO 1292
<211> LENGTH: 16
<212> TYPE: PRT
<213> ORGANISM: H. sapiens

<400> SEQUENCE: 1292

Ala Ser Thr Leu Thr Ile Gly Trp Arg Ala Gln Glu Met Ser Glu Lys
 1               5                   10                  15

<210> SEQ ID NO 1293
<211> LENGTH: 9
<212> TYPE: PRT
<213> ORGANISM: H. sapiens

<400> SEQUENCE: 1293

Asp Leu Glu Phe Glu Glu Asp Gln Arg
 1               5

<210> SEQ ID NO 1294
<211> LENGTH: 5
<212> TYPE: PRT
<213> ORGANISM: H. sapiens

<400> SEQUENCE: 1294

Asp Val Leu Glu Lys
```

-continued

<210> SEQ ID NO 1295
<211> LENGTH: 15
<212> TYPE: PRT
<213> ORGANISM: H. sapiens

<400> SEQUENCE: 1295

Glu Met Phe Leu Met Ala Ala Met Gly Pro Pro Gly Gly Gly Arg
1               5                   10                  15

<210> SEQ ID NO 1296
<211> LENGTH: 16
<212> TYPE: PRT
<213> ORGANISM: H. sapiens

<400> SEQUENCE: 1296

Phe His Ala Leu Ser Leu Gly Gln Gly Gln Ala Pro Ile Ala Ala Arg
1               5                   10                  15

<210> SEQ ID NO 1297
<211> LENGTH: 19
<212> TYPE: PRT
<213> ORGANISM: H. sapiens

<400> SEQUENCE: 1297

Phe Leu Ile Leu Gln Thr Glu Thr Met Glu Thr Thr Ala His Gly Leu
1               5                   10                  15

Phe Arg Arg

<210> SEQ ID NO 1298
<211> LENGTH: 15
<212> TYPE: PRT
<213> ORGANISM: H. sapiens

<400> SEQUENCE: 1298

Ile Asp Ser Tyr Leu Arg Glu Ile Glu Gly Ser Phe Pro Asn Lys
1               5                   10                  15

<210> SEQ ID NO 1299
<211> LENGTH: 11
<212> TYPE: PRT
<213> ORGANISM: H. sapiens

<400> SEQUENCE: 1299

Leu Val Glu Asp Leu Gly Leu Phe Pro Gly Arg
1               5                   10

<210> SEQ ID NO 1300
<211> LENGTH: 8
<212> TYPE: PRT
<213> ORGANISM: H. sapiens

<400> SEQUENCE: 1300

Met Phe Glu Lys Leu Ile Asn Lys
1               5

<210> SEQ ID NO 1301
<211> LENGTH: 7
<212> TYPE: PRT
<213> ORGANISM: H. sapiens

<400> SEQUENCE: 1301

Met Met Glu Asp Ala Leu Arg

```
-continued
                1               5

<210> SEQ ID NO 1302
<211> LENGTH: 7
<212> TYPE: PRT
<213> ORGANISM: H. sapiens

<400> SEQUENCE: 1302

Asn Cys His Leu Ala Leu Arg
1               5

<210> SEQ ID NO 1303
<211> LENGTH: 9
<212> TYPE: PRT
<213> ORGANISM: H. sapiens

<400> SEQUENCE: 1303

Asn Met Glu Gly Gly Gln Gly Leu Lys
1               5

<210> SEQ ID NO 1304
<211> LENGTH: 9
<212> TYPE: PRT
<213> ORGANISM: H. sapiens

<400> SEQUENCE: 1304

Gln Glu Leu Leu Ala Gln Ala Asn Lys
1               5

<210> SEQ ID NO 1305
<211> LENGTH: 14
<212> TYPE: PRT
<213> ORGANISM: H. sapiens

<400> SEQUENCE: 1305

Val Glu Leu Asp Ala Leu Gln Gln Ile Trp Glu Ile Ala Arg
1               5                   10

<210> SEQ ID NO 1306
<211> LENGTH: 11
<212> TYPE: PRT
<213> ORGANISM: H. sapiens

<400> SEQUENCE: 1306

Val Gly Arg Asn Gly Gly Glu Ala Glu Glu Lys
1               5                   10

<210> SEQ ID NO 1307
<211> LENGTH: 19
<212> TYPE: PRT
<213> ORGANISM: H. sapiens

<400> SEQUENCE: 1307

Val Ile Gly Gln Pro Arg Gly Asn Met Leu Leu Val Gly Ile Gly Gly
1               5                   10                  15

Ser Gly Arg

<210> SEQ ID NO 1308
<211> LENGTH: 18
<212> TYPE: PRT
<213> ORGANISM: H. sapiens

<400> SEQUENCE: 1308

Tyr Ile Arg Glu Met Phe Leu Met Ala Ala Met Gly Pro Pro Gly Gly
```

```
                1               5                  10                 15

Gly Arg

<210> SEQ ID NO 1309
<211> LENGTH: 6
<212> TYPE: PRT
<213> ORGANISM: H. sapiens

<400> SEQUENCE: 1309

Ala Ala Ser Gly Pro Lys
 1               5

<210> SEQ ID NO 1310
<211> LENGTH: 15
<212> TYPE: PRT
<213> ORGANISM: H. sapiens

<400> SEQUENCE: 1310

Gly Phe Leu Asn Phe Met Asn Thr Val Leu Val Ala Phe Thr Lys
 1               5                  10                 15

<210> SEQ ID NO 1311
<211> LENGTH: 14
<212> TYPE: PRT
<213> ORGANISM: H. sapiens

<400> SEQUENCE: 1311

Leu Leu Pro Ile Ser Pro Thr Trp Pro Phe Thr Glu Val Arg
 1               5                  10

<210> SEQ ID NO 1312
<211> LENGTH: 5
<212> TYPE: PRT
<213> ORGANISM: H. sapiens

<400> SEQUENCE: 1312

Leu Leu Tyr Glu Lys
 1               5

<210> SEQ ID NO 1313
<211> LENGTH: 4
<212> TYPE: PRT
<213> ORGANISM: H. sapiens

<400> SEQUENCE: 1313

Leu Tyr Glu Lys
 1

<210> SEQ ID NO 1314
<211> LENGTH: 12
<212> TYPE: PRT
<213> ORGANISM: H. sapiens

<400> SEQUENCE: 1314

Arg Ser Thr Tyr Pro Leu Ala Asp Ser Thr Glu Arg
 1               5                  10

<210> SEQ ID NO 1315
<211> LENGTH: 9
<212> TYPE: PRT
<213> ORGANISM: H. sapiens

<400> SEQUENCE: 1315

Ser Val Ser Asn Leu Asn Tyr Gln Arg
```

```
                1               5

<210> SEQ ID NO 1316
<211> LENGTH: 6
<212> TYPE: PRT
<213> ORGANISM: H. sapiens

<400> SEQUENCE: 1316

Val Glu Leu Asp Thr Arg
1               5

<210> SEQ ID NO 1317
<211> LENGTH: 10
<212> TYPE: PRT
<213> ORGANISM: H. sapiens

<400> SEQUENCE: 1317

Ala Ser Asp Ser Gln Glu Asp Gln Glu Lys
1               5                   10

<210> SEQ ID NO 1318
<211> LENGTH: 8
<212> TYPE: PRT
<213> ORGANISM: H. sapiens

<400> SEQUENCE: 1318

Glu Leu Ile Ala Ala Ala Ser Arg
1               5

<210> SEQ ID NO 1319
<211> LENGTH: 17
<212> TYPE: PRT
<213> ORGANISM: H. sapiens

<400> SEQUENCE: 1319

Glu Thr Pro Pro Leu Glu Asp Leu Ala Ala Asn Gln Ser Glu Asp Pro
1               5                   10                  15

Arg

<210> SEQ ID NO 1320
<211> LENGTH: 10
<212> TYPE: PRT
<213> ORGANISM: H. sapiens

<400> SEQUENCE: 1320

Ala Asp Leu Ala Gln Leu Ala Ile Ile Arg
1               5                   10

<210> SEQ ID NO 1321
<211> LENGTH: 7
<212> TYPE: PRT
<213> ORGANISM: H. sapiens

<400> SEQUENCE: 1321

Gly Ser Trp Gly Ser Gly Lys
1               5

<210> SEQ ID NO 1322
<211> LENGTH: 18
<212> TYPE: PRT
<213> ORGANISM: H. sapiens

<400> SEQUENCE: 1322

Ile Asp Thr Ile Ala Ala Asp Glu Ser Phe Thr Glu Leu Asp Leu Gly
```

```
                1               5                  10                  15

Asp Arg

<210> SEQ ID NO 1323
<211> LENGTH: 8
<212> TYPE: PRT
<213> ORGANISM: H. sapiens

<400> SEQUENCE: 1323

Ala Ser Ile Asp Gly Phe Asp Arg
 1               5

<210> SEQ ID NO 1324
<211> LENGTH: 7
<212> TYPE: PRT
<213> ORGANISM: H. sapiens

<400> SEQUENCE: 1324

Leu Thr Gln Thr Ser Pro Arg
 1               5

<210> SEQ ID NO 1325
<211> LENGTH: 14
<212> TYPE: PRT
<213> ORGANISM: H. sapiens

<400> SEQUENCE: 1325

Asn Thr Ile Glu Glu Thr Gly Asn Leu Ala Glu Gln Ala Arg
 1               5                  10

<210> SEQ ID NO 1326
<211> LENGTH: 15
<212> TYPE: PRT
<213> ORGANISM: H. sapiens

<400> SEQUENCE: 1326

Val Asp Leu Val Leu Pro Glu Asp Thr Thr Glu Tyr Phe Val Arg
 1               5                  10                  15

<210> SEQ ID NO 1327
<211> LENGTH: 8
<212> TYPE: PRT
<213> ORGANISM: H. sapiens

<400> SEQUENCE: 1327

Ala Val Thr Glu Val Leu Ala Arg
 1               5

<210> SEQ ID NO 1328
<211> LENGTH: 11
<212> TYPE: PRT
<213> ORGANISM: H. sapiens

<400> SEQUENCE: 1328

Ala Ala Asp Gly Ser Leu Asp Thr Gln Pro Lys
 1               5                  10

<210> SEQ ID NO 1329
<211> LENGTH: 8
<212> TYPE: PRT
<213> ORGANISM: H. sapiens

<400> SEQUENCE: 1329

Val Ala Gln Gly Tyr His Gln Arg
```

```
<210> SEQ ID NO 1330
<211> LENGTH: 6
<212> TYPE: PRT
<213> ORGANISM: H. sapiens

<400> SEQUENCE: 1330

Ser Ile Thr Asn Pro Arg
1               5

<210> SEQ ID NO 1331
<211> LENGTH: 8
<212> TYPE: PRT
<213> ORGANISM: H. sapiens

<400> SEQUENCE: 1331

Ser Leu Ala Ala Ala Phe Pro Arg
1               5

<210> SEQ ID NO 1332
<211> LENGTH: 15
<212> TYPE: PRT
<213> ORGANISM: H. sapiens

<400> SEQUENCE: 1332

Val Asp Leu Val Leu Pro Glu Asp Thr Thr Glu Tyr Phe Val Arg
1               5                   10                  15

<210> SEQ ID NO 1333
<211> LENGTH: 13
<212> TYPE: PRT
<213> ORGANISM: H. sapiens

<400> SEQUENCE: 1333

Glu Glu Leu Glu Glu Glu Leu Asp Glu Ala Val Glu Arg
1               5                   10

<210> SEQ ID NO 1334
<211> LENGTH: 11
<212> TYPE: PRT
<213> ORGANISM: H. sapiens

<400> SEQUENCE: 1334

Thr Leu Asn Gly Ala Glu Met Ala Pro Ile Arg
1               5                   10

<210> SEQ ID NO 1335
<211> LENGTH: 10
<212> TYPE: PRT
<213> ORGANISM: H. sapiens

<400> SEQUENCE: 1335

Leu Pro Thr Asp Ser Glu Leu Ala Pro Arg
1               5                   10

<210> SEQ ID NO 1336
<211> LENGTH: 6
<212> TYPE: PRT
<213> ORGANISM: H. sapiens

<400> SEQUENCE: 1336

Asn Gln Leu Ile Gln Lys
1               5
```

```
<210> SEQ ID NO 1337
<211> LENGTH: 12
<212> TYPE: PRT
<213> ORGANISM: H. sapiens

<400> SEQUENCE: 1337

Ile Thr Ile Pro Leu Pro Asn Ala Ala Leu Thr Arg
1               5                   10

<210> SEQ ID NO 1338
<211> LENGTH: 11
<212> TYPE: PRT
<213> ORGANISM: H. sapiens

<400> SEQUENCE: 1338

Gly Ala Thr Thr Thr Phe Ser Ala Val Glu Arg
1               5                   10

<210> SEQ ID NO 1339
<211> LENGTH: 14
<212> TYPE: PRT
<213> ORGANISM: H. sapiens

<400> SEQUENCE: 1339

Glu Ala Glu Ala Trp Ala Lys Pro Gly Ala Ala Ala Arg Arg
1               5                   10

<210> SEQ ID NO 1340
<211> LENGTH: 7
<212> TYPE: PRT
<213> ORGANISM: H. sapiens

<400> SEQUENCE: 1340

Ala Ala Gln Ala Leu Asn Arg
1               5

<210> SEQ ID NO 1341
<211> LENGTH: 10
<212> TYPE: PRT
<213> ORGANISM: H. sapiens

<400> SEQUENCE: 1341

Ala Gly Gly Ser His Ser Asp Pro Gly Arg
1               5                   10

<210> SEQ ID NO 1342
<211> LENGTH: 7
<212> TYPE: PRT
<213> ORGANISM: H. sapiens

<400> SEQUENCE: 1342

Val Ser Gly Gly Gly Glu Lys
1               5

<210> SEQ ID NO 1343
<211> LENGTH: 14
<212> TYPE: PRT
<213> ORGANISM: H. sapiens

<400> SEQUENCE: 1343

Ser Gln Gly Gly Glu Pro Thr Tyr Asn Val Ala Val Gly Arg
1               5                   10

<210> SEQ ID NO 1344
```

```
<211> LENGTH: 9
<212> TYPE: PRT
<213> ORGANISM: H. sapiens

<400> SEQUENCE: 1344

Gly Asp Pro Gly Asp Ala Gly Pro Arg
1               5

<210> SEQ ID NO 1345
<211> LENGTH: 7
<212> TYPE: PRT
<213> ORGANISM: H. sapiens

<400> SEQUENCE: 1345

Ala Asp Ser Ser Pro Val Lys
1               5

<210> SEQ ID NO 1346
<211> LENGTH: 11
<212> TYPE: PRT
<213> ORGANISM: H. sapiens

<400> SEQUENCE: 1346

Ala Ser Leu Gln His Gly Gln Ala Ala Glu Lys
1               5                   10

<210> SEQ ID NO 1347
<211> LENGTH: 9
<212> TYPE: PRT
<213> ORGANISM: H. sapiens

<400> SEQUENCE: 1347

Gly Leu Ala Glu Ala Ala Gly Pro Arg
1               5

<210> SEQ ID NO 1348
<211> LENGTH: 16
<212> TYPE: PRT
<213> ORGANISM: H. sapiens

<400> SEQUENCE: 1348

Tyr Phe Ser Thr Thr Glu Asp Tyr Asp His Glu Ile Thr Gly Leu Arg
1               5                   10                  15

<210> SEQ ID NO 1349
<211> LENGTH: 7
<212> TYPE: PRT
<213> ORGANISM: H. sapiens

<400> SEQUENCE: 1349

Thr Leu Gln Ser Thr Pro Arg
1               5

<210> SEQ ID NO 1350
<211> LENGTH: 13
<212> TYPE: PRT
<213> ORGANISM: H. sapiens

<400> SEQUENCE: 1350

Trp Leu Cys Val Val Gly Gly Trp Asp Gly Ser Arg Arg
1               5                   10

<210> SEQ ID NO 1351
<211> LENGTH: 13
<212> TYPE: PRT
```

```
<213> ORGANISM: H. sapiens

<400> SEQUENCE: 1351

Trp Leu Cys Val Val Gly Gly Trp Asp Gly Ser Arg Arg
 1               5                  10

<210> SEQ ID NO 1352
<211> LENGTH: 10
<212> TYPE: PRT
<213> ORGANISM: H. sapiens

<400> SEQUENCE: 1352

Gly Phe Leu Ser Gln Arg Leu Phe Ala Arg
 1               5                  10

<210> SEQ ID NO 1353
<211> LENGTH: 15
<212> TYPE: PRT
<213> ORGANISM: H. sapiens

<400> SEQUENCE: 1353

Leu Glu Gly Ile Gly Glu Gly Glu Phe Leu Val Leu Asp Gln Arg
 1               5                  10                  15
```

BIOMARKERS FOR NEURODEGENERATIVE DISORDERS

CROSS-REFERENCE

This application claims the benefit of U.S. Provisional Application No. 60/731,339, filed Oct. 27, 2005, which application is incorporated herein by reference in its entirety.

GOVERNMENT RIGHTS

This invention was made with government support under federal grant nos. R01AG025327 and R01ES012703 awarded by National Institutes of Health. The United States Government may have certain rights in this invention.

SEQUENCE LISTING

The present specification incorporates herein by reference, each in its entirety, the sequence information on the Compact Disks (CDs) labeled Copy 1 and Copy 2. The CDs are formatted on IBM-PC, with operating system compatibility with MS-Windows. The files on each of the CDs are as follows:

Copy 1—Seqlist.txt 214 KB created Jul. 28, 2006; and

Copy 2—Seqlist.txt 214 KB created Jul. 28, 2006.

BACKGROUND OF THE INVENTION

Neurodegenerative disorders, e.g. Alzheimer's disease (AD), Parkinson's disease (PD), and dementia with Lewy body (DLB) diseases, are diagnosed primarily by clinical presentations, limited laboratory investigations and, more recently, structural and functional neuroimaging analysis (Bacskai et al., J Cereb Blood Flow Metab, 2002. 22(9): p. 1035-41; Klunk et al., J Neuropathol Exp Neurol, 2002. 61(9): p. 797-805; and Small et al., J Mol Neurosci, 2002. 19(3): p. 323-7). However the diagnosis based on these approaches is unsatisfactory. As determined by pathological examination, diagnostic accuracy of various neurodegenerative diseases varies between 50% to 85% depending on the disease involved, the experience of physicians and the stages of the diseases (Jankovic et al., Arch Neurol, 2000. 57(3): p. 369-72; Hughes et al., Brain, 2002. 125(Pt 4): p. 861-70; Litvan et al., Arch Neurol, 1998. 55(7): p. 969-78; Rajput et al., Can J Neurol Sci, 1991. 18(3): p. 275-8; Hughes et al., J Neurol Neurosurg Psychiatry, 1992. 55(3): p. 181-4; and McKeith et al., Semin Clin Neuropsychiatry, 2003. 8(1): p. 46-57). The fact that the diagnosis cannot be made with reasonable certainty until the latter stages of the diseases possibly underlies the current state of clinical management, i.e. none of the available therapies, particularly those aimed at preventing disease's progression, is effective; this could simply be due to the fact that most neurons are already degenerated by the time diagnosis is made. It is also noteworthy that it is common for patients with various neurodegenerative diseases to go undetected using current approaches (Love et al., Histopathology, 2004. 44(4): p. 309-17).

Biomarkers are biological characteristics used to indicate or to measure disease risk, presence, and progression. Ideally, an optimal biomarker should be precise, reliable, inexpensive, as well as reflect the pathophysiological mechanisms of neurodegenerative diseases. Presently, no established diagnostic biomarkers can confirm AD, PD or DLB or monitor their progression with high sensitivity at high specificity. Furthermore, markers are most useful if they can detect at an early or even preclinical stages of diseases. In searching for biochemical markers in body fluids, including plasma, urine, and cerebrospinal fluid (CSF), only limited success has been achieved despite decades of research. It has been felt recently that this is largely due to the heterogeneity of all neurodegenerative diseases, i.e. several markers may be needed to detect subpopulations of patients (Olsson et al., Clin Chem, 2005. 51(2): p. 336-45).

The development of genomics, proteomics, and metabolomics has greatly enhanced the ability to discover multiple markers that are not only useful for diagnosis of AD, PD and DLB but also shed more lights on their pathogenesis. However, these studies are limited, as none has taken other neurodegenerative diseases into consideration, and in addition, very few studies have been performed using cases with pathological verification. The present invention addresses this need.

Relevant Literature

Bacskai et al., J Cereb Blood Flow Metab, 2002. 22(9): p. 1035-41; Klunk et al., J Neuropathol Exp Neurol, 2002. 61(9): p. 797-805; Small et al., J Mol Neurosci, 2002. 19(3): p. 323-7; Jankovic et al., Arch Neurol, 2000. 57(3): p. 369-72; Hughes et al., Brain, 2002. 125(Pt 4): p. 861-70; Litvan et al., Arch Neurol, 1998. 55(7): p. 969-78; Rajput et al., Can J Neurol Sci, 1991. 18(3): p. 275-8; Hughes et al., J Neurol Neurosurg Psychiatry, 1992. 55(3): p. 181-4; McKeith et al., Semin Clin Neuropsychiatry, 2003. 8(1): p. 46-57; Love et al., Histopathology, 2004. 44(4): p. 309-17; Olsson et al., Clin Chem, 2005. 51(2): p. 336-45; Zhang et al., Neurobiol Aging, 2005. 26(2): p. 207-27; and Zhang et al., J Alzheimers Dis, 2005. 7(2): p. 125-33.

SUMMARY OF THE INVENTION

The present invention provides methods for diagnosing neurodegenerative disease, such as Alzheimer's Disease, Parkinson's Disease, and dementia with Lewy body disease by detecting a pattern of gene product (e.g., protein) expression in a cerebrospinal fluid sample and comparing the pattern of gene product expression from the sample to a library of gene product expression pattern known to be indicative of the presence or absence of a neurodegenerative disease. Also provided are kits, systems and devices for practicing the subject methods.

The present invention provides a method for detecting presence or absence of a neurodegenerative disease in a subject by detecting a pattern of gene product expression present in a cerebrospinal fluid sample obtained from a subject; and comparing the pattern of gene product expression from the cerebrospinal fluid sample to a library of gene product expression pattern known to be indicative of the presence or absence of a neurodegenerative disease, wherein the comparing indicates the presence or absence of a neurodegenerative disease.

In some embodiments, the gene product is a polypeptide. In some embodiments, the detecting is by mass spectrometry. In other embodiments, the detecting is by immunoassay. In certain embodiments, the immunoassay is enzyme linked immunosorbent assay (ELISA). In other embodiments, the detecting by a Luminex xMAP system. In certain embodiments, the neurodegenerative disease is Alzheimer's disease, Parkinson's disease, or dementia with Lewy body disease.

The present invention also provides a method for monitoring progression of a neurodegenerative disease in a subject by detecting a first pattern of expression of gene products present in a cerebrospinal fluid sample obtained from a subject at a first time point, wherein said first pattern is indicative of a neurodegenerative disease; detecting a second pattern of expression of gene products present in a cerebrospinal fluid sample obtained from a subject at a second time point; and comparing the first and second patterns of expression of gene products from the cerebrospinal fluid samples, wherein the comparing provides for monitoring of the progression of the neurodegenerative disease from the first time point to the second time point.

In some embodiments, the gene product is a polypeptide. In some embodiments, the detecting is by mass spectrometry. In other embodiments, the detecting is by immunoassay. In certain embodiments, the immunoassay is enzyme linked immunosorbent assay (ELISA). In other embodiments, the detecting by a Luminex xMAP system. In certain embodiments, the neurodegenerative disease is Alzheimer's disease, Parkinson's disease, or dementia with Lewy body disease.

The present invention also provides a method of providing a differential diagnosis between Alzheimer's disease (AD), Parkinson's disease (PD), and dementia with Lewy body disease (DLB) in a subject by detecting a pattern of gene product expression present in a cerebrospinal fluid sample obtained from a subject; and comparing the pattern of gene product expression from the cerebrospinal fluid sample to a library of gene product expression patterns known to be indicative of the presence or absence of AD, PD and DLB, wherein the comparing providing a differential diagnosis between AD, PD, and DLB.

In some embodiments, the gene product is a polypeptide. In some embodiments, the detecting is by mass spectrometry. In other embodiments, the detecting is by immunoassay. In certain embodiments, the immunoassay is enzyme linked immunosorbent assay (ELISA). In other embodiments, the detecting by a Luminex xMAP system.

The present invention also provides a system, including a computing environment; an input device, connected to the computing environment, to receive data from a user, wherein the data received includes a pattern of gene product expression from a cerebrospinal fluid sample obtained from a subject; an output device, connected to the computing environment, to provide information to the user; and a computer readable storage medium having stored thereon at least one algorithm to provide for comparing the pattern of gene product expression from the cerebrospinal fluid sample to a library of gene product expression pattern known to be indicative of the presence or absence of a neurodegenerative disease. In some embodiments, the computing environment includes a local computer local to the user and a remote computer at a site remote to the user, wherein the local computer and the remote computer are connected through a network, and wherein the computer readable storage medium is provided on the remote computer.

The present invention also provides a computer readable medium including a program stored thereon, wherein the program provides for execution of one or more algorithms to provide for comparing a pattern of gene product expression from a cerebrospinal fluid sample obtained from a subject to a library of gene product expression pattern known to be indicative of the presence or absence of a neurodegenerative disease.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 2 shows confirmation of β-Fibrinogen with Western blot in pooled and individual samples. Proteomic data showed that β fibrinogen increased significantly over controls with pooled samples. Panel A: with standard Western blot protocol, pooled samples were analyzed with an antibody against β fibrinogen (1:2000) both based on total loading amount (10 μg, i.e. similar to proteomic analysis) or CSF volume (10 μl). Panel B: with identical approach in Panel A, but β fibrinogen was analyzed again in individual samples. AD: Alzheimer's disease; PD: Parkinson's disease; DLB: dementia with Lewy body disease; CT: age-matched controls.

FIGS. 5A-5YY is a table showing the proteins that have changes in expression levels unique to AD, PD, or DLB. The table is presented in six sections (I) proteins unique to AD and identified by two or more peptides; (II) proteins unique to AD and identified by a single peptide; (III) proteins unique to PD and identified by two or more peptides; (IV) proteins unique to PD and identified by a single peptide; (V) proteins unique to DLP and identified by two or more peptides; and (VI) proteins unique to DLB and identified by a single peptide. The identified proteins have also been grouped based on function within each category. Exemplary functional groupings include neuronal activities/signal transduction, cell structure/motility/transport/traffic, and extracellular matrix/cell adhesion, immunity/defense. The assignment of function of each protein is putative, as most, if not all, proteins have multiple functions. A legend of the symbols used in the table are: ↑↑: Increase (AD, PD or DLB vs. control>1.5); ↓↓: Decrease (AD, PD or DLB vs. control<0.67); ↑: Increase (AD, PD or DLB vs. control between 1.2 and 1.5); ↓: Decrease (AD, PD or DLB vs. control between 0.67 and 0.83); and NC: No change (AD, PD or DLB vs. control between 0.83 and 1.2).

FIGS. 6A-6T a table showing proteins identified in CSF samples using multidimensional peptide separation techniques, followed by 4700 TOF-TOF analysis.

FIGS. 7A-7V a table showing proteins identified in CSF samples using multidimensional peptide separation techniques, followed by 4700 TOF-TOF analysis that were identified as single-hits. Single-hits refers to the fact that a protein is identified from the MS/MS spectrum of a single peptide as opposed to those proteins identified with multiple peptide tandem mass spectra as listed in FIGS. 6A-6T.

DEFINITIONS

Figure 1:
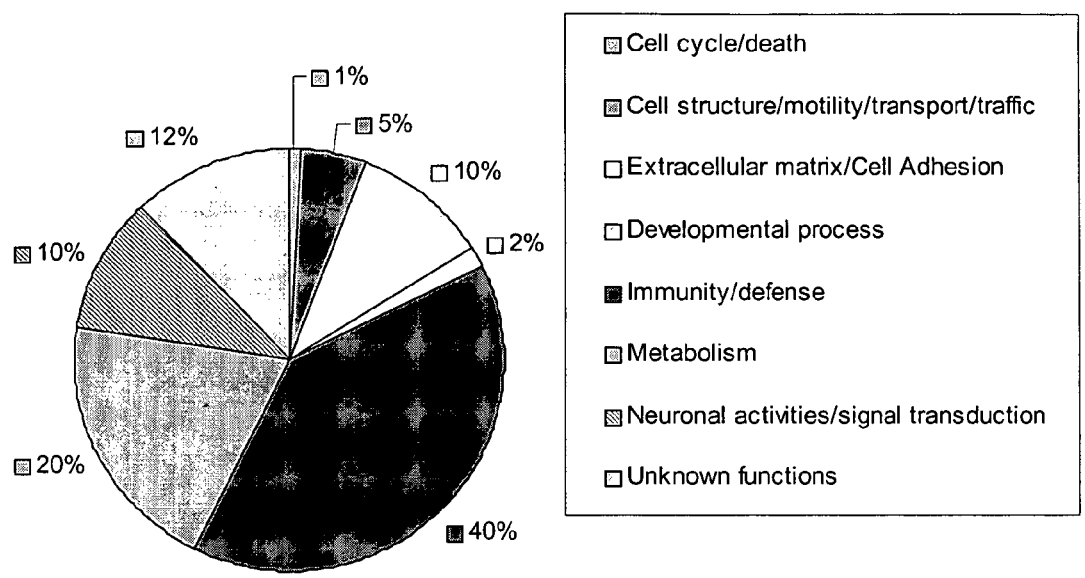
FIG. 1 shows a pie chart depicting the 1,540 proteins characterized by nano-LC-MALDI-TOF-TOF. A complete list of the identified proteins is provided in FIGS. 6A-6T and FIGS. 7A-V.

A "neurodegenerative disease", as used in the current context, is readily understood by one of ordinary skill in the art to include any abnormal physical or mental behavior or experience where the death or dysfunction of neuronal cells is involved in the etiology of the disorder, or is affected by the disorder. As used herein, neurodegenerative diseases encompass disorders affecting the central and peripheral nervous systems, and include such afflictions as memory loss, stroke, dementia, personality disorders, gradual, permanent or episodic loss of muscle control. Examples of neurodegenerative diseases for which the current invention can be used preferably include, but are not limited to, Alzheimer's Disease, Parkinson's Disease, Huntington's Disease, Dementia with Lewy Body, amyotrophic lateral sclerosis, epilepsy, myasthenia gravis, neuropathy, ataxia, dementia, chronic axonal neuropathy and stroke.

As used herein "Parkinson's disease" or "PD" refer to a condition of disturbance of voluntary movement in which muscles become stiff and sluggish, movement becomes clumsy and difficult and uncontrollable rhythmic twitching of groups of muscles produces characteristic shaking or tremor. The condition is believed to be caused by a degeneration of pre-synaptic dopaminergic neurons in the brain. The absence of adequate release of the chemical transmitter dopamine during neuronal activity thereby leads to the Parkinsonian symptomatology.

As used herein "Alzheimer's disease" or "AD" refers to a condition characterized by the abnormal deposition of amyloid in the brain of a patient in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein (βA4, also referred to as Aβ, β-protein and βAP) which is a proteolytic product of a precursor protein of much larger size. The symptoms of Alzheimer's disease are similar to those of other dementias. They include memory loss, changes in personality, problems using language, disorientation, difficulty doing daily activities, and disruptive behavior.

As used herein "dementia with Lewy body" or "DLB" refers to a condition characterized by widespread neurodegeneration with formation of Lewy bodies not only in the dopaminergic system but also in other brain regions. The major symptoms of DLB are fluctuating cognition, visual hallucinations and parkinsonian signs. This is a disease considered by some as a collision between AD and PD; its clinical diagnosis is extremely challenging.

A "gene product" is a biopolymeric product that is expressed or produced by a gene, such as a peptide or protein. A gene product may be, for example, an unspliced RNA, an mRNA, a splice variant mRNA, a polypeptide, a post-translationally modified polypeptide, a splice variant polypeptide etc. Also encompassed by this term are biopolymeric products that are made using an RNA gene product as a template (i.e., cDNA of the RNA). A gene product may be made enzymatically, recombinantly, chemically, or within a cell to which the gene is native. In many embodiments, if the gene product is proteinaceous, it exhibits a biological activity. In many embodiments, if the gene product is a nucleic acid, it can be translated into a proteinaceous gene product that exhibits a biological activity.

The terms "polypeptide" and "protein", interchangeably used herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "polynucleotide" refers to polymeric forms of nucleotides of any length, either ribonucleotides or deoxynucleotides. Thus, these terms include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. These terms further include, but are not limited to, mRNA or cDNA that comprise intronic sequences (see, e.g., Niwa et al. (1999) Cell 99(7):691-702). The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. Peyrottes et al. (1996) Nucl. Acids Res. 24:1841-1848; Chaturvedi et al. (1996) Nucl. Acids Res. 24:2318-2323. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. The term "polynucleotide" also encompasses peptidic nucleic acids (Pooga et al Curr Cancer Drug Targets. (2001) 1:231-9).

A composition (e.g. a polynucleotide, polypeptide, antibody, or host cell) that is "isolated" or "in substantially isolated form" refers to a composition that is in an environment different from that in which the composition naturally occurs. For example, a polynucleotide that is in substantially isolated form is outside of the host cell in which the polynucleotide naturally occurs, and could be a purified fragment of DNA, could be part of a heterologous vector, or could be contained within a host cell that is not a host cell from which the polynucleotide naturally occurs. The term "isolated" does not refer to a genomic or cDNA library, whole cell total protein or mRNA preparation, genomic DNA preparation, or an isolated human chromosome. A composition which is in substantially isolated form is usually substantially purified.

As used herein, the term "substantially purified" refers to a compound (e.g., a polynucleotide, a polypeptide or an antibody, etc.,) that is removed from its natural environment and is usually at least 60% free, preferably 75% free, and most preferably 90% free from other components with which it is naturally associated. Thus, for example, a composition containing A is "substantially free of" B when at least 85% by weight of the total A+B in the composition is A. Preferably, A comprises at least about 90% by weight of the total of A+B in the composition, more preferably at least about 95% or even 99% by weight. In the case of polynucleotides, "A" and "B" may be two different genes positioned on different chromosomes or adjacently on the same chromosome, or two isolated cDNA species, for example.

DETAILED DESCRIPTION OF THE INVENTION

The present invention provides methods for diagnosing neurodegenerative disease, such as Alzheimer's Disease, Parkinson's Disease, and dementia with Lewy body disease by detecting a pattern of gene product (e.g., protein) expression in a cerebrospinal fluid sample and comparing the pattern of gene product expression from the sample to a library of gene product expression pattern known to be indicative of the presence or absence of a neurodegenerative disease. Also provided are kits and devices for practicing the subject methods.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the marker" includes reference to one or more markers and equivalents thereof known to those skilled in the art, and so forth.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Overview

The present invention is based on the identification and quantification of cerebrospinal fluid (CSF) proteins using an unbiased quantitative proteomic approach called iTRAQ (isobaric Tagging for Relative and Absolute protein Quantification) to label pre-fractionated human CSF, and followed by MudPIT (Multidimensional Protein Identification Technology), prior to mass spectrometry (MS) analysis. This multiplex format allowed simultaneous comparison of the proteome of CSF in AD, PD, DLB patients and healthy controls. This analysis not only identified 1,540 CSF proteins (see FIGS. 6A-6T and FIGS. 7A-7V), thereby greatly expanding the current knowledge about the human CSF proteome, but also detected 136, 73, and 100 proteins that displayed quantitative changes unique to AD, PD, and DLB, respectively. Finally, the sensitivity at 95% specificity of each of eight exemplary markers or composite markers was calculated, demonstrating that the combination of several markers could distinguish between AD, PD and DLB patients not only from controls, but also from each other with high sensitivity at 95% specificity.

In addition, several exemplary panels of unique makers are capable of distinguishing AD, PD and DLB patients from each other as well as from controls with high sensitivity at 95% specificity (see e.g., FIGS. 5A-5YY).

Methods of the Invention

The invention features methods for diagnosing neurodegenerative disease, such as Alzheimer's Disease, Parkinson's Disease, and dementia with Lewy body disease by detecting a pattern of gene product (e.g., proteins/peptides) expression in a cerebrospinal fluid sample and comparing the pattern of gene product expression from the sample to a library of gene product expression pattern (e.g., FIGS. 5A-5YY) known to be indicative of the presence or absence of a neurodegenerative disease. In general, the detection of a pattern of gene product expression in a CSF sample obtained form a subject as described herein can be accomplished using any acceptable methodology.

The term's "neurodegeneration" and "neurodegenerative condition or disease" as used in the present application stand for the same and are used interchangeable throughout the application. These terms include any condition of the brain that is associated with a neuronal malfunctioning. Various diseases associated with neurodegeneration include Alzheimer's disease, Parkinson disease, dementia with Lewy Body, Huntington' disease, Creutzfeld Jacob disease, frontal temporal lobe dementia, normal Pressure Hydrocephalus, and amyotrophic lateral sclerosis. However, this list is not complete. Other diseases known to be associated with neuronal malfilrictioning are included as well. In certain embodiments of the present invention, the neurodegenerative disease or condition to be specifically detected, monitored, quantified and/or differentially diagnosed is chosen from the group consisting of Alzheimer's disease, and dementia with Lewy Body.

In general, the method for detecting the presence or absence of a neurodegenerative disease in a subject includes detecting a pattern of gene product expression present in a cerebrospinal fluid sample obtained from a subject; and comparing the pattern of gene product expression from the cerebrospinal fluid sample to a library of gene product expression pattern known to be indicative of the presence or absence of a neurodegenerative disease, wherein the comparing indicates the presence or absence of a neurodegenerative disease.

Any possible combination of gene product(s), such as proteins and peptides, that have an altered level in a CSF sample obtained form a subject under a certain neurological condition can be used for the detection of the presence or absence of a neurological disease, the monitoring of a neurological disease, including assessing therapeutic effects of a treatment regimen (e.g., administration of a therapeutic drug), or the differential diagnosis of AD, PD, or DLB. An exemplary list of candidate gene products that are suitable for use in the detection, monitoring, and differential diagnosis methods of the present invention are summarized in FIGS. 5A-5YY.

Detection of an alerted marker expression pattern(s) in a CSF sample obtained from a subject as compared to that of a normal subject (e.g., a subject known to not have a neurodegenerative disease) is an indicator of neurodegenerative disease, such as AD, PD, or DLB. As with all controls mentioned herein, the control is preferably derived from CSF of subjects without any neurological diseases or taking any medicines for any conditions that might influence neurological functions.

In general, at least enough gene products from FIGS. 5A-5YY are selected for the subject methods that provide for the specific detection of the presence or absence of a neurodegenerative disease. In most embodiments, at least two ore more gene products from FIGS. 5A-5YY are selected for determining the presence or absence of a neurodegenerative disease. In some embodiments, a least three or more genes are selected, including about four or more gene products, and about five or more gene products.

The present invention also provides a method for differential diagnosis between Alzheimer's disease (AD), Parkinson's disease (PD), and dementia with Lewy body disease (DLB) in a subject by detecting a pattern of gene product expression present in a cerebrospinal fluid sample obtained from a subject; and comparing the pattern of gene product expression from the cerebrospinal fluid sample to a library of gene product expression patterns known to be indicative of the presence or absence of AD, PD and DLB, wherein said comparing providing a differential diagnosis between AD, PD, and DLB.

It will be appreciated that the number of gene products selected for use in the present methods will be in part dictated by the specific gene products that are selected for the analysis and whether a general diagnosis of neurodegenerative disease is desired or a differential diagnosis of PD, AD, or DLB is desired. As will be readily apparent to one having skill in the art, the expression level of certain gene products will be modulated as compared to a control in certain conditions and will not be modulated (i.e., decrease or increased) in other conditions as compared to a control. For example, as shown in FIG. 5A, a decrease in expression of BDNF1 is witnessed in AD, while no change (NC) in expression as compared to a control is witnessed in PD or DLB. Likewise, as shown in FIG. 5B, a decrease in expression of Chromogranin B is witnessed in AD, while an increase in expression is witnessed in PD and no change in expression is witnessed in DLB.

As such, in some embodiments, the pattern of gene product expression will be detected and compared to the library of gene product expression patterns known to be indicative of the presence or absence of a neurodegenerative disease. In certain embodiments, the assessment of gene product expression of a single gene product will provide a preliminary result and will be followed up with the assessment of at least a second gene product expression.

The present invention also provides a method for monitoring progression of a neurodegenerative disease in a subject by detecting a first pattern of expression of gene products present in a cerebrospinal fluid sample obtained from a subject at a first time point, wherein said first pattern is indicative of a neurodegenerative disease; detecting a second pattern of expression of gene products present in a cerebrospinal fluid sample obtained from a subject at a second time point; and comparing the first and second patterns of expression of gene products from the cerebrospinal fluid samples, wherein the comparing provides for monitoring of the progression of the neurodegenerative disease from the first time point to the second time point.

In certain embodiments, the method of monitoring progression of a neurodegenerative disease in a subject will include detecting a pattern of expression of gene products present in a CSF sample obtained from a subject at more than two time points, such as three or more. In general, the time points for detecting a pattern of expression of gene products can be separated by any amount of time that is desired. For example, the first time point and second time point can be separated by about 3 months, about 6 months, or about 1 year or more, such as about 3 or more years.

In general, it will be appreciated by one of skill in the art that the duration of time between the first time point and the second time point must be sufficient to provide for a monitoring of the progression of the neurodegenerative disease.

In certain embodiments, the monitoring of the neurodegenerative disease in the subject will be conducted in parallel with a treatment regimen for the neurodegenerative disease. In such embodiments, the method of monitoring the neurodegenerative disease during treatment will provide information of whether the treatment is improving the condition, or having no effect or an adverse effect on the condition. In such embodiments, the first time point may be either just before, concurrent with, or just after the in initiation of a treatment regimen and the second time point may be a time point following a desired treatment period. For example, in such embodiments, the second time point may be about 6 month or more following initiation of treatment, including about 1 year, about 2 years, or more. For example, the detection of the pattern of expression of gene products present in a CSF sample obtained from the subject may be determined about once every 6 months to monitor progression of the disease and efficacy of the treatment regimen.

In general, methods of the invention involving detection of a gene product (e.g., proteins or polypeptides). In one embodiment, the methods involve contacting a sample with a probe specific for the gene product of interest (e.g., marker polypeptide). "Probe" as used herein in such methods is meant to refer to a molecule that specifically binds a gene product of interest (e.g., the probe binds to the target gene product with a specificity sufficient to distinguish binding to target over non-specific binding to non-target (background) molecules). "Probes" include, but are not necessarily limited to, antibodies (e.g., antibodies, antibody fragments that retain binding to a target epitope, single chain antibodies, and the like), or other polypeptide, peptide, or molecule (e.g., receptor ligand) that specifically binds a target gene product of interest.

The probe and sample suspected of having the gene product of interest are contacted under conditions suitable for binding of the probe to the gene product. For example, contacting is generally for a time sufficient to allow binding of the probe to the gene product (e.g., from several minutes to a few hours), and at a temperature and conditions of osmolarity and the like that provide for binding of the probe to the gene product at a level that is sufficiently distinguishable from background binding of the probe (e.g., under conditions that minimize non-specific binding). Suitable conditions for probe-target gene product binding can be readily determined using controls and other techniques available and known to one of ordinary skill in the art.

The probe can be an antibody or other polypeptide, peptide, or molecule (e.g., receptor ligand) that specifically binds a target polypeptide of interest.

The detection methods can be provided as part of a kit. Thus, the invention further provides kits for detecting the presence/absence and/or a level of expression of a marker of the invention, and/or a polypeptide in a human CSF sample. The kits of the invention for detecting a marker polypeptide generally comprise a moiety that specifically binds the polypeptide, which may be a specific antibody. The kit may optionally provide additional components that are useful in the procedure, including, but not limited to, buffers, developing reagents, labels, reacting surfaces, means for detection, control samples, standards, instructions, and interpretive information.

Detecting a Marker Polypeptide in Diagnosing Neurodegenerative Disease

The gene products according to the methods of the present invention can be detected by any suitable method. Detection paradigms that can be employed to this end include enzymatic methods, including immunological-based methods, optical methods, electrochemical methods (voltametry and amperometry techniques), atomic force microscopy, and radio frequency methods, e.g., multipolar resonance spectroscopy. It is to be understood that the present invention is not limited to a particular detection method. However, in some embodiments detection is by, for example, fluorescent detection, spectrometric detection, chemiluminescent detection, matrix assisted laser desorption-time-of flight (MALDI-TOF) detection, high pressure liquid chromatographic detection, charge detection, mass detection, radio frequency detection, and light diffraction detection. Exemplary detection methods that are suitable for use with the subject methods are described herein.

Detection by Capture Agent

In some embodiments, detection of gene products is by use of capture reagents specific to the gene products (e.g., polypeptides). In general, the biospecific capture reagent is bound to a solid phase, such as a bead, a plate, a membrane or a chip. Methods of coupling biomolecules, such as antibodies, to a solid phase are well known in the art. They can employ, for example, bifunctional linking agents, or the solid phase can be derivatized with a reactive group, such as an epoxide or an imidizole, that will bind the molecule on contact. Biospecific capture reagents against different gene products can be mixed in the same place, or they can be attached to solid phases in different physical or addressable locations. For example, one can load multiple columns with derivatized beads, each column able to capture a single gene product. Alternatively, one can pack a single column with different beads derivatized with capture reagents against a variety of gene products, thereby capturing all the analytes in a single place. Accordingly, antibody-derivatized bead-based technologies, such as Multi-Analyte Profiling (xMAP™) technology of Luminex (Austin, Tex.) can be used to detect the gene products.

Luminex xMAP™ is based on polystyrene particles (microspheres) that are internally labeled with two different fluorophores. When excited by a 635-nm laser, the fluorophores emit light at different wavelengths, e.g., 658 and 712 nm. By varying the 658-nm/712-nm emission ratios, the beads are individually classified by the unique Luminex 100 IS analyzer. A third fluorophore coupled to a reporter molecule allows for quantification of the interaction that has occurred on the microsphere surface. The Luminex xMAP™ technology is described, for example, in U.S. Pat. Nos. 5,736,330, 5,981,180, and 6,057,107, all of which are specifically incorporated by reference.

In yet another embodiment, the surfaces of biochips can be derivatized with the capture reagents directed against specific gene products (e.g., selected from FIGS. 5A-5YY). Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

Detection by Mass Spectrometry

In some embodiments, the gene products (e.g., polypeptides) are detected by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer and hybrids of these. In such embodiments, the relative levels of gene products in each sample can be determined with mass spectrometry where a standard curve can be generated using corresponding synthetic peptides without isotope labeling. Alternatively, the gene products (e.g., polypeptides) in the sample can be identified and quantified when the identical synthetic peptides are isotope labeled and spiked in the sample.

In certain embodiments the mass spectrometer is a laser desorption/ionization mass spectrometer. In laser desorption/ionization mass spectrometry, the analytes are placed on the surface of a mass spectrometry probe, a device adapted to engage a probe interface of the mass spectrometer and to present an analyte to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer.

In general, a probe with an adsorbent surface is contacted with the CSF sample obtained from a subject for a period of time sufficient to allow gene products (e.g., peptides) that may be present in the sample to bind to the adsorbent surface. After an incubation period, the substrate is washed to remove unbound material. Any suitable washing solutions can be used; such as an aqueous solution. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. An energy absorbing molecule is then applied to the substrate with the bound gene products.

The gene products bound to the substrate are then detected in a gas phase ion spectrometer such as a time-of-flight mass spectrometer or an ion trap mass spectrometer. The gene products are ionized by an ionization source such as a laser, the generated ions are collected by an ion optic assembly, and then a mass analyzer disperses and analyzes the passing ions. The detector then translates information of the detected ions into mass-to-charge ratios. Detection of a gene product typically will involve detection of signal intensity. Thus, both the quantity and mass of the gene product can be determined.

In another mass spectrometry method, the gene product(s) (e.g., polypeptides) can be first captured on a chromatographic resin that binds the target molecules. For example, the resin can be derivatized with anti-gene product proteins antibodies. Alternatively, this method could be preceded by chromatographic fractionation before application to the bio-affinity resin. After elution from the resin, the sample can be analyzed by MALDI, electrospray, or another ionization method for mass spectrometry. In another alternative, one could fractionate on an anion exchange resin and detect by MALDI or electrospray mass spectrometry directly. In yet another method, one could capture the gene product(s) on an immuno-chromatographic resin that comprises antibodies that bind the target molecules, wash the resin to remove unbound material, elute the bound molecules from the resin and detect the eluted proteins by MALDI, electrospray mass spectrometry or another ionization mass spectrometry method.

Detection by Immunoassay

Any of a variety of known immunoassay methods can be used for detection, including, but not limited to, immunoassay, using an antibody specific for the encoded polypeptide, e.g., by enzyme-linked immunosorbent assay (ELISA), radioimmunoassay (RIA), and the like; and functional assays for the encoded polypeptide, e.g., binding activity or enzymatic activity.

For example, an immunofluorescence assay can be easily performed on fractionated or non-fractionated human CSF. It is also possible to perform such assays in plasma if sufficient markers are diffused from human CSF to plasma.

To increase the sensitivity of the assay, the immunocomplex may be further exposed to a second antibody, which is labeled and binds to the first antibody, which is specific for the encoded polypeptide. Typically, the secondary antibody is detectably labeled, e.g., with a fluorescent marker. The cells which express the encoded polypeptide will be fluorescently labeled and easily visualized under the microscope. See, for example, Hashido et al. (1992) *Biochem. Biophys. Res. Comm.* 187:1241-1248.

As will be readily apparent to the ordinarily skilled artisan upon reading the present specification, the detection methods and other methods described herein can be varied. Such variations are within the intended scope of the invention. For example, in the above detection scheme, the probe for use in detection can be immobilized on a solid support, and the test sample (e.g., human CSF or plasma) contacted with the immobilized probe. Binding of the test sample to the probe can then be detected in a variety of ways, e.g., by detecting a detectable label bound to the test sample.

Thus generally the methods comprise: a) contacting the sample with an antibody specific for a gene product (e.g., a marker selected from FIGS. 5A-5YY); and b) detecting binding between the antibody and molecules of the sample. The level of antibody binding (either qualitative or quantitative) indicates the susceptibility of the patient to a neurodegenerative disease. For example, where the marker polypeptide is present at a level greater than that associated with a negative control level, then the patient is susceptive to neurodegenerative disease.

Suitable controls include a sample known not to contain the marker polypeptide; a sample contacted with an antibody not specific for the marker polypeptide; a sample having a level of polypeptide associated with neurodegenerative disease. A variety of methods to detect specific antibody-antigen interactions are known in the art and can be used in the method, including, but not limited to, standard immunohistological methods, immunoprecipitation, an enzyme immunoassay, and a radioimmunoassay.

In general, the specific antibody will be detectably labeled, either directly or indirectly. Direct labels include radioisotopes; enzymes having detectable products (e.g., luciferase, β-galactosidase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin, aequorin (green fluorescent protein), and the like.

The antibody may be attached (coupled) to an insoluble support, such as a polystyrene plate or a bead. Indirect labels include second antibodies specific for antibodies specific for the encoded polypeptide ("first specific antibody"), wherein the second antibody is labeled as described above; and members of specific binding pairs, e.g., biotin-avidin, and the like. The biological sample may be brought into contact with and immobilized on a solid support or carrier, such as nitrocellulose, that is capable of immobilizing cells, cell particles, or soluble proteins. The support may then be washed with suitable buffers, followed by contacting with a detectably-labeled first specific antibody. Detection methods are known in the art and will be chosen as appropriate to the signal emitted by the detectable label. Detection is generally accomplished in comparison to suitable controls, and to appropriate standards.

Polypeptide Arrays

Polypeptide arrays provide a high throughput technique that can assay a large number of polypeptides in a sample. This technology can be used as a tool to test for expression of a marker polypeptide and assessment of neurodegenerative disease. Of particular interest are arrays which comprise a probe for detection of one or more of the gene products selected from FIGS. 5A-5YY.

A variety of methods of producing arrays, as well as variations of these methods, are known in the art and contemplated for use in the invention. For example, arrays can be created by spotting polypeptide probes onto a substrate (e.g., glass, nitrocellulose, etc.) in a two-dimensional matrix or array having bound probes. The probes can be bound to the substrate by either covalent bonds or by non-specific interactions, such as hydrophobic interactions.

Samples of polypeptides can be detectably labeled (e.g., using radioactive or fluorescent labels) and then hybridized to the probes. Alternatively, the polypeptides of the test sample can be immobilized on the array, and the probes detectably labeled and then applied to the immobilized polypeptides. In most embodiments, the "probe" is detectably labeled. In other embodiments, the probe is immobilized on the array and not detectably labeled. In such embodiments, the sample is applied to the polypeptide array and bound gene products (e.g., peptides) are detected using secondary labeled probes Examples of such protein arrays are described in the following patents or published patent applications: U.S. Pat. No. 6,225,047; PCT International Publication No. WO 99/51773; U.S. Pat. No. 6,329,209, PCT International Publication No. WO 00/56934 and U.S. Pat. No. 5,242,828.

Computer-Based Systems and Methods

The invention also provides a variety of computer-related embodiments. Specifically, the automated means for performing the methods described above may be controlled using computer-readable instructions, i.e., programming. Accordingly, in some embodiments the invention provides computer programming for analyzing and comparing a pattern of gene product expression present in a CSF sample obtained from a subject to a library of gene product expression patterns known to be indicative of the presence or absence of a neurodegenerative disease, wherein the comparing indicates the presence or absence of a neurodegenerative disease.

In another embodiment, the invention provides computer programming for analyzing and comparing a first and a second pattern of expression of gene products from CSF samples takes from a subject in at least two different time points, wherein the first pattern is indicative of a neurodegenerative disease. In such embodiments, the comparing provides for monitoring of the progression of the neurodegenerative disease from the first time point to the second time point.

In yet another embodiment, the invention provides computer programming for analyzing and comparing a pattern of gene product expression from CSF sample to a library of gene product expression patterns known to be indicative of the presence or absence of AD, PD and DLB, wherein the comparing providing a differential diagnosis between AD, PD, and DLB.

The methods and systems described herein can be implemented in numerous ways. In one embodiment of particular interest, the methods involve use of a communications infrastructure, for example the internet. Several embodiments of the invention are discussed below. It is also to be understood that the present invention may be implemented in various forms of hardware, software, firmware, processors, or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site (e.g., at a service provider's facility).

For example, during or after data input by the user, portions of the data processing can be performed in the user-side computing environment. For example, the user-side computing environment can be programmed to provide for defined test codes to denote platform, carrier/diagnostic test, or both; processing of data using defined flags, and/or generation of flag configurations, where the responses are transmitted as processed or partially processed responses to the reviewer's computing environment in the form of test code and flag configurations for subsequent execution of one or more algorithms to provide a results and/or generate a report in the reviewer's computing environment.

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which generally includes test data (e.g., specific gene products assayed), and test result data (e.g., the pattern of gene product expression for a sample). This information received can be stored at least temporarily in a database, and data analyzed in comparison to a library of gene product expression patterns known to be indicative of the presence or absence of a neurodegenerative disease, including PD, AD, and DLB, as described above.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include email, interactive television, and the like. In an embodiment of particular interest, all or a portion of the input data and/or all or a portion of the output data (e.g., usually at least the library of gene product expression patterns known to be indicative of the presence or absence of a neurodegenerative disease) are maintained on a server for access, preferably confidential access. The results may be accessed or sent to professionals as desired.

A system for use in the methods described herein generally includes at least one computer processor (e.g., where the method is carried out in its entirety at a single site) or at least two networked computer processors (e.g., where gene product expression data for a CSF sample obtained from a subject is to be input by a user (e.g., a technician or someone performing the activity assays)) and transmitted to a remote site to a second computer processor for analysis (e.g., where the pattern of gene expression is compared to a library of gene product expression patterns known to be indicative of the presence or absence of a neurodegenerative disease), where the first and second computer processors are connected by a network, e.g., via an intranet or internet). The system can also include a user component(s) for input; and a reviewer component(s) for review of data, and generation of reports, including detection of neurodegenerative disease, differential diagnosis of PD, AD, and DLB, or monitoring the progression of a neurodegenerative disease. Additional components of the system can include a server component(s); and a database(s) for storing data (e.g., as in a database of report elements, e.g., a library of gene product expression patterns known to be indicative of the presence or absence of a neurodegenerative disease, or a relational database (RDB) which can include data input by the user and data output. The computer processors can be processors that are typically found in personal desktop computers (e.g., IBM, Dell, Macintosh), portable computers, mainframes, minicomputers, or other computing devices.

The networked client/server architecture can be selected as desired, and can be, for example, a classic two or three tier client server model. A relational database management system (RDMS), either as part of an application server component or as a separate component (RDB machine) provides the interface to the database.

In one embodiment, the architecture is provided as a database-centric user/server architecture, in which the user application generally requests services from the application server which makes requests to the database (or the database server) to populate the activity assay report with the various report elements as required, especially the assay results for each activity assay. The server(s) (e.g., either as part of the application server machine or a separate RDB/relational database machine) responds to the user's requests.

The input components can be complete, stand-alone personal computers offering a full range of power and features to run applications. The user component usually operates under any desired operating system and includes a communication element (e.g., a modem or other hardware for connecting to a network), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe and offers data management, information sharing between clients, network administration and security. The application and any databases used can be on the same or different servers.

Other computing arrangements for the user and server(s), including processing on a single machine such as a mainframe, a collection of machines, or other suitable configuration are contemplated. In general, the user and server machines work together to accomplish the processing of the present invention.

Where used, the database(s) is usually connected to the database server component and can be any device which will hold data. For example, the database can be any magnetic or optical storing device for a computer (e.g., CDROM, internal hard drive, tape drive). The database can be located remote to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc. as desired.

Computer-Readable Storage Media

The invention also contemplates a computer-readable storage medium (e.g. CD-ROM, memory key, flash memory card, diskette, etc.) having stored thereon a program which, when executed in a computing environment, provides for implementation of algorithms to carry out all or a portion of the methods described herein, including detection of neurodegenerative disease, differential diagnosis of PD, AD, and DLB, or monitoring the progression of a neurodegenerative disease. Where the computer-readable medium contains a complete program for carrying out the methods described herein, the program includes program instructions for collecting, analyzing and comparing a pattern of gene product expression patterns from a CSF sample obtained from a subject to a library of gene product expression patterns known to be indicative of the presence or absence of a neurodegenerative disease, and generally includes computer readable code devices for interacting with a user as described herein, processing that data in conjunction with analytical information, and generating unique printed or electronic media for that user.

Where the storage medium provides a program which provides for implementation of a portion of the methods described herein (e.g., the user-side aspect of the methods (e.g., data input, report receipt capabilities, etc.)), the program provides for transmission of data input by the user (e.g., via the internet, via an intranet, etc.) to a computing environment at a remote site. Processing or completion of processing of the data may be carried out at the remote site to provide for detection of neurodegenerative disease, differential diagnosis of PD, AD, and DLB, or monitoring the progression of a neurodegenerative disease. The computer-readable storage medium can also be provided in combination with one or more reagents for carrying out one or more of the activity assays (e.g., control compounds, cells, probes, arrays, or other activity assay test kit components).

Kits

Also provided by the subject invention are kits for practicing the subject methods, as described above, including detection of neurodegenerative disease, differential diagnosis of PD, AD, and DLB, or monitoring the progression of a neurodegenerative disease. The subject kits include at least one or more of: a probe or primer for detection of a marker polynucleotide, a marker polypeptide, or an anti-marker polypeptide antibody. Other optional components of the kit include: restriction enzymes, control primers and plasmids; nucleic acid or polypeptide standards; buffers; reaction mixtures (e.g., for carrying out the assay); enzymes (e.g., DNA polymerase, reverse transcriptase, and the like); cells; and the like. The various components of the kit may be present in separate containers or certain compatible components may be precombined into a single container, as desired.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

The following methods and materials are used in the examples below.

Chemicals and Antibodies

All reagents were purchased from Sigma Aldrich (St. Louis, Mo.) unless otherwise specified. Antibody list: Apolipoprotein (Apo)CI (goat anti-human, Biodesign International, Kennebunkport, Me.); ApoD (mouse monoclonal; Vision Biosystems, Norwell, Mass.); ApoH (rabbit polyclonal, Accurate Chemical & Scientific Corporation, Westbury, N.Y.); calcium/calmodulin-dependent protein kinase IIB isoform 8 (Ca/CaMKIIB; rabbit polyclonal, Stratagen, Cedar Creek, Tex.); ceruloplasmin (sheep polyclonal, Abcam, Cambridge, Mass.), chromogranin B (rabbit polyclonal, Abcam); Cu/Zn superoxide dismutase (Cu/Zn SOD; mouse anti-human, Calbiochem, La Jolla, Calif.); β-fibrinogen (goat polyclonal, Santa Cruz Biotechnology, Santa Cruz, Calif.); furin convertase (MON-148; mouse monoclonal, Alexis Biochemicals, San Diego, Calif.); α-1B-glycoprotein (A1BG; rabbit polyclonal, Aviva Systems Biology, San Diego, Calif.); haptoglobin (chicken polyclonal, Abcam), osteonectin (SPARC; mouse anti-human, Haematologic Technologies, Essex Junction, Vt.); semaphorin 7A (CDW108; mouse monoclonal, Chemicon International, Temecula, Calif.); T-cadherin (H-126; rabbit polyclonal, Santa Cruz Biotechnology); and vitamin D binding protein ((VitD BP) or Gc-globulin (chicken polyclonal; GenWay Biotech, San Diego, Calif.). Secondary antibodies included rabbit anti-chicken IgG-HRP, rabbit anti-sheep IgG-HRP, rabbit anti-goat IgG-HRP, and goat anti-rabbit IgG-HRP (Sigma-Aldrich). Rabbit anti-mouse IgG-HRP was purchased from Abcam.

Patients

All individuals underwent evaluation that consisted of medical history, physical and neurologic examinations, laboratory tests, and neuropsychological assessment. Laboratory evaluation included complete blood count: serum electrolytes, blood urea nitrogen, creatinine, glucose, vitamin B12, and thyroid stimulating hormone; all results were within normal limits. A brief summary on inclusion and exclusion criteria is provided below for normal controls as well as patients with AD, PD or DLB. Demographic information is listed in Table 1 for all subjects/patients.

TABLE 1

Characteristics of patients and age-matched controls

| | | M:F Ratio | Age (Mean ± SD) | MMSE (Mean ± SD) | Time of CSF Tap to Autopsy (years) |
|---|---|---|---|---|---|
| Control | 10 | 7:3 | 67 ± 6 | 29.3 + 0.68 | NA |
| AD | 10 | 6:4 | 72 ± 9 | 13.1 + 6.87 | 2.38 + 1.52 |
| PD | 10 | 7:3 | 63 ± 7 | 29.7 + 0.36 | NA |
| DLB | 5 | 5:0 | 69 ± 11 | 19.9 + 5.47 | 2.51 + 0.71 |

Normal aged controls: The control subjects were community volunteers in good health. Neuropsychological evaluation included: the Mini-Mental State Exam (MMSE) (Folstein et al., J Psychiatr Res, 1975. 12(3): p. 189-98), Trail-Making Tests A and B (Reitan et al., Percept Mot Skills, 1958. 8: p. 271-276). Clinical Dementia Rating Scale (CDR (Morris, Int Psychogeriatr, 1997. 9(Suppl 1): p. 173-6; discussion 177-8)), the Mattis and Coblentz Dementia Rating Scale score (DRS (Mattis et al., , S. and J. Coblentz, *Mental status examination for organic mental syndrome in the elderly patient*. Geriatric psychiatry: A handbook for psychiatrists and primary care physicians, ed. L. Belleck and T. Karasu. 1976, New York: Grune and Stratton. 77-121)) and -the New York University (NYU) version of the Logical Memory II subscale (Immediate and Delayed Paragraph Recall) from the Wechsler Memory Scale—Revised (Flicker et al., Neurology, 1991. 41(7): p. 1006-9). Control subjects had no signs or symptoms suggesting cognitive decline or neurologic disease; all subjects had a MMSE score between 28 and 30; a CDR score of 0, and NYU paragraph recall scores (immediate and delayed)>6. Exclusion criteria also included heavy cigarette smoking (more than 10 packs/year), alcohol use other than socially, and any psychotherapeutic use. Finally, it should be emphasized that although no pathological confirmation had been obtained in any of these subjects, all of them had been followed for approximately three years without demonstrating any symptoms or signs of neurological disorders, including mild cognitive impairment (MCI).

AD: Patients were diagnosed with probable AD according to NINDS-ADRDA criteria confirmed by a clinical team consensus conference at the Oregon Aging and Alzheimer's Disease Research Center and concurred by investigators at the UW-Alzheimer's Disease Search Center. One important aspect of this study was that only subjects with post-mortem pathological confirmation of AD according to NIA-Ragan criteria (high) were included in this study. CSF was collected during life and maintained at −70° C. until analysis. The average time from CSF collected to autopsy was 2.8 years (also see Table 1).

PD: Only clinically probable PD patients defined with NINDS criteria, which is based on those described by Drs. Calne (Calne et al., Ann Neurol, 1992. 32(Suppl): p. S125-7) and Gelb (Gelb et al., Arch Neurol, 1999. 56(1): p. 33-9), were included. Essentially, patients were required to have three Group A signs, i.e. resting tremor, bradykinesia, rigidity and asymmetric onset, and have sustained response to levodopa or a DA agonist. Patients with the following features (Group B signs) were excluded: 1) prominent postural instability in the first three years after symptom onset, 2) freezing phenomenon in the first three years, 3) hallucinations unrelated to medications in the first three years, 4) dementia preceding motor symptoms or in the first year, 5) supranuclear gaze palsy (other than restriction of upward gaze) or slowing of vertical saccades, 6) severe, symptomatic dysautonomia unrelated to medications, and 7) documentation of a condition known to produce parkinsonism and plausibly connected to the patient's symptoms (such as suitably located focal brain lesions or neuroleptic use within the past six months). Please note, like the control patients, all of these patients were still alive at the time of proteomic analysis, i.e. no pathological confirmation of PD had been obtained yet. Nonetheless, all patients included in this study had sustained response to DA drugs for at least three years and there was no need to revise clinical diagnosis on any of these patients after follow-up evaluation when this manuscript was written.

DLB: These patients were initially diagnosed with probable AD according to NINDS-ADRDA criteria, but each developed parkinsonism, fluctuation cognition, and visual hallucinations, characteristic of DLB, shortly after CSF was obtained, yielding a revised diagnosis clinically. As mentioned early, as sensitivity and specificity of clinical criteria for DLB diagnosis are not high (McKeith et al., Semin Clin Neuropsychiatry, 2003. 8(1): p. 46-57), only subjects with post-mortem pathological confirmation of DLB were included in this study. More specifically, all subjects had AD pathology in addition to cortical Lewy bodies. One caveat is that some pathologists may classify this entity as a Lewy body variant of AD (LBV-AD). Another major variant of DLB is dementia cases with diffuse Lewy bodies in the cortex in the absence of AD pathology, which overlaps with PD plus dementia both clinically and pathologically. Finally, it should be noted that this group of patients was hardest to obtain, particularly when the quality of CSF was taken into consideration (see below), and thus this study was limited to include only five DLB cases.

Collection of CSF and Quality Control

Following written informed consent, individuals were placed in the lateral decubitus position and the L4-5 interspace was infiltrated with 1% lidocaine. Lumbar puncture (LP) was performed with a 20 g or 24 g spinal needle. Individuals remained at bed rest for one hour following LP. All CSF for proteomic analysis was taken from the $15^{th}$ to $25^{th}$ ml collected to limit variations arising from rostral-caudal gradient. In addition, all LP was performed in the morning to limit potential circadian fluctuation of CSF proteins and metabolites.

The protein concentration in CSF is relatively low compared to plasma (CSF:plasma=1/20), and in addition, the protein profiles in CSF are similar to those in plasma (Blennow et al., Eur Neurol, 1993. 33(2): p. 129-33), suggesting that even a minor contamination of CSF with blood could significantly confound the interpretation of quantitative proteomic analysis of CSF. To minimize blood contamination in the CSF samples, only CSF samples with <10 RBCs/ml and a serum: CSF ApoB (a protein not generated in CNS) ratio >6000 were included in this study. This approach has been utilized successfully in previous CSF proteomics studies (Zhang et al., Neurobiol Aging, 2005. 26(2): p. 207-27; Zhang et al., J Alzheimers Dis, 2005. 7(2): p. 125-33).

Sample Preparation Before Proteomic Analysis

Previous experience has shown that extensive analysis of well-characterized pooled samples is more productive than analyzing individual samples. This is largely due to the limitation of current MS technology, i.e. a low reproducibility when an identical sample is analyzed multiple times (Zhang et al., Neurobiol Aging, 2005. 26(2): p. 207-27; Zhou et al., J Biol Chem, 2004. 279(37): p. 39155-64). For example, if profiling is done with an individual sample, when a marker is identified in one individual (e.g. an AD patient) but not the other, there is no way of telling whether it is due to the nature of the subject/patient or variation in ionization of MS unless an independent validation process is performed, which is not currently available in a high throughput manner. To circumvent this difficulty, the following strategy was adopted: discovering potential biomarkers with pooled samples (diseased vs. controls) with extensive chromatographic separation of peptides and multiple injections to reach the "bottom of the iceberg". After potential biomarkers are identified, individual samples were confirmed and/or validated to achieve information related to the sensitivity and specificity of each marker (Zhang et al., Neurobiol Aging, 2005. 26(2): p. 207-27; Zhang et al., J Alzheimers Dis, 2005. 7(2): p. 125-33). Hence, in the current study, in discovery phase CSF samples were pooled from 10 AD, 10 PD, 5 DLB, and 10 controls before proteomic analysis.

The other issue related to CSF proteomics has to do with its unique profiles, i.e. overtly enriched in albumin and immunoglobulins (IgGs) (Blennow et al., Eur Neurol, 1993. 33(2): p. 129-33) with a dynamic range of protein concentrations $\sim 10^9$ as opposed to a dynamic range of $\sim 10^8$ for typical cell lysates (Corthals et al., Electrophoresis, 2000. 21(6): p. 1104-15). Because all current proteomic techniques are inheritably biased toward abundant proteins (Yuan et al., Electrophoresis, 2002. 23(7-8): p. 1185-96), fractionation of CSF is required before detailed proteomic analysis of CSF can be achieved. Thus, a graduated organic fractionation approach was followed that was recently developed to process CSF before standard MudPIT analysis of CSF proteins (Zhang et al., Neurobiol Aging, 2005. 26(2): p. 207-27). Briefly, pooled CSF was mixed with 1.5 volume of acetonitrile (ACN) first to generate the first pellet (P1), and then the supernatant was further mixed with final 3.0 volume of ACN to generate the second pellet (P2) and a supernatant (S2), which was dialyzed with a porous (500 D) membrane to desalt. With this approach, more than 90% of albumin and IgGs are found in the first pellet (Zhang et al., Neurobiol Aging, 2005. 26(2): p. 207-27).

iTRAQ Labeling and Two Dimensional Liquid Chromatography

Three fractions from each pooled CSF sample, i.e. P1, P2, and S2, were matched across all four groups of patients/subjects, forming three iTRAQ experiments. Briefly, 100 µg protein from each corresponding fraction (e.g. P1 fraction from AD, PD, DLB and controls) was digested in parallel with trypsin and then labeled with one of the four-iTRAQ™ reagents following the manufacturer's instructions. Next, four samples labeled with iTRAQ reagents were combined (a total of 400 g proteins), and loaded onto a strong cation exchange (SCX) column (0.5 mm×200 mm) that had been equilibrated in 0.05% formic acid/20% ACN and pH 3.0 (buffer A) at a flow rate of 200 µl/min. Peptides were eluted by applying a linear gradient from 0 to 100% buffer B (500 mM ammonium formiate/20% ACN, pH 3.0). 11 fractions were collected from each sample and dried down in a SpeedVac (Thermo Savant, Holbrook, N.Y.).

SCX fractionated peptides from each sample were then dissolved in 0.5% trifluoroacetic acid (TFA) and separated using reverse phase (RP) chromatography. Nano-capillary liquid chromatography (LC) was performed using the LC Packings UltiMate™ with Famos™ autosampler and Switchos™ automated switching valve (LC Packings, Sunnyvale, Calif.). Samples were loaded onto a capillary precolumn cartridge (Dionex, Sunnyvale, Calif.). The trap column was washed with mobile phase A containing 2% ACN and 0.1% TFA in HPLC water. The flow rate was set at 0.4 µl/min. The sample was then loaded onto a 15 cm×100 µm ID Magic C18 3 µm, 100-angstrom packing capillary LC column (Michrome BioResources Inc., Auburn, Calif.). The gradient run was from 5% mobile phase B (80% ACN, 20% HPLC water, 0.08% TFA) to 90% mobile phase B for 85 minutes. The eluted gradient was mixed with 7 mg/ml re-crystallized α-cyano-4-hydroxycinnamic acid (Sigma) in 60% ACN, 2.6% (5 mg/ml) ammonium citrate with internal standard (AB's 4700 Mass Standard Kit) and spotted onto a stainless steel MALDI plate with the Probot™ (LC Packings). Samples were spotted at 5-seconds intervals using a 24×24 array pattern for a total of 576 spots per plate. In total, 36 LC MALDI plates were spotted and analyzed by a 4700 Proteomic System.

MS Analysis and Protein Identification

Quantitative MS analysis was carried out using the 4700 Proteomics Analyzer with TOF/TOF Optics (Applied Biosystems or AB, Foster City, Calif.). MS reflector positive ion mode with automated acquisition of 800-4000 m/z range was used with 1000 shots per spectrum. A maximum of 15 peaks were selected per spot, with a minimum signal-noise (S/N) ratio of 75 and cluster area of 500. Greater than 36000 precursors were selected and were submitted for MS/MS, where a positive ion mode with CID cell on and 1 kV collision energy were used, and 3000 shots accumulated per spectrum. For each spotted plate, a total of 576 MS, and more than 1200 MS/MS spectra, were acquired. Identification of proteins was achieved using Mascot (Matrix Science, Boston, Mass.) algorithm and searched against the International Protein Index (IPI; Version 3.01), a database also used in one of the recent studies of human CSF (Xu et al., Int. Rev. of Neurobiol, 2005). In addition, protein identification was determined with a newer version of the IPI database (3.10) as well as with the Celera Discovery System™ database (20050302) that is typically used by AB's 4700 Proteomic System. Finally, identified proteins were further filtered by ProteinProphet, a program routinely used in the lab to enhance the accuracy of protein identification. Protein quantification was achieved by averaging ratios of all peptides of each identified protein; normalization, assuming a Gaussian distribution with median of 1 when all peptides were considered between control and experimental groups, was performed before ratios were calculated.

Western Blot

Western blot analysis was performed as described previously (Andreasen, et al., Clin Neurol Neurosurg, 2005. 107 (3): p. 165-73) with minor modifications. In brief, equal amounts of human CSF proteins (and equal volumes as well for pooled samples) were run on SDS/PAGE Tris-HCl Criterion Gels (Bio-Rad Laboratories, Hercules, Calif.) under reducing conditions, transferred to PVDF membranes (Bio-Rad), blocked, and probed overnight at 4° C. with primary antibodies of ApoC1 (1:2000), ApoD (1:10000), ApoH (1:1000), A1BG (1:10000), chromogranin B (1:10000), Ca/CaMKIIB (1:500), ceruloplasmin (1:2000), β-fibrinogen (1:2000), furin (1:5000), haptoglobin (1:2000), semaphorin 7A (1:500), SPARC (1:5000), Cu/Zn-SOD (1:10000), T-cadherin (1:250), or VitD BP (1:4000). The secondary antibodies were added, and detected by enhanced chemiluminescence or by ECL plus western blotting detection system (Amersham Biosciences, N.J.). Relative levels of each protein were quantified by measuring optical densities (OD) of the corresponding bands compared to a pooled sample containing all cases. Protein concentration of the CSF was determined by the Bradford method with bovine serum albumin (Pierce, Ill.) as the standard.

Quantifying the Diagnostic Ability of Candidate Markers

Quantifying the diagnostic ability of a single marker: The performance of each of the eight confirmed candidate markers was evaluated both graphically and statistically with receiver operating characteristic (ROC) curve methods. ROC curves associate the sensitivity of a diagnostic test to the entire range of the possible false positive rate (FPR). The FPR is equal to one minus the test specificity. The area under the ROC curve (AUC) indicates the average sensitivity of a marker over the entire ROC curve. The sensitivity of each marker was computed at 95% specificity. Establishing statistical significance of a single marker was performed by the Wilcoxon rank-sum test, which evaluates the significance of the entire ROC curve. To aid interpretation of the data when comparing markers, raw data was transformed with the natural log so their behavior among healthy subjects more accurately reflected a normal distribution with a mean of 0 and unit standard deviation (McIntosh et al., Gynecol Oncol, 2004. 95(1): p. 9-15). Standardization of the markers, which leaves the ROC curves unchanged, also facilitates the comparison of two different markers because the units of measurement are now similar, i.e. the number of standard deviations above the average normal subject.

Combining markers: After the eight candidate markers were ranked based on the sensitivity at 95% specificity, p-value from Wilcoxon rank-sum test, and the area under curve (AUC) value, the top five markers were chosen for calculation of composite markers (CM). This was accomplished by evaluating a linear combination, which can be easily interpreted, or by the weighting of any two standardized markers from the top five markers identified. Logistic regression was used to optimize marker combination and estimate the weights. Logistic regression has several theoretical properties that make it convenient for applied biomarker research (McIntosh et al., Biometrics, 2002. 58: p. 657-664). For instance, its P values evaluate whether the marker combination, compared to the single marker, significantly increases the "distance" between cases and controls. If the model is correctly specified, the sensitivity of the resulting CM is maximized at all specificities simultaneously, although the theoretically correct model cannot ever be known in practice. After establishing significance, resulting ROC curves were then examined to evaluate the quality of the composite marker.

Example 1

CSF Proteome

Using pooled, well characterized CSF samples and multi-dimensional peptide separation techniques, followed by 4700 TOF-TOF analysis, a total of 1,540 proteins were identified (FIGS. 6A-6T and FIGS. 7A-V). Of these, 804 were called single hits (FIGS. 7A-V). Single-hits refers to the fact that a protein is identified from the MS/MS spectrum of a single peptide and is therefore judged as being less reliably identified than those proteins identified with multiple peptide tandem mass spectra. Nonetheless, all protein identification was based on meeting the criteria of having at least one peptide whose individual score was above the 95% confidence interval threshold (p<0.05) and also identified as the top-ranked matching sequence for that spectrum. Furthermore, all proteins also had a probability of being more than 95% correct as determined by ProteinProphet.

When the list of identified proteins was compared to the previous analysis of human CSF, where close to 1,000 proteins were identified (Xu et al., Int. Rev. of Neurobiol, 2005) using the same database, 449 of those proteins were identified again in the current study. To state it differently, 1,091 new proteins were identified in the current study, thereby increasing the total identified CSF proteins to 1,883. Of note was also the observation that 51 proteins identified previously by a single peptide were now identified by more than two peptides. Examples included testican-1 precursor, ApoM, neuroligin 2 precursor, xylosyltransferase 1, and sortilin 1 preprotein. On the other hand, 90 proteins identified previously by more than two peptides were now identified by only a single peptide. These included cathepsin L precursor, collagen alpha 1(III) chain precursor, Mn-SOD, mitochondrial precursor, gelsolin precursor, and peroxiredoxin 2. Thus, technically, the proteins identified by more than two peptides were 1,097 when all of the studies are combined.

Classification of the 1,540 proteins identified in this study, shown in FIG. 1, is based on a modified scheme developed in previous publications (Zhang et al., Neurobiol Aging, 2005. 26(2): p. 207-27; Zhang et al., J Alzheimers Dis, 2005. 7(2): p. 125-33); it includes cell cycle/death, cell structure/motility/transport/traffic, extracellular matrix/adhesion, developmental process, immunity/defense, metabolism, neuronal activities/signal transduction, and unknown functions. However, as demonstrated in Table 2, the database used for protein identification can have a significant role in not only the number of proteins identified but also classifications of proteins (Xu et al., Int. Rev. of Neurobiol, 2005). As a result, IPI 3.01 (a database used in the recent CSF study) was used rather than an updated version IPI 3.10 in this study to make sure the data can be compared meaningfully. However, to further illustrate the contribution of databases on the outcome of protein identification, the identical MS data generated by 10 plates of 1.5P fraction were searched against the updated IPI version (3.10) as well as the newest Celera Discovery System (CDS) database (20050302) that is provided by Applied Biosystems, the manufacturer for the 4700 proteomic station. The results for database comparison are listed in Table 2 with several major points noted below. First, the overlap was only 26.0% between IPI 3.01 and CDS database if common protein names were used, but improved to 86.8% when peptides were considered regardless of protein names. Second, the overlap was much higher between two different versions of IPI database; and, consistent with previous results, the overlap was higher for proteins identified by more than two peptides than those by single peptide. Finally, although the IPI database appears to be maturing, the difference in protein identification between 3.01 and an earlier version (Xu et al., Int. Rev. of Neurobiol, 2005) vs. 3.01 and 3.10 was about the same, i.e. a change in the database when an identical MS data set was used resulted in about 10% difference in protein identification.

TABLE 2

Identification of proteins with the same MS data against different database

| | Proteins Identified | | | Overlap | |
|---|---|---|---|---|---|
| | IPI (3.01) | IPI (3.10) | Celera | IPI 3.10 vs. 3.01 | Celera vs. IPI 3.01 |
| Common names | 567 | 559 | 782 | 62.9% | 26.0% |
| Two peptides | 250 | 291 | 569 | 65.4% | 30.5% |
| Single peptide | 317 | 268 | 213 | 58.9% | 23.2% |
| Peptides regardless of protein name | 1584 | 1759 | 1506 | 96.7% | 86.8% |

Compared with previous results, 1,091 new proteins were identified, expanding the total CSF proteome to 1,883 proteins, the most. extensive characterization of human CSF proteins today. The significant increase in the number of protein identification in this study largely resulted from two major factors, namely better separation of peptides by extensive chromatography and utilization of a more advanced MS instrument. The advantage of using better instrumentation is obvious, regardless of proteomic platforms used. Extensive chromatography is essential in LC based proteomics, even when MudPIT is used, as complex samples usually yield hundreds of thousands of peptides after proteins are digested. This issue is especially challenging in proteomic analysis of CSF or plasma, where albumin and IgGs constitute more than 75% of total proteins (Blennow et al., Eur Neurol, 1993. 33(2): p. 129-33), i.e. unless peptides are separated well, protein identification by MS will be centered on abundant proteins. Here, extensive peptide separation was achieved by utilizing two consecutive processes: 1) perform RP separation with a nano-capillary LC system that increases sensitivity by at least 10 fold as compared to a conventional microcapillary LC system, resulting in less peptides eluted onto each MALDI plate; and 2) spot each LC run to 24×24 (576) arrays on an MALDI plate instead of a standard 198 spot array, thereby further separating peptides. Good peptide separation is evidenced by the fact that more than 400 (417 to be precise) proteins were identified in 1.5P fraction, notwithstanding it was overtly enriched in albumin and IgGs (Zhang et al., Neurobiol Aging, 2005. 26(2): p. 207-27).

The significance of extensive identification of the human CSF proteome is apparent, as it not only expands substantially the current knowledge regarding human CSF proteins, but also supplies the necessary information to appropriately interpret protein biomarkers of age-related neurodegenerative diseases. In addition, the impact of this data goes beyond neurodegenerative diseases because intense interest has also been expressed in other CNS diseases, including multiple sclerosis (Hammack et al., Mult Scler, 2004. 10(3): p. 245-60), acute brain injury (Siman et al., Neurobiol Dis, 2004. 16(2): p. 311-20), and CNS tumors (Zheng et al., J Neuropathol Exp Neurol, 2003. 62(8): p. 855-62).

Example 2

Chances in CSF Proteome Associated with AD, PD, and DLB

Individual quantification of the identified peptides were based on the individual ratios from signature ion peak areas of the iTRAQ reagents tags of the identified peptides from AD, PD and DLB samples compared with the healthy individuals' signature ion peak areas. Peptide ratios from each protein were grouped and averaged together to give protein level modulations ratios for 1,520 identified proteins. Modulated proteins were found to be involved in several biological processes such as cellular metabolism, immunity and defense, signal transductions and neural activities, and synaptic transmissions. Some of these modulations exceeded two or three folds up or down. As the first step towards selecting candidate proteins for further study, changes with more than 50% increase or decrease were defined as significant. Changes that were less than <20% and >20% but less than 50% were defined as non-significant and ambiguous, respectively.

With these criteria, AD, PD, and DLB patients had a total of 388, 282, and 380 proteins that displayed significant changes from controls. Next, the focus was further narrowed on the protein markers that were unique only to AD, PD, or DLB. For instance, a protein marker, e.g. calreticulin precursor (IPI00020599), was excluded if it were significantly increased not only in AD vs. controls but also PD vs. controls. It should be noted, however, if a marker, e.g. DJ977L11.1 (IPI00478622), displayed a significant increase in AD vs.

controls, but a decrease in PD vs. controls, the marker was considered not only unique to AD but also to PD. With this approach, 154, 81, and 113 proteins were identified that were uniquely altered with AD, PD and DLB, respectively (FIGS. 5A-5YY).

Example 3

Confirmation of Candidate Protein Markers for Each Neurological Disease

As demonstrated by data presented in Table 2, the numbers, as well as the types of proteins identified changed significantly when the database was altered. Given that none of the current databases is complete, it is imperative to confirm candidate protein markers not only for their identifications but also for their quantifications as determined by proteomics with alternative means before extensively pursuing their utilities in clinical diagnosis. Currently, there is no high throughput method available for this purpose, so consequently, Western blot analysis was used achieve this goal. Several criteria were used in selecting candidate proteins for further confirmation, including: 1) proteins had to be identified by more than two unique peptides; 2) markers should be unique to each disease, i.e. a marker common to two diseases was not considered; 3) markers with known biological functions were preferred; 4) markers identified by both IPI and Celera database were preferred with exception of those with appealing biological functions; and 5) commercial antibodies needed to be available. With these caveats in mind, 15 antibodies were purchased and tested initially with pooled samples that were also used for proteomic analysis. The antibodies chosen were A1BG, ApoCI, ApoC-III, ApoD, ApoH, Ca/CaMKIIB, ceruloplasmin, chromogranin B, β-fibrinogen, furrin, haptoglobin, semaphorin 7A precursor, sparc (osteonectin), Cu/Zn-SOD, T-cadherin, and VitD BP.

Among the 15 antibodies tested with pooled samples, only 8 of them were confirmed not only with respect to their identification, i.e. a distinct band was observed in human CSF at appropriate molecular weight for each marker, but also their quantification, meaning that quantitative changes as determined by Western blot were consistent with proteomic assessment for at least one of the diseases. These markers were ApoCI, ApoH, ceruloplasmin, chromogranin B, β-fibrinogen, haptoglobin, T-cadherin, and VitD BP. Western blot results are shown for β-fibrinogen as an example in FIG. 2, panel A, where quantification was performed with samples being normalized to the amount of protein as well as CSF volume.

To calculate the sensitivity/specificity for each marker in their ability of differentiating one disease from controls or from each other, all eight antibodies were then studied in individual samples. Of note, these samples were saved before pooled samples were generated for proteomic analysis and initial confirmation with Western blot analysis mentioned above. The results on Western blot analysis on individual samples is summarized in Table 3, and an actual gel blot is shown in FIG. 2 panel B, again for β-fibrinogen as an example with the samples being normalized to the amount of proteins loaded only. Notably, data shown in Table 3 was obtained initially by correcting the OD value of each band to a pooled sample containing all testing samples and run on the same gel. Next, the data was transformed to percent of controls for the sake of ease of comparison with proteomic data. As seen in the Table 3, Western quantification of each marker correlated with proteomic analysis reasonably well, with exception of chromogranin B and T-cadherin, meaning that the results obtained in pooled samples were not replicated in individual ones when tested with Western blot using these two antibodies. It should be emphasized, though, that a 20% decrease in a protein, e.g. ApoH, in PD patients does not necessarily disagree with a 50% decrease as determined by proteomic analysis. This is for the reason that the dynamic range of a Western blot is not as good as MS analysis, particularly when there is no purified antigen to optimize the Western blot run and establish a standard curve from which each band can be quantified more reasonably.

TABLE 3

Measurements of each markers in individual cases

| Protein | AD | PD | DLB | Control |
|---|---|---|---|---|
| Apo H | 1.29 | 1.07 | 1.33 | 1.30 ± 0.036 |
|  | [0.99] | [0.82] | [1.02] |  |
|  | (↑) | (↓↓) | (*) |  |
| Apo C1 | 1.83 | 1.89 | 1.49 | 2.06 ± 0.49 |
|  | [0.89] | [0.92] | [0.72] |  |
|  | (*) | (*) | (↓↓) |  |
| Ceruloplasmin | 1.07 | 0.90 | 1.00 | 1.06 ± 0.031 |
|  | [1.01] | [0.85] | [0.94] |  |
|  | (*) | (↓↓) | (*) |  |
| Chromogranin B | 1.14 | 1.20 | 1.01 | 1.18 ± 0.071 |
|  | [0.97] | [1.02] | [0.86] |  |
|  | (↓↓) | (↑) | (*) |  |
| β-Fibrinogen | 1.28 | 1.07 | 1.05 | 0.95 ± 0.035 |
|  | [1.35] | [1.13] | [1.11] |  |
|  | (↑↑) | (*) | (*) |  |
| Haptoglobin | 2.40 | 1.75 | 1.16 | 0.95 ± 0.033 |
|  | [2.53] | [1.84] | [1.22] |  |
|  | (↑↑) | (↑) | (*) |  |
| T-Cadherin | 1.28 | 1.10 | 1.13 | 1.12 ± 0.077 |
|  | [1.14] | [0.98] | [1.01] |  |
|  | (*) | (*) | (↓↓) |  |
| Vit-D BP | 1.45 | 1.03 | 0.98 | 1.19 ± 0.082 |
|  | [1.22] | [0.87] | [0.82] |  |
|  | (*) | (↓↓) | (*) |  |

Values (mean ± SE) for each marker are calculated first by correcting OD of each distinct band with the OD of the same band derived from a pooled sample containing all cases and run on the same gel.
Value expressed in [ ] are derived from the raw data divided by the mean of control cases shown in the last column, i.e. expressed as percent of controls. The rationale behind data transformation was to replicate the way that proteomic data were obtained.
↑↑: Proteomic changes greater than 50% as compared to controls;
↑: Proteomic changes greater than 20% but less than 50% as compared to controls;
*Proteomic changes less than 20% as compared to controls.

Example 4

Calculation of Sensitivity of Each Marker

Table 4 summarizes the overall discrimination ability of each marker (its AUC) to classify different diseases and controls, their ROC Curves, and the P values from Wilcoxon sum-rank tests. It appeared that two markers, i.e. β-fibrinogen and VitD BP, can differentiate AD from controls as well as other diseases with AUC as 78% and 88%, respectively, and 40% to 50% sensitivity at 95% specificity. Both Wilcoxon p values are less than 0.05. Similarly, ApoH and ceruloplasmin appeared to be able to segregate PD from controls and other diseases very well. ApoH has the largest AUC and the smallest P value over the eight markers: AUC=87%, P value=0.004, and sensitivity at 95% specificity=67%. Ceruloplasmin was the next best maker with AUC=77%, P value=0.03 and sensitivity at 95% specificity=56%. However, none of the eight markers are statistically significant predictors of DLB over control or other diseases. Their Wilcoxon P values range from 0.07 to 0.9, probably because the small sample size tested for DLB cases (five for discovery and four for confirmation).

does not necessarily mean it will perform better when the combination approach is taken. This can be illustrated in PD markers, where both ApoH (67%) and ceruloplasmin (56%)

TABLE 4

Summaries of ROC curves for the eight markers

| | Case Group | | | | | | | | |
|---|---|---|---|---|---|---|---|---|---|
| | AD | | | | PD | | | DLB | |
| Control Group | PD | DLB | CT | Non-AD | DLB | Cont | Non-PD | CT | Non-DLB |
| Apo C1 | | | | | | | | | |
| AUC | 0.478 | 0.625 | 0.633 | 0.536 | 0.667 | 0.605 | 0.495 | 0.667 | 0.656 |
| Sense (0.95) | 0.000 | 0.100 | 0.000 | 0.000 | 0.222 | 0.000 | 0.000 | 0.000 | 0.250 |
| Wilcoxon P value | 0.659 | 0.536 | 0.360 | 0.984 | 0.412 | 0.489 | 0.740 | 0.412 | 0.354 |
| Apo H | | | | | | | | | |
| AUC | 0.806 | 0.550 | 0.525 | 0.610 | 0.861 | 0.944 | 0.869 | 0.391 | 0.593 |
| Sense (0.95) | 0.600 | 0.400 | 0.300 | 0.100 | 0.778 | 0.778 | 0.667 | 0.250 | 0.250 |
| Wilcoxon P value | 0.038* | 0.835 | 0.896 | 0.329 | 0.078 | 0.008* | 0.004* | 0.461 | 0.580 |
| Chromogranin B | | | | | | | | | |
| AUC | 0.611 | 0.750 | 0.574 | 0.525 | 0.847 | 0.525 | 0.621 | 0.806 | 0.801 |
| Sense (0.95) | 0.111 | 0.556 | 0.000 | 0.111 | 0.667 | 0.000 | 0.111 | 0.000 | 0.000 |
| Wilcoxon P value | 0.438 | 0.214 | 0.603 | 0.779 | 0.101 | 0.862 | 0.315 | 0.131 | 0.073 |
| Ceruloplasmin | | | | | | | | | |
| AUC | 0.772 | 0.708 | 0.457 | 0.672 | 0.667 | 0.809 | 0.765 | 0.722 | 0.440 |
| Sense (0.95) | 0.444 | 0.444 | 0.111 | 0.444 | 0.556 | 0.556 | 0.556 | 0.000 | 0.000 |
| Wilcoxon P value | 0.811 | 0.336 | 0.728 | 0.168 | 0.413 | 0.041* | 0.030* | 0.270 | 0.620 |
| Fibrinogen | | | | | | | | | |
| AUC | 0.733 | 0.725 | 0.844 | 0.777 | 0.556 | 0.756 | 0.493 | 0.722 | 0.531 |
| Sense (0.95) | 0.500 | 0.500 | 0.600 | 0.500 | 0.333 | 0.444 | 0.000 | 0.250 | 0.000 |
| Wilcoxon P value | 0.111 | 0.251 | 0.023* | 0.020* | 0.821 | 0.095 | 0.967 | 0.270 | 0.888 |
| Haptoglobin | | | | | | | | | |
| AUC | 0.594 | 0.675 | 0.811 | 0.702 | 0.667 | 0.815 | 0.600 | 0.722 | 0.545 |
| Sense (0.95) | 0.300 | 0.500 | 0.600 | 0.300 | 0.333 | 0.667 | 0.000 | 0.250 | 0.000 |
| Wilcoxon P value | 0.496 | 0.375 | 0.038* | 0.087* | 0.413 | 0.041 | 0.364 | 0.270 | 0.800 |
| T-cadherin | | | | | | | | | |
| AUC | 0.622 | 0.625 | 0.589 | 0.609 | 0.556 | 0.549 | 0.578 | 0.500 | 0.554 |
| Sense (0.95) | 0.200 | 0.300 | 0.400 | 0.300 | 0.222 | 0.111 | 0.000 | 0.250 | 0.000 |
| Wilcoxon P value | 0.402 | 0.535 | 0.548 | 0.347 | 0.821 | 0.794 | 0.507 | 0.940 | 0.932 |
| Vit D | | | | | | | | | |
| AUC | 0.950 | 0.975 | 0.767 | 0.880 | 0.555 | 0.685 | 0.758 | 0.778 | 0.777 |
| Sense (0.95) | 0.800 | 0.900 | 0.400 | 0.400 | 0.222 | 0.222 | 0.222 | 0.000 | 0.000 |
| Wilcoxon P value | 0.005 | 0.021* | 0.071 | 0.002* | 0.821 | 0.233 | 0.037* | 0.168 | 0.092 |

AUC denotes the area under ROC curve whereas Sense (0.95) denotes the sensitivity at 95% specificity of the ROC curve. The Wilcoxon sum-rank test with P value less than 0.05 was marked by an asterisk.

The fact that none of the single markers could detect AD, PD or DLB with 100% sensitivity at 95% specificity is expected, simply because all neurodegenerative diseases, including AD, PD, and DLB, are heterogeneous in nature, i.e. subgroups of patients may show different markers. Consequently, whether higher sensitivity could be achieved by combining individual markers was next investigated, and the results, shown in Table 5, appeared to show that this was indeed the case. Several conclusions can be drawn from the results presented in Table 5. First, the combination of two markers could achieve a higher sensitivity than a single marker alone. For instance, at 95% specificity, β-fibrinogen and VitD BD had 50% and 40% sensitivity, respectively, when tested alone in differentiating AD from controls and other diseases; but the sensitivity increased to 100% when the two markers were combined. Second, a better single marker had better sensitivity than chromogranin B (11%) when tested alone; but when ApoH was combined with ceruloplasmin and chromogranin B, respectively, the sensitivity remained the same for ceruloplasmin, but improved to 78% for ApoH when combined with chromogranin B. In addition, both p values were now at or lower than 0.05 after two markers were combined, showing that chromogranin B, not ceruloplasmin, helps ApoH outperform ApoH alone. Furthermore, when VitD BP and ApoC were combined, the sensitivity for differentiating DLB from other diseases also increased to 50% at 95% specificity and with p value for VitD BP as 0.04 and for ApoC as 0.09. Last, but not least, no overt improvement was seen when a third maker was added to composite marker panel. Combination of more than three markers was not pursued to avoid the over-fitting problem in a data set that is underspecified.

TABLE 5

Summaries for composite markers

| | Marker 1 | Marker 2 | AUC | Sense (0.95) | P-value for marker 1 | P-value for marker 2 |
|---|---|---|---|---|---|---|
| AD versus all others | Vit D BP | β-Fibrinogen | 0.99 | 1.00 | 0.0635 | 0.0207 |
| | Ceruloplasmin | β-Fibrinogen | 0.94 | 0.89 | 0.0142 | 0.0199 |
| PD versus all others | ApoH | Chromogranin B | 0.92 | 0.78 | 0.0086 | 0.0560 |
| | Ceuloplasmijn | Chromogranin B | 0.93 | 0.22 | 0.0052 | 0.0203 |
| DLB versus all others | ApoC1 | Chromogranin B | 0.92 | 0.50 | 0.0737 | 0.086 |
| | ApoC! | Vit D BP | 0.86 | 0.50 | 0.0394 | 0.0890 |

AUC denotes the area under ROC curve whereas Sense (0.95) represents the sensitivity at 95% specificity of the ROC curve for CM of marker 1 and 2. P value for marker 1 represents the likelihood ratio P value from logistic regression for marker 1 given marker 2, whereas P value for marker 2 represents the P value of marker 2 given marker 1 in the logistic regression model.

Figure 3:
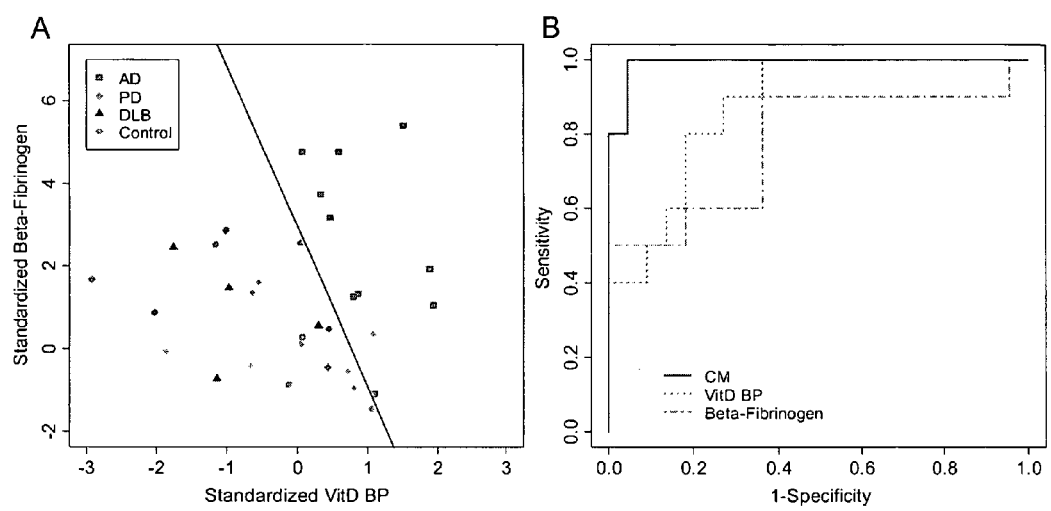
FIG. 3 shows composite markers for AD vs. other neurodegenerative diseases. Panel A is a scatter plot showing the association between standardized β fibrinogen and standardized VitD BP with AD, PD, and DLB cases and healthy controls as well. Line in plot represents the composite marker defined from logistic regression. The actual line represented here gives the classification rule for 95% specificity. Panel B shows ROC curves for VitD BP β fibrinogen and the composite marker (CM). The following statistics are obtained from CM: AUC (area under curve)=0.99; Sensitivity at 95%=1.00 with p-value for VitD BP=0.0635 and p-value for β-fibrinogen=0.0207.
Figure 4:
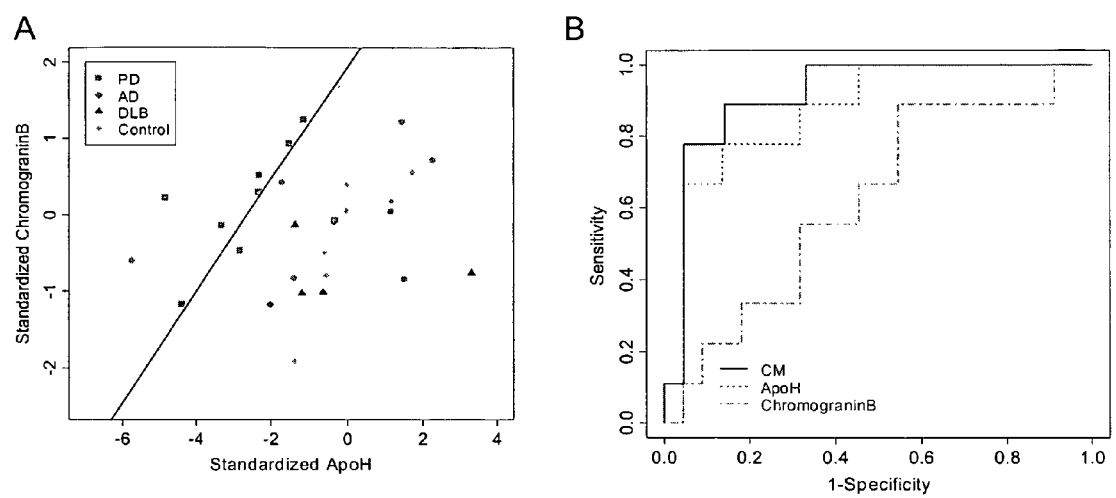
FIG. 4 shows composite markers for PD vs. other neurodegenerative diseases. Panel A is a scatter plot showing the association between standardized Chromogranin B and standardized ApoH with AD, PD and DLB cases and healthy controls as well. Line in plot represents the composite marker defined from the logistic regression. The actual line represented here gives the classification rule for 95% specificity. Panel B: ROC curves for chromogranin B, ApoH and the composite marker (CM). The following statistics are obtained from CM: AUC (area under curve)=0.92; Sensitivity at 95%=0.78 with p-value for chromogranin B=0.0056 and p-value for ApoH=0.0068.

Results on the performance of CM as well as ROC curves for both single and CM are also shown graphically in FIG. 3 and FIG. 4, where the joint behaviors of standardized markers among disease and control groups were displayed. As clearly shown in FIG. 3 and FIG. 4, the ability of CM to separate AD or PD from other diseases or healthy controls with higher sensitivity at high specificity was better when two dimensions instead of one was used. Similarly, both ROC curve plots show the improvement of sensitivity over all the ranges of specificity of CM compared to each individual marker. The statistical significance of the logistic regression proves that both markers are significant and important contributors to the resulting CM ROC curve.

Many candidate markers were discovered for AD patients in this study. As many groups, including us, have investigated AD CSF markers in the past with proteomic approaches (Zhang et al., J Alzheimers Dis, 2005. 7(2): p. 125-33; Puchades et al., Brain Res Mol Brain Res, 2003. 118(1-2): p. 140-6; Carrette et al., Proteomics, 2003. 3(8): p. 1486-94; Blennow et al., Expert Rev Mol Diagn, 2005. 5(5): p. 661-72; and Choe et al., Electrophoresis, 2002. 23(14): p. 2247-51), one would wonder how the current results compare with those reported in the literature. A fair comparison between the results with those of other groups is very hard. This is because there are many variables involved in proteomic studies, including difference in sample preparation, quality control of CSF samples (potential blood supplement in particular), patient population, proteomic platforms used, criteria used for protein identification, whether identified proteins have been confirmed or validated, and type of database used, which is a critical issue as demonstrated in this and previous studies (Xu et al., Rev. of Neurobiol, 2005). Nonetheless, all of the results generated by all platforms of proteomics were compiled in Table 7, demonstrating, as expected, that only a very small fraction of proteins change in the same direction, whether increase or decrease in AD vs. controls, among all or most studies. The increased proteins are albumin precursor, amyloid beta A4 protein precursor, α-1- antitrypsin precursor, ApoA-II precursor, complement C4 precursor, a hypothetical protein, β-2-microglobulin (isoforms) (with one exception), neuronal pentraxin I precursor, retinol binding protein (with one exception), and thioredoxin (except in the previous study where this protein was not quantified). There is only one consistently decreased protein, i.e. β-1,3-N-acetylglucosaminyltransferase bGnT-6, EWI2, when AD patients are compared to controls.

TABLE 7

Comparison of AD CSF markers across all proteomic studies

| No. | Name (IPI) | Common Name | Previous study [13] | Peer Literature | Current study |
|---|---|---|---|---|---|
| 1 | IPI00244477 | Similar to fem-1 homolog a | ↑↑ | NI | NI |
| 2 | IPI00171473 | Spondin 1, (f-spondin) extracellular matrix protein | ↑↑ | NI | NC |
| 3 | IPI00181232 | $Ca^{2+}$-dependent activator protein for secretion 2 | ↑↑ | NI | NI |
| 4 | IPI00001508 | Proinsulin precursor | ↑↑ | NI | NI |
| 5 | IPI00245370 | Insulin-like growth factor binding protein 2 (36 kD) | ↑↑ | NI | NI |
| 6 | IPI00032220 | Angiotensinogen precursor | ↑↑ | NI | NC |
| 7 | IPI00006608 | Amyloid beta A4 protein precursor | ↑↑ | NI | NC |
| | IPI00219182 | | | NI | ↑ |
| | IPI00219189 | | | NI | NI |
| 8 | IPI00233778 | Complement component 1, r subcomponent | ↑↑ | NI | NI |
| 9 | IPI00300241 | Hypothetical protein | ↑↑ | NI | ↑↑ |
| 10 | IPI00032258 | Complement C4 precursor | ↑↑ | NI | ↑ |
| 11 | IPI00234495 | Cathepsin B preproprotein* | ↑↑ | NI | NI |
| 12 | IPI00332161 | Ig gamma-1 chain C region | ↑↑ | NI | NI |
| | IPI00328111 | Factor VII active site mutant immunoconjugate | ↑↑ | NI | |
| 13 | IPI00064607 | MEGF10 protein* | ↑↑ | NI | NI |
| 14 | IPI00013299 | Neuroblastoma, suppression of tumorigenicity 1 | ↑↑ | NI | NI |

TABLE 7-continued

Comparison of AD CSF markers across all proteomic studies

| No. | Name (IPI) | Common Name | Previous study [13] | Peer Literature | Current study |
|---|---|---|---|---|---|
| 15 | IPI00333982 | Hypothetical protein | ↑↑ | NI | NI |
|  | IPI00168728 | FLJ00385 protein | ↑↑ | NI | NI |
| 16 | IPI00219020 | a. Splice isoform 1 of Q13748 Tubulin alpha-2 chain | ↑↑ | NI | NI |
|  | IPI00177441 | b. Similar to Tubulin alpha-3/alpha-7 chain |  | NI | NI |
|  | IPI00180675 | c. Hypothetical protein |  | NI | NI |
|  | IPI00179709 |  |  | NI | NI |
|  | IPI00183040 |  |  | NI | NI |
|  | IPI00166768 |  |  |  |  |
|  | IPI00216005 | d. Tubulin alpha-8 chain | ↑↑ | NI | NI |
|  | IPI00218345 | e. Tubulin, alpha 2 isoform 2 | ↑↑ | NI | NI |
| 17 | IPI00022371 | Histidine-rich glycoprotein precursor | ↑↑ | NI | NC |
| 18 | IPI00220562 | Neuronal pentraxin I precursor | ↑↑ | NI | ↑ |
| 19 | IPI00004656 | a. Alpha-2-microglobulin precursor | ↑↑ | NI | NI |
|  | IPI00182398 | b. Hypothetic protein | ↑↑ | NI | NI |
| 20 | IPI00021854 | Apolipoprotein A-II precursor # | ↑↑ | NI | ↑↑ |
| 21 | IPI00009997 | Beta-1,3-N-acetylglucosaminyltransferase bGnT-6 | ↓↓ | NI | ↓ |
| 22 | IPI00298853 | Vitamin D-binding protein precursor | ↓↓ | NI | NC |
| 23 | IPI00257600 | Cell adhesion molecule with homology to L1CAM precursor | ↓↓ | NI | NI |
| 24 | IPI00027425 | Prion protein | ↓↓ | NI | NC |
|  | IPI00022284 |  |  |  |  |
| 25 | IPI00293592 | Hypothetical protein AF447587* | ↓↓ | NI | NI |
|  | IPI00168464 | Hypothetical protein* | ↓↓ | NI | NI |
| 26 | IPI00056478 | EWI2 | ↓↓ | NI | ↓ |
|  | IPI00186736 | LIR-D1 | ↓↓ | NI | NC |
| 27 | IPI00020984 | Calnexin* | ↓↓ | NI | NI |
| 28 | IPI00232736 | Similar to RIKEN cDNA 2410146L05* | ↓↓ | NI | NI |
| 29 | IPI00027547 | Dermcidin precursor | ↓↓ | NI | ↑↑ |
| 30 | IPI00025456 | LJ00053 protein | ↓↓ | NI | NI |
| 31 | IPI00045498 | a. Hypothetical protein, JKTBP1delta6 ( ) | ↓↓ | NI | NI |
|  | IPI00011274 | b. Heterogeneous nuclear ribonucleoprotein D-like |  | NI | NI |
| 32 | IPI00183616 | a. Hypothetic protein | ↓↓ | NI | NI |
|  | IPI00218719 | b. Splice isoform 2 of P78527 DNA-dependent protein kinase catalytic subunit |  | NI | NI |
|  | IPI00233252 | c. DNA-dependent protein kinase catalytic subunit |  | NI | NI |
| 33 | IPI00155723 | a. Leukophysin | ↓↓ | NI | NI |
|  | IPI00215638 | b. DEAD/H (Asp-Glu-Ala-Asp/His) box polypeptide 9 isoform 1 | ↓↓ | NI |  |
| 34 | IPI00032292 | Metalloproteinase inhibitor 1 precursor* | ↓↓ | NI | NC |
| 35 | IPI00027381 | Lymphocyte antigen 75 precursor | ↓↓ | NI | NI |
| 36 | IPI00033086 | a. Disks large-associated protein 2* | ↓↓ | NI | NI |
|  | IPI00221115 | b. Splice isoform 2 of Q9P1A6 Disks large-associated protein 2 |  | NI | NI |
|  | IPI00221116 | c. Splice isoform 3 of Q9P1A6 Disks large-associated protein 2 |  | NI | NI |
| 37 | IPI00170706 | KIAA1412 protein* | ↓↓ | NI | NI |
| 38 | IPI00170548 | PRO2000 protein* | ↓↓ | NI | NI |
| 39 | IPI00479805 | ApoA4 | NI | ↓ [53] | ↑↑ |
| 40 |  | 7.7 kDa unknown protein | NI | ↑ [35] | NI |
| 41 | IPI00305457 | Alpha-1-antitrypsin precursor | ↑↑ | ↑ [34] | ↑ |
| 42 | IPI00216722 | Alpha-1β glycoprotein | NC | ↓ [34, 54] | NI |
| 43 | IPI00022431 | Alpha-2-HS glycoprotein | ↑ | ↓ [34] | NI |
| 44 | IPI00022434 | Albumin precursor | ↑ | ↓ [34] | ↑↑ |
| 45 | NCBI 178775* | ApoA1 | Identified | ↓ [34] | NI |

TABLE 7-continued

Comparison of AD CSF markers across all proteomic studies

| No. | Name (IPI) | Common Name | Previous study [13] | Peer Literature | Current study |
|---|---|---|---|---|---|
| 46 | NCBI 4557325; 178848* | ApoE | Identified | ↓ [34, 53] | NI |
| 47 | NCBI 178855* | ApoJ | Identified | ↓ [34] | NI |
| 48 | GenBank ID 4557327* | Apolipoprotein H precursor | NI | ↓ [54] | NI |
| 49 | * | Beta-amyloid (1-42) | NI | ↓ [37] ELISA ↓ [55] non-protemics | NI |
| 50 | NCBI 4758048* | Cell cycle progression 8 protein | NI | ↓ [34] | NI |
| 51 | GenBank ID 4557018* | Chitinase 3-like 1 | NI | ↑ [54] | NI |
| 52 | GenBank ID 181387* | Cystatin C | NC | ↑ [35, 54] | NI |
| 53 | * | Kininogen precursor | Identified | ↓ [34] | NI |
| 54 | * | Phospho-tau | NI | ↑ [55] non-proteomics | NI |
| 55 | 178775* | Proapolipoprotein | NI | ↓ [53] | NI |
| 56 | NCBI 730305; GenBank ID 455962672* | Protaglandin D2 synthase | NC | ↓ [34] ↑ [54] | NI |
| 57 | IPI00479848 | Retinol binding protein | ↑ | ↓ [34] ↑ [53] | ↑ |
| 58 | * | Tau | NI | ↓ [37] WB ↑ [55] non-proteomics | NI |
| 59 | IPI00216298 | Thioredoxin | NI | ↑ [54] | ↑ |
| 60 | NCBI 4557871* | Transferrin precursor | ↑ | ↓ [34] | NI |
| 61 | IPI00022432 | Transthyretin | ↑ | ↓ [34] ↑ [53] | NC |
| 62 | IPI00383014 | VGF protein | Identified | ↓ [35] | ↑ |
| 63 | 4699583* | Zn-a-2 glycoprotein | NI | ↑ [53] | NI |
| 64 | IPI00004656 | β-2-Microglobulin (isoforms) | ↑↑ | ↑ [35, 53, 54] ↓ [34] | ↑ |

↑↑: Increase (Ratio of AD vs. control >1.5)
↓↓: Decrease (Ratio of AD vs. control <0.67)
↑: Increase (Ratio of AD vs. control >1.2 but <1.5)
↓: Decrease (Ratio of AD vs. control >0.67 but <0.83)
NC: No change (Ratio of AD vs. control between 1.2~0.83)
NI: Not Identified.
*No IPI number as they are identified by others using different database.
: Protein unique to AD as listed in FIGS. 5A-5YY.
Cited References:
[13] - Zhang et al., J Alzheimers Dis, 2005. 7(2): p. 125-33
[34] - Puchades et al., Brain Res Mol Brain Res, 2003. 118(1-2): p. 140-6
[35] - Carrette et al., Proteomics, 2003. 3(8): p. 1486-94
[37] - Choe et al., Electrophoresis, 2002. 23(14): p. 2247-51
[53] - Davidsson et al., Neuroreport, 2002. 13(5): p. 611-5
[54] - Hu et al., Mol Cell Proteomics, 2005.
[55] - Davidsson et al., Dis Markers, 2005. 21(2): p. 81-92
Multiple entries in a box without letter designation signify one protein with multiple names.
Multiple entries designated by letters indicate multiple possible protein candidates from the sequenced peptides, typically isoforms and precursors.
IPI: International Protein Index.

The concordance between the previous and current studies is higher, as in addition to the proteins mentioned above, the following proteins also demonstrate similar quantitative changes: afamin precursor, chemokine (C-X-C motif) ligand 16, β-galactosidase binding lectin precursor, GM2 activator precursor, ganglioside, α-2-macroglobulin precursor, and selenium-binding protein 1. Finally, 7 proteins displayed significant changes in the current study (FIGS. 5A-5YY) in the same direction, whether increased or decreased in AD vs. controls, as those listed in the previous publication where they have changes >20% but <50% alternations (Zhang et al., J Alzheimers Dis, 2005. 7(2): p. 125-33), and consequently are not listed in Table 7. These proteins are: dystroglycan precursor, haptoglobin, hemopexin precursor, insulin-like growth factor binding protein 2 precursor, ribonuclease 6 precursor, mimecan precursor, and tetranectin precursor.

What is most remarkable is that among all of the proteins with consistent changes in most experiments, only very few are unique to AD, i.e. most previous "candidate" markers were also changing more or less in the same direction in PD or DLB cases. Because it is not difficult for an experienced clinician to diagnose demented subjects from controls, the utility of these "non-unique" markers diminishes significantly. The only unique marker that has been consistently found in all studies is ApoA-II precursor. The other close possibility is haptoglobin, which is why this protein was selected for further confirmation even though it also displayed more than 20% changes in PD vs. controls. These results emphasize again that it is imperative to include other disease controls in addition to age-matched controls when the goal is to identify unique disease markers.

Candidate markers unique to AD fall into four major categories: immune/inflammation, transportation related proteins, e.g. ApoII-A, ApoC1 and ApoH, cellular metabolism, and neural transmission (FIGS. 5A-5YY). It is not practical to discuss each of the candidate proteins in detail; thus, the discussion will be focused on three confirmed markers demonstrating relatively high sensitivity, i.e. β-fibrinogen, haptoglobin, and VitD BP. β-Fibrinogen, best known for its role in coagulation and inflammation, has at least two isoforms, α and β, and it is not clear whether this protein is synthesized in the brain or transported via the blood brain barrier (BBB) (Strohmeyer et al., Brain Res Mol Brain Res, 2000. 81(1-2): p. 7-18). Nonetheless, it has been recognized for some time now that the activity of fibrinogen is increased in the plasma of AD patients (Gupta et al., Int J Clin Pract, 2005. 59(1): p. 52-7). The role of increased β-fibrinogen in AD CSF is not clear, but it can be at least hypothesized that it could potentially enhance microglial activation, a process implicated as one of the major mechanisms of cell death in PD (Shie et al., Am J Pathol, 2005. 166(4): p. 1163-72). On the other hand, an increase in haptoglobin in CSF has been associated with a subpopulation of AD patients, and it is initially (Pantoni et al., Acta Neurol Scand, 1995. 91(3): p. 225) thought to be due to an abnormal penetration of haptoglobin in AD patients secondary to compromised BBB (Alafuzoff et al., Acta Neuropathol (Berl), 1987. 73(2): p. 160-6; Tomimoto et al., Stroke, 1996. 27(11): p. 2069-74). Some studies have also associated with haptoglobin with increased risk in some AD patients, although contradictory results have also been reported (Matsuyama et al., Hum Hered, 1986. 36(2): p. 93-6). Nonetheless, several studies preformed with conventional methods also show that the level of haptoglobin increases in AD patients (Johnson et al., Appl Theor Electrophor, 1992. 3(2): p. 47-53). However, as demonstrated in this study, an increase in haptoglobin alone is not sufficient to differentiate AD from other neurological diseases. VitD BP has been classically associated with calcium metabolism and bone remodeling, although recently it has been noted that mRNA levels for this protein are decreased in the hippocampus in Alzheimer's patients (Sutherland et al., Brain Res Mol Brain Res, 1992. 13(3): p. 239-50). Nevertheless, like haptoglobin, the role of VitD BP in the pathogenesis of AD is largely unknown.

Prior to this study, very little was known about markers unique to PD and DLB. Three confirmed good candidate markers for PD are ceruloplasmin, chromogranin B and ApoH. Ceruloplasmin is an interesting protein because it has been implicated to play a central role in PD pathogenesis owing to two observations: 1) iron deposition in PD substantia nigra correlates with the severity of the disease (Hochstrasser et al., Neurology, 2004. 63(10): p. 1912-7); and 2) ceruloplasmin, an important protein for iron transportation, is decreased in the blood of PD patients (Torsdottir et al., Pharmacol Toxicol, 1999. 85(5): p. 239-43). Finally, It should be emphasized that this protein did not decrease in all PD patients in an earlier study (Loeffler et al., Alzheimer Dis Assoc Disord, 1994. 8(3): p. 190-7), consistent with the facts that this disease is heterogeneous in nature and that it is probably not sufficient by itself to detect PD patients with high sensitivity at high specificity. The influence of chromogranin B, a non-significant marker by itself in confirmation studies, on the overall performance of ApoH is also remarkable, as it significantly improved the sensitivity of ApoH to differentiate PD from controls as well as other diseases. Notably, a study performed years ago has suggested that although chromogranin B cannot differentiate AD or PD from controls by itself, the ratio between chromogranin A and B may be a correcting factor for neuropeptides seen in human CSF (Eder et al., J Neural Transm, 1998. 105(1): p. 39-51). The third marker that might be important in PD is ApoH, a protein clearly reported to be present in human CSF (Koch et al., J Lipid Res, 2001. 42(7): p. 1143-51), although its role in PD or in neurodegenerative diseases in general remains to be defined.

The markers unique to DLB also appeared to be related to two lipoproteins, i.e. ApoC1 and ApoH. Again, the role of ApoH in DLB or neurodegenerative disease in general is largely unknown, although given the fact that it is also increased in PD, one might argue its role in Lewy body disease. Very little is known about the role of ApoC in Lewy body disease, including PD and DLB, or dementia. However, several issues are worth commenting. First, one does not need to know the function of a protein in order for it to be a diagnostic tool; a good example of this type of use is the presence of oligoclonal bands in the CSF in the absence of identical bands in serum, which has been widely used clinically to aide the diagnosis of multiple sclerosis (McLean et al., Brain, 1990. 113(Pt 5): p. 1269-89). Second, all of these novel proteins should be studied further not only for their diagnostic use, but also for their roles in the pathogenesis of neurodegenerative diseases. Finally, given the limited DLB cases studied, caution needs to be excised with respect to the significance of these proteins.

Accordingly, the results show that examples of potential good combination of markers included β-fibrinogen plus Vit D BP or ceruloplasmin for AD, chromogranin B plus ceuloplamin or ApoH for PD and ApoC1 plus chormgranin B or VitD BP for DLB (Table 5).

Example 5

Diagnosis of Alzheimer's Disease

A patient's CSF providing the following protein expression pattern is diagnosed as having Alzheimer's disease (AD) and not Parkinson's disease (PD) or dementia with Lewy body (DLB): a decrease in angiotensinogen precursor and enolase 2, an increase in ADAM 10 precursor, an increase in Hect domain and RLD 4, and an increase in KIAA1291 protein. This determination is based on the results provided in FIGS. 5A-5YY, which show that (1) both angiotensinogen precursor and enolase 2 decrease in AD, do not change in PD, but increase in DLB; (2) ADAM 10 precursor increases in AD, but does not change in PD or DLB; and (3) Hect domain and RLD 4 increase in AD, decrease in PD, but do not change in DLB.

| Change in Expression | Protein Name |
|---|---|
| ↓ | Angiotensinogen precursor |
| ↑ | ADAM 10 precursor |

-continued

| Change in Expression | Protein Name |
|---|---|
| ↓ | Enolase 2 |
| ↑ | Hect domain and RLD 4 |
| ↑ | KIAA1291 protein |

Example 6

Diagnosis of Alzheimer's Disease

A patient's CSF providing the following protein expression pattern is diagnosed as having Alzheimer's disease (AD) and not Parkinson's disease (PD) or dementia with Lewy body (DLB): a decrease in IL-17RC and PLXDC2 protein, an increase in Golgi phosphoprotein 2, an increase in spondin 1 precursor, and an increase in ZNF627 protein. This determination is based on the results provided in FIGS. 5A-5YY, which show that (1) Golgi phosphoprotein 2 increases in AD, does not change in PD, but decreases in DLB; (2) IL-17RC decreases in AD but does not change in PD or DLB; (3) PLXDC2 protein decreases in AD, does not change in PD but increases in DLB; and (4) spondin 1 precursor and ZNF627 protein increase in AD, but do not change in PD or DLB.

| Change in Expression | Protein Name |
|---|---|
| ↑ | Golgi phosphoprotein 2 |
| ↓ | IL-17RC |
| ↓ | PLXDC2 protein |
| ↑ | Spondin 1 precursor |
| ↑ | ZNF627 protein |

Example 7

Diagnosis of Alzheimer's Disease

A patient's CSF providing the following protein expression pattern is diagnosed as having Alzheimer's disease (AD) and not Parkinson's disease (PD) or dementia with Lewy body (DLB): a decrease in chromogranin A and divalent cation tolerant protein CUTA, an increase in apolipoprotein D, an increase in haptoglobin precursor, and an increase in reticulocalbin 2 precursor. This determination is based on the results provided in FIGS. 5A-5YY, which show that (1) apolipoprotein D precursor and reticulocalbin 2 precursor increase in AD but do not change in PD or DLB; (2) chromogranin A decreases in AD but does not change in PD or DLB; (3) divalent cation tolerant protein CUTA decreases in AD, does not change in PD, but increases in DLB; and (4) haptoglobin precursor increases in AD and PD, but does not change in DLB.

| Change in Expression | Protein Name |
|---|---|
| ↑ | Apolipoprotein D precursor |
| ↓ | Chromogranin A |
| ↓ | Divalent cation tolerant protein CUTA |

| Change in Expression | Protein Name |
|---|---|
| ↑ | Haptoglobin precursor |
| ↑ | Reticulocalbin 2 precursor |

Example 8

Diagnosis of Alzheimer's Disease

A patient's CSF providing the following protein expression pattern is diagnosed as having Alzheimer's disease (AD) and not Parkinson's disease (PD) or dementia with Lewy body (DLB): a decrease in secretogranin I precursor, a decrease in splice isoform 2 of insulin receptor, an increase in AMBP protein precursor, an increase in kallikrein 6 precursor, and an increase in TRIF-related adapter molecular. This determination is based on the results provided in FIGS. 5A-5YY, which show that (1) AMBP protein precursor and TRIF-related adapter molecule increase in AD but do not change in PD or DLB; (2) kallikrein 6 precursor increases in AD, decreases in PD, but does not change in DLB; and (3) secretogranin I precursor and splice isoform 2 of insulin receptor precursor decrease in AD but do not change in PD or DLB.

| Change in Expression | Protein Name |
|---|---|
| ↑ | AMBP protein precursor |
| ↑ | Kallikrein 6 precursor |
| ↓ | Secretogranin I precursor |
| ↓ | Splice isoform 2 of insulin receptor precursor |
| ↑ | TRIF-related adapter molecule |

Example 9

Diagnosis of Alzheimer's Disease

A patient's CSF providing the following protein expression pattern is diagnosed as having Alzheimer's disease (AD) and not Parkinson's disease (PD) or dementia with Lewy body (DLB): a decrease in brain-derived neurotrophic factor BDNF1, a decrease in interleukin-1 receptor-associated kinase-like 2, a decrease in neurexin 1-alpha precursor, and an increase in alpha 1 type XIII collagen isoform 3. This determination is based on the results provided in FIGS. 5A-5YY, which show that (1) alpha 1 type XIII collagen isoform 3 increases in AD, decreases in PD but does not change in DLB; (2) brain-derived neurotrophic factor BDNF1 and interleukin-1 receptor-associated kinase-like 2 decrease in AD but do not change in PD or DLB; (3) latent transforming growth factor beta binding protein 2 increases in AD, does not change in PD, but decreases in DLB; and (4) neurexin 1-alpha precursor decreases in AD, increases in PD but does not change in DLB.

| Change in Expression | Protein Name |
|---|---|
| ↑ | Alpha 1 type XIII collagen isoform 3 |
| ↓ | Brain-derived neurotrophic factor BDNF1 |

| Change in Expression | Protein Name |
|---|---|
| ↓ | Interleukin-1 receptor-associated kinase-like 2 |
| ↑ | Latent transforming growth factor beta binding protein 2 |
| ↓ | Neurexin 1-alpha precursor |

Example 10

Diagnosis of Alzheimer's Disease

A patient's CSF providing the following protein expression pattern is diagnosed as having Alzheimer's disease (AD) and not Parkinson's disease (PD) or dementia with Lewy body (DLB): a decrease in cadherin-13 precursor, an increase in ADAM 10 precursor, an increase in fibrinogen beta chain precursor, an increase in HLA class I histocompatibility antigen, an increase in E alpha chain precursor and an increase in Zinc finger protein 95. This determination is based on the results provided in FIGS. 5A-5YY, which show that (1) ADAM 10 precursor, fibrinogen beta chain precursor, HLA class I histocompatibility antigen, E alpha chain precursor and zinc finger protein 95 homolog increase in AD but do not change in PD or DLB; and (2) cadherin-13 precursor decreases in AD but does not change in PD or DLB.

| Change in Expression | Protein Name |
|---|---|
| ↑ | ADAM 10 precursor |
| ↓ | Cadherin-13 precursor |
| ↑ | Fibrinogen beta chain precursor |
| ↑ | HLA class I histocompatibility antigen, E alpha chain precursor |
| ↑ | Zinc finger protein 95 homolog |

Example 11

Diagnosis of Alzheimer's Disease

A patient's CSF providing the following protein expression pattern is diagnosed as having Alzheimer's disease (AD) and not Parkinson's disease (PD) or dementia with Lewy body (DLB): a decrease in PPIB protein, a decrease in prostatic binding protein, a decrease in SAYY8238, a decrease in transcriptional activator SRCAP, and an increase in inter-alpha-trypsin inhibitor heavy chain HI precursor. This determination is based on the results provided in FIGS. 5A-5YY, which show that (1) inter-alpha-trypsin inhibitor heavy chain HI precursor increases in AD but does not change in PD or DLB; and (2) PPIB protein, prostatic binding protein, SAYY8238, and transcriptional activator SRCAP decrease in AD but do not change in PD or DLB.

| Change in Expression | Protein Name |
|---|---|
| ↑ | Inter-alpha-trypsin inhibitor heavy chain H1 precursor |
| ↓ | PPIB protein |
| ↓ | Prostatic binding protein |

| Change in Expression | Protein Name |
|---|---|
| ↓ | SAYY8238 |
| ↓ | Transcriptional activator SRCAP |

Example 12

Diagnosis of Alzheimer's Disease

A patient's CSF providing the following protein expression pattern is diagnosed as having Alzheimer's disease (AD) and not Parkinson's disease (PD) or dementia with Lewy body (DLB): a decrease in cell growth regulator with EF hand domain 1, a decrease in metallothionein-III, a decrease in neuronal pentraxin receptor, an increase in heat shock 10 kDa protein 1 (chaperonin 10), and an increase in integral membrane protein 2B. This determination is based on the results provided in FIGS. 5A-5YY, which show that (1) cell growth regulator with EF hand domain 1 decreases in AD, increases in PD, but does not change in DLB; (2) heat shock 10 kDa protein 1 and integral membrane protein 2B increase in AD but do not change in PD or DLB; and (3) metallothionein-III and neuronal pentraxin receptor decrease in AD but do not change in PD or DLB.

| Change in Expression | Protein Name |
|---|---|
| ↓ | Cell growth regulator with EF hand domain 1 |
| ↑ | Heat shock 10 kDa protein 1 (chaperonin 10) |
| ↑ | Integral membrane protein 2B |
| ↓ | Metallothionein-III |
| ↓ | Neuronal pentraxin receptor |

Example 13

Diagnosis of Alzheimer's Disease

A patient's CSF providing the following protein expression pattern is diagnosed as having Alzheimer's disease (AD) and not Parkinson's disease (PD) or dementia with Lewy body (DLB): a decrease in apolipoprotein E precursor, a decrease in glucosidase II beta subunit precursor, a decrease in neural proliferation differentiation, a decrease in control protein-1 precursor, an increase in cytokine-like protein C17 precursor, and an increase in voltage-dependent calcium channel gamma-6 subunit. This determination is based on the results provided in FIGS. 5A-5YY, which show that (1) apolipoprotein E precursor, glucosidase II beta subunit precursor, neural proliferation differentiation and control protein-1 precursor decrease in AD, but do not change in PD or DLB; and (2) cytokine-like protein C17 precursor and voltage-dependent calcium channel gamma-6 subunit increase in AD, but do not change in PD or DLB.

| Change in Expression | Protein Name |
|---|---|
| ↓ | Apolipoprotein E precursor |
| ↑ | Cytokine-like protein C17 precursor |

-continued

| Change in Expression | Protein Name |
|---|---|
| ↓ | Glucosidase II beta subunit precursor |
| ↓ | Neural proliferation differentiation and control protein-1 precursor |
| ↑ | Voltage-dependent calcium channel gamma-6 subunit |

Example 14

Diagnosis of Alzheimer's Disease

A patient's CSF providing the following protein expression pattern is diagnosed as having Alzheimer's disease (AD) and not Parkinson's disease (PD) or dementia with Lewy body (DLB): a decrease in inhibin beta A chain precursor, a decrease in neurofascin isoform 2, a decrease in receptor-type tyrosine-protein phosphatase-like N precursor, an increase in antigen MLAA-20, an increase in HLA class I histocompatibility antigen, and an increase in B-27 alpha chain precursor. This determination is based on the results provided in FIGS. 5A-5YY, which show that (1) antigen MLAA-20, HLA class I histocompatibility antigen and B-27 alpha chain precursor increase in AD but do not change in PD or DLB; and (2) inhibin beta A chain precursor, neurofascin isoform 2 and receptor-type tyrosine-protein phosphatase-like N precursor decrease in AD but do not change in PD or DLB.

| Change in Expression | Protein Name |
|---|---|
| ↑ | Antigen MLAA-20 |
| ↑ | HLA class I histocompatibility antigen, B-27 alpha chain precursor |
| ↓ | Inhibin beta A chain precursor |
| ↓ | Neurofascin isoform 2 |
| ↓ | Receptor-type tyrosine-protein phosphatase-like N precursor |

Example 15

Diagnosis of Alzheimer's Disease

A patient's CSF providing the following protein expression pattern is diagnosed as having Alzheimer's disease (AD) and not Parkinson's disease (PD) or dementia with Lewy body (DLB): a decrease in chromogranin B, a decrease in neuronal pentraxin I precursor, an increase in alpha-1-acid glycoprotein1 precursor, an increase in KARCA1 protein, and an increase in sortilin 1 preprotein. This determination is based on the results provided in FIGS. 5A-5YY, which show that (1) alpha-1-acid glycoprotein 1 precursor increases in AD, decreases in PD, but does not change in DLB; (2) chromogranin B decreases in AD, increases in PD, but does not change in DLB; (3) KARACA1, and sortilin I preprotein increase in AD, do not change in PD, but decrease in DLB; and (4) neuronal pentraxin 1 precursor decreases in AD, does not change in PD, but increases in DLB.

| Change in Expression | Protein Name |
|---|---|
| ↑ | Alpha-1-acid glycoprotein 1 precursor |
| ↓ | Chromogranin B |
| ↑ | KARCA1 protein |
| ↓ | Neuronal pentraxin I precursor |
| ↑ | Sortilin 1, preproprotein |

Example 16

Diagnosis of Alzheimer's Disease

A patient's CSF providing the following protein expression pattern is diagnosed as having Alzheimer's disease (AD) and not Parkinson's disease (PD) or dementia with Lewy body (DLB): a decrease in G protein-coupled sphingolipid receptor, a decrease in superoxide dismutase 1, soluble, an increase in apolipoprotein H, an increase in mosaic serine protease, and an increase in myosin-reactive immunoglobulin heavy chain variable region. This determination is based on the results provided in FIGS. 5A-5YY, which show that (1) apolipoprotein H increases in AD, decreases in PD, but does not change in DLB; (2) G protein-coupled sphingolipid receptor decreases in AD, but does not change in PD or DLB; (3) mosaic serine protease and myosin-reactive immunoglobulin heavy chain variable region increase in AD, but do not change in PD or DLB; and (4) superoxide dismutase 1, soluble decreases in AD, does not change in PD, but increases in DLB.

| Change in Expression | Protein Name |
|---|---|
| ↑ | Apolipoprotein H |
| ↓ | G protein-coupled sphingolipid receptor |
| ↑ | Mosaic serine protease |
| ↑ | Myosin-reactive immunoglobulin heavy chain variable region |
| ↓ | Superoxide dismutase 1, soluble |

Example 17

Diagnosis of Alzheimer's Disease

A patient's CSF providing the following protein expression pattern is diagnosed as having Alzheimer's disease (AD) and not Parkinson's disease (PD) or dementia with Lewy body (DLB): a decrease in vacuolar ATP synthase subunit S1 precursor, an increase in apolipoprotein C-1 precursor, an increase in matrix Gla-protein precursor, an increase in SAA1 protein, and an increase in splice isoform 2 of insulin-like growth factor II precursor. This determination is based on the results provided in FIGS. 5A-5YY, which show that (1) apolipoprotein C-1 precursor and SAA1 protein increase in AD, decrease in PD, but do not change in DLB; (2) matrix Gla-protein precursor and splice isoform 2 of insulin-like growth factor II precursor increase in AD, but do not change in PD or DLB; and (3) vacuolar ATP synthase subunit S1 precursor decreases in AD, but does not change in PD or DLB.

| Change in Expression | Protein Name |
| --- | --- |
| ↑ | Apolipoprotein C-1 precursor |
| ↑ | Matrix Gla-protein precursor |
| ↑ | SAA1 protein |
| ↑ | Splice isoform 2 of insulin-like growth factor II precursor |
| ↓ | Vacuolar ATP synthase subunit S1 precursor |

Example 18

Diagnosis of Parkinson's Disease

A patient's CSF providing the following protein expression pattern is diagnosed as having Parkinson's disease (PD) and not Alzheimer's disease (AD) or dementia with Lewy body (DLB): a decrease in amyloid-like protein 1 precursor, a decrease in extracellular matrix protein 1, a decrease in HRPE773, a decrease in selenoprotein M precursor, and an increase in Golgi autoantigen, golgin subfamily B member 1. This determination is based on the results provided in FIGS. 5A-5YY, which show that (1) amyloid-like protein 1 precursor and extracellular matrix protein 1 decrease in PD, but do not change in AD or DLB; (2) Golgi autoantigen, golgin subfamily B member 1 increases in PD, decreases in AD, but does not change in DLB; (3) HRPE773 decreases in PD, does not change in AD, but increases in DLB; and (4) selenoprotein M precursor decreases in PD but does not change in AD or DLB.

| Change in Expression | Protein Name |
| --- | --- |
| ↓ | Amyloid-like protein 1 precursor |
| ↓ | Extracellular matrix protein 1 |
| ↑ | Golgi autoantigen, golgin subfamily B member 1 |
| ↓ | HRPE773 |
| ↓ | Selenoprotein M precursor |

Example 19

Diagnosis of Parkinson's Disease

A patient's CSF providing the following protein expression pattern is diagnosed as having Parkinson's disease (PD) and not Alzheimer's disease (AD) or dementia with Lewy body (DLB): a decrease in alpha 1 type XIII collagen isoform 3, a decrease in prothrombin precursor, a decrease in retinol binding protein 4, a decrease in plasma and vitamin D-binding protein precursor, and an increase in putative 4 repeat voltage-gated ion channel. This determination is based on the results provided in FIGS. 5A-5YY, which show that (1) alpha 1 type XIII collagen isoform 3 decreases in PD, increases in AD, but does not change in DLB; (2) prothrombin precursor, retinol binding protein 4, plasma and vitamin D-binding protein precursor decrease in PD but do not change in AD or DLB; and (3) putative 4 repeat voltage-gated ion channel increases in PD, decreases in AD, but does not change in DLB.

| Change in Expression | Protein Name |
| --- | --- |
| ↓ | Alpha 1 type XIII collagen isoform 3 |
| ↓ | Prothrombin precursor |
| ↑ | Putative 4 repeat voltage-gated ion channel |
| ↓ | Retinol binding protein 4, plasma |
| ↓ | Vitamin D-binding protein precursor |

Example 20

Diagnosis of Parkinson's Disease

A patient's CSF providing the following protein expression pattern is diagnosed as having Parkinson's disease (PD) and not Alzheimer's disease (AD) or dementia with Lewy body (DLB): a decrease in cochlin precursor, a decrease in cystatin C precursor, a decrease in KRT8 protein, a decrease in metabotropic glutamate receptor 3 precursor, and an increase in neurexin 1-alpha precursor. This determination is based on the results provided in FIGS. 5A-5YY, which show that (1) cochlin precursor decreases in PD, increases in AD, but does not change in DLB; (2) cystatin C precursor and KRT8 protein decrease in PD, but do not change in AD or DLB; (3) metabotropic glutamate receptor 3 precursor decreases in PD, does not change in AD, but increases in DLB; and (4) neurexin 1-alpha precursor increases in PD, decreases in AD, but does not change in DLB.

| Change in Expression | Protein Name |
| --- | --- |
| ↓ | Cochlin precursor |
| ↓ | Cystatin C precursor |
| ↓ | KRT8 protein |
| ↓ | Metabotropic glutamate receptor 3 precursor |
| ↑ | Neurexin 1-alpha precursor |

Example 21

Diagnosis of Parkinson's Disease

A patient's CSF providing the following protein expression pattern is diagnosed as having Parkinson's disease (PD) and not Alzheimer's disease (AD) or dementia with Lewy body (DLB): a decrease in alpha-1-acid glycoprotein 1 precursor, a decrease in Hook homolog 3, a decrease in Kallikrein 6 precursor, an increase in ATP-binding cassette, an increase in sub-family A, member 1 and an increase in pyruvate kinase 3 isoform 2. This determination is based on the results provided in FIGS. 5A-5YY, which show that (1) alpha-1-acid glycoprotein 1 precursor and Kallikrein 6 precursor decrease in PD, increase in AD, but do not change in DLB; (2) ATP-binding cassette, sub-family A, member 1 and pyruvate kinase 3 isoform 2 increase in PD, but do not change in AD or DLB; and (3) Hook homolog 3 decreases in PD, but does not change in AD or DLB.

| Change in Expression | Protein Name |
| --- | --- |
| ↓ | Alpha-1-acid glycoprotein 1 precursor |
| ↑ | ATP-binding cassette, sub-family A, member 1 |

-continued

| Change in Expression | Protein Name |
|---|---|
| ↓ | Hook homolog 3 |
| ↓ | Kallikrein 6 precursor |
| ↑ | Pyruvate kinase 3 isoform 2 |

Example 22

Diagnosis of Parkinson's Disease

A patient's CSF providing the following protein expression pattern is diagnosed as having Parkinson's disease (PD) and not Alzheimer's disease (AD) or dementia with Lewy body (DLB): a decrease in ceruloplasmin precursor, a decrease in heparin-binding EGF-like growth factor precursor, a decrease in SAA1 protein, an increase in cell growth regulator with EF hand domain 1 and an increase in selenium binding protein 1. This determination is based on the results provided in FIGS. 5A-5YY, which show that (1) cell growth regulator with EF hand domain 1 increases in PD, decreases in AD, but does not change in DLB; (2) ceruloplasmin precursor and heparin-binding EGF-like growth factor precursor decrease in PD, but do not change in AD or DLB; (3) SAA1 protein decreases in PD, increases in AD, but does not change in DLB; and (4) selenium binding protein 1 increases in PD but does not change in AD or DLB.

| Change in Expression | Protein Name |
|---|---|
| ↑ | Cell growth regulator with EF hand domain 1 |
| ↓ | Ceruloplasmin precursor |
| ↓ | Heparin-binding EGF-like growth factor precursor |
| ↓ | SAA1 protein |
| ↑ | Selenium binding protein 1 |

Example 23

Diagnosis of Parkinson's Disease

A patient's CSF providing the following protein expression pattern is diagnosed as having Parkinson's disease (PD) and not Alzheimer's disease (AD) or dementia with Lewy body (DLB): a decrease in apolipoprotein A-II precursor, a decrease in mammalian ependymin related protein 1, a decrease in splice isoform 1 of lysosomal trafficking regulator, a decrease in splice isoform 2 of integrin alpha-7 precursor, and an increase in C-type natriuretic peptide precursor. This determination is based on the results provided in FIGS. 5A-5YY, which show that (1) apolipoprotein A-II precursor decreases in PD, increases in AD, but does not change in DLB; (2) C-type natriuretic peptide precursor increases in PD, but does not change in AD or DLB; (3) mammalian ependymin related protein 1 decreases in PD, does not change in AD, but increases in DLB; and (4) splice isoform 1 of lysosomal trafficking regulator and splice isoform 2 of integrin alpha-7 precursor decrease in PD, but do not change in AD or DLB.

| Change in Expression | Protein Name |
|---|---|
| ↓ | Apolipoprotein A-II precursor |
| ↑ | C-type natriuretic peptide precursor |
| ↓ | Mammalian ependymin related protein 1 |
| ↓ | Splice isoform 1 of lysosomal trafficking regulator |
| ↓ | Splice Isoform 2 of integrin alpha-7 precursor |

Example 24

Diagnosis of Parkinson's Disease

A patient's CSF providing the following protein expression pattern is diagnosed as having Parkinson's disease (PD) and not Alzheimer's disease (AD) or dementia with Lewy body (DLB): a decrease in apolipoprotein C-I precursor, a decrease in insulin-like growth factor binding protein 5 precursor, a decrease in splice isoform 1 of transcription factor E2-alpha, an increase in ribonuclease 4 precursor and an increase in splice isoform 1 of basigin precursor. This determination is based on the results provided in FIGS. 5A-5YY, which show that (1) apolipoprotein C-I precursor and insulin-like growth factor binding protein 5 precursor decrease in PD, increase in AD, but do not change in PD; (2) ribonuclease 4 precursor increases in PD, but does not change in AD or DLB; (3) splice isoform 1 of basigin precursor increases in PD, does not change in AD, but decreases in DLB; and (4) splice isoform 1 of transcription factor E2-alpha decreases in PD, does not change in AD, but increases in DLB.

| Change in Expression | Protein Name |
|---|---|
| ↓ | Apolipoprotein C-I precursor |
| ↓ | Insulin-like growth factor binding protein 5 precursor |
| ↑ | Ribonuclease 4 precursor |
| ↑ | Splice isoform 1 of basigin precursor |
| ↓ | Splice isoform 1 of transcription factor E2-alpha |

Example 25

Diagnosis of Parkinson's Disease

A patient's CSF providing the following protein expression pattern is diagnosed as having Parkinson's disease (PD) and not Alzheimer's disease (AD) or dementia with Lewy body (DLB): a decrease in activating receptor pilrbeta, a decrease in apolipoprotein M, a decrease in polymeric-immunoglobulin receptor precursor, an increase in CD99L2 protein and an increase in chromogranin B. This determination is based on the results provided in FIGS. 5A-5YY, which show that (1) activating receptor pilrbeta decreases in PD, does not change in AD, but increases in DLB; (2) apolipoprotein M decreases in PD, but does not change in AD or DLB; (3) CD99L2 protein increases in PD, does not change in AD, but decreases in DLB; (4) chromogranin B increases in PD, decreases in AD, but does not change in DLB; and (5) polymeric-immunoglobulin receptor precursor decreases in PD, does not change in AD, but increases in DLB.

| Change in Expression | Protein Name |
| --- | --- |
| ↓ | Activating receptor pilrbeta |
| ↓ | Apolipoprotein M |
| ↑ | CD99L2 protein |
| ↑ | Chromogranin B |
| ↓ | Polymeric-immunoglobulin receptor precursor |

Example 26

Diagnosis of Parkinson's Disease

A patient's CSF providing the following protein expression pattern is diagnosed as having Parkinson's disease (PD) and not Alzheimer's disease (AD) or dementia with Lewy body (DLB): a decrease in KIAA1265 protein, a decrease in ribosomal protein L3-like, an increase in laminin gamma-1 chain precursor, an increase in prion protein, and an increase in protein tyrosine phosphatase, non-receptor type substrate 1 precursor. This determination is based on the results provided in FIGS. 5A-5YY, which show that (1) KIAA1265 protein decreases in PD, does not change in AD, but increases in DLB; (2) laminin gamma-1 chain precursor and protein tyrosine phosphatase, non-receptor type substrate 1 precursor increase in PD, do not change in AD, but decrease in DLB; (3) prion protein increases in PD, but does not change in AD or DLB; and (4) ribosomal protein L3-like decreases in PD, but does not change in AD or DLB.

| Change in Expression | Protein Name |
| --- | --- |
| ↓ | KIAA1265 protein |
| ↑ | Laminin gamma-1 chain precursor |
| ↑ | Prion protein |
| ↑ | Protein tyrosine phosphatase, non-receptor type substrate 1 precursor |
| ↓ | Ribosomal protein L3-like |

Example 27

Diagnosis of Parkinson's Disease

A patient's CSF providing the following protein expression pattern is diagnosed as having Parkinson's disease (PD) and not Alzheimer's disease (AD) or dementia with Lewy body (DLB): a decrease in apolipoprotein H, a decrease in DJ977L11.1, a decrease in serine/threonine-protein kinase PLK2, an increase in Ig kappa chain V-I region HK102 precursor and an increase in Rho-GTPase activating protein 10. This determination is based on the results provided in FIGS. 5A-5YY, which show that (1) apolipoprotein H and DJ977L11.1 decrease in PD, increase in AD, but do not change in DLB; (2) Ig kappa chain V-I region HK102 precursor and serine/threonine-protein kinase PLK2 increase in PD, but do not change in AD or DLB; and (3) Rho-GTPase activating protein 10 increases in PD, does not change in AD, but does decrease in DLB.

| Change in Expression | Protein Name |
| --- | --- |
| ↓ | Apolipoprotein H |
| ↓ | DJ977L11.1 |
| ↑ | Ig kappa chain V-I region HK102 precursor |
| ↑ | Rho-GTPase activating protein 10 |
| ↓ | Serine/threonine-protein kinase PLK2 |

Example 28

Diagnosis of Dementia with Lewy Body

A patient's CSF providing the following protein expression pattern is diagnosed as having dementia with Lewy body (DLB) and not Alzheimer's disease (AD) or Parkinson's disease (PD): a decrease in Rho-GTPase activating protein 10, a decrease in somatostatin precursor, a decrease in sortilin 1, preprotein, an increase in angiotensinogen precursor and an increase in myosin. This determination is based on the results provided in FIGS. 5A-5YY, which show that (1) angiotensinogen precursor and myosin increase in DLB, but do not change in AD or PD; (2) Rho-GTPase activating protein 10 decreases in DLB, does not change in AD, but increases in PD; (3) somatostatin precursor decreases in DLB, but does not change in AD or PD; and (4) sortilin 1, preprotein decreases in DLB, increases in AD, but does not change in PD.

| Change in Expression | Protein Name |
| --- | --- |
| ↑ | Angiotensinogen precursor |
| ↑ | Myosin |
| ↓ | Rho-GTPase activating protein 10 |
| ↓ | Somatostatin precursor |
| ↓ | Sortilin 1, preproprotein |

Example 29

Diagnosis of Dementia with Lewy Body

A patient's CSF providing the following protein expression pattern is diagnosed as having dementia with Lewy body (DLB) and not Alzheimer's disease (AD) or Parkinson's disease (PD): a decrease in coagulation factor V, a decrease in SCMH1 protein, an increase in KIAA1265 protein, an increase in neuronal pentraxin I precursor and an increase in profilin 2 isoform. This determination is based on the results provided in FIGS. 5A-5YY, which show that (1) coagulation factor V and SCMH1 protein decrease in DLB, but do not change in AD or PD; (2) KIAA1265 protein increases in DLB, does not change in AD, but decreases in PD; (3) neuronal pentraxin I precursor increases in DLB, decreases in AD, but does not change in PD; and (4) profilin 2 isoform increases in DLB, but does not change in AD or PD.

| Change in Expression | Protein Name |
| --- | --- |
| ↓ | Coagulation factor V |
| ↑ | KIAA1265 protein |

-continued

| Change in Expression | Protein Name |
|---|---|
| ↑ | Neuronal pentraxin I precursor |
| ↑ | Profilin 2 isoform |
| ↓ | SCMH1 protein |

Example 30

Diagnosis of Dementia with Lewy Body

A patient's CSF providing the following protein expression pattern is diagnosed as having dementia with Lewy body (DLB) and not Alzheimer's disease (AD) or Parkinson's disease (PD): a decrease in neurexophilin 4, a decrease in neuronal pentraxin receptor isoform 1, an increase in enolase 2, an increase in N-acetyllactosaminide beta-1,3,-N-acetylglucosaminyltransferase and an increase in parvalbumin. This determination is based on the results provided in FIGS. 5A-5YY, which show that (1) enolase 2 increases in DLB, decreases in AD, but does not change in PD; (2) N-acetyllactosaminide beta-1,3,-N-acetylglucosaminyltransferase and parvalbumin increase in DLB, but do not change in AD or PD; and (3) neurexophilin 4 and neuronal pentraxin receptor isoform 1 decrease in DLB, but do not change in AD or PD.

| Change in Expression | Protein Name |
|---|---|
| ↑ | Enolase 2 |
| ↑ | N-acetyllactosaminide beta-1,3-N-acetylglucosaminyltransferase |
| ↓ | Neurexophilin 4 |
| ↓ | Neuronal pentraxin receptor isoform 1 |
| ↑ | Parvalbumin |

Example 31

Diagnosis of Dementia with Lewy Body

A patient's CSF providing the following protein expression pattern is diagnosed as having dementia with Lewy body (DLB) and not Alzheimer's disease (AD) or Parkinson's disease (PD): a decrease in Fas apoptotic inhibitory molecule 2, a decrease in protein tyrosine phosphatase, non-receptor type substrate 1 precursor, an increase in brain abundant, membrane attached signal protein 1, an increase in divalent cation tolerant protein CUTA, and an increase in superoxide dismutase 1, soluble. This determination is based on the results provided in FIGS. 5A-5YY, which show that (1) brain abundant, membrane attached signal protein 1, divalent cation tolerant protein CUTA and superoxide dismutase 1, soluble increase in DLB, decrease in AD, but do not change in PD; (2) Fas apoptotic inhibitory molecule 2 decreases in DLB, but does not change in AD or PD; and (3) protein tyrosine phosphatase, non-receptor type substrate 1 precursor decreases in DLB, does not change in AD, but increases in PD.

| Change in Expression | Protein Name |
|---|---|
| ↑ | Brain abundant, membrane attached signal protein 1 |
| ↑ | Divalent cation tolerant protein CUTA |
| ↓ | Fas apoptotic inhibitory molecule 2 |
| ↓ | Protein tyrosine phosphatase, non-receptor type substrate 1 precursor |
| ↑ | Superoxide dismutase 1, soluble |

Example 32

Diagnosis of Dementia with Lewy Body

A patient's CSF providing the following protein expression pattern is diagnosed as having dementia with Lewy body (DLB) and not Alzheimer's disease (AD) or Parkinson's disease (PD): a decrease in latent transforming growth factor beta binding protein 2, a decrease in T-cadherin, a decrease in transcription elongation regulator 1, an increase in apolipoprotein C-III precursor and an increase in lysozyme C precursor. This determination is based on the results provided in FIGS. 5A-5YY, which show that (1) apolipoprotein C-III precursor increases in DLB, does not change in AD, but decreases in PD; (2) latent transforming growth factor beta binding protein 2 and transcription elongation regulator 1 decrease in DLB, increase in AD, but do not change in PD; (3) lysozyme C precursor increases in DLB, but does not change in AD or PD; and (4) T-cadherin decreases in DLB, but does not change in AD or PD.

| Change in Expression | Protein Name |
|---|---|
| ↑ | Apolipoprotein C-III precursor |
| ↓ | Latent transforming growth factor beta binding protein 2 |
| ↑ | Lysozyme C precursor |
| ↓ | T-Cadherin |
| ↓ | Transcription elongation regulator 1 |

Example 33

Diagnosis of Dementia with Lewy Body

A patient's CSF providing the following protein expression pattern is diagnosed as having dementia with Lewy body (DLB) and not Alzheimer's disease (AD) or Parkinson's disease (PD): a decrease in apolipoprotein C1, a decrease in dermatopontin precursor, a decrease in proenkephalin A precursor, a decrease in Rho-associated protein kinase 1 and an increase in tetranectin precursor. This determination is based on the results provided in FIGS. 5A-5YY, which show that (1) apolipoprotein C1, dermatopontin precursor, proenkephalin A precursor and Rho-associated protein kinase 1 decrease in DLB, but do not change in AD or PD; and (2) tetranectin precursor increases in DLB, decreases in AD, but does not change in PD.

| Change in Expression | Protein Name |
|---|---|
| ↓ | Apolipoprotein C1 |
| ↓ | Dermatopontin precursor |
| ↓ | Proenkephalin A precursor |
| ↓ | Rho-associated protein kinase 1 |
| ↑ | Tetranectin precursor |

Example 34

Diagnosis of Dementia with Lewy Body

A patient's CSF providing the following protein expression pattern is diagnosed as having dementia with Lewy body (DLB) and not Alzheimer's disease (AD) or Parkinson's disease (PD): a decrease in splice isoform 1 of basigin precursor, a decrease in splice isoform 2 of glutaryl-CoA dehydrogenase, mitochondrial precursor, a decrease in splice isoform 2 of sodium/potassium/calcium exchanger 2 precursor, an increase in metabotropic glutamate receptor 3 precursor and an increase in polymeric-immunoglobulin receptor precursor. This determination is based on the results provided in FIGS. 5A-5YY, which show that (1) metabotropic glutamate receptor 3 precursor and polymeric-immunoglobulin receptor precursor increase in DLB, do not change in AD, but decrease in PD; (2) splice isoform 1 of basigin precursor decrease in DLB, do not change in AD, but increase in PD; and (3) splice isoform 2 of glutaryl-CoA dehydrogenase, mitochondrial precursor and splice isoform 2 of sodium/potassium/calcium exchanger 2 precursor decrease in DLB, but do not change in AD or PD.

| Change in Expression | Protein Name |
|---|---|
| ↑ | Metabotropic glutamate receptor 3 precursor |
| ↑ | Polymeric-immunoglobulin receptor precursor |
| ↓ | Splice isoform 1 of basigin precursor |
| ↓ | Splice isoform 2 of glutaryl-CoA dehydrogenase, mitochondrial precursor |
| ↓ | Splice isoform 2 of sodium/potassium/calcium exchanger 2 precursor |

Example 35

Diagnosis of Dementia with Lewy Body

A patient's CSF providing the following protein expression pattern is diagnosed as having dementia with Lewy body (DLB) and not Alzheimer's disease (AD) or Parkinson's disease (PD): a decrease in 2'-phophodiesterase, a decrease in laminin gamma-1 chain precursor, a decrease in splice isoform 3 of reelin precursor, an increase in apolipoprotein C-II precursor and an increase in splice isoform 3 of integrin alpha-7 precursor. This determination is based on the results provided in FIGS. 5A-5YY, which show that (1) 2'-phosphodiesterase and splice isoform 3 of reelin precursor decrease in DLB, but do not change in AD or PD; (2) apolipoprotein C-II precursor and splice isoform 3 of integrin alpha-7 precursor increase in DLB, but do not change in AD or PD; and (3) laminin gamma-1 chain precursor decreases in DLB, does not change in AD, but increases in PD.

| Change in Expression | Protein Name |
|---|---|
| ↓ | 2'-phosphodiesterase |
| ↑ | Apolipoprotein C-II precursor |
| ↓ | Laminin gamma-1 chain precursor |
| ↑ | Splice isoform 3 of integrin alpha-7 precursor |
| ↓ | Splice isoform 3 of reelin precursor |

Example 36

Diagnosis of Dementia with Lewy Body

A patient's CSF providing the following protein expression pattern is diagnosed as having dementia with Lewy body (DLB) and not Alzheimer's disease (AD) or Parkinson's disease (PD): a decrease in MGAT3 protein, a decrease in sulfatase 2 isoform b precursor, an increase in activating receptor pilrbeta, an increase in nucleobindin 1 precursor and an increase in selenoprotein P precursor. This determination is based on the results provided in FIGS. 5A-5YY, which show that (1) activating receptor pilrbeta increases in DLB, does not change in AD, but decreases in PD; (2) MGAT3 protein and sulfatase 2 isoform b precursor decrease in DLB, but do not change in AD or PD; and (3) nucleobindin 1 precursor and selenoprotein P precursor increase in DLB, but do not change in AD or PD.

| Change in Expression | Protein Name |
|---|---|
| ↑ | Activating receptor pilrbeta |
| ↓ | MGAT3 protein |
| ↑ | Nucleobindin 1 precursor |
| ↑ | Selenoprotein P precursor |
| ↓ | Sulfatase 2 isoform b precursor |

Example 37

Diagnosis of Dementia with Lewy Body

A patient's CSF providing the following protein expression pattern is diagnosed as having dementia with Lewy body (DLB) and not Alzheimer's disease (AD) or Parkinson's disease (PD): a decrease in protein C20 orf 98, a decrease in SH3-domain GRB2-like 1, an increase in hemopexin precursor, an increase in latent transforming growth factor-beta-binding protein 2 precursor and an increase in transthyretin precursor. This determination is based on the results provided in FIGS. 5A-5YY, which show that (1) hemopexin precursor, latent transforming growth factor-beta-binding protein 2 precursor and transthyretin precursor increase in DLB, but do not change in AD or PD; and (2) protein C20 orf98 and SH3-domain GRB2-like 1 decrease in DLB, but do not change in AD or PD.

| Change in Expression | Protein Name |
|---|---|
| ↑ | Hemopexin precursor |
| ↑ | Latent transforming growth factor-beta-binding protein 2 |

-continued

| Change in Expression | Protein Name |
|---|---|
| | precursor |
| ↓ | Protein C20 orf98 |
| ↓ | SH3-domain GRB2-like 1 |
| ↑ | Transthyretin precursor |

Example 38

Diagnosis of Dementia with Lewy Body

A patient's CSF providing the following protein expression pattern is diagnosed as having dementia with Lewy body (DLB) and not Alzheimer's disease (AD) or Parkinson's disease (PD): a decrease in Kelch/ankyrin repeat containing cyclin A1 interacting protein, a decrease in splice isoform 1 of SWI/SNF-related, matrix associated, actin-dependent regulator, a decrease in splice isoform 2 of metabotropic glutamate receptor 8 precursor, an increase in neuroendocrine convertase 2 precursor and an increase in sortilin-related receptor precursor. This determination is based on the results provided in FIGS. 5A-5YY, which show that (1) Kelch/ankyrin repeat containing cyclin A1 interacting protein and splice isoform 1 of SWI/SNF-related, matrix associated, actin-dependent regulator decrease in DLB, increase in AD, but do not change in PD; (2) neuroendocrine convertase 2 precursor and sortilin-related receptor precursor increase in DLB, do not change in AD or PD; and (3) splice isoform 2 of metabotropic glutamate receptor 8 precursor decreases in DLB, but does not change in AD or PD.

| Change in Expression | Protein Name |
|---|---|
| ↓ | Kelch/ankyrin repeat containing cyclin A1 interacting protein |
| ↑ | Neuroendocrine convertase 2 precursor |
| ↑ | Sortilin-related receptor precursor |
| ↓ | Splice isoform 1 of SWI/SNF-related, matrix associated, actin-dependent regulator |
| ↓ | Splice isoform 2 of metabotropic glutamate receptor 8 precursor |

Example 39

Diagnosis of Dementia with Lewy Body

A patient's CSF providing the following protein expression pattern is diagnosed as having dementia with Lewy body (DLB) and not Alzheimer's disease (AD) or Parkinson's disease (PD): a decrease in neural cell adhesion molecule 1, 140 kDa isoform precursor, a decrease in splice isoform 2 of collagen alpha 2(VI) chain precursor, an increase in DNA-directed RNA polymerase I largest subunit, an increase in latent transforming growth factor-beta binding protein 4 and an increase in protein FAM3C precursor. This determination is based on the results provided in FIGS. 5A-5YY, which show that (1) DNA-directed RNA polymerase I largest subunit increases in DLB, decreases in AD, but does not change in PD; (2) latent transforming growth factor-beta binding protein 4 and protein FAM3C precursor increase in DLB, but do not change in AD or PD; and (3) neural cell adhesion molecule 1, 140 kDa isoform precursor and splice isoform 2 of collagen alpha 2(VI) chain precursor decrease in DLB, but do not change in AD or PD.

| Change in Expression | Protein Name |
|---|---|
| ↑ | DNA-directed RNA polymerase I largest subunit |
| ↑ | Latent transforming growth factor-beta binding protein 4 |
| ↓ | Neural cell adhesion molecule 1, 140 kDa isoform precursor |
| ↑ | Protein FAM3C precursor |
| ↓ | Splice isoform 2 of collagen alpha 2(VI) chain precursor |

Example 40

Diagnosis of Alzheimer's Disease and/or Parkinson's Disease

A patient's CSF providing the following protein expression pattern is diagnosed as having Alzheimer's disease (AD) and/or Parkinson's disease (PD) and not dementia with Lewy body (DLB): a decrease in apolipoprotein A-II precursor, a decrease in cochlin precursor, a decrease in serine/threonine-protein kinase PLK2, a decrease in splice isoform 3 of integrin alpha-7 precursor, and an increase in hepatocellular carcinoma associated protein TB6. This determination is based on the results provided in FIGS. 5A-5YY, which show that (1) apolipoprotein A-II precursor and cochlin precursor increase in AD, decrease in PD, but do not change in DLB; (2) hepatocellular carcinoma associated protein TB6 increases in AD, but does not change in PD or DLB; and (3) serine/threonine-protein kinase PLK and splice isoform 3 of integrin alpha-7 precursor do not change in AD, decrease in PD, but do not change in DLB. The presence of quantitative changes in unique markers of two diseases indicates either an overlap of AD and PD or an uncharacterized disease having a CSF protein profile featuring both AD and PD.

| Change in Expression | Protein Name |
|---|---|
| ↓ | Apolipoprotein A-II precursor |
| ↓ | Cochlin precursor |
| ↑ | Hepatocellular carcinoma associated protein TB6 |
| ↓ | Serine/threonine-protein kinase PLK2 |
| ↓ | Splice isoform 3 of integrin alpha-7 precursor |

Example 41

Diagnosis of Parkinson's Disease and/or Dementia with Lewy Body

A patient's CSF providing the following protein expression pattern is diagnosed as having Parkinson's disease (PD) and/or dementia with Lewy body (DLB) and not Alzheimer's disease (AD): a decrease in apolipoprotein C-III precursor, a decrease in CD99L2 protein, a decrease in HRPE773, a decrease in polymeric-immunoglobulin receptor precursor and an increase in activating receptor pilrbeta. This determination is based on the results provided in FIGS. 5A-5YY, which show that (1) activating receptor pilrbeta, apolipoprotein C-III precursor, HRPE773 and polymeric-immunoglobulin receptor precursor do not change in AD, decrease in PD, but increase in DLB; and (2) CD99L2 protein does not change in AD, increases in PD, but decreases in DLB.

| Change in Expression | Protein Name |
|---|---|
| ↑ | Activating receptor pilrbeta |
| ↓ | Apolipoprotein C-III precursor |
| ↓ | CD99L2 protein |
| ↓ | HRPE773 |
| ↓ | Polymeric-immunoglobulin receptor precursor |

Example 42

Diagnosis of Alzheimer's Disease and/or Dementia with Lewy Body

A patient's CSF providing the following protein expression pattern is diagnosed as having Alzheimer's disease (AD) and/or dementia with Lewy body (DLB) and not Parkinson's disease (PD): a decrease in brain abundant, membrane attached signal protein 1, a decrease in KARCA1 protein, an increase in golgi phosphoprotein 2, an increase in tetranectin precursor and an increase in transcription elongation regulator 1. This determination is based on the results provided in FIGS. 5A-5YY, which show that (1) brain abundant, membrane attached signal protein 1 and tetranectin precursor decrease in AD, do not change in PD, but increase in DLB; and (2) Golgi phosphoprotein 2, KARCAI protein, and transcription elongation regulator 1 increase in AD, do not change in PD, but decrease in DLB.

| Change in Expression | Protein Name |
|---|---|
| ↓ | Brain abundant, membrane attached signal protein 1 |
| ↑ | Golgi phosphoprotein 2 |
| ↓ | KARCA1 protein |
| ↑ | Tetranectin precursor |
| ↑ | Transcription elongation regulator 1 |

Example 43

Diagnosis of Neurogenerative Disease

A patient's CSF providing the following protein expression pattern is diagnosed as having a neurodegenerative disease in general and not specifically Alzheimer's disease (AD) ,Parkinson's disease (PD) or dementia with Lewy body (DLB): a decrease in hect domain and RLD4, a decrease in secretogranin III precursor, a decrease in splice isoform 2 of ephrin type-A receptor 5 precursor, an increase in apolipoprotein C-III precursor and an increase in splice isoform 7 of amyloid beta A4 protein precursor. This determination is based on the results provided in FIGS. 5A-5YY, which show that (1) apolipoprotein C-III precursor does not change in AD, decreases in PD, but increases in DLB; (2) hect domain and RLD 4 increase in AD, decrease in PD, but do not change in DLB; (3) secretogranin III precursor decreases in AD, but does not change in PD or DLB; (4) splice isoform 2 of ephrin type-A receptor 5 precursor does not change in AD or PD, but decreases in DLB; and (5) splice isoform 7 of amyloid beta A4 protein precursor does not change in AD, increases in PD, but does not change in DLB.

| Change in Expression | Protein Name |
|---|---|
| ↑ | Apolipoprotein C-III precursor |
| ↓ | Hect domain and RLD 4 |
| ↓ | Secretogranin III precursor |
| ↓ | Splice isoform 2 of ephrin type-A receptor 5 precursor |
| ↑ | Splice isoform 7 of amyloid beta A4 protein precursor |

Example 44

Diagnosis of Neurogenerative Disease

A patient's CSF providing the following protein expression pattern is diagnosed as having a neurodegenerative disease in general and not specifically Alzheimer's disease (AD) ,Parkinson's disease (PD) or dementia with Lewy body (DLB): a decrease in golgi autoantigen, golgin subfamily B member 1, a decrease in reticulon 4, isoform D, a decrease in splice isoform 1 of transcription factor E2-alpha, an increase in collagen alpha 2(I) chain precursor, and an increase in splice isoform 1 of neuroendocrine protein 7B2 precursor. This determination is based on the results provided in FIGS. 5A-5YY, which show that (1) collagen alpha 2(I) chain precursor increases in AD, but does not change in PD or DLB; (2) Golgi autoantigen, golgin subfamily B member 1 decreases in AD, increases in PD, but does not change in DLB; (3) reticulon 4, isoform D does not change in AD, decreases in PD, but does not change in DLB; (4) splice isoform 1 of neuroendocrine protein 7B2 precursor does not change in AD or PD, but increases in DLB; and (5) splice isoform 1 of transcription factor E2-alpha does not change in AD, decreases in PD, but increases in DLB.

| Change in Expression | Protein Name |
|---|---|
| ↑ | Collagen alpha 2(I) chain precursor |
| ↓ | Golgi autoantigen, golgin subfamily B member 1 |
| ↓ | Reticulon 4, isoform D |
| ↑ | Splice isoform 1 of neuroendocrine protein 7B2 precursor |
| ↓ | Splice isoform 1 of transcription factor E2-alpha |

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

---

That which is claimed is:

1. A method of aiding in a differential diagnosis between Alzheimer's disease (AD), Parkinson's disease (PD), and dementia with Lewy body disease (DLB) in a subject having clinical presentations of neurodegenerative diseases, said method comprising:
   detecting a pattern of gene product expression for at least five gene products listed in FIGS. 5A-5YY in a cerebrospinal fluid sample from the subject; and
   comparing the detected pattern of gene product expression from the cerebrospinal fluid sample to a library of gene product expression patterns known to provide a differential diagnosis between AD, PD and DLB as represented in FIGS. 5A-5YY,
   wherein when the detected pattern corresponds to a pattern as represented in FIGS. 5A-5YY a differential diagnosis between AD, PD, and DLB is made.

2. The method of claim 1, wherein said gene product is a polypeptide.

3. The method of claim 1, wherein said detecting is by mass spectrometry.

4. The method of claim 1, wherein said detecting is by immunoassay.

5. The method of claim 4, wherein said immunoassay is enzyme linked immunosorbent assay (ELISA).

6. The method of claim 1, wherein said detecting is by an antibody-derivatized bead-based technology.

* * * * *

UNITED STATES PATENT AND TRADEMARK OFFICE
CERTIFICATE OF CORRECTION

| | |
|---|---|
| PATENT NO. | : 7,575,876 B2 |
| APPLICATION NO. | : 11/441384 |
| DATED | : August 18, 2009 |
| INVENTOR(S) | : Jing Zhang |

It is certified that error appears in the above-identified patent and that said Letters Patent is hereby corrected as shown below:

Column 1, lines 12-15 insert the following paragraph:
--This invention was made with government support under federal grant nos. R01AG025327 and R01ES012703 awarded by National Institutes of Health. The United States Government has certain rights in this invention.--

Signed and Sealed this
Fifteenth Day of February, 2011

David J. Kappos
*Director of the United States Patent and Trademark Office*